(12) United States Patent
Rosson et al.

(10) Patent No.: US 6,743,609 B1
(45) Date of Patent: Jun. 1, 2004

(54) LINOLEATE ISOMERASE

(75) Inventors: Reinhardt A. Rosson, Manitowoc, WI (US); Alan D. Grund, Manitowoc, WI (US); Ming-De Deng, Manitowoc, WI (US); Fernando Sanchez-Riera, Manitowoc, WI (US)

(73) Assignee: Arkion Life Sciences LLC, Wilmington, DE (US)

( * ) Notice: Subject to any disclaimer, the term of this patent is extended or adjusted under 35 U.S.C. 154(b) by 0 days.

(21) Appl. No.: 09/221,014

(22) Filed: Dec. 23, 1998

Related U.S. Application Data

(60) Provisional application No. 60/068,617, filed on Dec. 23, 1997, and provisional application No. 60/089,560, filed on Jun. 17, 1998.

(51) Int. Cl.$^7$ .......................... C12P 7/64; C12N 11/02; C12N 11/14; C12N 9/58
(52) U.S. Cl. ..................... 435/134; 435/176; 435/177; 435/233
(58) Field of Search ............................... 435/134, 232, 435/233, 176, 177

(56) References Cited

U.S. PATENT DOCUMENTS

| | | | | |
|---|---|---|---|---|
| 5,856,149 A | * | 1/1999 | Pariza et al. ................. | 435/134 |
| 6,015,833 A | | 1/2000 | Sæbø ........................ | 514/558 |

FOREIGN PATENT DOCUMENTS

| | | |
|---|---|---|
| WO | WO 96/38137 | 12/1996 |
| WO | WO 99/29886 | 6/1999 |

OTHER PUBLICATIONS

Hart et al., "Complete nucleotide sequence and transcriptional analysis of shakehead fish retrovirus," J. Virol. vol. 70 pp. 3606–3616, Nov. 1996.*
Burgess et al., Lipids, 26(2):162–165 (1991).
Chibata, 1978, Immobilized Enzymes, pp. 73–81, Halsted Press, Japan.
Eyssen et al., Amer. J. Clin. Nutrition, 27:1329–1340 (1974).
Eyssen et al., Applied and Environmental Microbiol., 47(1):39–43 (1984).
Faber, Ch 3. Special Techniques, pp. 270–340. In (ed.), Biotransformations in organic chemistry (1995).
Fujimoto et al., Bioscience and Biotechnology Biochemistry, 57(6):1026–1027 (1993).
Fukui et al., Endeavour, New Series, 9(1):10–17 (1985).
Garcia et al., Biochimica et Biophysica Acta, 424:296–302 (1976).
Giesel–Bühler et al., 1986, The anearobic transformation of linoleic acid by Acetobacterium woodii. International Symposium—Biocatalysis in organic media. Wageningen, The Netherlands. Elsevier Science Publishers B.V.
Hamberg, Biochem. and Biophys. Res. Comm., 188(3):1220–1227 (1992).
Hughes et al., J. Biological Chemistry, 257(7):3643–3649 (1982).
Hunter et al., J. Biological Chemistry, 251(8):2241–2247 (1976).
Jack et al., Clinica Chimica Acta, 224:139–146 (1994).
Jiang et al., J. Applied Microbiology, 85:95–102 (1998).
Kemp et al., J. General Microbiology, 130:527–533 (1984).
Kemp et al., British J. Nutrition, 52:165–170 (1984).
Kemp et al., British J. Nutrition, 52:171–177 (1984).
Kemp et al., J. General Microbiology, 90:100–114 (1975).
Kepler et al., J. Biological Chemistry, 242(24):5686–5692 (1967).
Kepler et al., Methods in Enzymology, 14:105–110 (1969).
Kepler et al., J. Biological Chemistry, 241(6):1350–1354 (1966).
Kepler et al., J. Biological Chemistry, 245(14):3612–3620 (1970).
Kepler et al., J. Biological Chemistry, 246(9):2765–2771 (1971).
Kil et al., Infect. Immun., 62:2440–2449 (sequence search) (1994).
Klein et al., 1983, Immobilized Microbial Cells, vol. 4, pp. 11–51, "Methods for the Immobilization of Microbial Cells", In Wingard & Katchalski–Katzir (eds.) Academic Press.
Koritala et al., Applied Microbiology and Biotechnology, 32:299–304 (1989).
Lanser, J. American Oil Chemists Society, 75(12):1809–1813 (1998).
Lilly, Chemical Engineering Science, 49(2):151–159 (1994).
Mills et al., Australian J. of Biological Sciences, 23:1109–1113 (1970).
Mortimer et al., J. Biological Chemistry, 249(9):2833–2842 (1974).
Niehaus, Mechanisms of cis–trans isomerization of unstaturated fatty acids, pp. 229–245, In E.E. van Tamelen (ed.) Bioorganic Chemistry, Academic Press, New York, 1989.
Niehaus et al., J. Bacteriology, 134(1):177–183 (1978).
Niehaus et al., J. Biological Chemistry, 245(15):3790–3797 (1970).
Niehaus et al., J. Biological Chemistry, 245(15):3802–3809 (1970).
Park et al., J. Food Sci. and Nutr., 1(2):244–251 (1996).
Polan et al., J. Bacteriology, 88(4):1056–1064 (1964).
Powell, 1996, Chapter 2.14—Immobilized Enzymes, pp. 267–272, In T. Godfrey and S. West (ed.), Industrial Enzymology. The Nature Press, New York.
Sako et al., Nucleic Acids Res., 11:7679–7693 (sequence search) (1983).

(List continued on next page.)

Primary Examiner—Rebecca E. Prouty
Assistant Examiner—David J Steadman
(74) Attorney, Agent, or Firm—Sheridan Ross P.C.

(57) ABSTRACT

The present invention provides an isolated linoleate isomerase and its nucleic acid and amino acid sequence. The present invention also provides a method for producing CLA from an oil using an immobilized bacterial cell or an isolated linoleate isomerase.

47 Claims, 42 Drawing Sheets

OTHER PUBLICATIONS

Schwab et al., *Chemical Reviews*, 90:1203–1245 (1990).
Seltzer, 1972, Cis–Trans Isomerization, pp. 381–406, In P.D. Boyer (ed.), The Enzymes, Academic Press, New York.
Seo et al., *Agricultural Biological Chemistry*, 45(9):2025–2030 (1981).
Swaisgood, 1985, Chapter 1—Enzymes and Immobilized Cells in Biotechnology, pp. 1–24, In Allen I. Laskin (ed.), New Jersey Center for Advanced Biotechnology and Medicine, New Jersey.
Tulloch, *Lipids*, 17:544–550 (1982).
Uchida, *Biochimica et Biophysica Acta*, 348:86–93 (1974).
Uchida, *Agricultural and Biological Chemistry*, 39(2):561–563 (1975).
Uchida et al., *J. General and Applied Microbiology*, 18:109–129 (1972).
Uchida et al., *J. General and Applied Microbiology*, 19:233–249 (1973).
Van Sonsbeek et al., *Enzyme and Microbial Technology*, 15:722–729 (1993).
Verhulst et al., *Systematic and Applied Microbiology*, 9:12–15 (1987).
Verhulst et al., *Microbiology*, 51(3):532–538 (1986).
Verhulst et al., *FEMS Microbiology Ecology*, 31:255–259 (1985).
Wise et al., *Biochemistry*, 36(10):2985–2992 (1998).
Wise et al., *Experientia*, 52:88–92 (1996).
Yamazaki et al., *J. Biological Chemistry*, 254(10):3812–3817 (1979).
Miskin et al., *Microbiology*, 143:1745–1755 (1997).
Steiner et al., *Can. J. Microbiol.*, 43:315–321 (1997).
Yang, "Isolation, identification and characterization of linoleate isomerase from *Lactobacillus reuteri*" (1997) 180 pp., UMI Order No. DA9823268.

* cited by examiner

```
                          A — T
                          A — T
                          A — T
                          G — C
                       T        G
                          C — G
                          G — C
                          A — T
                          A — T
                          G — C
                          A — T
                          A — T
5'-TTA CTA TAA AGA TGA — TTTTTATA-3'
    L   L   STOP
```

FIG. 10

Tested Two Constructs

New Construct #3:

New Construct #4:

Expression System:
  HapII promoter
  LAT promoter
  — with the secretion signal peptide
  — without the secretion signal peptide

LINOLEATE ISOMERASE

CROSS REFERENCE TO RELATED APPLICATIONS

This application claims priority to U.S. Provisional Application No. 60/068,617, filed Dec. 23, 1997, and U.S. Provisional Application No. 60/089,560, filed Jun. 17, 1998, both of which are incorporated herein by reference in their entirety.

FIELD OF THE INVENTION

The present invention relates to an isolated linoleate isomerase enzyme, an nucleic acid molecule encoding a linoleate isomerase enzyme, to immobilized cells containing a linoleate isomerase enzyme, and to a method for converting linoleic acid or linolenic acid to CLA using the isolated linoleate isomerase enzyme, nucleic acid molecule and/or immobilized cells.

BACKGROUND OF THE INVENTION

The term "CLA" is used herein as a generic term to describe both conjugated linoleic acid and conjugated linolenic acid. The CLA compounds (cis,trans)-9,11-linoleic acid and (trans,cis)-10,12-linoleic acid are recognized nutritional supplements and effective inhibitors of epidermal carcinogenesis and forestomach neoplasia in mice, and of carcinogen-induced rat mammary tumors. CLA has also been shown to prevent adverse effects caused by immune stimulation in chicks, mice and rats, and has been shown to decrease the ratio of low density lipoprotein cholesterol to high density lipoprotein cholesterol in rabbits fed an atherogenic diet. CLA also reduces body fat in mouse, rat, chick and pig models. CLA has also been shown to be effective in treating skin. lesions when included in the diet.

CLA occurs naturally in various amounts in virtually all foods. The principle natural sources of CLA are dairy products, beef and foods derived from ruminant animals. In the U.S., beef, beef tallow, veal, lamb (3–4 mg CLA/g fat; 84% cis-9, trans-11) and dairy products (3–7 mg CLA/g fat; 80–90% cis-9, trans-11) have the highest concentration of CLA. CLA concentrations 2–3 times higher are found in Australian dairy products and pasture-fed beef and lamb. Very low concentrations of CLA (0.1–0.7 mg CLA/g fat; ca. 40% each cis-9, trans-11 and trans-10, cis-12) are found in commercial vegetable oils.

CLA is a normal intermediate of linoleic acid metabolism. In cows, (cis,trans)-9,11-CLA produced by natural bacterial flora that is not further metabolized is incorporated into lipids and then into host tissues and milk. Animals take up and incorporate CLA into normal tissue and milk from dietary sources such as milk, milk products or meat containing CLA, or from CLA dietary supplements.

CLA can be synthetically obtained from alkaline isomerization of linoleic or linolenic acid, or of vegetable oils which contain linoleic acid, linolenic acid or their derivatives. Heating vegetable oil at about 180° C. under alkaline conditions catalyzes two reactions: (1) fatty acid ester bonds from the triglyceride lipid backbone are hydrolyzed, producing free fatty acids; and (2) unconjugated unsaturated fatty acids with two or more appropriate double bonds are conjugated. Commercial CLA oils available at the present time, typically made from sunflower oil, are sold without further purification. They contain a mixture of CLA isomers as well as other saturated and unsaturated fatty acids. Generally, chemical synthesis produces about 20–35% (cis, trans)-9,11-CLA and about 20–35% (trans,cis)-10,12-CLA, and the balance as a variety of other isomers. The presence of the non-active, non-natural isomers introduces the need to purify (cis,trans)-9,11-CLA and/or (trans,cis)-10,12-CLA, or to demonstrate the safety and seek regulatory approval of these non-beneficial, non-natural isomers for human use. It is not feasible economically, however, to isolate single isomers of CLA from the CLA made by alkaline isomerization. Using a fractional crystallization procedure, it is possible to enrich 9,11-CLA relative to 10,12-CLA and vice versa. Another approach, described in WO 97/18320 to Loders Croklaan B. V. uses lipases to selectively esterify 10,12-CLA and thus enrich the 9,11-CLA fraction. None of the above-described methods, however, allow for the production of high purity, single isomer CLA.

One method of overcoming the shortcomings of chemical transformation is a whole cell transformation or an enzymatic transformation of linoleic acid, linolenic acid or their derivatives to CLA. It is well known that a biological system can be an effective alternative to chemical synthesis in producing a desired chemical compound where such a biological system is available. The existence of linoleate isomerase enzyme to convert linoleic acid to CLA has been known for over thirty years, however, no one has yet successfully isolated the enzyme. And because it has not yet been isolated, the linoleate isomerase enzyme has not been sequenced.

In many microorganisms, the linoleate isomerase enzyme converts linoleic acid to CLA as an intermediate in the biohydrogenation step. Kepler and Tove have identified this enzyme in *Butyrivibrio fibrisolvens*. Kepler and Tove, *J. Biol. Chem.*, 1966, 241, 1350. However, they could not solubilize the activity, i.e., they were unable to isolate the enzyme in any significantly pure form. Kepler and Tove, *J. Biol. Chem.*, 1967, 242, 5686. In addition, earlier studies have indicated that only compounds which possess a free carboxyl group and a cis-9, cis-12 double bond moieties are isomerized by linoleate isomerase. See Kepler and Tove, *Methods in Enzymology*, 1969, 14, 105–109, and Kepler et al., *J. Biol. Chem.*, 1970, 245, 3612.

Therefore, there remains a need for purifying and identifying a linoleate isomerase enzyme and/or producing one by recombinant techniques. There also remains a need for finding and identifying an linoleate isomerase enzyme which does not require presence of a free carboxylic acid group in the fatty acid for isomerization. In addition, there remains a need for a method for producing CLA utilizing whole cells or isolated linoleate isomerase enzyme.

SUMMARY OF THE INVENTION

The present invention generally relates to isolated linoleate isomerase nucleic acid molecules, isolated linoleate isomerase proteins, immobilized bacterial cells having a genetic modification that increases the action of linoleate isomerase, and methods of using such nucleic acid molecules, proteins and cells to produce CLA.

One embodiment of the invention relates to an isolated linoleate isomerase. Included in the invention are linoleate isomerases from Lactobacillus, Clostridium, Propionibacterium, Butyrivibrio and Eubacterium, and particularly, from *Lactobacillus reuteri, Clostridium sporogenes, Propionibacterium acnes, Butyrivibrio fibrisolvens, Propionibacterium acidipropionici, Propionibacterium freudenreichii* and *Eubacterium lentum*. Particularly preferred linoleate isomerases include linoleate isomerases from *Lactobacillus reuteri, Clostridium sporogenes,* and *Propionibacterium acnes*.

In one embodiment, an isolated linoleate isomerase of the present invention converts linoleic acid and linolenic acid to CLA, including (cis, trans)-9,11-linoleic acid and/or (trans, cis)-10,12-linoleic acid. A linoleate isomerase of the present invention includes linoleate isomerases having one or more of the following biochemical characteristics: a size of about 50 kDa or about 67 kDa; an optimum pH of about 6.8 or about 7.5; a specific linoleic acid isomerization activity of at least about 1000 nmoles mg$^{-1}$ min$^{-1}$; a Km of about 8.1 $\mu$M for linoleic acid, a pH optimum of about 7.5, and a Ki of about 80 $\mu$M for oleic acid; and/or an initial velocity that decreases at about 60 $\mu$M linoleic acid. A linoleate isomerase of the present invention can be either a membrane bound or a soluble enzyme. The linoleate isomerase of the present invention can include lipid material.

In another embodiment, an isolated linoleate isomerase of the present invention includes an amino acid sequence encoded by a nucleic acid molecule that hybridizes under stringent hybridization conditions to a nucleic acid molecule comprising the complement of a sequence selected from the group of SEQ ID NO:4, SEQ ID NO:8, SEQ ID NO:10, SEQ ID NO:14, SEQ ID NO:15, SEQ ID NO:16, SEQ ID NO:17 and SEQ ID NO:26. In another embodiment, the isolated linoleate isomerase is encoded by a nucleic acid molecule which includes a nucleic acid sequence having at least 24 contiguous nucleotides having 100% identity with nucleic acid sequence SEQ ID NO:17. In yet another embodiment, an isolated linoleate isomerase of the present invention includes an amino acid sequence with at least about 70% identity with an amino acid sequence selected from the group of SEQ ID NO:1, SEQ ID NO:5, SEQ ID NO:9, SEQ ID NO:11 and SEQ ID NO:18.

Preferably, an isolated linoleate isomerase is encoded by a nucleic acid molecule comprising a nucleic acid sequence selected from the group of SEQ ID NO:4, SEQ ID NO:8, SEQ ID NO:10, SEQ ID NO:14, SEQ ID NO:15, SEQ ID NO:16, SEQ ID NO:17 and SEQ ID NO:26, with SEQ ID NO:17 being the most preferred. Isolated linoleate isomerases of the present invention include proteins having an amino acid sequence selected from the group of SEQ ID NO:1, SEQ ID NO:5, SEQ ID NO:9, SEQ ID NO:11, SEQ ID NO:18, with SEQ ID NO:18 being most preferred. Also included in the present invention are homologues of linoleate isomerase proteins, including proteins having an amino acid sequence having at least 8 contiguous amino acids with 100% identity to SEQ ID NO:18, and proteins encoded by naturally occurring allelic variants of linoleate isomerase nucleic acid molecules.

In one embodiment, the linoleate isomerase is bound to a solid support, which includes, but is not limited to organic supports, biopolymer supports and inorganic supports.

Another embodiment of the present invention relates to an isolated antibody that selectively binds to the isolated linoleate isomerase of the present invention.

Yet another embodiment of the present invention relates to a method for producing CLA, including contacting an oil, which comprises a compound selected from the group of linoleic acid and linolenic acid, with an isolated linoleate isomerase enzyme of the present invention to convert at least a portion of the compound to CLA. In one embodiment, the compound is in the form of a triglyceride and the method further includes contacting the oil with a hydrolysis enzyme to convert at least a portion of the triglyceride to free fatty acids. Such a hydrolysis enzyme can include lipases, phospholipases and esterases. The method of the present invention can also include a step of recovering the CLA. The CLA can included (cis, trans)-9,11-linoleic acid and/or (trans, cis)-10,12-linoleic acid. The oil can include, but is not limited to, sunflower oil, safflower oil, corn oil, linseed oil, palm oil, rapeseed oil, sardine oil, herring oil, mustard seed oil, peanut oil, sesame oil, perilla oil, cottonseed oil, soybean oil, dehydrated castor oil and walnut oil. In one embodiment of the method, the linoleate isomerase enzyme is bound to a solid support, which can include organic supports, biopolymer supports and inorganic supports.

Another aspect of the present invention relates to an isolated nucleic acid molecule selected from the group of: (a) a nucleic acid molecule comprising a nucleic acid sequence that encodes a protein having an amino acid sequence selected from the group of SEQ ID NO:1, SEQ ID NO:5, SEQ ID NO:9, SEQ ID NO:11, and SEQ ID NO:18; (b) a nucleic acid molecule encoding a homologue of any of such amino acid sequences of (a), wherein the homologue comprises at least 8 contiguous amino acids having 100% identity with amino acids in such amino acid sequences; (c) a nucleic acid molecule comprising a naturally occurring allelic variant of a nucleic acid molecule encoding any of such amino acid sequences of (a);

and, (d) a nucleic acid molecule that is complementary to any of the nucleic acid molecules of (a), (b) or (c). Preferably, an isolated nucleic acid molecule of the present invention encodes a linoleate isomerase, including a linoleate isomerase homologue. In one embodiment, such an isolated nucleic acid molecule hybridizes under stringent conditions to a nucleic acid molecule having a nucleic acid sequence selected from the group of SEQ ID NO:4, SEQ ID NO:8, SEQ ID NO:10, SEQ ID NO:14, SEQ ID NO:15, SEQ ID NO:16, SEQ ID NO:17, SEQ ID NO:26, and/or the complement of any of such nucleic acid sequences. In another embodiment, an isolated nucleic acid molecule of the present invention includes a nucleic acid sequence having at least about 70% identity with a nucleic acid sequence selected from the group of SEQ ID NO:4, SEQ ID NO:8, SEQ ID NO:10, SEQ ID NO:14, SEQ ID NO:15, SEQ ID NO:16, SEQ ID NO:17 and SEQ ID NO:26. In yet another embodiment, an isolated nucleic acid molecule of the present invention includes a nucleic acid sequence having at least 24 contiguous nucleotides having 100% identity with nucleic acid sequence SEQ ID NO:17. Preferred nucleic acid molecules of the present invention include molecules that hybridize under stringent hybridization conditions with a nucleic acid molecule selected from the group of nCLA$_{87}$, nCLA$_{596}$, nCLA$_{1709}$, nCLA$_{3551}$, nCLA$_{1776}$ and nCLA$_{7113}$. More preferably, an isolated nucleic acid molecule of the present invention has a sequence selected from the group of SEQ ID NO:4, SEQ ID NO:8, SEQ ID NO:10, SEQ ID NO:14, SEQ ID NO:15, SEQ ID NO:16, SEQ ID NO:17 and SEQ ID NO:26, with SEQ ID NO:17 being more preferred. An isolated nucleic acid molecule of the present invention preferably encodes a linoleate isomerase protein of the present invention as described above.

The isolate nucleic acid molecule of the present invention includes linoleate isomerase nucleic acid molecules from microorganisms including, but not limited to, Lactobacillus, Clostridium, Propionibacterium, Butyrivibrio, and Eubacterium, with *Lactobacillus reuteri, Clostridium sporogenes, Propionibacterium acnes, Butyrivibrio fibrisolvens, Propionibacterium acidipropionici, Propionibacterium freudenreichii* and *Eubacterium lentum* being particularly preferred. Most preferred linoleate isomerase nucleic acid molecules are from *Lactobacillus reuteri, Clostridium sporogenes,* or *Propionibacterium acnes.*

Also included in the present invention are recombinant molecules, recombinant viruses and recombinant cells which include an isolated nucleic acid molecule of the present invention. In one embodiment, as recombinant cell of the present invention is from a microorganism which includes, but is not limited to, *Lactobacillus reuteri, Clostridium sporogenes, Propionibacterium acnes, Propionibacterium freudenreichii, Propionibacterium acidipropionici, Escherichia coli, Bacillus subtilis, Bacillus licheniformis, Butyrivibrio fibrisolvens,* or *Eubacterium lentum,* with *Escherichia coli, Bacillus subtilis* and *Bacillus licheniformis* being most preferred.

Yet another embodiment of the present invention relates to a method to produce linoleate isomerase, comprising culturing a recombinant cell transformed with an isolated nucleic acid molecule encoding linoleate isomerase.

Another embodiment of the present invention relates to a method for producing CLA, including contacting an oil which comprises a compound selected from the group of linoleic acid and linolenic acid, with an isolated linoleate isomerase enzyme encoded by the isolated nucleic acid molecule of the present invention to convert at least a portion of the compound to CLA.

Yet another embodiment of the present invention relates to an immobilized bacterial cell having a genetic modification that increases the action of linoleate isomerase. The cell can be a microorganism which includes, but is not limited to Lactobacillus, Clostridium, Propionibacterium, Butyrivibrio, Escherichia, Bacillus or Eubacterium cells. In one embodiment, the genetic modification results in over-expression of linoleate isomerase by the bacterial cell. The genetic modification can result in at least one amino acid modification selected from the group consisting of deletion, insertion, inversion, substitution and derivatization of at least one amino acid residue of the linoleate isomerase, wherein such modification results in increased linoleate isomerase action, reduced substrate inhibition, and/or reduced product inhibition. In another embodiment, the genetic modification includes transformation of the cell with a recombinant nucleic acid molecule encoding a linoleate isomerase of the present invention, wherein the recombinant nucleic acid molecule is operatively linked to a transcription control sequence. The recombinant nucleic acid molecule can include any of the isolated nucleic acid molecules described above, including a nucleic acid sequence encoding a homologue of linoleate isomerase. In one embodiment, such a homologue has an amino acid sequence having at least 8 contiguous amino acids with 100% identity to amino acid sequence SEQ ID NO:18.

In one embodiment, the recombinant nucleic acid molecule is integrated into the genome of the bacterial cell. In another embodiment, the recombinant nucleic acid molecule encoding linoleate isomerase comprises a genetic modification which increases the action of the linoleate isomerase and in another embodiment, the genetic modification reduces substrate and/or product inhibition of the linoleate isomerase.

In another embodiment, an immobilized bacterial cell of the present invention can be lysed. The cell can be immobilized by crosslinking with a bifunctional or multifunctional crosslinking agent, including, but not limited to glutaraldehyde.

Yet another embodiment of the present invention relates to a method for producing CLA, including contacting an oil which includes a compound selected from the group of linoleic acid and linolenic acid, with an immobilized bacterial cell having a linoleate isomerase, to convert at least a portion of the compound to CLA. The bacterial cell can be from a microorganism including Lactobacillus, Clostridium, Propionibacterium, Butyrivibrio, Escherichia, Bacillus and Eubacterium cells, preferably *Lactobacillus reuteri, Clostridium sporogenes, Propionibacterium acnes, Propionibacterium freudenreichii, Propionibacterium acidipropionici, Escherichia coli, Bacillus subtilis, Bacillus licheniformis, Butyrivibrio fibrisolvens,* and *Eubacterium lentum,* and most preferably, *Escherichia coli, Bacillus subtilis* or *Bacillus licheniformis.* The cell can be a naturally occurring bacterial cell having a linoleate isomerase, or a genetically modified microorganism as described above. Preferably, a genetically modified microorganism has increased linoleate isomerase action. The compound can include compounds in the form of a triglyceride such that at least a portion of the triglycerides are converted to free fatty acids. Other features of the method are as described above in the method to produce CLA.

BRIEF DESCRIPTION OF THE DRAWINGS

FIG. 10 is a schematic illustration of the putative transcription terminator in the linoleate isomerase gene.

DETAILED DESCRIPTION OF THE INVENTION

Figure 1A:
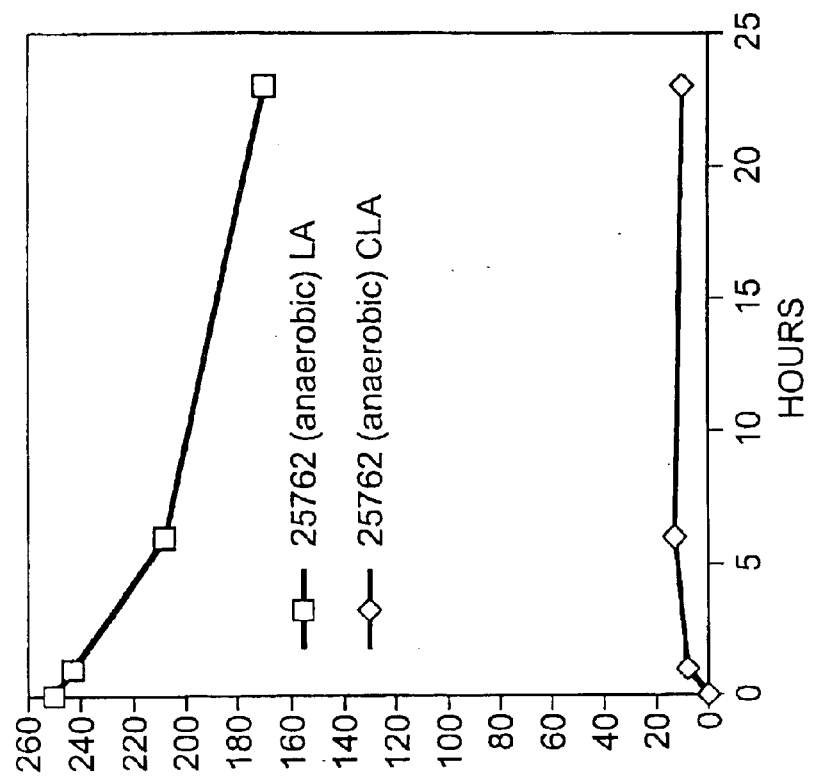
FIG. 1A is a line graph showing whole cell biotransformation of CLA from linoleic acid by *Clostridium sporogenes* ATCC 25762 under aerobic conditions.

One embodiment of the present invention is an isolated linoleate isomerase enzyme. The isolated linoleate isomerase can be used to produce CLA from linoleic acid, linolenic acid or their derivatives. More specifically, isolated linoleate isomerase can convert linoleic acid to conjugated linoleic acid and/or linolenic acid to conjugated linolenic acid. The term "conjugated" refers to a molecule which has two or more double bonds which alternate with single bonds in an unsaturated compound. Linoleate isomerase is a part of a biohydrogenation pathway in microorganisms which convert linoleic acid and other unsaturated fatty acids containing a 9,12-diene moiety into a 9,11-conjugate diene moiety which is then further metabolized to other fatty acids containing a 9-11 monoene moiety. For example, most linoleate isomerase converts (cis,cis)-9,12-linoleic acid to (cis,trans)-9,11-linoleic acid as an intermediate in the biohydrogenation pathway. In many cases, the formation of CLA is followed by metabolism to other CLA isomers as well as metabolism to non-CLA compounds, such as a monoene fatty acid. *Lactobacillus reuteri*, however, produces and accumulates CLA as an end product. Other microorganisms such as *Propionibacterium acnes* convert (cis,cis)-9,12-linoleic acid to (trans,cis)-10,12-linoleic acid.

The term "isolated linoleate isomerase" refers to a linoleate isomerase outside of its natural environment in a pure enough form to achieve a significant increase in activity over crude extracts having linoleate isomerase activity. Such a linoleate isomerase can include, but is not limited to, purified linoleate isomerase, recombinantly produced linoleate isomerase, membrane bound linoleate isomerase, linoleate isomerase complexed with lipids, linoleate isomerase having an artificial membrane, soluble linoleate isomerase and isolated linoleate isomerase containing other proteins. An "artificial membrane" refers to any membrane-like structure that is not part of the natural membrane which contain linoleate isomerase.

An isolated linoleate isomerase of the present invention can be characterized by its specific activity. A "specific activity" refers to the rate of conversion of linoleic acid to CLA by the enzyme. More specifically, it refers to the number of molecules of linoleic acid converted to CLA per mg of the enzyme per time unit. Preferably, the isolated linoleate isomerase of the present invention has a specific activity of at least about 1000 nmoles $mg^{-1}$ $min^{-1}$, more preferably at least about 10,000 nmoles $mg^{-1}$ $min^{-1}$, and most preferably at least about 100,000 nmoles $mg^{-1}$ $min^{-1}$.

Another way to characterize the isolated linoleate isomerase is by its Michaelis-Menten constant. ($K_m$) $K_m$ is a kinetic (i.e., rate) constant of the enzyme-linoleic acid complex under conditions of the steady state. Preferably, the isolated linoleate isomerase of the present invention has $K_m$ of at least about 8.1 μM at a pH of about 7.5 and at a temperature of about 20° C.

Yet another way to characterize the linoleate isomerase is by oleic acid inhibition rate constant ($K_i$). Specifically, $K_i$ is a dissociation rate of the oleic acid-enzyme complex. Preferably, the isolated linoleate isomerase of the present invention has $K_i$ of from about 50 μM to about 100 μM at a pH of about 7.5 and at a temperature of about 20° C., and more preferably, greater than 100 μM, with no inhibition being most preferred.

Still another way to characterize the isolated linoleate isomerase is by its initial velocity ($v_0$), i.e., initial rate of product formation. The initial velocity ($v_0$) refers to the initial conversion rate of linoleic acid to CLA by the enzyme. Specifically, it refers to the number of molecules of linoleic acid converted to CLA per mg of the enzyme per time unit. Preferably, the maximum initial velocity rate of the isolated linoleate isomerase at a pH of about 7.5 is least about 100 nmoles/(sec-mg of protein), more preferably at least about 1,000 nmoles/(sec-mg of protein), and most preferably at least about 10,000 nmoles/(sec-mg of protein).

The isolated linoleate isomerase can be further characterized by its optimum pH. The optimum pH refers to the pH at which the linoleate isomerase has a maximum initial velocity. Preferably the optimum pH is between about 5 and about 10, more preferably between about 6 and about 8, and most preferably from about 6.8 to about 7.5.

Further embodiments of the isolated linoleate isomerase of the present invention include proteins which are encoded by any of the nucleic acid molecules which are described below.

Further embodiments of the present invention include nucleic acid molecules that encode linoleate isomerases. In one embodiment, such nucleic acid molecules include isolated nucleic acid molecules that hybridize under stringent hybridization conditions with: the complement of a gene encoding a naturally occurring linoleate isomerase, a nucleic acid molecule comprising the complement of a nucleic acid molecule encoding an amino acid sequence selected from the group consisting of SEQ ID NO:1, SEQ ID NO:5, SEQ ID NO:9, SEQ ID NO:11 and/or SEQ ID NO:18, or a nucleic acid molecule comprising the complement of a nucleic acid molecule having a nucleic acid sequence SEQ ID NO:4, SEQ ID NO:8, SEQ ID NO:10, SEQ ID NO:14, SEQ ID NO:15, SEQ ID NO:16, SEQ ID NO:17 or SEQ ID NO:26. In other embodiments, the present invention includes an isolated nucleic acid molecule that encodes a protein comprising amino acid sequence selected from the group consisting of SEQ ID NO:1, SEQ ID NO:5, SEQ ID NO:9, SEQ ID NO:11 and/or SEQ ID NO:18 and an isolated nucleic acid molecule having a nucleic acid sequence of SEQ ID NO:4, SEQ ID NO:8, SEQ ID NO:10, SEQ ID NO:14, SEQ ID NO:15, SEQ ID NO:16, SEQ ID NO:17 or SEQ ID NO:26.

As used herein, a linoleate isomerase gene (i.e., nucleic acid molecule which encodes a linoleate isomerase) of the present invention can include an isolated natural linoleate isomerase gene or a homologue thereof, the latter of which is described in more detail below. A nucleic acid molecule of the present invention can include one or more regulatory regions that control production of the linoleate isomerase protein encoded by that gene (such as, but not limited to, transcription, translation or post-translation control regions) as well as a full-length or partial coding region itself. It is to be noted that an isolated linoleate isomerase nucleic acid molecule of the present invention need not encode a protein having linoleate isomerase activity. A linoleate isomerase nucleic acid molecule can encode a truncated, mutated or inactive protein, for example. Such genes and the proteins encoded by such genes are useful in diagnostic assays, for example, or for other purposes such as antibody production, as is described in the Examples below.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, stringent hybridization and washing conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 TO 9.62.

Preferred linoleate isomerase nucleic acid molecules of the present invention include nucleic acid molecules which comprise a nucleic acid sequence having at least about 70%, more preferably, at least about 80% and most preferably, at least about 90% identity with a nucleic acid sequence selected from SEQ ID NO:4, SEQ ID NO:8, SEQ ID NO:10, SEQ ID NO:14, SEQ ID NO:15, SEQ ID NO:16, SEQ ID NO:17 and/or SEQ ID NO:26.

Preferred linoleate isomerase nucleic acid molecules of the present invention also include nucleic acid molecules which comprise a nucleic acid sequence selected from SEQ ID NO:4, SEQ ID NO:8, SEQ ID NO:10, SEQ ID NO:14, SEQ ID NO:15, SEQ ID NO:16, SEQ ID NO:17 and/or SEQ ID NO:26. Preferred linoleate isomerase nucleic acid molecules of the present invention also include nucleic acid molecules which comprise a nucleic acid molecule selected from nCLA$_{87}$, nCLA$_{596}$, nCLA$_{1709}$, nCLA$_{1.1}$, nCLA$_{2.3}$, nCLA$_{3551}$, nCLA$_{1776}$ and/or nCLA$_{7113}$. As used herein, reference to a percent (%) identity refers to a BLAST homology search with the default parameters identified in Table 1.

TABLE 1

BLAST Search Parameters

| | |
|---|---|
| HISTOGRAM | Display a histogram of scores for each search; default is yes. (See parameter H in the BLAST Manual). |
| DESCRIPTIONS | Restricts the number of short descriptions of matching sequences reported to the number specified; default limit is 100 descriptions. (See parameter V in the manual page). See also EXPECT and CUTOFF. |
| ALIGNMENTS | Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual). |
| EXPECT | The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual). |
| CUTOFF | Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT. |
| MATRIX | Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response. |
| STRAND | Restrict a TBLASTN search to just the top or bottom strand of the database sequences; or restrict BLASTN, BLASTX or TBLASTX search to just reading frames on the top or bottom strand of the query sequence. |
| FILTER | Mask off segments of the query sequence that have low compositional complexity, as determined by the SEG program of Wootton & Federhen (Computers and Chemistry, 1993), or segments consisting of short-periodicity internal repeats, as determined by the SNU program of Claverie & States (Computers and Chemistry, 1993), or, for BLASTN, by the DUST program of Tatusov and Lipman (in preparation). Filtering can eliminate statistically significant but biologically uninteresting reports from the blast output (e.g., hits against common acidic-, basic- or proline-rich regions), leaving the more biologically interesting regions of the query sequence available for specific matching against database sequences. Low complexity sequence found by a filter program is substituted using the letter "N" in nucleotide sequence (e.g., "NNNNNNNNNNNNN") and the letter "X" in protein sequences (e.g., "XXXXXXXXX"). Users may turn off filtering by using the "Filter" option on the "Advanced options for the BLAST server" page. Filtering is only applied to the query sequence (or its translation products), not to database sequences. Default filtering is DUST for BLASTN, SEG for other programs. It is not unusual for nothing at all to be masked by SEG, SNU, or both, when applied to |

TABLE 1-continued

BLAST Search Parameters

| | |
|---|---|
| | sequences in SWISS-PROT, so filtering should not be expected to always yield an effect. Furthermore, in some cases, sequences are masked in their entirety, indicating that the statistical significance of any matches reported against the unfiltered query sequence should be suspect. |
| NCBI-gi | Causes NCBI gi identifiers to be shown in the output, in addition to the accession and/or locus name. |

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated linoleate isomerase nucleic acid molecule of the present invention can be isolated from its natural source or produced using recombinant DNA technology (e.g., polymerase chain reaction (PCR) amplification, cloning) or chemical synthesis. Isolated linoleate isomerase nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a linoleate isomerase of the present invention or to form stable hybrids under stringent conditions with natural gene isolates (i.e., a linoleate isomerase nucleic acid homologue). An isolated linoleate isomerase nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a linoleate isomerase of the present invention can vary due to degeneracies.

A linoleate isomerase nucleic acid molecule homologue can be produced using a number of methods known to those skilled in the art (see, for example, Sambrook et al.) . For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologues can be selected by hybridization with a linoleate isomerase gene or by screening the function of a protein encoded by a nucleic acid molecule (e.g., ability to convert linoleic acid to CLA). Additionally, a nucleic acid molecule homologues of the present invention can include nucleic acid sequences comprising at least 24 contiguous nucleotides having 100% identity with nucleic acid sequence SEQ ID NO:17, and more preferably, at least about 30, and even more preferably, at least about 42 contiguous mucleotides having 100% identity with nucleic acid sequence SEQ ID NO:17. Similarly, nucleic acid molecule homologues encode proteins having an amino acid sequence comprising at least 8, and preferably 10, and even more preferably 14 contiguous amino acid residues having 100% identity with amino acid sequence SEQ ID NO:18. According to the present invention, the term "contiguous" means to be connected in an unbroken sequence. For a first sequence to have "100% identity" with a second sequence means that the first sequence exactly matches the second sequence with no gaps between nucleotides or amino acids.

One embodiment of the present invention includes a recombinant vector, which includes at least one isolated nucleic acid molecule of the present invention, inserted into any vector capable of delivering the nucleic acid molecule into a host cell to form a recombinant cell. Such a vector contains heterologous nucleic acid sequences, that is nucleic acid sequences that are not naturally found adjacent to nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of linoleate isomerase nucleic acid molecules of the present invention. The vector can be expressed as an extrachromosomal element (e.g., a plasmid) or it can be integrated into the chromosome. The entire vector can remain in place, or under certain conditions, the plasmid DNA can be deleted leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome.

One type of recombinant vector, referred to herein as a recombinant molecule, includes a nucleic acid molecule of the present invention operatively linked to one or more transcription control sequences to form a recombinant molecule. As used herein, the phrase "recombinant molecule" primarily refers to a nucleic acid molecule or nucleic acid sequence operatively linked to a transcription control sequence, but can be used interchangeably with the phrase "nucleic acid molecule". According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a linoleate isomerase of the present invention. A variety of such transcription control sequences are known to those skilled in the art. Preferred transcription control sequences include those which function in bacterial, fungal (e.g., yeast), insect, plant or animal cells.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed linoleate isomerase to be secreted from the cell that produces the protein. Suitable signal segments include a signal segment that is naturally associated with a linoleate isomerase of the present invention or any heterologous signal segment capable of directing the secretion of a linoleate isomerase according to the present invention. In another embodiment, a recombinant molecule of the present invention comprises a leader sequence to enable an expressed linoleate isomerase to be delivered to and inserted into the membrane of a host cell. Suitable leader sequences include a leader sequence that is naturally associated with a linoleate isomerase of the present invention, or any heterologous leader sequence capable of directing the delivery and insertion of a linoleate isomerase to the membrane of a cell.

One or more recombinant molecules of the present invention can be used to produce an encoded product (i.e., a linoleate isomerase protein) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include any bacterial, fungal (e.g., yeast), insect, plant or animal cell that can be transfected. Host cells can be either untransfected cells or cells that are already transformed with at least one nucleic acid molecule. Preferred host cells for use in the present invention include any microorganism cell which is suitable for expression of a linoleate isomerase of the present invention, including, but not limited to, bacterial cells of the genera Lactobacillus, Clostridium, Propionibacterium, Butyrivibrio, Eubacterium, Escherichia and Bacillus. Particularly preferred host cells include bacterial cells suitable as industrial expression hosts including, but not limited to *Escherichia coli* and Bacillus species, and particularly including, but not limited to *Escherichia coli, Bacillus subtilis* and *Bacillus licheniformis*.

In one embodiment, an isolated linoleate isomerase protein of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a linoleate isomerase protein of the present invention. Such medium typically comprises an aqueous medium having assimilable carbon, nitrogen and phosphate sources, and appropriate salts, minerals, metals and other nutrients, such as vitamins. Examples of suitable media and culture conditions are discussed in detail in the Examples section. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli;* or be retained on the outer surface of a cell or viral membrane.

The phrase "recovering the protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a biocatalyst or other reagent.

Another type of recombinant vector, referred to herein as a recombinant virus, includes a recombinant molecule of the present invention that is packaged in a viral coat and that can be expressed in a cell after delivery of the virus to the cell. A number of recombinant virus particles can be used, including, but not limited to, those based on alphaviruses, baculoviruses, poxviruses, adenoviruses, herpesviruses, and retroviruses.

As used herein, descriptions of nucleic acid molecules in relation to linoleate isomerase proteins (e.g., nucleic acid molecules which encode a linoleate isomerase) refer to isolated linoleate isomerases which can be full-length linoleate isomerase proteins, truncated linoleate isomerase proteins, fusion proteins, or any homologue of such a protein. According to the present invention, a linoleate isomerase protein homologue includes linoleate isomerase proteins in which at least one or a few, but not limited to one or a few, amino acids have been deleted (e.g., a truncated version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol). A linoleate isomerase protein homologue includes proteins having an amino acid sequence comprising at least 8, and preferably at least 10, and more preferably, at least 14, contiguous amino acid residues having 100% identity to any of the linoleate isomerase amino acid sequences disclosed herein, and particularly, to amino acid sequence SEQ ID NO:18. Similarly, a linoleate isomerase protein homologue includes proteins encoded by a nucleic acid sequence comprising at least 24, and preferably at least 30, and more preferably at least 42, contiguous nucleotides having 100% identity to any of the linoleate isomerase nucleic acid molecules disclosed herein, and particularly, to SEQ ID NO:17. A linoleate isomerase protein homologue can also be identified as a protein having at least one epitope which elicits an immune response against a protein having an amino acid sequence selected from the group of SEQ ID NO:1, SEQ ID NO:5, SEQ ID NO:9, SEQ ID NO:11 and/or SEQ ID NO:18. In some embodiments, a linoleate isomerase protein homologue has measurable linoleate isomerase enzymatic activity. In another embodiment, a homologue of a linoleate isomerase is a protein having an amino acid sequence that is sufficiently similar to a natural linoleate isomerase amino acid sequence that a nucleic acid sequence encoding the homologue is capable of hybridizing under stringent conditions to (i.e., with) a nucleic acid molecule encoding the natural linoleate isomerase (i.e., to the complement of the nucleic acid strand encoding the natural linoleate isomerase amino acid sequence). A nucleic acid sequence complement of nucleic acid sequence encoding linoleate isomerase of the present invention refers to the nucleic acid sequence of the nucleic acid strand that is complementary to (i.e., can form a complete double helix with) the strand for which the nucleic acid sequence encodes linoleate isomerase. It will be appreciated that a double stranded DNA which encodes a given amino acid sequence comprises a single strand DNA and its complementary strand having a sequence that is a complement to the single strand DNA. As such, nucleic acid molecules which encode the linoleate isomerase of the present invention can be either double-stranded or single-stranded, and include those nucleic acid molecules that form stable hybrids under stringent hybridization conditions with a nucleic acid sequence that encodes the amino acid sequence selected from the group consisting of SEQ ID NO:1, SEQ ID NO:5, SEQ ID NO:9, SEQ ID NO:11 and/or SEQ ID NO:18, and/or with the complement of the nucleic acid that encodes amino acid sequence selected from the group consisting of SEQ ID NO:1, SEQ ID NO:5, SEQ ID NO:9, SEQ ID NO:11 and/or SEQ ID NO:18. Methods to deduce a complementary sequence are known to those skilled in the art. It should be noted that since amino acid sequencing and nucleic acid sequencing technologies are not entirely error-free, the sequences presented herein, at best, represent apparent sequences of linoleate isomerase of the present invention.

Linoleate isomerase homologues can be the result of natural allelic variation or natural mutation. Linoleate isomerase homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding linoleate isomerase is a gene that occurs at essentially the same locus (or loci) in the genome as the gene which encodes an amino acid sequence selected from the group consisting of SEQ ID NO:1, SEQ ID NO:5, SEQ ID NO:9, SEQ ID NO:11 and/or SEQ ID NO:18, but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art and would be expected to be found within a given bacterial species since the genome is haploid and/or among a group of two or more bacterial species.

Linoleate isomerase proteins also include expression products of gene fusions (for example, used to overexpress soluble, active forms of the recombinant enzyme), of mutagenized genes (such as genes having codon modifications to enhance gene transcription and translation), and of truncated genes (such as genes having membrane binding domains removed to generate soluble forms of a membrane enzyme, or genes having signal sequences removed which are poorly tolerated in a particular recombinant host). It is noted that linoleate isomerase proteins and protein homologues of the present invention include proteins which do not have linoleate isomerase enzymatic activity. Such proteins are useful, for example, for the production of antibodies and for diagnostic assays.

An isolated linoleate isomerase of the present invention, including full-length proteins, truncated proteins, fusion proteins and homologues, can be identified in a straightforward manner by: the proteins' ability to convert linoleic acid and/or linolenic acid to CLA, such as is illustrated in the Examples; the biochemical properties of the protein as described in the Examples; by selective binding to an antibody against a linoleate isomerase; and/or by homology with other linoleate isomerase amino acid and nucleic acid sequences as disclosed in the Examples.

The minimal size of a protein and/or homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 18 bases in length if they are AT-rich. As such, the minimal size of a nucleic acid molecule used to encode linoleate isomerase protein or homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of linoleate isomerase protein or homologue of the present invention is from about 4 to about 6 amino acids in length, with preferred sizes depending on whether a full-length, multivalent (i.e., fusion protein having more than one domain each of which has a function), or functional portions of such proteins are desired.

Preferred linoleate isomerases of the present invention include proteins which comprise an amino acid sequence having at least about 70%, more preferably, at least about 80% and most preferably, at least about 90% identity with an amino acid sequence selected from SEQ ID NO:1, SEQ ID NO:5, SEQ ID NO:9, SEQ ID NO:11 and/or SEQ ID NO:18. Preferred linoleate isomerases of the present invention also include proteins which comprise an amino acid sequence selected from SEQ ID NO:1, SEQ ID NO:5, SEQ ID NO:9, SEQ ID NO:11 and/or SEQ ID NO:18. Preferred linoleate isomerases of the present invention also include proteins which comprise a protein selected from $PCLA_{35}$, $PCLA_{28}$, $PCLA_{158}$, $PCLA_{324}$ and/or $PCLA_{591}$.

The present invention also includes a fusion protein that includes a linoleate isomerase-containing domain attached to one or more fusion segments. Suitable fusion segments for use with the present invention include, but are not limited to, segments that can: enhance a protein's stability; provide other enzymatic activity (e.g., lipase, phospholipase, or esterase to hydrolyze esters of 9,12-diene fatty acids to 9,12-fatty acids); and/or assist purification of a linoleate isomerase (e.g., by affinity chromatography). A suitable fusion segment can be a domain of any size that has the desired function (e.g., imparts increased stability, solubility, action or activity; provides other enzymatic activity such as hydrolysis of esters; and/or simplifies purification of a protein). Fusion segments can be joined to amino and/or carboxyl termini of the linoleate isomerase-containing domain of the protein and can be susceptible to cleavage in order to enable straight-forward recovery of a linoleate isomerase. Fusion proteins are preferably produced by culturing a recombinant cell transformed with a fusion nucleic acid molecule that encodes a protein including the fusion segment attached to either the carboxyl and/or amino terminal end of a linoleate isomerase-containing domain.

Linoleate isomerases can be isolated from a various microorganisms including bacteria and fungi. For example, bacterial genera such as Lactobacillus, Clostridium, Propionibacterium, Butyrivibrio, and Eubacterium have linoleate isomerase activity. In particular, bacterial species such as *Lactobacillus reuteri, Clostridium sporogenes, Propionibacterium acnes, Butyrivibrio fibrisolvens, Propionibacterium acidipropionici, Propionibacterium freudenreichii* and *Eubacterium lentum* contain linoleate isomerase. A particularly preferred linoleate isomerase is *Lactobacillus reuteri* linoleate isomerase. Other preferred linoleate isomerases are linoleate isomerases from *Propionibacterium acnes* and *Clostridium sporogenes*.

To produce significantly high yields of CLA by the methods of the present invention, a microorganism is genetically modified to increase the action of linoleate isomerase, and preferably, to enhance production of linoleate isomerase, and thereby, CLA. As used herein, a genetically modified microorganism, such as any of the preferred genera of bacteria described herein, has a genome which is modified (i.e., mutated or changed) from its normal (i.e., wild-type or naturally occurring) form such that the desired result is achieved (i.e., increase the action of linoleate isomerase). Genetic modification of a microorganism can be accomplished using classical strain development and/or molecular genetic techniques. Such techniques are generally disclosed, for example, in Sambrook et al., 1989, *Molecular Cloning: A Laboratory Manual,* Cold Spring Harbor Labs Press. The reference Sambrook et al., ibid., is incorporated by reference herein in its entirety. Additionally, techniques for genetic modification of a microorganism through recombinant technology are described in detail in the Examples section.

A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

According to the present invention, a genetically modified microorganism includes a microorganism that has been modified using recombinant technology. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications which result in an increase in gene expression or function can be referred to as amplification, overproduction, overexpression, activation, enhancement, addition, or up-regulation of a gene.

In one embodiment of the present invention, a genetic modification of a microorganism increases or decreases the action of a linoleate isomerase. Such a genetic modification includes any type of modification and specifically includes modifications made by recombinant technology and by classical mutagenesis. It should be noted that reference to increasing the action (or activity) of linoleate isomerase refers to any genetic modification in the microorganism in question which results in increased functionality of the enzyme and includes higher activity of the enzymes (e.g., specific activity or in vivo enzymatic activity), reduced inhibition or degradation of the enzymes and overexpression of the enzymes. For example, gene copy number can be increased, expression levels can be increased by use of a promoter that gives higher levels of expression than that of the native promoter, or a gene can be altered by genetic engineering or classical mutagenesis to increase the action of an enzyme. Similarly, reference to decreasing the action of an enzyme refers to any genetic modification in the microorganism in question which results in decreased functionality of the enzymes and includes decreased activity of the enzymes (e.g., specific activity), increased inhibition or degradation of the enzymes and a reduction or elimination of expression of the enzymes. For example, the action of an enzyme of the present invention can be decreased by blocking or reducing the production of the enzyme, "knocking out" the gene encoding the enzyme, reducing enzyme activity, or inhibiting the activity of the enzyme. Blocking or reducing the production of an enzyme can include placing the gene encoding the enzyme under the control of a promoter that requires the presence of an inducing compound in the growth medium. By establishing conditions such that the inducer becomes depleted from the medium, the expression of the gene encoding the enzyme (and therefore, of enzyme synthesis) could be turned off. Blocking or reducing the activity of an enzyme could also include using an excision technology approach similar to that described in U.S. Pat. No. 4,743,546, incorporated herein by reference. To use this approach, the gene encoding the enzyme of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In one embodiment of the present invention, a genetically modified microorganism includes a microorganism which has an enhanced ability to synthesize CLA. According to the present invention, "an enhanced ability to synthesize" a product refers to any enhancement, or up-regulation, in a pathway related to the synthesis of the product such that the microorganism produces an increased amount of the product compared to the wild-type microorganism cultured under the same conditions. In one embodiment of the present invention, enhancement of the ability of a microorganism to synthesize CLA is accomplished by amplification of the expression of the linoleate isomerase gene. Amplification of the expression of linoleate isomerase can be accomplished in a bacterial cell, for example, by introduction of a recombinant nucleic acid molecule encoding the linoleate isomerase gene, or by modifying regulatory control over a native linoleate isomerase gene.

Therefore, it is an embodiment of the present invention to provide a bacteria which is transformed with a recombinant nucleic acid molecule comprising a nucleic acid sequence encoding a linoleate isomerase gene. Preferred recombinant nucleic acid molecules comprising such a nucleic acid sequence include recombinant nucleic acid molecules comprising a nucleic acid sequence which encodes a linoleate isomerase comprising an amino acid sequence selected from SEQ ID NO:1, SEQ ID NO:5, SEQ ID NO:9, SEQ ID NO:11 or SEQ ID NO:18. Other preferred recombinant nucleic acid molecules of the present invention include nucleic acid molecules which comprise a nucleic acid sequence selected from the group of SEQ ID NO:4, SEQ ID NO:8, SEQ ID NO:10, SEQ ID NO:14, SEQ ID NO:15, SEQ ID NO:16, SEQ ID NO:17 or SEQ ID NO:26. The above identified nucleic acid molecules represent nucleic acid molecules comprising wild-type (i.e., naturally occurring) nucleic acid sequences encoding linoleate isomerases. Genetically modified nucleic acid molecules which include nucleic acid sequences encoding homologues of (i.e., modified and/or mutated) linoleate isomerases are also encompassed by the present invention and are described in detail herein.

Therefore, it is yet another embodiment of the present invention to provide a microorganism having a linoleate isomerase with reduced substrate inhibition and/or reduced product inhibition. A linoleate isomerase with reduced substrate and/or product inhibition can be a mutated (i.e., genetically modified) linoleate isomerase gene, for example, and can be produced by any suitable method of genetic modification. For example, a recombinant nucleic acid molecule encoding linoleate isomerase can be modified by any method for inserting, deleting, and/or substituting nucleotides, such as by error-prone PCR. In this method, the gene is amplified under conditions that lead to a high frequency of misincorporation errors by the DNA polymerase used for the amplification. As a result, a high frequency of mutations are obtained in the PCR products. The resulting linoleate isomerase gene mutants can then be screened for reduced substrate and/or product inhibition by testing the mutant genes for the ability to confer increased CLA production onto a test microorganism, as compared to a microorganism carrying the non-mutated recombinant linoleate isomerase nucleic acid molecule. It should be noted that decreased substrate and/or product inhibition of linoleate isomerase will typically result in a linoleate isomerase with increased action, even when the specific activity of the enzyme is remains the same, or actually is decreased, relative to a naturally occurring linoleate isomerase enzyme. Therefore, it is an embodiment of the present invention to produce a genetically modified linoleate isomerase with increased action and increased in vivo enzymatic activity, which has unmodified or even decreased specific activity as compared to a naturally occurring linoleate isomerase. Also encompassed by the present invention are genetically modified linoleate isomerases with increased specific activity.

Therefore, it is an embodiment of the present invention to provide a microorganism which is transformed with a genetically modified recombinant nucleic acid molecule comprising a nucleic acid sequence encoding a mutant, or homologue, linoleate isomerase. Such linoleate isomerases can be referred to herein as linoleate isomerase homologues. Protein homologues are described in detail herein. Preferred recombinant nucleic acid molecules comprising such a nucleic acid sequence include recombinant nucleic acid molecules comprising a nucleic acid sequence which encodes a linoleate isomerase comprising an amino acid sequence selected from the group of SEQ ID NO:1, SEQ ID NO:5, SEQ ID NO:9, SEQ ID NO:11 or SEQ ID NO:18. Other preferred recombinant nucleic acid molecules comprise a nucleic acid sequence selected from the group of SEQ ID NO:4, SEQ ID NO:8, SEQ ID NO:10, SEQ ID NO:14, SEQ ID NO:15, SEQ ID NO:16, SEQ ID NO:17 or SEQ ID NO:26. Particularly preferred genetically modified recombinant nucleic acid molecules useful in the present invention include nucleic acid molecules comprising nucleic acid molecules selected from the group of $nCLA_{87}$, $nCLA_{596}$, $nCLA_{1709}$ $nCLA_{141}$ $nCLA_{2.3}$, $nCLA_{3551}$, $nCLA_{1776}$ and/or $nCLA_{7113}$.

Another embodiment of the present invention is a method for producing CLA from an oil using an isolated linoleate isomerase enzyme. The method can be operated in batch or continuous mode using a stirred tank, a plug-flow column reactor or other apparatus known to those skilled in the art. The oil comprises a compound selected from the group consisting of free fatty acids, salts of free fatty acids (e.g., soaps), and mixtures containing linoleic acid, linolenic acid and mixtures thereof. Preferably the oil comprises at least about 50% by weight of the compound, more preferably at least about 60% by weight, and most preferably at least about 80% by weight. The method of the present invention converts at least a portion of the compound to CLA. Preferably at least about 50% of the oil is converted to CLA, more preferably at least about 70%, and most preferably at least about 95%.

A variety of animal and plant sources are available which contain oil that is useful for the foregoing method of the present invention. Preferably, the oil is selected from the group consisting of sunflower oil, safflower oil, corn oil, linseed oil, palm oil, rapeseed oil, sardine oil, herring oil, mustard seed oil, peanut oil, sesame oil, perilla oil, cottonseed oil, soybean oil, dehydrated castor oil and walnut oil.

When the compound is in the form of a triglyceride, the method includes contacting the oil with a hydrolysis enzyme to convert at least a portion of the triglyceride to free fatty acids. Hydrolysis enzymes include any enzyme which can cleave an ester bond of a triglyceride to provide a free fatty acid. Preferably, hydrolysis enzyme is selected from the group consisting of lipases, phospholipases, and esterases. Use of enzymes to hydrolyze a triglyceride is well known to one skilled in the art.

Alternatively, the oil comprising a triglyceride of a fatty acid can be chemically hydrolyzed to convert at least a portion of the triglyceride to free fatty acids. Chemical conversion of triglyceride to free fatty acids is well known to one skilled in the art. For example, a triglyceride can be hydrolyzed to provide a free fatty acid under a basic condition using a base such as hydroxides, carbonates and bicarbonates. Exemplary bases include sodium hydroxide, calcium hydroxide, potassium hydroxide, sodium carbonate, lithium hydroxide, magnesium hydroxide, calcium carbonate, sodium bicarbonate, lithium carbonate, and lithium bicarbonate. Alternatively, triglycerides can be hydrolyzed to provide a free fatty acid under an acidic condition using an acid. Exemplary acids include, hydrochloric acid, sulfuric acid, phosphoric acid, and carboxylic acids such as acetic acid and formic acid.

In a preferred method of the present invention, the linoleate isomerase is bound to a solid support, i.e., an immobilized enzyme. As used herein, a linoleate isomerase bound to a solid support (i.e., an immobilized linoleate isomerase) includes immobilized isolated linoleate isomerases, immobilized bacterial cells which contain a linoleate isomerase enzyme, stabilized intact cells and stabilized cell/membrane homogenates. Stabilized intact cells and stabilized cell/membrane homogenates include cells and homogenates from naturally occurring microorganisms expressing linoleate isomerase or from genetically modified microorganisms as disclosed elsewhere herein. Thus, although methods for immobilizing linoleate isomerase are discussed below, it will be appreciated that such methods are equally applicable to immobilizing bacterial cells and in such an embodiment, the cells can be lysed.

A variety of methods for immobilizing an enzyme are disclosed in Industrial Enzymology 2nd Ed., Godfrey, T. and West, S. Eds., Stockton Press, New York, N.Y., 1996, pp. 267–272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, California, 1985; and Applied Biochemistry and Bioengineering, Vol. 4, Chibata, I. and Wingard, Jr., L. Eds, Academic Press, New York, N.Y., 1983, which are incorporated herein in their entirety.

Briefly, a solid support refers to any solid organic, biopolymer or inorganic supports that can form a bond with linoleate isomerase without significantly effecting the activity of isolated linoleate isomerase enzyme. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®) agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. Preferably, the solid support is selected from the group consisting of stabilized intact cells and/or crude cell homogenates. Preparation of such supports requires a minimum of handling and cost. Additionally, such supports provide excellent stability of the enzyme.

Stabilized intact cells and/or cell/membrane homogenates can be produced, for example, by using bifunctional crosslinkers (e.g., glutaraldehyde) to stabilize cells and cell homogenates. In both the intact cells and the cell membranes, the cell wall and membranes act as immobilizing supports. In such a system, integral membrane proteins are in the "best" lipid membrane environment. Whether starting with intact cells or homogenates, in this system the cells are either no longer "alive" or "metabolizing", or alternatively, are "resting" (i.e., the cells maintain metabolic potential and active linoleate isomerase, but under the culture conditions are not growing); in either case, the immobilized cells or membranes serve as biocatalysts.

Linoleate isomerase can be bound to a solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports in a bead form are particularly well-suited. The particle size of an adsorption solid support can be selected such that the immobilized enzyme is retained in the reactor by a mesh filter while the substrate (e.g., the oil) is allowed to flow through the reactor at a desired rate. With porous particulate supports it is possible to control the adsorption process to allow linoleate isomerases or bacterial cells to be embedded within the cavity of the particle, thus providing protection without an unacceptable loss of activity.

Cross-linking of a linoleate isomerase to a solid support involves forming a chemical bond between a solid support and a linoleate isomerase. It will be appreciated that although cross-linking generally involves linking a linoleate isomerase to a solid support using an intermediary compound, it is also possible to achieve a covalent bonding between the enzyme and the solid support directly without the use of an intermediary compound. Cross-linking commonly uses a bifunctional or multifunctional reagent to activate and attach a carboxyl group, amino group, sulfur group, hydroxy group or other functional group of the enzyme to the solid support. The term "activate" refers to a chemical transformation of a functional group which allows a formation of a bond at the functional group. Exemplary amino group activating reagents include water-soluble carbodiimides, glutaraldehyde, cyanogen bromide, N-hydroxysuccinimide esters, triazines, cyanuric chloride, and carbonyl diimidazole. Exemplary carboxyl group activating reagents include water-soluble carbodiimides, and N-ethyl-5-phenylisoxazolium-3-sulfonate. Exemplary tyrosyl group activating reagents include diazonium compounds. And exemplary sulfhydryl group activating reagents include dithiobis-5,5'-(2-nitrobenzoic acid), and glutathione-2-pyridyl disulfide. Systems for covalently linking an enzyme directly to a solid support include Eupergit®, a polymethacrylate bead support available from Rohm Pharma (Darmstadt, Germany), kieselguhl (Macrosorbs), available from Sterling Organics, kaolinite available from English China Clay as "Biofix" supports, silica gels which can be activated by silanization, available from W.R. Grace, and high-density alumina, available from UOP (Des Plains, Ill.).

Entrapment can also be used to immobilize linoleate isomerase. Entrapment of linoleate isomerase involves formation of, inter alia, gels (using organic or biological polymers), vesicles (including microencapsulation), semi-permeable membranes or other matrices. Exemplary materials used for entrapment of an enzyme include collagen, gelatin, agar, cellulose triacetate, alginate, polyacrylamide, polystyrene, polyurethane, epoxy resins, carrageenan, and egg albumin. Some of the polymers, in particular cellulose triacetate, can be used to entrap the enzyme as they are spun into a fiber. Other materials such as polyacrylamide gels can be polymerized in solution to entrap the enzyme. Still other materials such as polyglycol oligomers that are functionalized with polymerizable vinyl end groups can entrap enzymes by forming a cross-linked polymer with UV light illumination in the presence of a photosensitizer.

CLA produced by a method of the present invention can be recovered by conventional methods.

CLA can be produced in a two-phase aqueous-oil system with emulsified oil (e.g., emulsified with lecithin), in a co-solvent system, or most preferably, in a two-phase aqueous oil system comprising an oil stream containing very little water (i.e, only the minimum water required for enzyme activity). A further characteristic of linoleate isomerases of the present invention is that they are not inhibited by higher log P solvents. In fact, it has been surprisingly found that in some cases linoleate isomerases of the present invention provide higher conversion of linoleic acid to CLA when immiscible solvents are used. CLA can be produced using a variety of solvent systems. For example, CLA can be produced using an aqueous system or a combination of an aqueous and an organic system. Preferably, a solvent system for CLA production using a linoleate isomerase comprises a solvent selected from the group consisting of water, hexane decane, hexadecane, and propylene glycol.

Yet another embodiment of the present invention relates to a method for producing CLA which utilizes industrial expression systems formed from the microorganisms, nucleic acid molecules, and proteins of the present invention which have been disclosed herein. In this method, immobilized intact whole cells or cell/membrane homogenates formed from naturally occurring microorganisms expressing linoleate isomerase or from a genetically modified microorganism as described herein (including recombinant microorganisms), wherein the microorganism stably expresses a linoleate isomerase of the present invention, will be grown in a suitable culture system (e.g., fermentors). The stabilized cells or homogenates will serve as a biocatalyst in a biotransformation process to convert linoleic acid and/or linolenic acid to CLA, according to the parameters specified elsewhere herein. In one embodiment, the biocatalyst will be reused (i.e., recycled) several times. In a preferred embodiment, the linoleic and/or linolenic acid-containing oil stream is added to the biocatalyst in the presence of a minimum amount of water.

Yet another embodiment of the present invention relates to a nucleic acid molecule denoted $nCSN_{726}$, which is located on the strand of $nCLA_{3551}$ that is complementary to the nucleic acid sequence SEQ ID NO:16, and which comprises an open reading frame having nucleic acid sequence SEQ ID NO:21. SEQ ID NO:21 is positioned on the strand that is complementary to nucleotide positions 1 through 726 of SEQ ID NO:16, with a start codon approximately 275 nucleotides up-stream from the putative start codon of a nucleic acid molecule of the present invention which encodes a linoleate isomerase. The deduced amino acid sequence of SEQ ID NO:21 is represented by SEQ ID NO:22. A protein comprising SEQ ID NO:22 is referred to herein as $PCSN_{242}$. The C-terminal portion of the protein comprising SEQ ID NO:22 is not included in SEQ ID NO:22. The present inventors have shown (See Example 5) that the nucleic acid sequence of SEQ ID NO:21 is 66% identical to a competence-specific nuclease (DNA entry nuclease) from Streptococcus pneumoniae (Q03158), with the amino acid sequence SEQ ID NO:22 being 51–72% identical to the amino acid sequence for this competence-specific nuclease. Therefore, it is believed to be possible that $PCSN_{242}$ represents at least a portion of a competence-specific nuclease. $PCSN_{242}$ is contained within a protein denoted $PCSN_{247}$, which has an amino acid sequence represented herein by SEQ ID NO:34. SEQ ID NO:34 is encoded by a nucleic acid molecule denoted $nCSN_{744}$, which is represented herein by SEQ ID NO:33. The amino acid sequence SEQ ID NO:34 is about 57% identical and about 71% similar to the amino acid sequence for the above-mentioned competence-specific nuclease (BLAST, standard parameters).

Yet another embodiment of the present invention relates to a nucleic acid molecule denoted $nBSP_{941}$, which comprises an open reading frame located upstream from an open reading frame encoding a linoleate isomerase of the present invention, and having nucleic acid sequence SEQ ID NO:27. The deduced amino acid sequence of SEQ ID NO:27 is represented by SEQ ID NO:28. A protein comprising SEQ ID NO:28 is referred to herein as $PBSP_{312}$. The present inventors have shown (See Example 5) that the amino acid sequence of SEQ ID NO:28 is about 56% identical and about 74% similar (using standard BLAST parameters) to a permease from Bacillus subtilis (p54425). Therefore, it is believed to be possible that $PBSP_{312}$ represents at least a portion of a permease.

As described in Example 5 below, one embodiment of the present invention is a nucleic acid molecule, denoted $nUNK1_{656}$, which comprises an open reading frame located about 122 nucleotides downstream from an open reading frame encoding a linoleate isomerase of the present invention. The nucleic acid molecule $nUNK1_{656}$ comprises a nucleic acid sequence represented by SEQ ID NO:19, the deduced amino acid sequence of which is represented by SEQ ID NO:20. A protein having SEQ ID NO:20 is referred to herein as $PUNK1_{218}$. $PUNK1_{218}$ is contained within a larger protein, denoted $PUNK1_{513}$ having a deduced amino acid sequence represented by SEQ ID NO:36. SEQ ID NO:36 is encoded by a nucleic acid molecule denoted $nUNK1_{1540}$, the nucleic acid sequence of which is represented by SEQ ID NO:35. The C-terminal sequence of $PUNK1_{513}$ is incomplete.

Yet another embodiment of the present invention is a nucleic acid molecule, denoted $nUNK2_{600}$, which comprises an open reading frame located upstream from an open reading frame encoding a linoleate isomerase of the present invention. The nucleic acid molecule $nUNK2_{600}$ comprises a nucleic acid sequence represented by SEQ ID NO:29, the deduced amino acid sequence of which is represented by SEQ ID NO:30. A protein having SEQ ID NO:30 is referred to herein as PUNK2$_{199}$.

Yet another embodiment of the present invention is a nucleic acid molecule, denoted nUNK3$_{849}$, which comprises an open reading frame located upstream from an open reading frame encoding a linoleate isomerase of the present invention. The nucleic acid molecule nUNK3$_{849}$ comprises a nucleic acid sequence represented by SEQ ID NO:31, the deduced amino acid sequence of which is represented by SEQ ID NO:32. A protein having SEQ ID NO:32 is referred to herein as PUNK3$_{282}$.

EXAMPLES

It is to be noted that the Examples include a number of molecular biology, microbiology, immunology and biochemistry techniques considered to be known to those skilled in the art.

Disclosure of such techniques can be found, for example, in Sambrook et al., id. and related references. Unless otherwise noted, all column chromatography was performed at 4° C.

Example 1

This example illustrates CLA production from linoleic acid using whole cell biotransformations with a variety of microorganisms. The term "whole cell biotransformation" refers to a conversion of a suitable substrate to CLA by a microorganism.

A variety of other microorganisms were purchased from ATCC (American Type Culture Collection) and grown on Brain Heart Infusion Broth (Difco) supplemented with 0.5% yeast extract, 0.0005% hemin, 0.001% vitamin K$_1$, 0.05% cysteine, and 0.001% resazurin. Cultures were grown in closed containers with limited head space for about 12 to about 16 hours at 37° C., harvested and washed with fresh medium. Culture stocks were maintained in 10% glycerol at about −80° C.

*Lactobacillus reuteri* PYR8 (ATCC Accession No. 55739, deposited on Feb. 15, 1996 with the American Type Culture Collection (ATCC), 10801 University Boulevard, Manassas, Va. 20110, USA, in connection with U.S. Pat. No. 5,674,901 to Cook et al., issued Oct. 7, 1997, incorporated herein by reference in its entirety) was obtained from Dr. Michael Pariza of the Food Research Institute at University of Wisconsin at Madison. The organism was grown on MRS Lactobacillus Broth (BBL) in closed containers with limited head space. Large scale cultures were grown (1–2% inoculum) in 2-L bottles without agitation at 37° C. for about 36 to about 40 hours, harvested by centrifugation, washed once with 0.1 M Bis-Tris, 0.9% NaCl pH 6.0 buffer, and was used immediately or stored at about −80° C.

Cultures were grown and harvested as described above. Washed cells were resuspended in either fresh growth medium or 0.1 M Tris pH 8.0 buffer containing linoleic acid at various concentrations.

Aerobic biotransformations were carried out in baffled 250 mL shake flasks agitated at 200 rpm on a shaker at room temperature.

Anaerobic biotransformations were carried out in sealed 150 mL serum bottles under a 95% nitrogen/5% carbon dioxide head space at 37° C. Media were prepared anaerobically by boiling under a N$_2$/CO$_2$ atmosphere for 15 minutes, sealed with a crimped septum and autoclaved. MRS broth (BBL) was used with *L. reuteri*. Supplemented Brain Heart Infusion broth was used in anaerobic biotransformations with other microorganisms.

Samples were taken at appropriate intervals and analyzed for CLA as described in Example 2. In some experiments, various detergents were added to 0.1–0.5% final concentration. In experiments using organic solvents, linoleic acid was provided as a 5% (v/v) stock dissolved in hexane (log P=3.6), decane (log P=5.6) or hexadecane (log P=8.6). About 5 mL solvent was added to about 20 mL aqueous cell suspension in a 125 mL baffled shake flask incubated at room temperature.

Figure 1B:
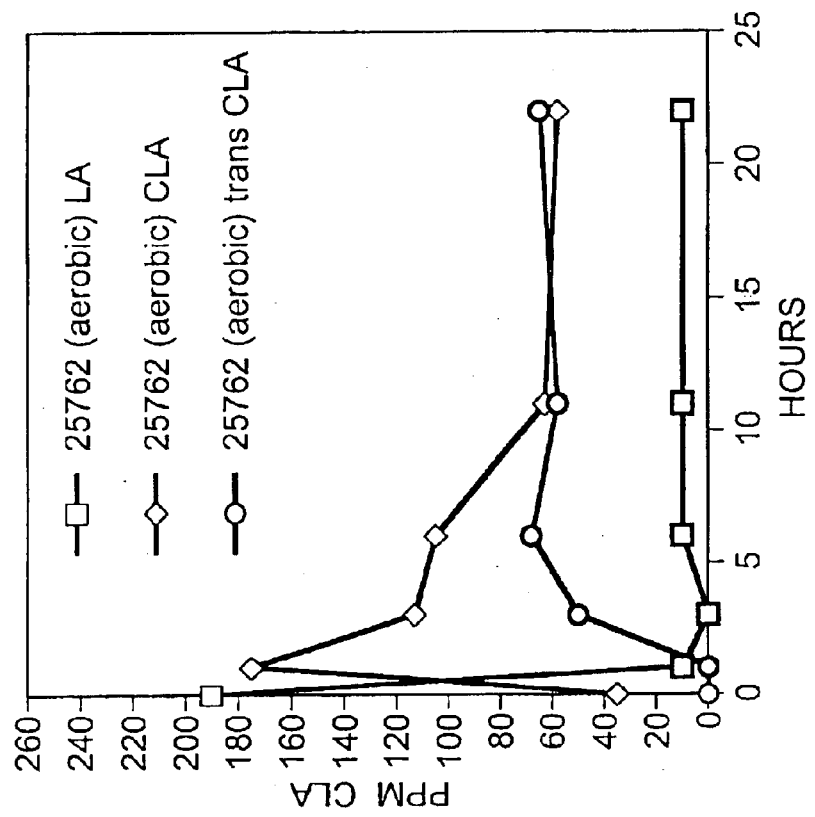
FIG. 1B is a line graph showing whole cell biotransformation of CLA from linoleic acid by *Clostridium sporogenes* ATCC 25762 under anaerobic conditions.

FIGS. 1A and 1B show the results of whole cell biotransformation by *Clostridium sporogenes* ATCC 25762 under aerobic (FIG. 1A) and anaerobic (FIG. 1B) conditions. As FIG. 1A shows, under aerobic conditions, *C. sporogenes* ATCC 25762 rapidly converts linoleic acid to (cis,trans)-9, 11-CLA. However, prolonged whole cell biotransformation results in a decrease in (cis,trans)-9,11-CLA and an increase in (trans,trans)-9,11-CLA and (trans,trans)-10,12-CLA. *C. sporogenes* ATCC 25762 also produces (cis,trans)-9,11-CLA from linoleic acid under anaerobic conditions (FIG. 1B); however, no (trans,trans)-CLA is observed under anaerobic conditions.

Figure 2B:
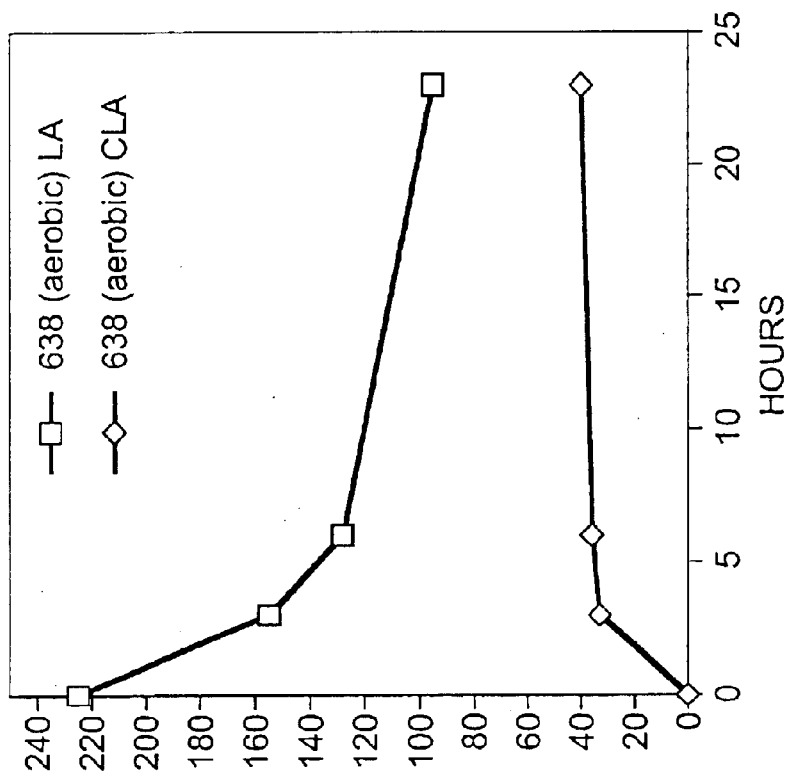
FIG. 2B is a line graph illustrating whole cell biotransformation of CLA from linoleic acid by *C. bifermentans* ATCC 638 under anaerobic conditions.
Figure 2A:
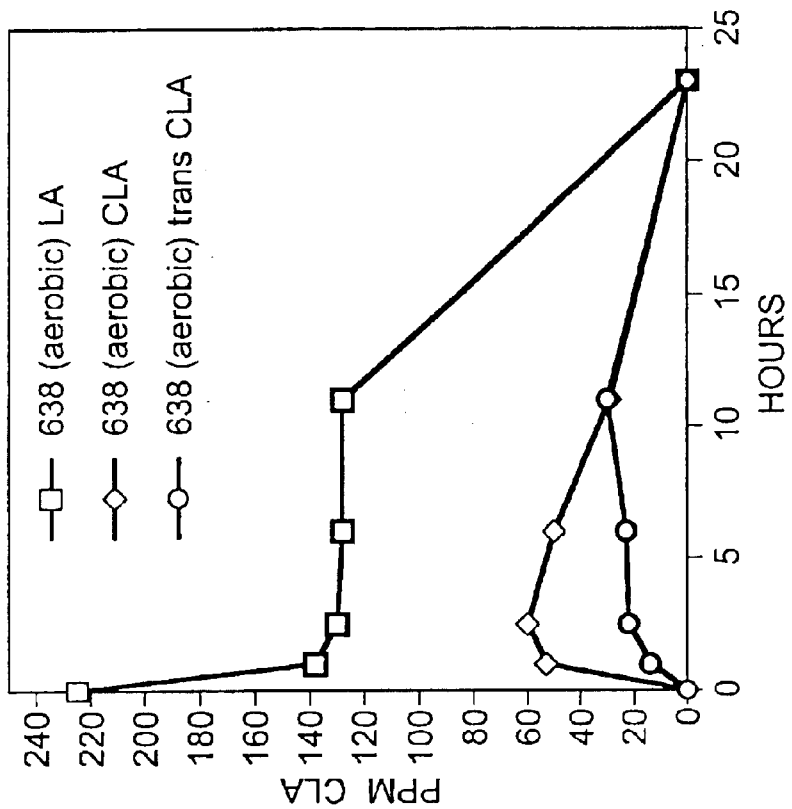
FIG. 2A is a line graph illustrating whole cell biotransformation of CLA from linoleic acid by *C. bifermentans* ATCC 638 under aerobic conditions.

FIGS. 2A and 2B show the results of whole cell biotransformation by *C. bifermentans* ATCC 638 under aerobic (FIG. 2A) and anaerobic (FIG. 2B) conditions. Linoleic acid is more rapidly converted to (cis,trans)-9,11-CLA by *C. bifermentans* ATCC 638 under aerobic conditions (FIG. 2A) than under anaerobic conditions (FIG. 2B). The highest (cis,trans)-9,11-CLA concentration is observed at about 1 to about 5 hours under aerobic conditions. *C. sordellii* ATCC 9714 also converts linoleic acid to (cis,trans)-9,11-CLA under both aerobic and anaerobic conditions (data not shown).

Figure 3B:
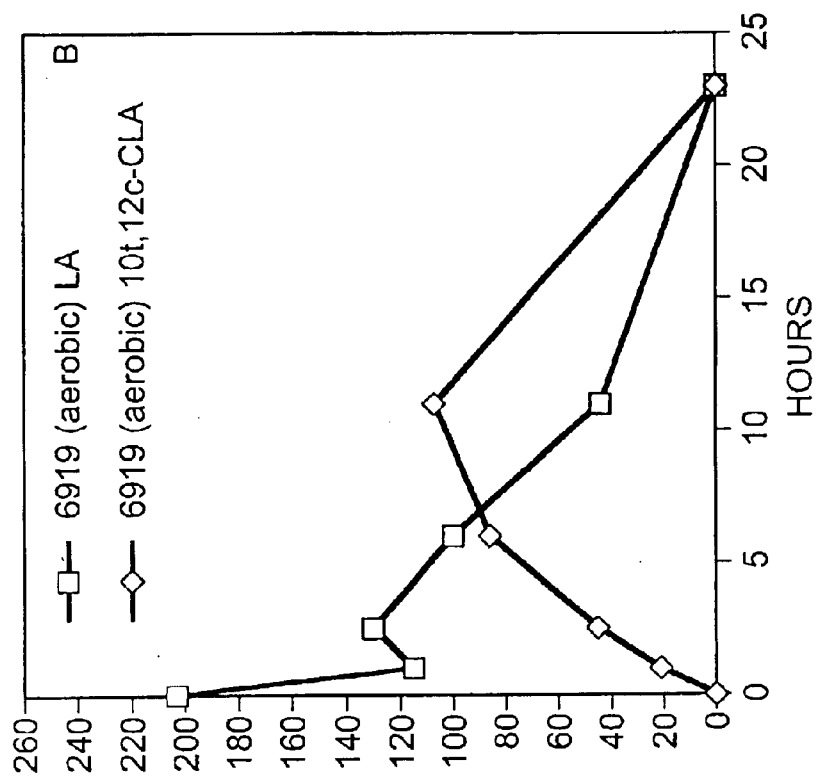
FIG. 3B is a line graph showing whole cell biotransformation of CLA from linoleic acid by *P. acnes* ATCC 6919.
Figure 3A:
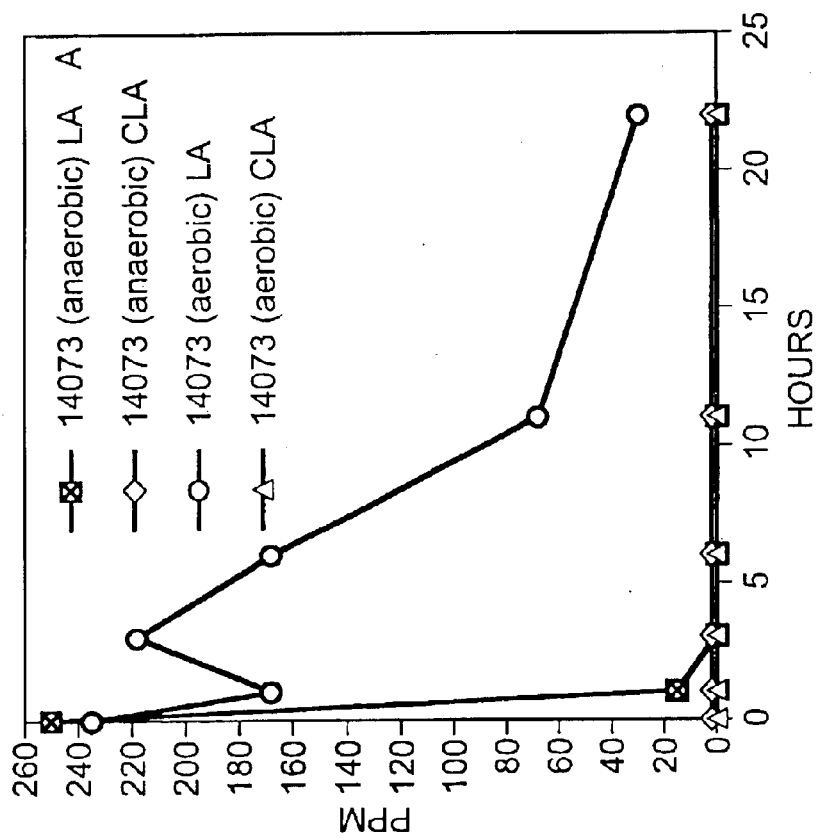
FIG. 3A is a line graph showing whole cell biotransformation of CLA from linoleic acid by *Propionibacterium jensenii* ATCC 14073.
Figure 4:
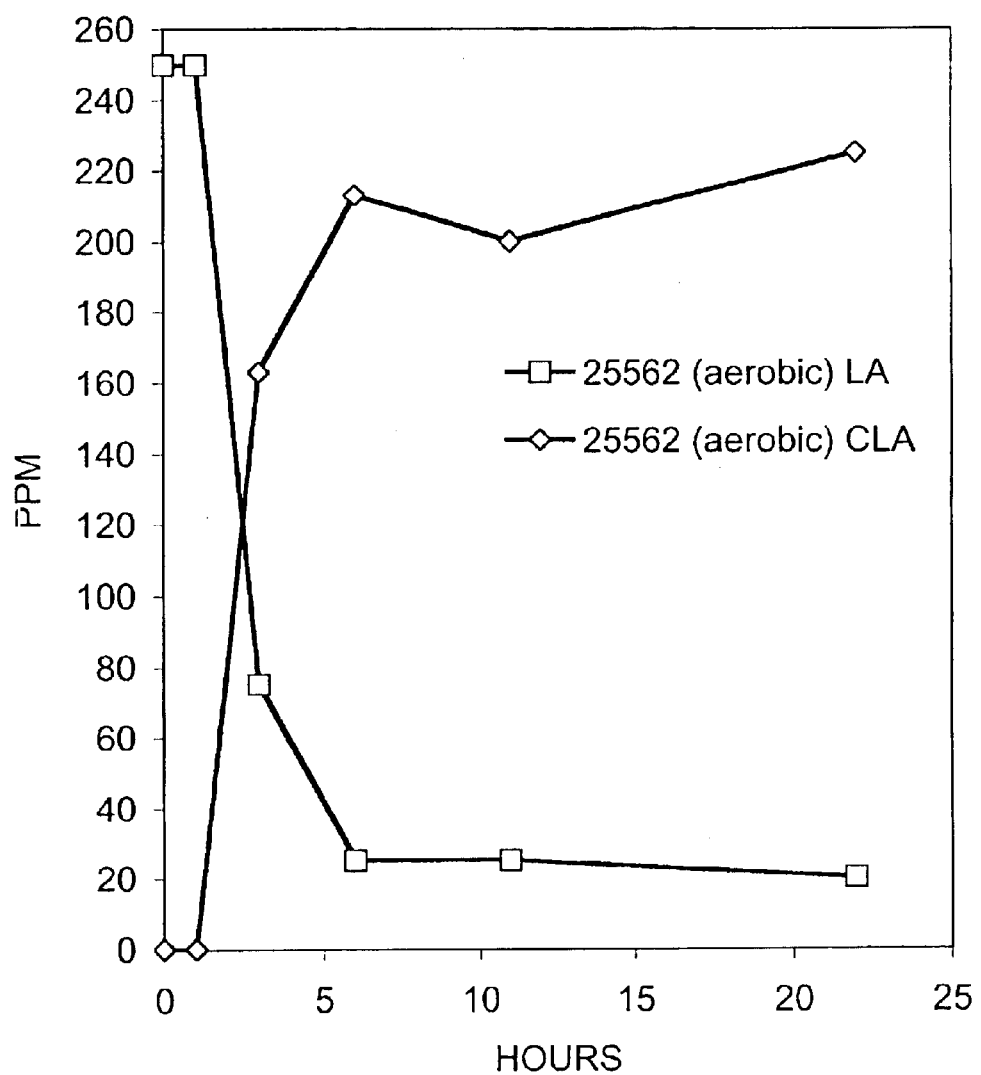
FIG. 4 is a line graph demonstrating whole cell biotransformation of CLA from linoleic acid by *P. acidipropionici* ATCC 25562.

FIGS. 3A, 3B and 4 show the results of whole cell biotransformation by *Propionibacterium jensenii* ATCC 14073 (FIG. 3A), *P. acnes* ATCC 6919 (FIG. 3B), and *P. acidipropionici* ATCC 25562 (FIG. 4), respectively. Interestingly, it has been found that while *P. acidipropionici* converts linoleic acid to (cis,trans)-9,11-CLA, *P. acnes* converts linoleic acid to (trans,cis)-10,12-CLA under aerobic conditions.

Figure 5:
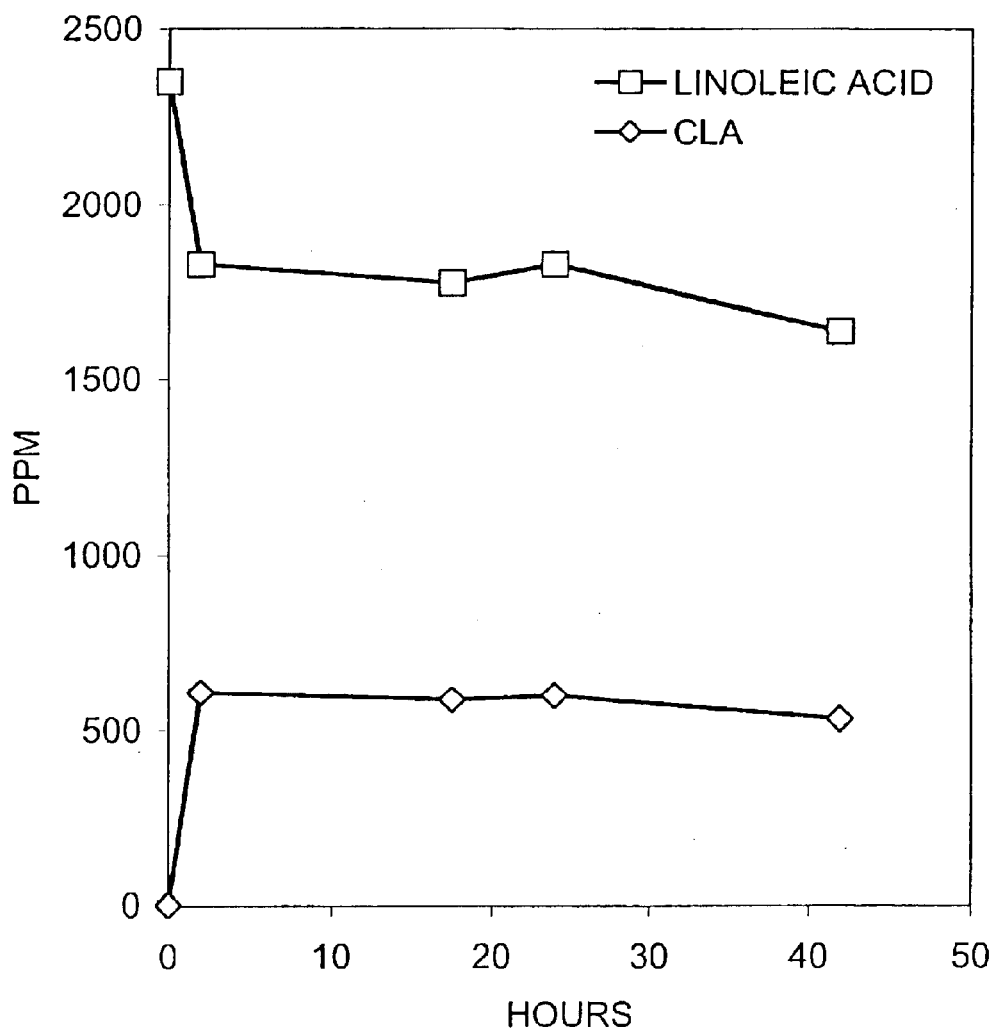
FIG. 5 is a line graph illustrating whole cell biotransformation of CLA from linoleic acid by *L. reuteri* PYR8.

FIG. 5 shows the results of whole cell biotransformation by *Lactobacillus reuteri*. Unlike other microorganisms, the concentration of (cis,trans)-9,11-CLA formed by *L. reuteri* from linoleic acid does not decrease significantly with time. Addition of various nonionic detergents, such as Tween-80 or Triton X-100, does not significantly increase (cis,trans)-9,11-CLA formation.

Example 2

This example describes a procedure for fatty acid analysis to determine the amount of conversion of linoleic acid to CLA.

Fatty acids were extracted from about 1 mL to about 2.5 mL aqueous samples with 0.5 mL of 5 M NaCl added. The samples were shaken with 5 mL of 2:1 mixture of chloroform/methanol in a glass screw cap tube with Teflon lined cap. The two phases were separated and about 1 to 2 mL of the chloroform layer was removed. The organic layer was dried with Na$_2$SO$_4$ and concentrated. The concentrated fatty acids were converted to methyl esters by a modification of the procedure of Chin et al., *J. Food Composition*, 1992, 5:185–192. About 6 mL of 4% HCl in methanol preheated to 60° C. was added to the glass tube containing the fatty acid sample. The tubes were sealed with a Teflon lined cap and incubated in a tube heater at 60° C. for 20 minutes, then cooled to room temperature, and 2 mL of water and 3 mL of hexane are added. After shaking, the organic layer was separated, dried with $Na_2SO_4$, and analyzed by gas chromatography. The order of four CLA peaks was (1) (cis,trans)-9,11-CLA, (2) (trans,cis)-10,12-CLA, (3) (cis,cis)-9-11-CLA and (cis,cis)-10,12-CLA, and (4) (trans,trans)-9,11-CLA and (trans,trans)-10,12-CLA.

Example 3

This Example describes the purification of linoleate isomerase from *L. reuteri*.

Detergent soluble protein fractions were prepared as follows. Frozen cells were thawed and suspended in breakage buffer on ice. The standard breakage buffer for *L. reuteri* comprised 0.1 M Bis-Tris (Calbiochem Ultrol grade) pH 5.8 (4° C.), 10 mM NaCl, 10% glycerol, 2 mM dithiothreitol. For other organisms, Tris buffer at pH 7.5 was used in place of Bis-Tris buffer. The cell suspensions were broken at 18,000 psi using a SLM Aminco French press. The extract was centrifuged at 12,000×g for 30 minutes. The supernatant was further fractionated by centrifugation at 100,000×g for 90 minutes to yield a soluble fraction and a membrane pellet. The membrane pellets were resuspended (approximately 5 mg/mL) and extracted with detergent buffer (0.1 M Bis-Tris pH 5.8, 0.25 M NaCl, 10% glycerol, 2 mM dithiothreitol, 0.3% octylthioglucopyranoside (OTGP, Calbiochem Ultrol grade)) at 4° C. for 4–18 hours with gentle stirring using a magnetic flea. After centrifugation at 100,000×g for 90 minutes, the supernatants (i.e., the detergent soluble protein fraction) were further purified by Method A, B or C, infra.

Method A

Figure 6:
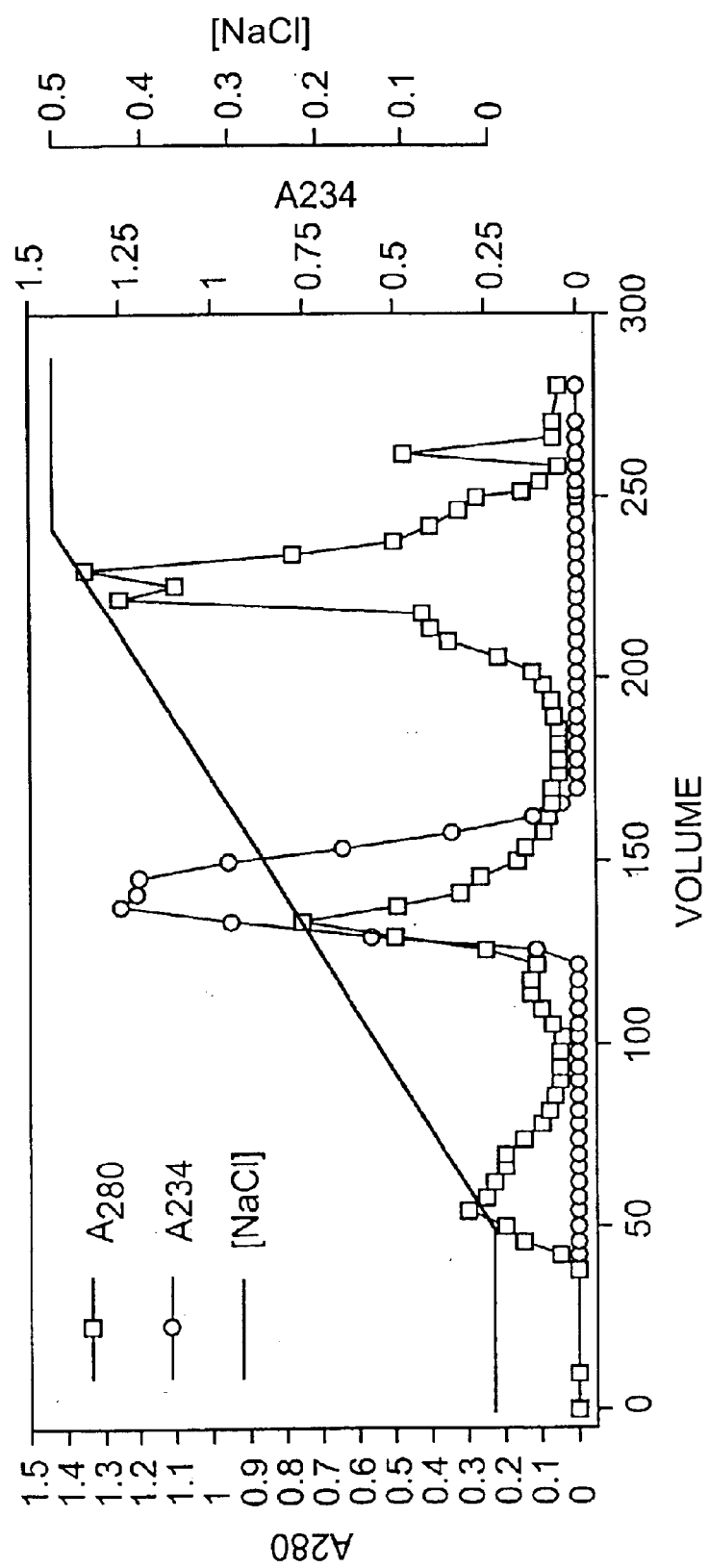
FIG. 6 is a line graph showing DEAE chromatography of detergent solubilized isomerase by *L. reuteri* PYR8.
Figure 7:
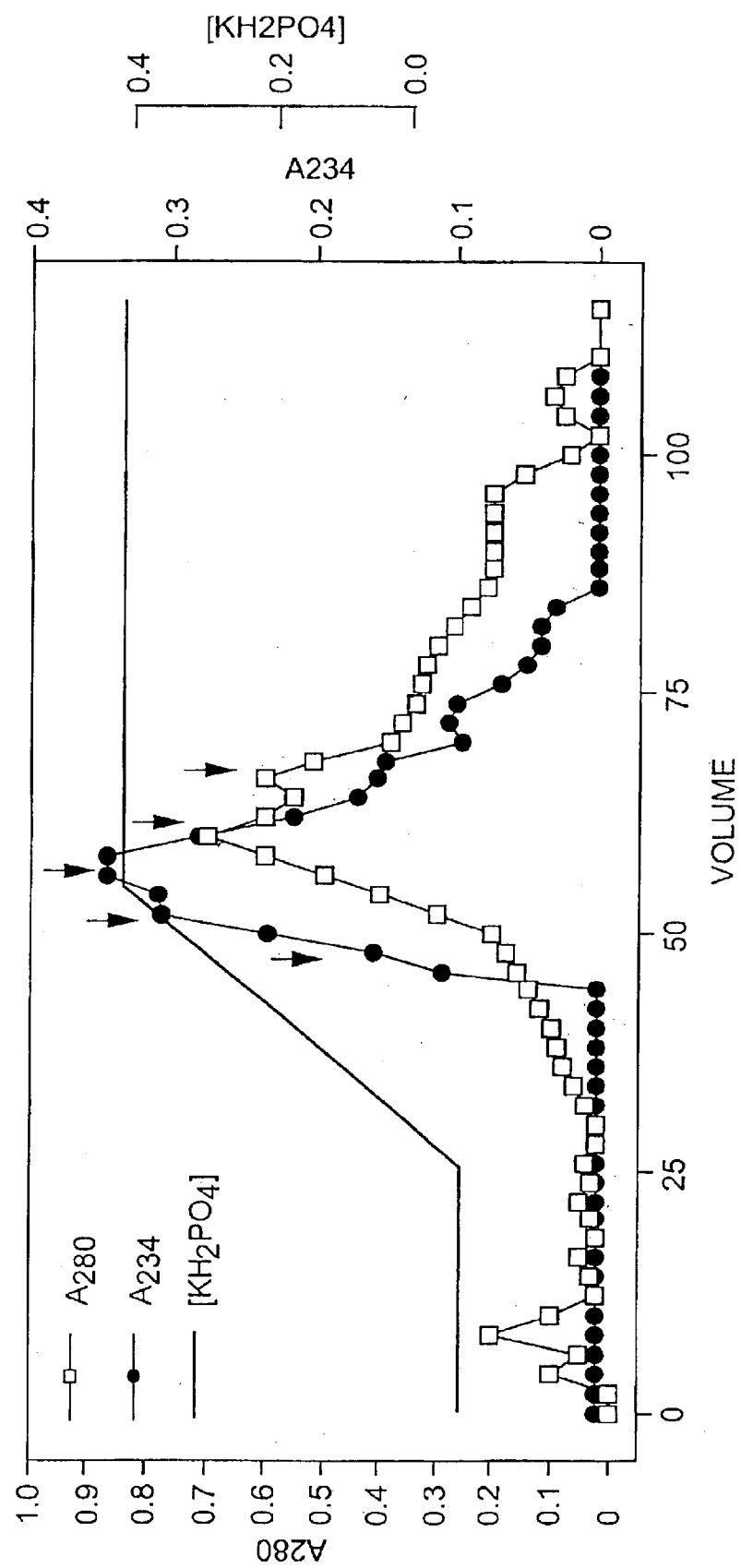
FIG. 7 is a line graph demonstrating hydroxyapatite chromatography of isomerase activity by *L. reuteri* PYR8.

Detergent soluble protein fractions were dialyzed overnight against low salt buffer (0.1 M Bis-Tris pH 5.8, 10 mM NaCl, 2 mM dithiothreitol, 10% glycerol, 0.3% OTGP), and applied to a 2.1×15 cm DEAE-5PW column (TosoHaas) previously equilibrated with low salt buffer. The column was washed (4 mL/min) with the same buffer containing 1 M NaCl (high salt buffer). The results of this step are shown in FIG. 6. Protein concentration was monitored continuously at 280 nm. About 4 mL fractions were collected and assayed for isomerase activity. Isomerase activity in the extracts was measured at 20 ppm linoleic acid. Fractions with significant isomerase activity were combined and concentrated using an Amicon ultrafiltration cell. Concentrated fractions were then applied to a 1.6×55 cm Superdex-200 (Pharmacia) gel filtration column. The column was developed with a buffer comprising 0.1 M Bis-Tris pH 5.8, 0.2 M NaCl, 10% glycerol, 2 mM dithiothreitol, 0.3% OTGP at 0.5 mL/min. Fractions of 2.0 mL were collected and assayed for isomerase activity. Active fractions were collected, concentrated and applied to a hydroxylapatite column (Bio-Rad 5 mL CHT-II cartridge) equilibrated with 0.1 M Bis-Tris pH 5.8, 10 mM $KH_2PO_4$, 10% glycerol, 2 mM dithiothreitol, 0.3% OTGP, 0.2 M NaCl. The column was washed (1 mL/min) with increasing phosphate using the same buffer containing 400 mM $KH_2PO_4$ with the results shown in FIG. 7. Active fractions were subjected to SDS PAGE using the Pharmacia Phast System on 12.5% acrylamide gels. The isomerase activity correlated with four bands on the gel, ranging from 45 to 70 kilodaltons (kD).

Method B

Detergent soluble protein fractions were applied to an affinity column. The affinity column was then sequentially washed (1 mL/min) with low salt buffer (75 mL), high salt buffer (50 mL) and linoleic acid buffer (100 mL) comprising 0.1 M Bis-Tris pH 5.8, 1 M NaCl, 0.3% OTGP, 2 mM dithiothreitol, 10% glycerol, 20% 1,2-propane diol.

The affinity column was prepared as follows. Pharmacia EAH Sepharose 4B was washed and suspended as a slurry in deionized water. A five-fold excess of ligand (linoleic acid or oleic acid) was added in an equal volume of 1,2-propane diol. Solid N-ethyl-N'-(3-dimethylaminopropyl) carbodiimide hydrochloride (EDC) was added to 0.1 M, pH adjusted to around 5.0, and the slurry was mixed by slow inversion overnight at room temperature. The gel was collected on a glass fritted funnel and extensively washed successively with 50% 1,2-propane diol, 0.1 M potassium acetate pH 4.0, 0.5 M NaCl, and 0.1 M tris pH 8.2. The resin was then washed, suspended in low salt buffer and used to prepare a 1.6×20 cm affinity column.

Method C

Figure 8:
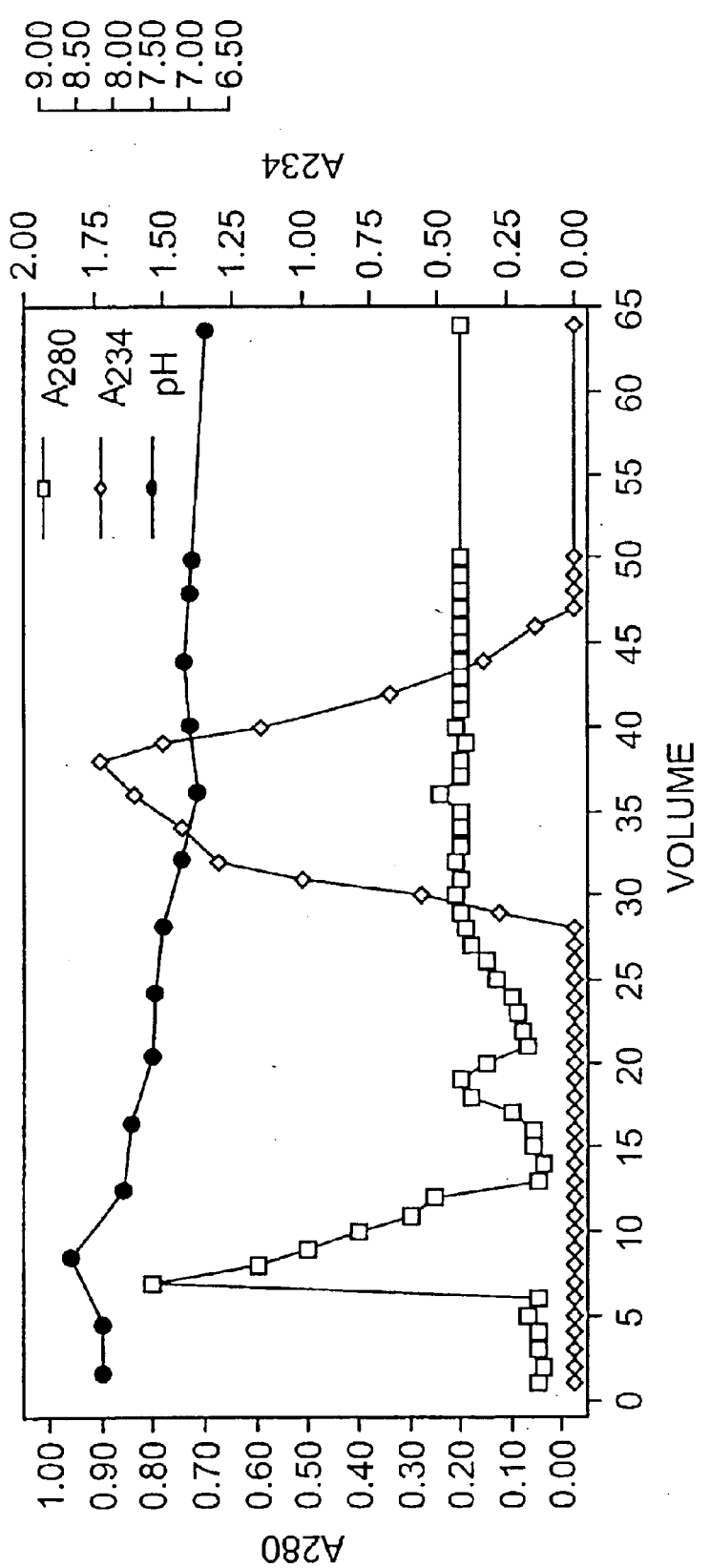
FIG. 8 is a line graph illustrating chromatofocusing of linoleic acid isomerase activity by *L. reuteri* PYR8.

Detergent soluble protein fractions were purified by a chromatography using DEAE-5PW column as described in Method A. The fractions containing isomerase activity were combined, concentrated, and desalted by ultrafiltration. The resulting sample was applied to a Mono PHR 5/20 column (Pharmacia, 0.5×20 cm) which has been previously equilibrated with a buffer comprising 25 mM triethanolamine, 1 mM dithiothreitol, 0.3% OTGP at pH 8.3. The column was then eluted with a buffer comprising 10% Polybuffer 96 (Pharmacia), 0.3% OTGP, 1 mM dithiothreitol at pH 6.5 and 1 mL fractions were collected. As shown in FIG. 8, some of the proteins were present in early fractions (fractions 5–15) and fractions containing isomerase activity were eluted typically between fractions 27 and 47. The fractions containing isomerase activity were combined and further purified by a chromatography using Superdex-200 gel filtration column as described in Method A. The fraction containing isomerase activity was eluted as a single band with a mass of about 160 kD. This same band was run on a denaturing SDS-PAGE gel and resulted in a single band of about 70 kD. This 70 kD band was excised and subjected to N-terminal amino acid sequencing using techniques known to those skilled in the art. A partial N-terminal amino acid sequence of about 35 amino acids was deduced and is represented herein as SEQ ID NO:1. A protein having the sequence of SEQ ID NO:1 is referred to herein as $PCLA_{35}$. It should be noted that since amino acid sequencing technology is not entirely error-free, SEQ ID NO:1 represents, at best, an apparent partial N-terminal amino acid sequence.

Example 4

This example describes the procedure for determining presence of isomerase activity of a fraction or a protein. This example also describes a method for conducting a kinetic assay.

Linoleic isomerase activity was assayed either via CLA quantification by gas chromatography as described in Example 2 or by spectrophotometry. The enzyme assay was carried out in 0.1 M Tris buffer pH 7.5, 10 mM NaCl, 1 mM dithiothreitol, with linoleic acid at 20 parts per million (ppm), unless otherwise noted.

About 50 to about 250 μL of enzyme sample was added to 1.5 mL of enzyme assay buffer for reaction. About 1 to about 2 mL of aqueous phase was separated from the enzyme reaction and was extracted with about 3 mL of hexane. In some experiments, and with chromatography fractions containing detergent, 0.5 mL of methanol and 0.5 mL of 5 M NaCl solution were first added to enhance phase separation. The organic layer was separated and the absorbance at 234 nm was measured using a HP 8452A diode array spectrophotometer. Depending on the level of activity, assay mixtures of chromatography fractions were incubated at room temperature from about 1 to about 24 hours before extraction with hexane.

Kinetic assays were performed directly in a 0.5 mL quartz cuvette at room temperature and were continuously monitored at 234 nm. Reactions were initiated by addition of linoleic acid from a concentrated stock prepared in 1,2-propane diol. Reaction buffer was the same as above except it contained 10% 1,2-propane diol.

Example 5

This Example shows the nucleic acid cloning and sequencing of a *Lactobacillus reuteri* linoleate isomerase nucleic acid molecule of the present invention.

It should be noted that since amino acid sequencing and nucleic acid sequencing technologies are not entirely error-free, the sequences presented in this example and those below, at best, represent apparent sequences of a linoleate isomerase of the present invention.

Two sets of fully degenerated oligonucleotide primers were synthesized, corresponding the sequences of the amino acid residues 1–7 and 23–29 of SEQ ID NO:1.

The first oligonucleotide primer, designated CLAO1, had the following sequence:
5'-cgt gaa ttc ATG TA(T/C) TA(T/C) (T/A)(C/G)N AA(T/C) GGN AA-3' (including an EcoRI site and 3 extra bases (shown as lower case letters) at the 5' end) (SEQ ID NO:2).

The second oligonucleotide primer, designated CLAO2, had the following sequence:
5'-act gga tCC NAC (T/A/G)AT (A/G)AT NGC (A/G)TG (C/T)TT-3' (including an Bam HI site and 3 extra bases (shown as lower case letters) at the 5' end) (SEQ ID NO:3).

PCR products were amplified from *L. reuteri* genomic DNA under optimized PCR conditions and gel purified. A single band of PCR product with the expected size (about 100 bp) was detected on 3% agarose gel. The PCR product was purified and cloned at the Srf I site into the vector pPCR-Script(Amp)SK(+) (Stratagen). Potential recombinant plasmids were analyzed by restriction digestion and sequenced.

Four clones which were sequenced contain inserts of about 87 nucleotides with the same sequence (SEQ ID NO:4) denoted herein as $nCLA_{87}$. The deduced amino acid sequence (SEQ ID NO:5) matches the N-terminal sequence of the linoleate isomerase identified in Example 3. A protein having the sequence of SEQ ID NO:5 is referred to herein as $PCLA_{28}$.

An approach of inverse PCR amplification was used to clone the DNA fragments flanking the N-terminus coding sequence, $nCLA_{87}$. Two oligonucleotide primers, designated CLAO3 and CLAO4 (SEQ ID NO:6 and SEQ ID NO:7, respectively) were designed for inverse PCR. CLAO3 corresponded to nucleotides 25–41 of $nCLA_{87}$ (SEQ ID NO:4), and CLAO4 nucleotides 46–67 of $nCLA_{87}$ (SEQ ID NO:4).

Genomic DNA from *Lactobacillus reuteri* PYR8 was digested with the restriction enzyme Bam HI, treated with T4 DNA ligase to circularize the molecules, and the resulting molecules were used as a template in PCR reactions. A PCR product of 592 nucleotides was purified and cloned at the Srf I site into the vector pPCR-Script(Amp)SK(+) (Stratagen) and sequenced. A 596 bp edited version of this molecule is denoted herein as $nCLA_{596}$ (SEQ ID NO:8). $nCLA_{596}$ contains both the 5' upstream and 3' downstream sequences of a linoleate isomerase gene. The site of Bam HI in the sequence would indicate the junction point. However, no Bam HI site was detected in the sequence. Therefore, the sequence in $nCLA_{596}$ was tentatively edited with reference to its ORF and the sequence $nCLA_{87}$. This tentatively edited sequence contains an ORF of 475 nucleotides. The deduced amino acid sequence of this ORF is denoted $PCLA_{158}$ (SEQ ID NO:9). A protein having the sequence of SEQ ID NO:9 is referred to herein as $PCLA_{158}$.

The sequences immediately flanking CLAO3 and CLAO4 are identical to the sequence in $nCLA_{87}$, confirming the identity of the cloned PCR product. $nCLA_{596}$ was labeled with $^{32}P$ and hybridized to a Southern blot of *Lactobacillus reuteri* PYR8 genomic DNA digested with different restriction enzymes. The partial linoleate isomerase sequence of $nCLA_{596}$ contains one AgeI site and one Eco 58 I site. As expected, two hybridization bands were observed on the Southern blot when the genomic DNA were digested with these two enzymes individually. Only one hybridization band was detected in the digests prepared with enzymes which do not cut the partial isomerase sequence such as BamHI, HindIII, PvuI, SalI, and XhoI while a more diffused hybridization signal in the high molecular mass region (>10 kb) was observed with EcoRI, SacI and SphI digests. These data indicate that the linoleate isomerase gene is present as a single copy in the genome of *Lactobacillus reuteri* PYR8.

In order to clone the entire linoleate isomerase gene, an approach of inverse PCR was followed. As set forth above, a restriction enzyme AgeI site is present in the middle of SEQ ID NO:8 ($nCLA_{596}$) at nucleotide position 295. Southern hybridization showed two bands in AgeI digests of *L. reuteri* PYR8 genomic DNA: about 1.1 and about 2.3 kb, respectively. Genomic DNA from *L. reuteri* PYR8 was digested with AgeI, religated with T4 DNA ligase and used as template in a PCR reaction. Under optimized conditions, a PCR product of about 1.1 kb was generated using the primer set of CLAO3 and CLAO4 as well as a product of 2.3 kb using the primer set CLAO5 and CLAO6 (SEQ ID NO:12 and SEQ ID NO:13, respectively). CLAO5 corresponds to nucleotides 326–342 of $nCLA_{596}$ and CLAO6 corresponds to nucleotides 396–414 of $nCLA_{596}$. These results are consistent with the Southern blot data.

Both of the PCR products were cloned into pPCR-Script (Amp)SK(+) (Stratagen). The clone containing the 1.1 kb fragment is denoted $nCLA_{1.1}$ and the clone with the 2.3 kb fragment is denoted $nCLA_{2.3}$. Initially, about 700 nucleotides of sequencing data upstream from CLAO3 in $nCLA_{1.1}$, and about 700 nucleotides of sequencing data down-stream of CLAO6 in $nCLA_{23}$ were obtained. The sequences of $nCLA_{596}$ partial $nCLA_{1.1}$, and partial $nCLA_{2.3}$ were edited to generate a composite sequence denoted herein as $nCLA_{1709}$ (SEQ ID NO:10). The deduced amino acid sequence of SEQ ID NO:10 is represented herein as SEQ ID NO:11. A protein having the sequence of SEQ ID NO:11 is referred to herein as $PCLA_{324}$.

$nCLA_{1709}$ contains part of the isomerase coding sequence as well as 5' upstream sequence. The 737 nucleotide sequence upstream from the ATG codon corresponding to the first amino acid of the purified polypeptide was compared against known sequences by using Blastx (open reading frames) and Blastn (nucleotides) searches of the BLAST network. No significant homology has been found with any entry, with the score being below 176 for Blastn and 153 for Blastx. The coding sequence downstream from the ATG start codon showed a homology with 67 kD myosin-crossreactive streptococcal antigen from *Streptococcus pyogenes* (U09352): 69% identity at the amino acid level and 66% at the nucleotide level. The longest stretch of identical nucleotides is of 23 nucleotides. The isomerase coding sequence shows also a homology to an ORF from

*Staphylococcus aureus* (L19300): 62% identity at both the amino acid level and the nucleotide level.

Figure 9:
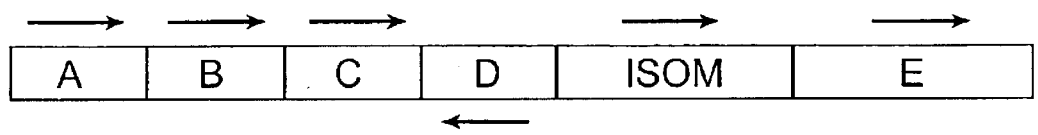
FIG. 9 is a schematic illustration of the linoleate somerase genes and flanking open reading frames in L. reuteriYR8.

Subsequent to the initial sequencing of nCLA$_{1.1}$ and nCLA$_{2.3}$, both clones were completely sequenced (SEQ ID NO:14 and SEQ ID NO:15, respectively) and these sequences, along with the sequence of nCLA$_{596}$ (SEQ ID NO: 8), were assembled to generate a nucleic acid sequence of 3551 nucleotides, which is denoted nCLA$_{3551}$ and which is represented herein by SEQ ID NO:16. SEQ ID NO:14 spans from nucleotide 1 to 1173 of SEQ ID NO:16, and SEQ ID NO:15 spans from nucleotide 1174 to 3551 of SEQ ID NO:16.

nCLA$_{3551}$ contains three open reading frames (FIG. 9; ISOM, D and E), with the first ORF (FIG. 9, ISOM) being an about 1.8 kb nucleic acid molecule spanning from nucleotide positions 1000 to 2775 of SEQ ID NO:16, and represented herein as SEQ ID NO:17. SEQ ID NO:17 encodes a linoleate isomerase of the present invention. A nucleic acid molecule having a nucleic acid sequence represented by SEQ ID NO:17 is referred to herein as nCLA$_{1776}$, and encodes an approximately 67 kD (deduced) protein of 591 amino acid residues having an amino acid sequence represented by SEQ ID NO:18. A protein having amino acid sequence SEQ ID NO:18 is referred to herein as PCLA$_{591}$. The deduced size of PCLA$_{591}$ is consistent with the size of the purified isomerase protein determined on an SDS gel. Seven nucleotides upstream from the initiation codon of this first ORF (SEQ ID NO:17) is a sequence similar to the consensus ribosome-binding-site which has been reported in Lactobacillus. Also, upstream from this first ORF are sequences similar to -10 and -35 promoter sequences. These sequence characteristics are consistent with a conclusion that the start codon at position 1000 of nCLA$_{3551}$ is the translation start codon. Alternatively, the sequence of nCLA$_{3551}$ has, upstream from the first ORF, at 36 nucleotides upstream from the start codon at position 1000, in frame, two ATG start codons in tandem. If one of these codons is a translation start codon, then a leader peptide of about 12 amino acids may be produced which is subsequently cleaved to form a mature isomerase.

The complete coding sequence for the linoleate isomerase gene determined as described above (SEQ ID NO:17) was compared against known sequences by using Blastx (open reading frames) and Blastn (nucleotides) searches of the BLAST network. The linoleate isomerase encoded by SEQ ID NO:17 showed 67% identity at the nucleic acid level and 70% identity at the amino acid level with the previously-mentioned *Staphylococcus pyogenes* (U09352) 67 kD myosin-crossreactive streptococcal antigen. The *Staphylococcus pyogenes* (U09352) protein has 590 amino acid residues. The homology between the linoleate isomerase encoded by SEQ ID NO:17 and the above-described *Streptococcus aureus* (L19300) gene is slightly lower: about 60% at the nucleic acid level and about 62% at the amino acid level. The BLAST Search Parameters with default values for these searches are shown in Table 1 (see above). No defined functions have been previously described for either the *Streptococcus pyogenes* (U09352) or the *Staphylococcus aureus* (L19300) sequences.

The second open reading frame of nCLA$_{3551}$ (FIG. 9, E) is from nucleotide positions 2896 to 3551 of SEQ ID NO:16, and is represented by SEQ ID NO:19. A nucleic acid molecule having SEQ ID NO:19 is referred to herein as nUNK1$_{656}$ which encodes a protein of about 218 amino acid residues having an amino acid sequence of SEQ ID NO:20. A protein having SEQ ID NO:20 is referred to herein as PUNK1$_{218}$. The function of PUNK1$_{218}$ is unknown. The sequence of nUNK1$_{656}$ was compared with known sequences for homology and no significant homology was identified. This second reading frame is located 122 nucleotides downstream from the first open reading frame (SEQ ID NO:17) encoding the linoleate isomerase.

The third open reading frame of nCLA$_{3551}$ (FIG. 9, D) is located on the strand of nCLA$_{3551}$ that is complementary to SEQ ID NO:16, and is represented herein as SEQ ID NO:21. SEQ ID NO:21 is positioned on the strand that is complementary to nucleotide positions 1 through 726 of SEQ ID NO:16, with start codon 275 nucleotides up-stream from position 1000 of the putative start codon of SEQ ID NO:17. A nucleic acid molecule having SEQ ID NO:21 is referred to herein as nCSN$_{726}$ which encodes at least a portion of a protein having an amino acid sequence of SEQ ID NO:22. The C-terminal portion of the protein comprising SEQ ID NO:22 was not present in the isolated clones. A 242 amino acid residue protein having SEQ ID NO:22 is referred to herein as PCSN$_{242}$. A database search (BLAST) showed that the nucleic acid sequence of this third ORF (SEQ ID NO:21) is about 66% identical to a competence-specific nuclease (DNA entry nuclease) from *Streptococcus pneumoniae* (Q03158), with the amino acid sequence SEQ ID NO:22 being about 51–72% identical to the amino acid sequence for this competence-specific nuclease. Therefore, it is believed to be possible that the third ORF identified on the complementary strand of SEQ ID NO:16 encodes a competence-specific nuclease.

Example 6

The following example demonstrates the cloning of sequences flanking the isomerase gene in the *L. reuteri* PYR8 genome.

A third round of inverse PCR was carried out on the circularized genomic DNA from *Lactobacillus reuteri* PYR8 as described in Example 5. This third round was designed to clone more sequences flanking the isomerase gene. Two oligonucleotide primers, designated CLAo9 and CLAo10 (SEQ ID NO:23 and SEQ ID NO:24, respectively) were designed for this round of PCR. CLAo9 (SEQ ID NO:23) was designed close to the 5' end of the sequence of nCLA$_{355}$. (nucleotides 63–40 of SEQ ID NO:16). CLAo10 was designed to correspond to the 3' end of the nCLA$_{3551}$ sequence (nucleotides 3505–3522 of SEQ ID NO:16).

More particularly, *L. reuteri* PYR8 genomic DNA was digested with SalI, religated and amplified with oligonucleotide primers CLAo9 and CLAo10. A PCR product of about 3.5–4.0 kb was cloned into pPCR-Script Amp SK(+) and sequenced. This nucleic acid molecule was denoted nSAL$_{3684}$ and is represented herein by SEQ ID NO:25.

The identity of nSAL$_{3684}$ was confirmed by the sequences flanking the primers CLAo9 and CLAo10. The sequence nSAL$_{3684}$ contains a unique SalI site, which indicates the junction point of the inverse PCR product. Therefore, the sequence nSAL$_{3648}$ was spliced at the SalI site and added to the 3' and 5' ends of the sequence of nCLA$_{3551}$ (SEQ ID NO:16). This approximately 7 kb nucleic acid molecule is denoted nCLA$_{7113}$ and is represented herein by SEQ ID NO:26.

The approximately 7 kb *L. reuteri* PYR8 genomic DNA (SEQ ID NO:26) contains 6 open reading frames, schematically illustrated in FIG. 9. There are four ORF's (A, B, C and D) located 5' upstream of the isomerase gene (ISOM) and one ORF located 3' downstream of the isomerase gene.

The first open reading frame of nCLA$_{7113}$ (FIG. 9, A) spans from nucleotide positions 1 to 941 of SEQ ID NO:26, and is represented by SEQ ID NO:27. A nucleic acid molecule having SEQ ID NO:27 is referred to herein as $nBSP_{941}$ which encodes a protein of about 312 amino acid residues having an amino acid sequence of SEQ ID NO:28. A protein having SEQ ID NO:28 is referred to herein as $PBSP_{312}$. A database search (BLAST) showed that the amino acid sequence (SEQ ID NO:28) of the protein encoded by this first ORF A (SEQ ID NO:27) is about 56% identical and 74% similar (using standard BLAST parameters) to a permease from Bacillus subtilis (p54425). Therefore, it is believed to be possible that the first ORF A of SEQ ID NO:26 encodes a permease.

The second open reading frame of $nCLA_{7113}$ (FIG. 9, B) spans from nucleotide positions 1146 to 1745 of SEQ ID NO:26, and is represented by SEQ ID NO:29. A nucleic acid molecule having SEQ ID NO:29 is referred to herein as $nUNK2_{600}$ which encodes a protein of about 199 amino acid residues having an amino acid sequence of SEQ ID NO:30. A protein having SEQ ID NO:30 is referred to herein as $PUNK2_{199}$. The function of $PUNK2_{199}$ is unknown. The sequence of $nUNK2_{600}$ was compared with known sequences for homology and no significant homology was identified. The highest Blastp score using standard defaults was 51.

The third open reading frame of $nCLA_{7113}$ (FIG. 9, C) spans from nucleotide positions 1742 to 2590 of SEQ ID NO:26, and is represented by SEQ ID NO:31. A nucleic acid molecule having SEQ ID NO:31 is referred to herein as $nUNK3_{849}$ which encodes a protein of about 282 amino acid residues having an amino acid sequence of SEQ ID NO:32. A protein having SEQ ID NO:32 is referred to herein as $PUNK3_{282}$. The function of $PUNK3_{282}$ is unknown. The sequence of $nUNK3_{849}$ was compared with known sequences for homology and no significant homology was identified. The highest Blastp score using standard defaults was 68.

The fourth open reading frame of $nCLA_{7113}$ (FIG. 9, D) spans from nucleotide positions 2662 to 3405 of SEQ ID NO:26, and is represented by SEQ ID NO:33. A nucleic acid molecule having SEQ ID NO:33 is referred to herein as $nCSN_{744}$ which encodes a protein having an amino acid sequence of SEQ ID NO:34. A 247 amino acid residue protein having SEQ ID NO:34 is referred to herein as $PCSN_{247}$. $PCSN_{242}$ (SEQ ID NO:22), described above in Example 5 (the third ORF identified in $nCLA_{3551}$) is included in $PCSN_{247}$ spanning from amino acid position 1 to 242 of SEQ ID NO:34. Similarly, the nucleic acid sequence of $nCSN_{726}$ (SEQ ID NO:21) spans from nucleotides 1 to 726 of SEQ ID NO:33. A database search (BLAST) showed that the amino acid sequence SEQ ID NO:34 is about 57% identical and about 71% similar (using standard parameters) to the amino acid sequence for the above-mentioned Streptococcus pneumoniae competence-specific nuclease.

The fifth open reading frame of $nCLA_{7113}$ (FIG. 9, ISOM) is a nucleic acid molecule ($nCLA_{1776}$, SEQ ID NO:17) encoding the linoleate isomerase ($PCLA_{591}$, SEQ ID NO:18) of the present invention, as described above in Example 5.

The sixth open reading frame of $nCLA_{7113}$ (FIG. 9, E) spans from nucleotide positions 5574–7113 of SEQ ID NO:26, and is represented by SEQ ID NO:35. A nucleic acid molecule having SEQ ID NO:35 is referred to herein as $nUNK1_{1540}$ which encodes a protein having an amino acid sequence of SEQ ID NO:36. A 513 amino acid residue protein having SEQ ID NO:36 is referred to herein as $PUNK1_{513}$. $PUNK1_{218}$ (SEQ ID NO:20), described above in Example 5 (the second ORF identified in $nCLA_{3551}$) is included in $PUNK1_{513}$, spanning from amino acid position 1 to 218 of SEQ ID NO:36. Similarly, the nucleic acid sequence of $nUNK1_{656}$ (SEQ ID NO:19) spans from nucleotides 1 to 656 of SEQ ID NO:35. The sequence of $nUNK1_{1540}$ was compared with known sequences for homology and no significant homology was identified. The highest Blastp score for $PUNK1_{513}$ using standard defaults was 51. The C-terminal sequence of $PUNK1_{513}$ is incomplete.

The isomerase gene is very likely transcribed as a monocistron. This conclusion is based on two observations. First, the ORF that is located immediately upstream from the isomerase gene (FIG. 9, D) is coded on the opposite strand. Secondly, a reverse-repeat DNA sequence was observed in the region downstream from the stop codon of the isomerase gene (FIG. 10). This 28 nucleotide structure (SEQ ID NO:37), starting at the base 6 after the stop codon, has only one unmatched base. This structure could function as a rho-dependent stem-loop transcription terminator of the isomerase gene. Therefore, it is concluded that the isomerase gene is most likely transcribed as a monocistron and that the open reading frame downstream from the isomerase gene seems to be in a separate transcription unit.

Linoleate isomerase from L. reuteri is a membrane protein since its activity is detected mostly in membrane fraction of cellular protein extracts and detergent is needed to solubilize the enzyme. Consistent with this data, the hydrophilicity plot of the isomerase ORF shows a major hydrophobic domain close to the N-terminal sequence, from amino acid residue 27 through 42. This hydrophobic domain may function as a transmembrane segment as well as part of an uncleaved signal peptide, which plays an important role in directing the protein into the membrane. Also, it is interesting to notice that the peptide contains 4 cysteine residues at amino acid positions 89, 124, 336 and 430, suggesting the native protein may have one or two internal disulfide bonds.

Example 7

The following example demonstrates the expression of L. reuteri linoleate isomerase in E. coli.

Two oligonucleotides were synthesized to amplify the isomerase gene (Promoter-ORF-Terminator) from L. reuteri PYR8 genomic DNA (described in Example 5). Nucleotide CLAo7 (SEQ ID NO:38), the forward primer, corresponds to the positions 3296 through 3314 of the sequence $nCLA_{7113}$ (SEQ ID NO:26) and it includes a SalI site and 3 extra bases at the 5' end (lower case):

5'-gcagtcgacGGAGTTAAGACTGAATTAG-3'

The nucleotide CLAo8B (SEQ ID NO:39), the reverse primer, corresponds to the positions 5577 through 5593 of the sequence $nCLA_{7113}$ (SEQ ID NO:26) and it includes a SalI site and 3 extra bases at the 5' end (lower case):

5'-ctagtcgacGCAGTTTCTGTCATGAC-3'

Figure 11:
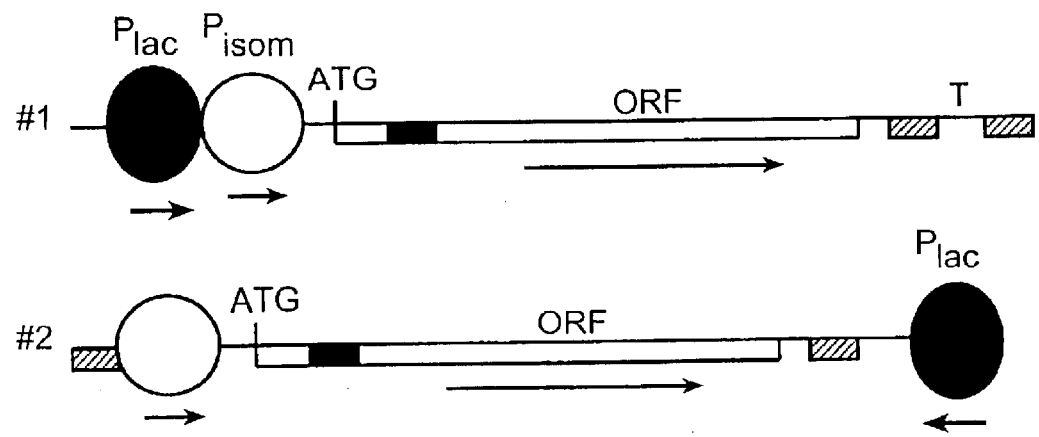
FIG. 11 is an illustration of several constructs for linoleate isomerase expression in *E. coli.*
Figure 11:
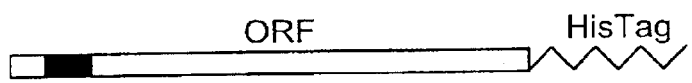
Figure 11:

The PCR product of 2.3 kb was ligated with blunt ends into pPCR-Script(Amp)SK at the SrfI site. Ligated DNA was transformed into E. coli cells. Clones with inserts in both orientations were selected and tested for expression of the isomerase gene. In the construct #1 (FIG. 11), the isomerase gene was placed downstream from the lac promoter. In the construct #2 (FIG. 11), the isomerase gene was placed reverse to the lac promoter.

To detect isomerase activity, E. coli cells transformed with the different isomerase constructs were grown to mid log phase, induced with or without IPTG for 1 to 3 hours and harvested for testing in an isomerase activity assay. Linoleic acid was incubated with *E. coli* cells (biotransformation) or with a crude cell lysate. Fatty acids were extracted by hexane and analyzed on gas chromatography. With both plasmid construct #1 and plasmid construct #2 in *E. coli*, no isomerase activity was detected by biotransformation or by crude cell lysate. SDS-gel analysis, however, showed that IPTG induced expression of a 67 kD protein in cells transformed with construct #1. The size of the expressed isomerase protein is that predicted from the isomerase gene sequence analysis and is in good agreement with the size of the native isomerase purified from *L. reuteri* PYR8. The lack of catalytic activity may be a result of incorrect folding and/or membrane insertion of the isomerase in the heterologous system.

pET vectors were used to develop isomerase gene constructs where the isomerase coding sequence is fused to a His tag at the C-terminus. Using a commercial antibody specific to His tag, it would be possible to monitor the levels of isomerase-His tag fusion protein synthesized in *E. coli*, Lactobacillus, Bacillus, or any other appropriate expression host by Western blot analysis, even if the enzyme was inactive. Since the constructs would be made with *E. coli* plasmids, *E. coli* systems could be used to test the method. The isomerase-His tag protein was expressed in *E. coli* to produce large amounts of isomerase protein. This protein can be further purified under denaturing conditions with nickel columns and used in the production of antibodies specific to the *L. reuteri* PYR8 linoleate isomerase. Isomerase expression in the native host and recombinant systems can be monitored with these antibodies. Additionally, the antibodies can be used in immunoscreening to identify new microorganism strains that produce linoleate isomerases, and eventually to aid in the cloning of additional linoleate isomerase genes.

In additional experiments, *E. coli* transformed with and expressing the PYR8 isomerase gene with a His tag (construct #3, FIG. 11) were grown under standard conditions to study expression of the isomerase protein. On Coomassie Blue stained SDS gel, a band between 60 and 70 kD was predominant in the cell lysate. This band was present at a high level even before induction. The addition of IPTG, however, induced a very strong overproduction of the protein (data not shown). The highest expression level was achieved two hours after IPTG induction. This protein band was strongly recognized by anti-His tag antibody on Western blot, confirming that this protein corresponds to the correct linoleate isomerase fusion protein (data not shown).

Figure 13:
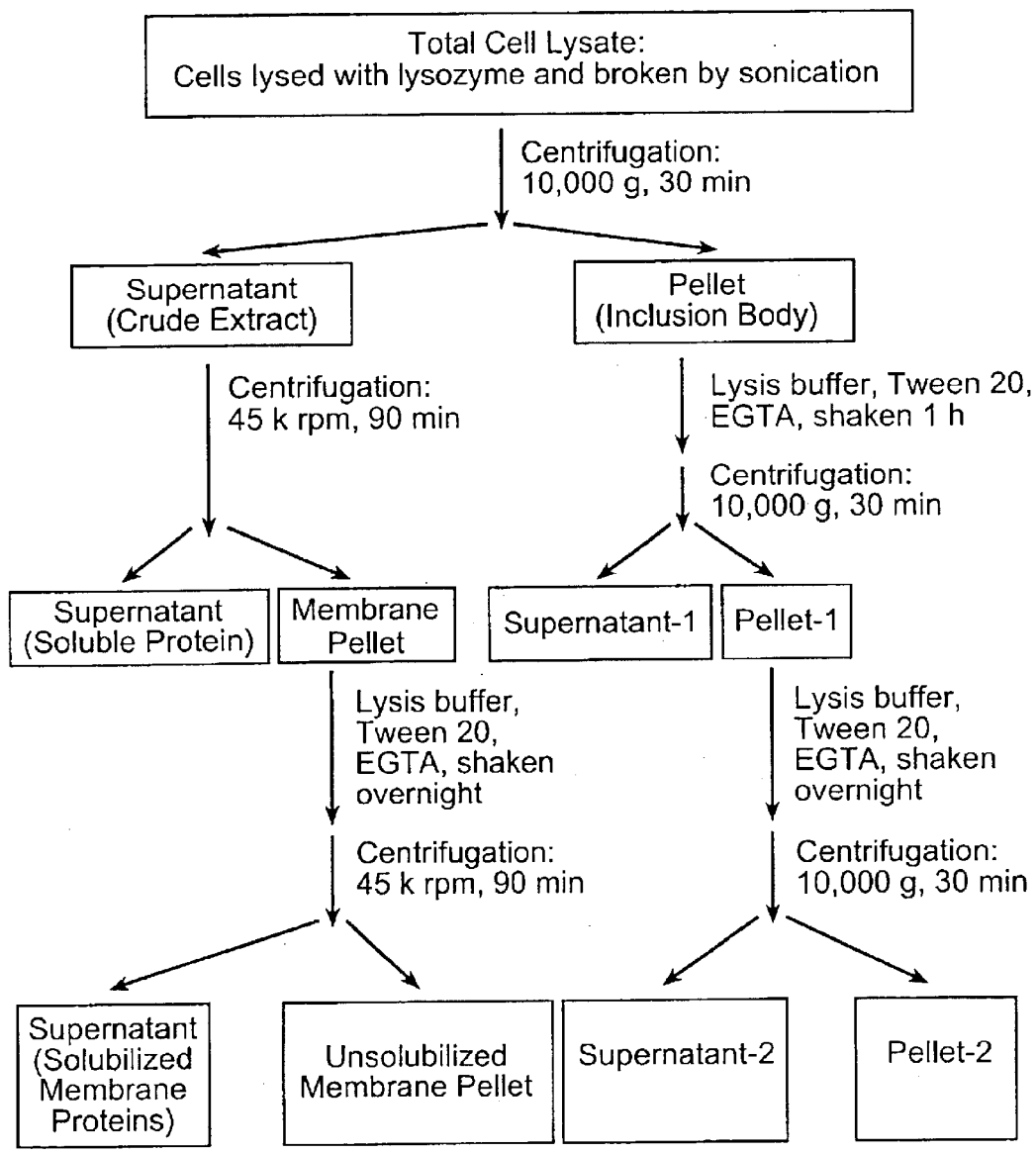
FIG. 13 is a flow diagram of the experimental protocol for the preparation of different protein fractions of *E. coli* which have expressed recombinant linoleate isomerase.

The cells expressing the linoleate isomerase gene were harvested four hours after IPTG induction and analyzed to determine the location of the isomerase-His fusion protein. FIG. 13 outlines the experimental protocol for the preparation of different protein fractions. Briefly, *E. coli* cells expressing the isomerase-His tag fusion protein were lysed in a non-denaturing buffer with lysozyme and broken by sonication. The total cell lysate was centrifuged at low speed to pellet the inclusion bodies. The crude inclusion bodies were washed twice with 0.25% Tween 20 and 0.1 mM EGTA. The proteins retained in the washed pellets were highly insoluble aggregates of improperly folded peptides (inclusion bodies). The supernatant generated by low speed centrifugation of the total cell lysate was subjected to an ultra centrifugation step to separate membrane (pellet) from soluble proteins. Detergent was used to solubilize membrane proteins, which were then separated from other insoluble membrane components by ultra-centrifugation. The total cell lysate and different protein fractions were analyzed on SDS gel and by Western blot. In the total cell lysate of *E. coli* cells expressing the isomerase gene, only the protein band between 60 and 70 kD can be seen after Coomassie staining. This protein band was recovered in the inclusion body fraction and was confirmed to be the isomerase-His tag fusion protein by Western blot. Under the conditions used in these experiments, the antibody did not cross-react with other proteins in the cell lysate of *E. coli* that did not contain the isomerase gene construct. The amount of fusion protein in the soluble and membrane fractions was under the detectable limit. The fusion protein in the inclusion body fraction was extensively washed with EGTA and Tween 20 to remove other contaminant proteins. The purified peptide will be used to produce antibodies specific for the PYR8 linoleate isomerase.

Additional strategies for expressing a linoleate isomerase of the present invention include, but are not limited to: (1) deleting the single hydrophobic domain of the sequence to try to convert the isomerase into a functional soluble protein for use in determination of fusion protein synthesis, solubility and isomerase activity; (2) developing constructs for production of the isomerase in *L. reuteri* using both the native promoter and non-native inducible or constitutive promoters, including an isomerase-His tag fusion gene under the control of the isomerase native promoter; (3) cloning the promoter from the erythromycin resistance gene for control of isomerase gene expression in *L. reuteri* ATCC 23272; and (4) knocking out the wild-type linoleate isomerase gene in the native *L. reuteri* PYR8 strain and recovering the activity by transforming the strain with the cloned isomerase gene. In this fourth strategy, a plasmid has been generated to knock out the wild-type gene which contains a non-functional isomerase gene interrupted by an erythromycin resistance gene as a selectable marker.

Example 8

The following example describes expression of a linoleate isomerase of the present invention in Bacillus.

To express the *L. reuteri* PYR8 linoleate isomerase gene described in Example 5 in *Bacillus subtilis* and *Bacillus licheniformis*, two oligonucleotides were synthesized to amplify isomerase coding sequence from *L. reuteri* genomic DNA. The forward primer (SEQ ID NO:40) corresponds to nucleotide positions 3678 through 3706 of nCLA$_{7113}$ (SEQ ID NO:26), with a NdeI site containing the ATG start codon at the 5' end (lower case):
5'catATGTATTATTCAAACGGGAATTATGAAGC-3'.

The reverse primer (SEQ ID NO:41) corresponds to nucleotide position 5579 through 5602 of the sequence nCLA$_{7113}$ (SEQ ID NO:26) with a BclI site at the 5' end (lower case):
5'tgatcaTCTATACCAGCAGTTTCTGTCATG-3'.

The PCR product of 1.9 kb was cloned as blunt ends at the SrfI site into pPCR-Script Amp SK and transformed into cells of *E. coli* strain NovaBlue. Since dam methylation in this host prevents BclI digestion, the recombinant plasmid was transformed into cells of *E. coli* strain GM2163, which is a dam minus strain. Recombinant plasmid DNA was digested with the restriction enzymes NdeI and BclI and ligated to the vector PBHAI which had been digested with NdeI and BamHI. Recombinant plasmid DNA was digested with SacI to remove the *E. coli* portion of the vector, recircularized, and transformed into *B. subtilis* 23856.

Figure 12:
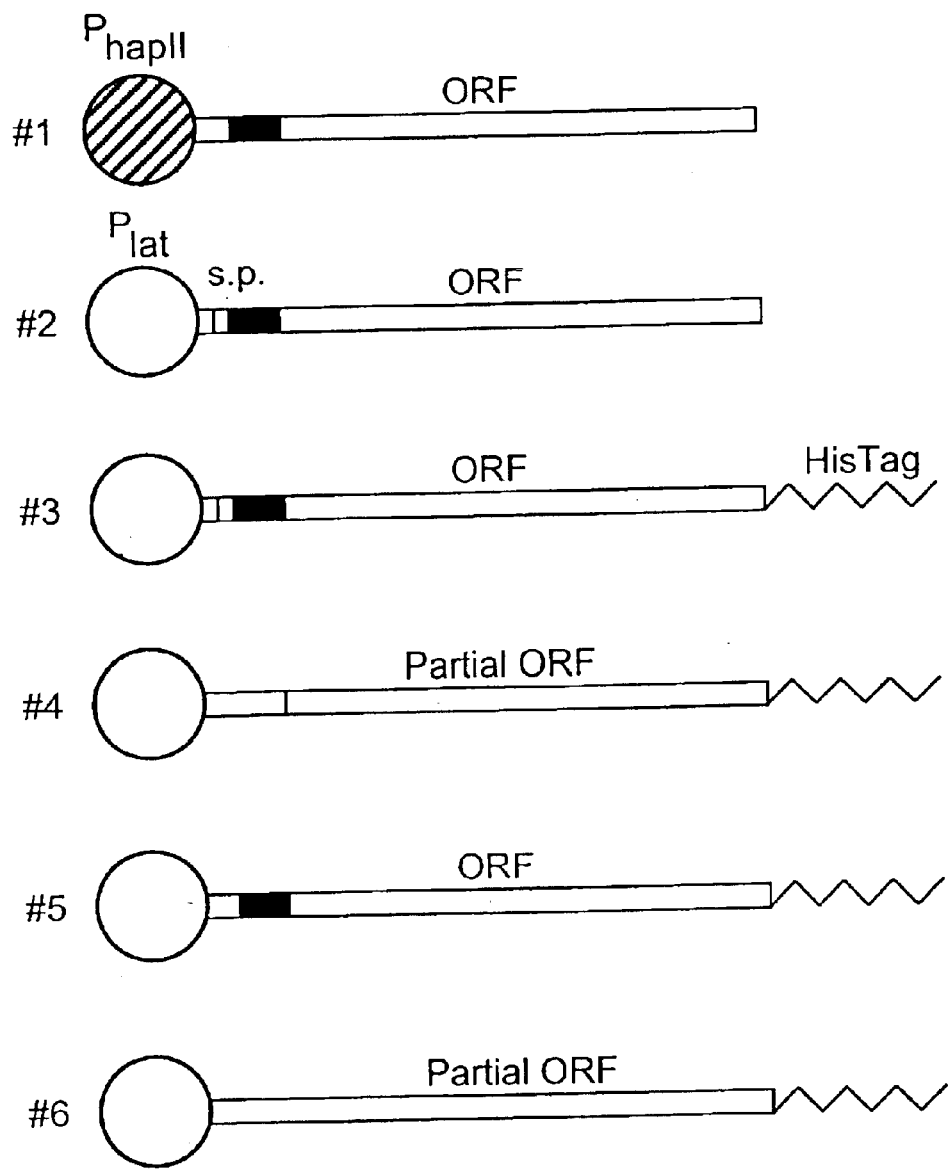
FIG. 12 is an illustration of several constructs for linoleate isomerase expression in Bacillus.

In this construct, the isomerase coding sequence was placed under the control of the HpaII promoter (FIG. 12, #1 construct) and its native ribosome-binding site was replaced by the counterpart in the vector. Clones of transformants were grown to mid-log phase and then harvested for biotransformation of linoleic acid. No CLA was detected by GC analysis in the hexane extract of fatty acids. However, after incubation for 1 hour, 2 hours, and 3 hours, the level of linoleic acid decreased drastically, being about 40% after a 3 hour incubation. The same results were observed with all sixteen *B. subtilis* clones tested. The use of linoleic acid was dependent on the presence of the cloned isomerase gene since the level of linoleic acid was constant during the incubation of *B. subtilis* wild type cell without the plasmid and the cells transformed with the empty vector. The same results were observed when the isomerase construct was transformed into *B. licheniformis* T399.

Experiments were carried out to investigate why CLA did not accumulate while linoleic acid was used up. One possibility was that linoleic acid might be converted to CLA, which was rapidly metabolized or degraded. That implied that *B. subtilis* and *B. licheniformis* cells have the ability to metabolize CLA. To test this hypothesis, Bacillus wild type cells and cell transformed with the isomerase gene construct were incubated with single 9,11 isomer produced in a biotransformation using *L. reuteri* PYR8 cells and with chemically synthesized CLA, which contains 9,11 and other CLA isomers. Bacillus cells could not metabolize the CLA. The same conclusion was also drawn with crude cell extracts.

Furthermore, a peak of unknown product (retention time= 20 minutes) on GC spectra of the biotransformation with cells containing the isomerase gene was observed. Also, the conversion of linoleic acid and formation of the unknown product seemed to be at a 1:1 ratio. Preliminary GC-MS analysis indicated that this unknown product has a molecular weight consistent with that of a hydroxylated linoleic acid derivative. Further structural analysis by different methods may help to determine the identity of the product.

Without being bound by theory, the present inventors believe that this unknown product may be an intermediate of linoleic acid conjugation. When this product was incubated with *L. reuteri* PYR8 cells or crude enzyme extracts, however, it could not be converted to CLA. It is possible that the intermediate has to be bound with the enzyme or membrane during the conjugation, and once it is released the conjugation could not be completed.

Further experiments include developing a series of constructs based on the vector pLAT10 to explore the advantage of including the His tag (FIG. 12). pLAT10 is a plasmid that can be used to directly transform *B. subtilis* and *B. licheniformis*. It has the promoter, coding sequence and the terminator of the LAT gene encoding α-amylase. Also present is a signal peptide sequence for mobilizing proteins into or across the Bacillus membrane. In construct #2, the isomerase coding sequence was placed under amylase promoter control as a fusion to its signal peptide. Normally, the LAT signal sequence directs the protein into or across the membrane. Soluble proteins typically are secreted into the culture broth and in the process, the signal peptide is removed by specific proteases. Membrane protein would migrate to and integrate into the membrane. Since the hydrophobic domain of the isomerase peptide may function both as an uncleaved signal sequence and transmembrane segment in *L. reuteri*, it is not known if such a domain of the protein would interfere with the proper function of the secretion machinery in Bacillus and the LAT signal-isomerase may not fold into proper conformation. In construct #3 (FIG. 12), the entire coding sequence of the isomerase gene is fused to His tag at the C-terminus while in construct #4, the isomerase sequence without the hydrophobic domain is fused to His tag. In constructs #5 and #6, the secretion signal peptide is removed. With these new constructs, it can be determined whether the isomerase protein is synthesized in Bacillus cells and in which cellular fractions the protein is located.

Example 9

The following example describes the purification of linoleate isomerase from Propionibacterium acnes.

Figure 14:
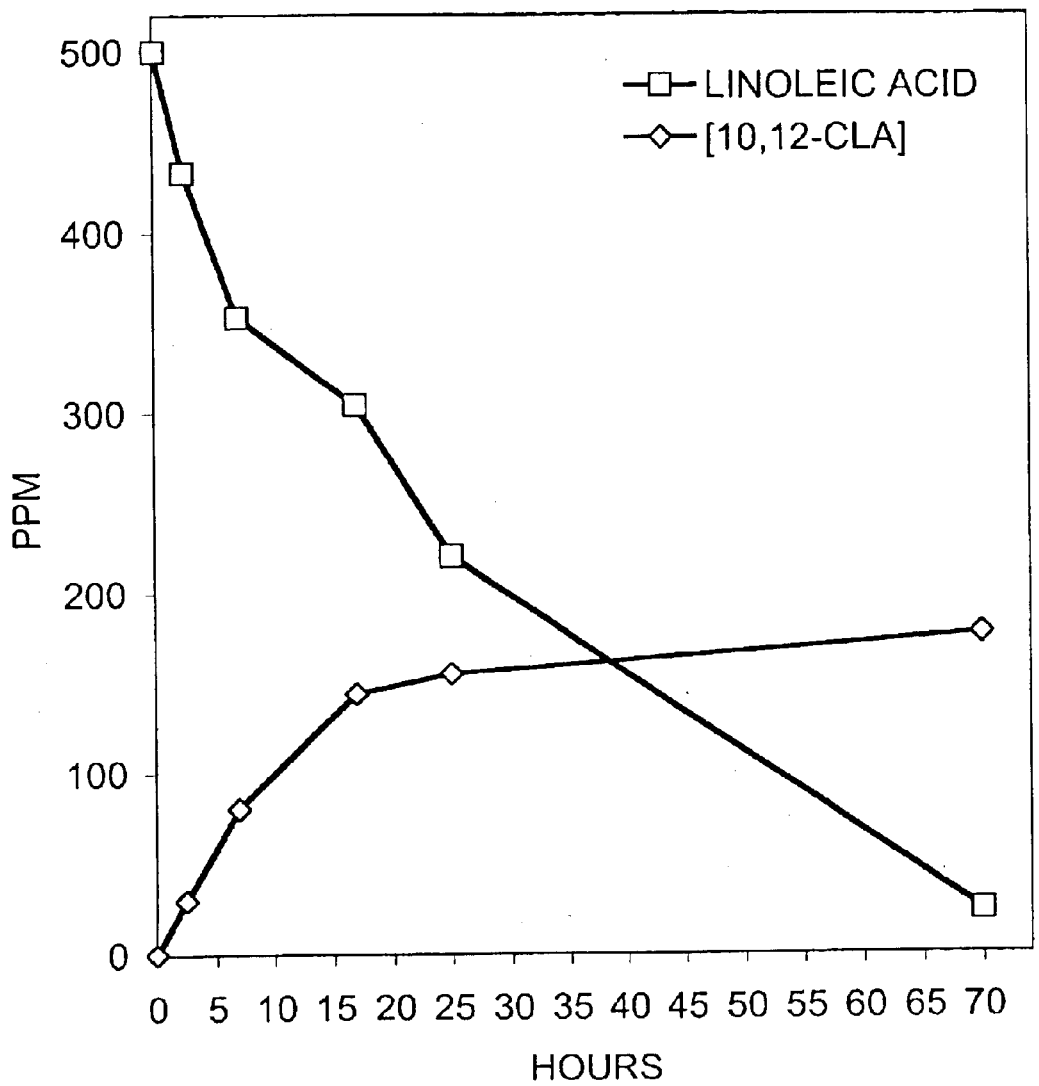
FIG. 14 is a line graph showing the formation of t10,c12-CLA from linoleic acid using whole cells of *P. acnes.*

*P. acnes* ATCC 6919 is the only microorganism known to produce t10,c12-CLA directly from linoleic acid. Experiments described in Example 1 using whole cells confirmed the presence of a 10,12-linoleate isomerase in this organism. Enzyme extracts were prepared by French Press. FIG. 14 shows the formation of t10,c12-CLA from linoleic acid using whole cells of *P. acnes*. Cultures were grown anaerobically to stationary phase in a complex brain heart infusion medium, harvested and resuspended in the same medium containing 500 ppm linoleic acid. Cells were incubated aerobically with shaking at ambient temperature. The level of linoleic acid decreased about 50% in 24 hours. About half of this missing linoleic acid could be detected as t10,c12-CLA. No c9,t11-CLA was observed. With prolonged incubation, the level of t10,c12-CLA changed only slightly, while nearly all remaining linoleic acid disappeared. At present it is unclear how linoleic acid is metabolized in this organism. In other experiments, t10,c12-CLA rose in concentration, but later disappeared completely, as did all of the linoleic acid (results not shown). This suggests that t10,c12-CLA may be subject to further metabolism, possibly by a reductase. Linoleic acid may also be a substrate for enzymes other than the isomerase.

Figure 15:
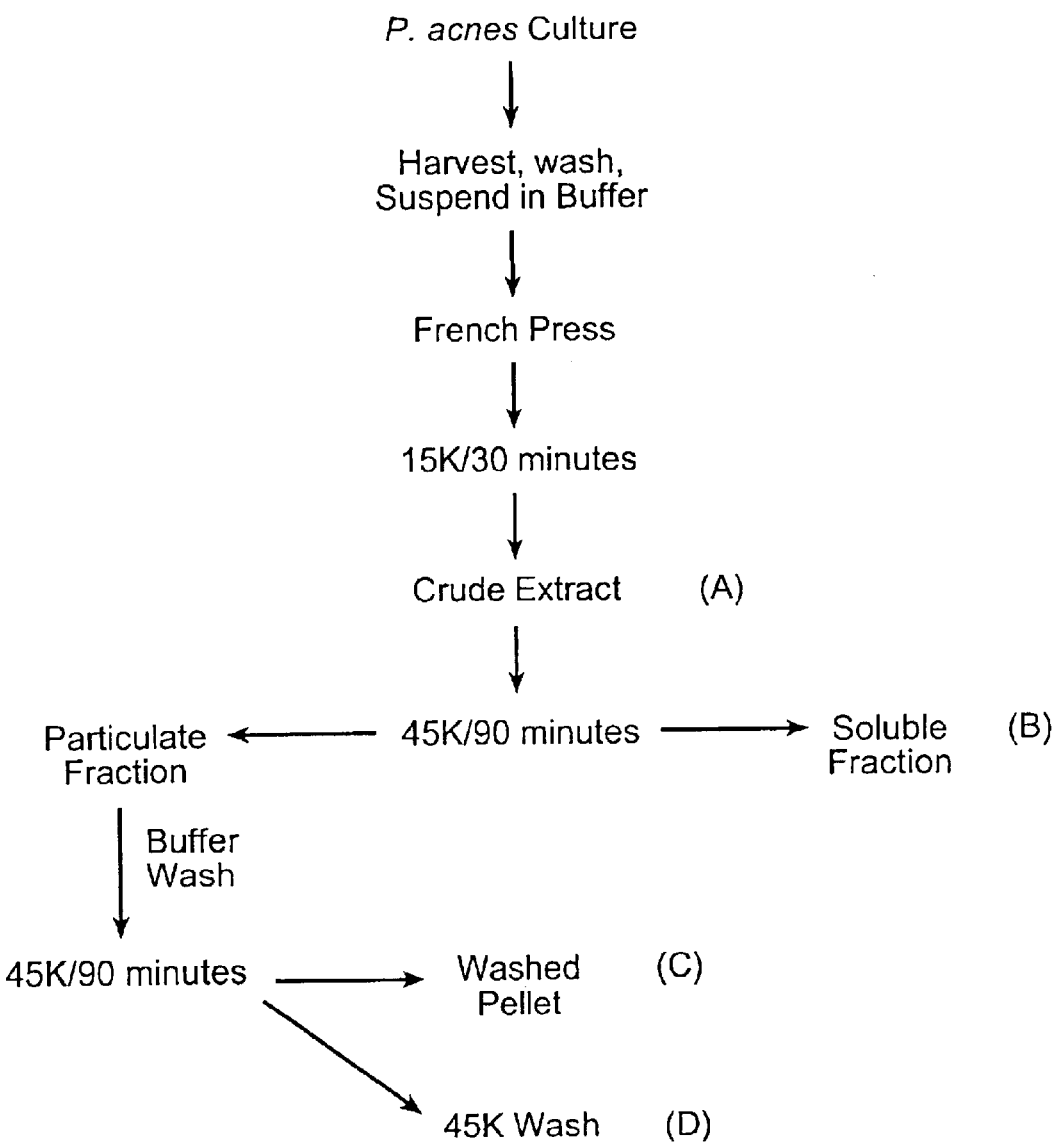
FIG. 15 is a flow diagram showing the cell fractionation protocol for *P. acnes* ATCC 6919.

Enzyme extracts were prepared by French Press and the extract fractionated as outlined in FIG. 15. Taking the total isomerase activity in fraction A as 100%, over 93% of the activity was detected in the soluble protein fraction (B) Less than 1% of the isomerase activity was found in the washed pellet, or membrane fraction (C). Approximately 2% of the activity was located in the buffer fraction (D), after the pellet washing and centrifugation steps. Thus, the *P. acnes* isomerase clearly is not a membrane protein, unlike the isomerase activities in *L. reuteri* PYR8 and other strains examined to date.

Isomerase activity, using a crude soluble enzyme preparation, was not significantly affected by overnight dialysis. A number of possible cofactors were tested for their effect on isomerase activity, including NAD, NADH, NADP, NADPH, FAD, FMN, ADP, ATP and glutathione. No significant effect was observed in 60 minute assays with any of these compounds. Calcium and magnesium also had no effect. Isomerase activity was not inhibited by the chelators EDTA (5 mM) or 1,10-phenanthroline (1 mM), or the sulfhydryl reagents p-chloromercuribenzoate (5 $\mu$M) or N-ethylmaleimide (100 $\mu$M).

Figure 16:
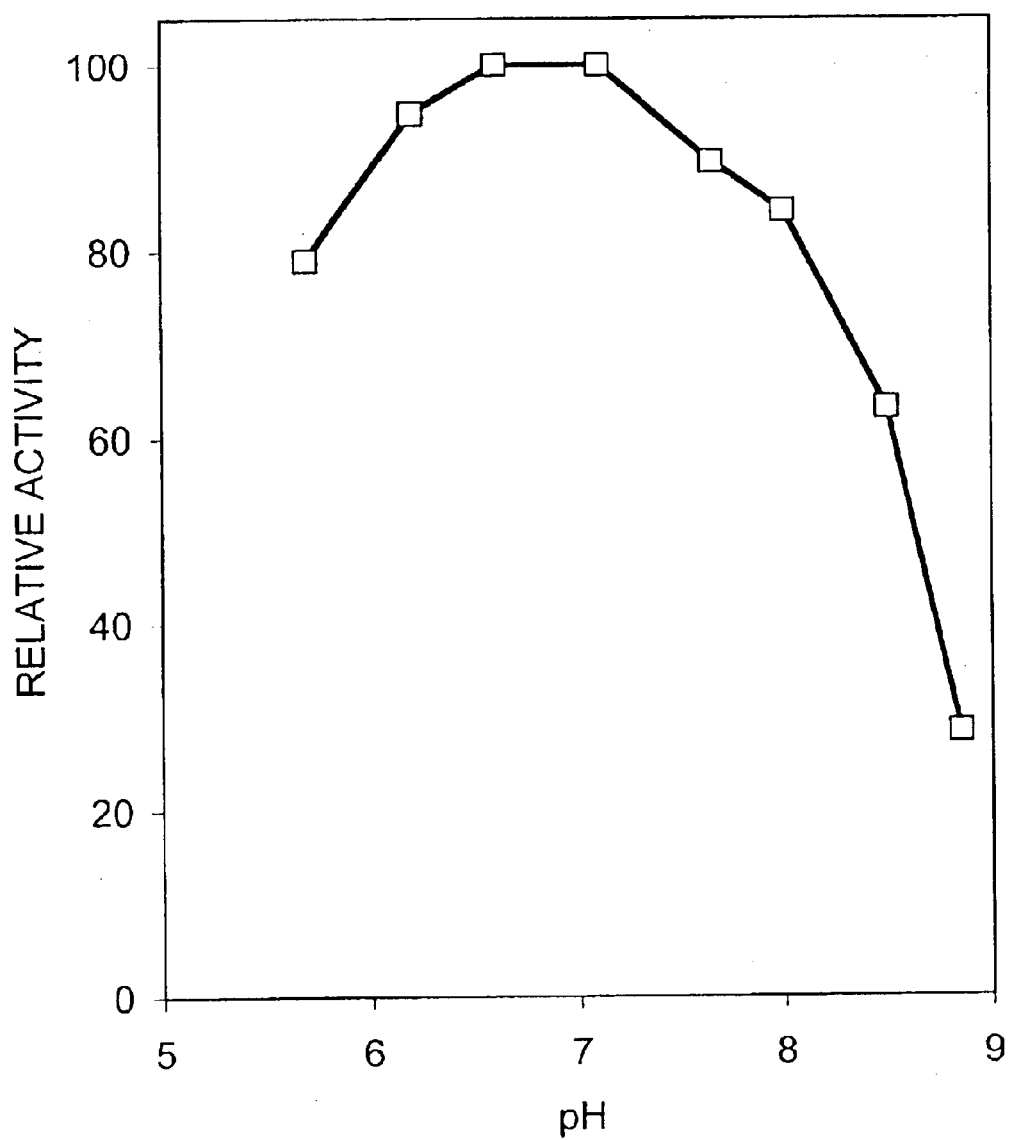
FIG. 16 is a line graph showing the effect of pH on linoleate isomerase activity in crude extracts of *P. acnes* ATCC 6919.

The effect of pH on enzyme activity in crude extracts was examined. The isomerase activity exhibits a pH optimum centered around 6.8 (FIG. 16).

Figure 17:
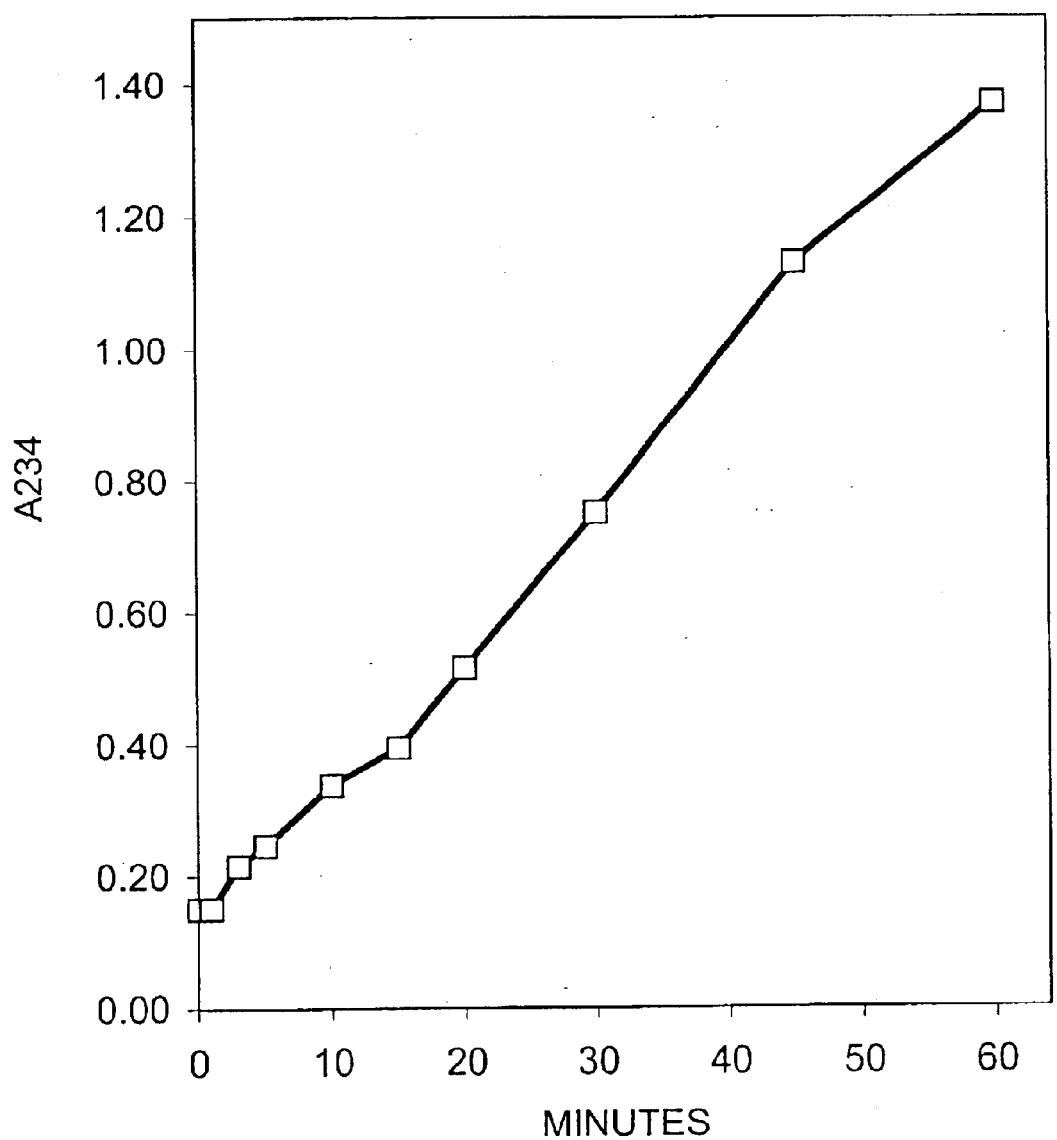
FIG. 17 is a line graph showing the time course of CLA formation in crude extracts of *P. acnes* ATCC 6919.
Figure 18:
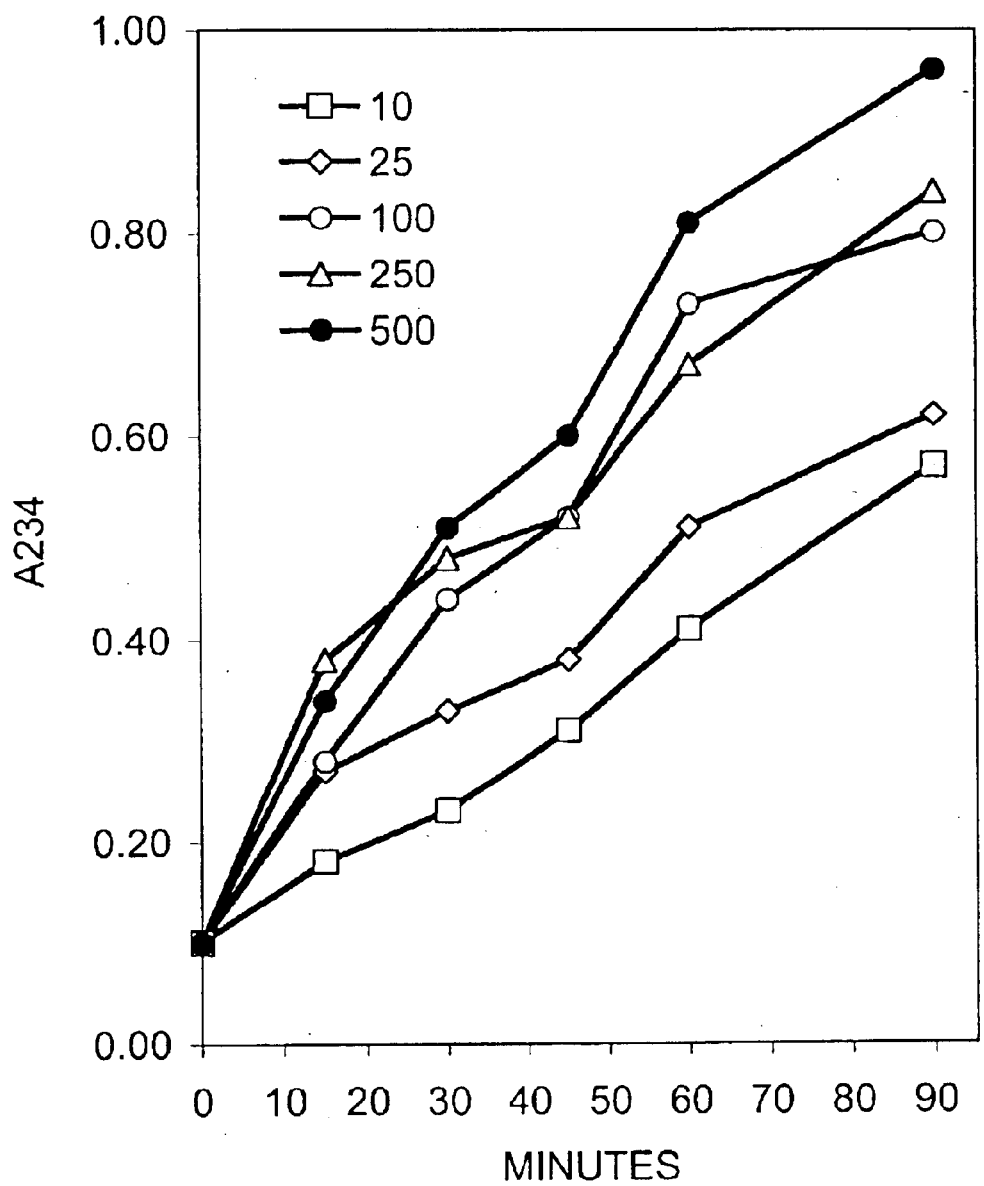
FIG. 18 is a line graph showing the time course for the formation of CLA in crude extracts of *P. acnes* ATCC 6919 at different levels of linoleic acid.
Figure 19:
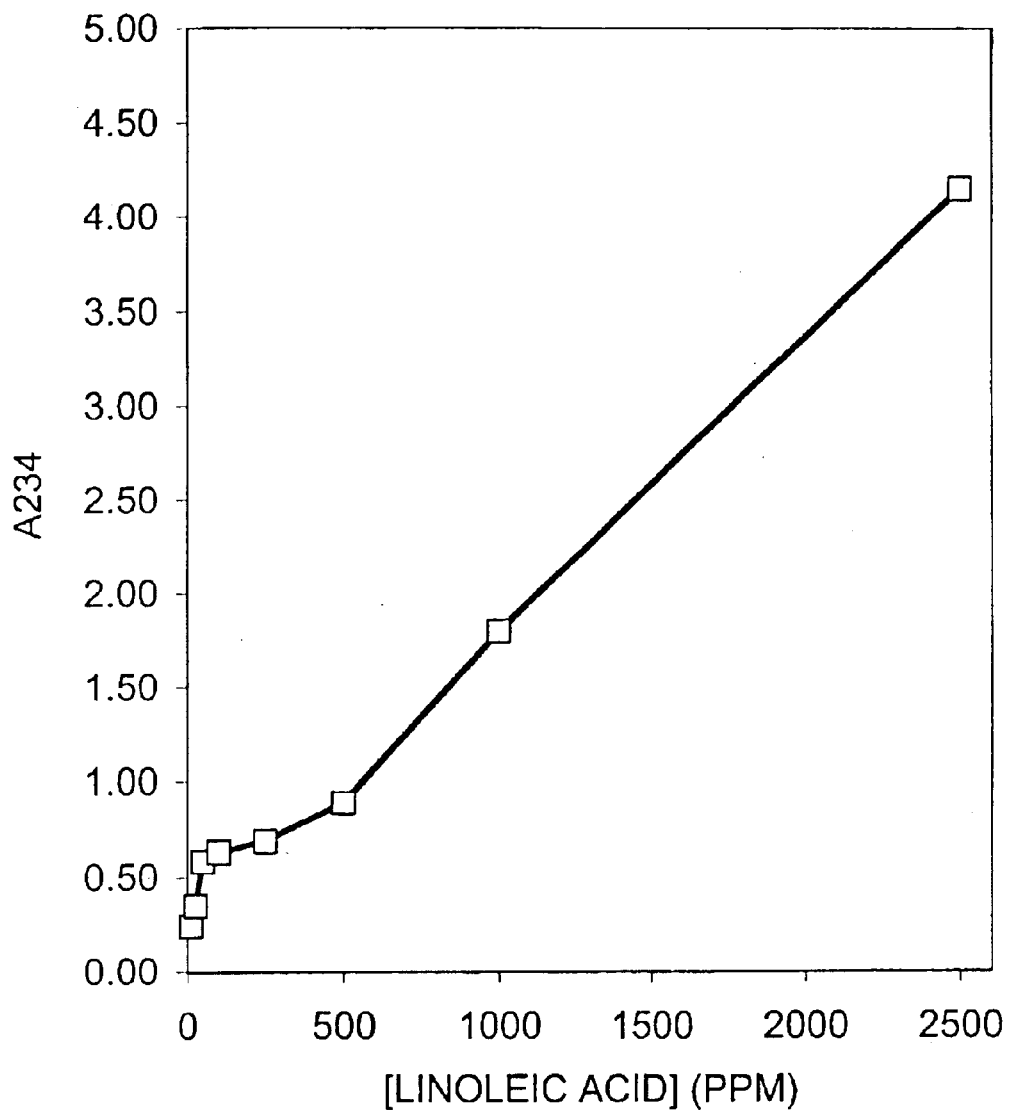
FIG. 19. is a line graph showing end point for formation of CLA in crude extracts of *P. acnes* ATCC 6919 at different levels of linoleic acid.

Formation of CLA was determined by measuring the absorbance at 234 nm. FIG. 17 shows a typical time course experiment using the crude isomerase extract as enzyme source. Generally, the isomerase was assayed using an endpoint assay after 30 to 60 minutes incubation at room temperature. FIG. 18 (time course assay at different linoleic acid levels) and FIG. 19 (end point assay at different linoleic acid levels) show the effect of increasing substrate concentration on formation of linoleic acid. These data suggest that the enzyme in *P. acnes* is not subject to the same type of substrate inhibition observed in the linoleic acid isomerases of C. sporogenes, L. reuteri and B. fibrisolvens.

The effect of temperature on isomerase activity has been examined to a limited extent. The enzyme works very slowly at 4° C., demonstrating much better activity at room temperature. CLA formation was virtually the same at 37° C. as at room temperature (data not shown). These results again differ significantly from those observed with the particulate L. reuteri isomerase.

Figure 20:
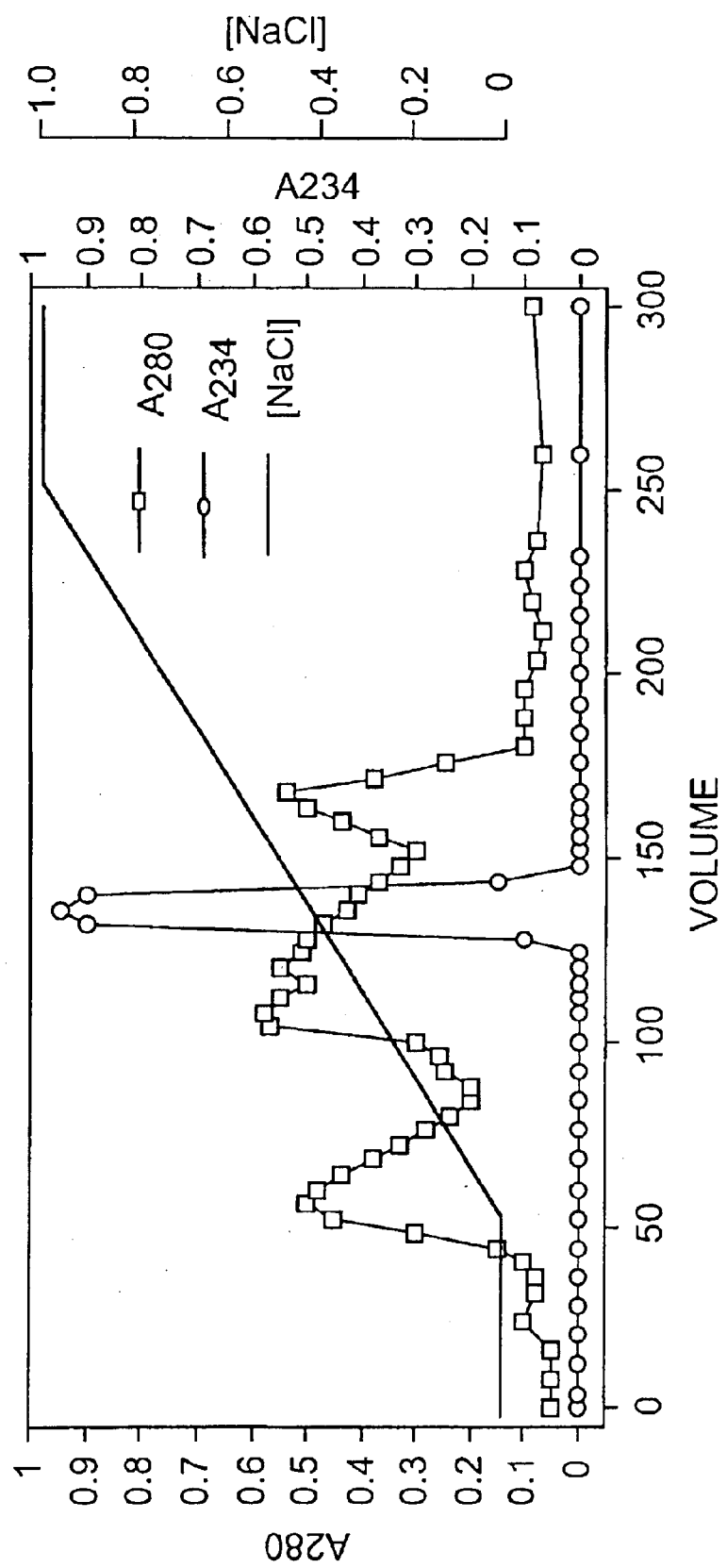
FIG. 20 is a graph illustrating DEAE ion exchange chromatography of total soluble protein from *P. acnes* ATCC 6919.
Figure 21:
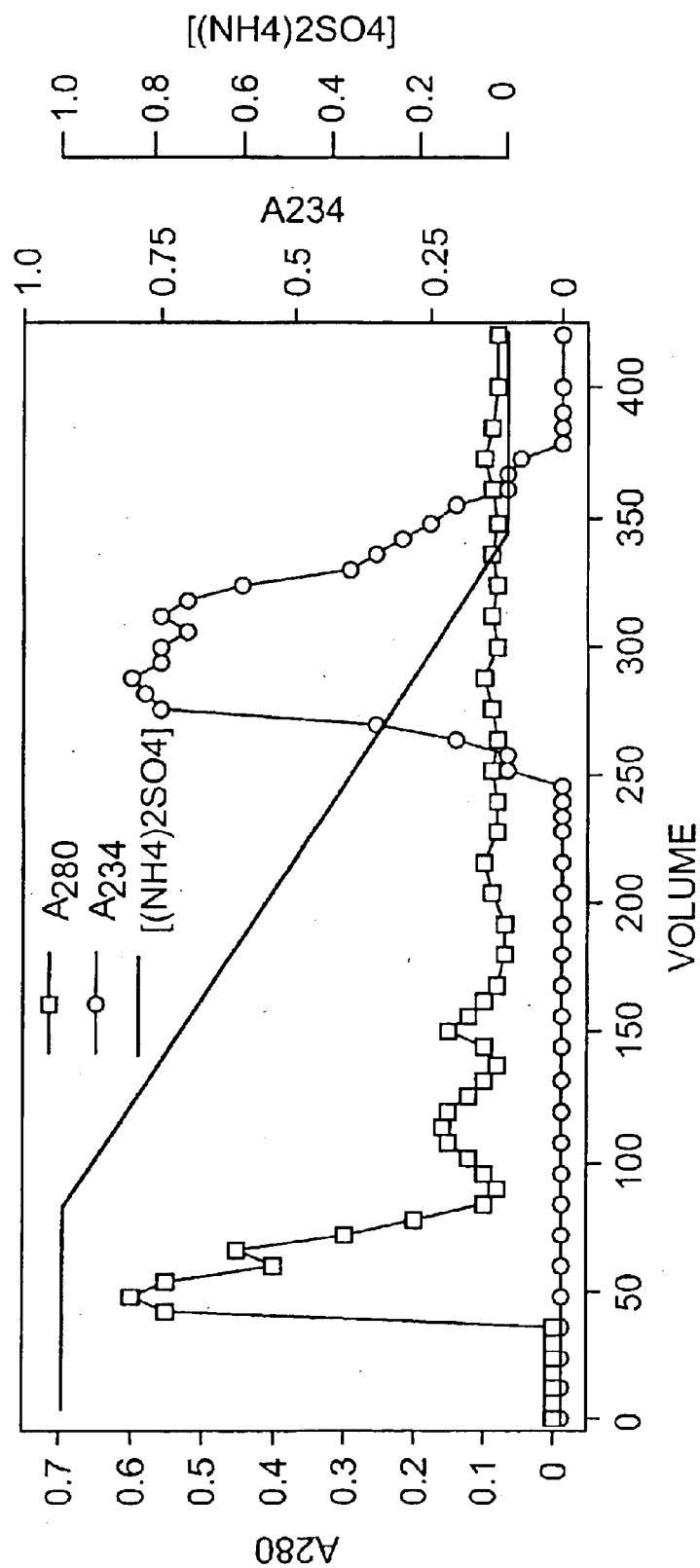
FIG. 21 is a graph illustrating hydrophobic interaction chromatography of total soluble protein from *P. acnes* ATCC 6919.

Purification of the linoleate isomerase in P. acnes was initiated. Following preparation of a centrifuged crude extract, samples were applied to several columns to determine applicability and suitable conditions. Typical chromatograms for some of these pilot experiments are shown in FIG. 20 and FIG. 21 for DEAE and hydrophobic interaction chromatography (HIC), respectively. The initial purification trial consisted of DEAE followed by HIC and gel filtration chromatography. After these three columns, however, multiple bands were seen on SDS PAGE.

This initial attempt at purification clearly highlighted the need to optimize separation conditions. The DEAE step was optimized further by altering the salt gradient program. Following a linear gradient to 0.175 M NaCl, the salt level was held at this level for 70 ml. The isomerase eluted at this point, after which time the gradient was continued to elute other proteins.

The isomerase binds very tightly to the phenyl HIC column, and is only released with ethylene glycol. A large number of other proteins were also released, however, with stepwise exposure to 20% ethylene glycol. The HIC chromatography step was altered by use of an ethylene glycol gradient from 5 to 30%. This resulted in a somewhat sharper elution profile for the isomerase than previously obtained (results not shown).

Following DEAE and HIC chromatography, chromatofocusing was employed. This method separates molecules on the basis of isoelectric point. Protein was applied to a weak anion exchange column at high pH, and eluted as the pH decreased by application of a lower pH "Polybuffer". Preliminary experiments showed that a pH gradient from 6.5 to 4.0 resulted in elution of the isomerase at a pH around 4.4. Clearly the isomerase is a fairly acidic protein.

Figure 22:
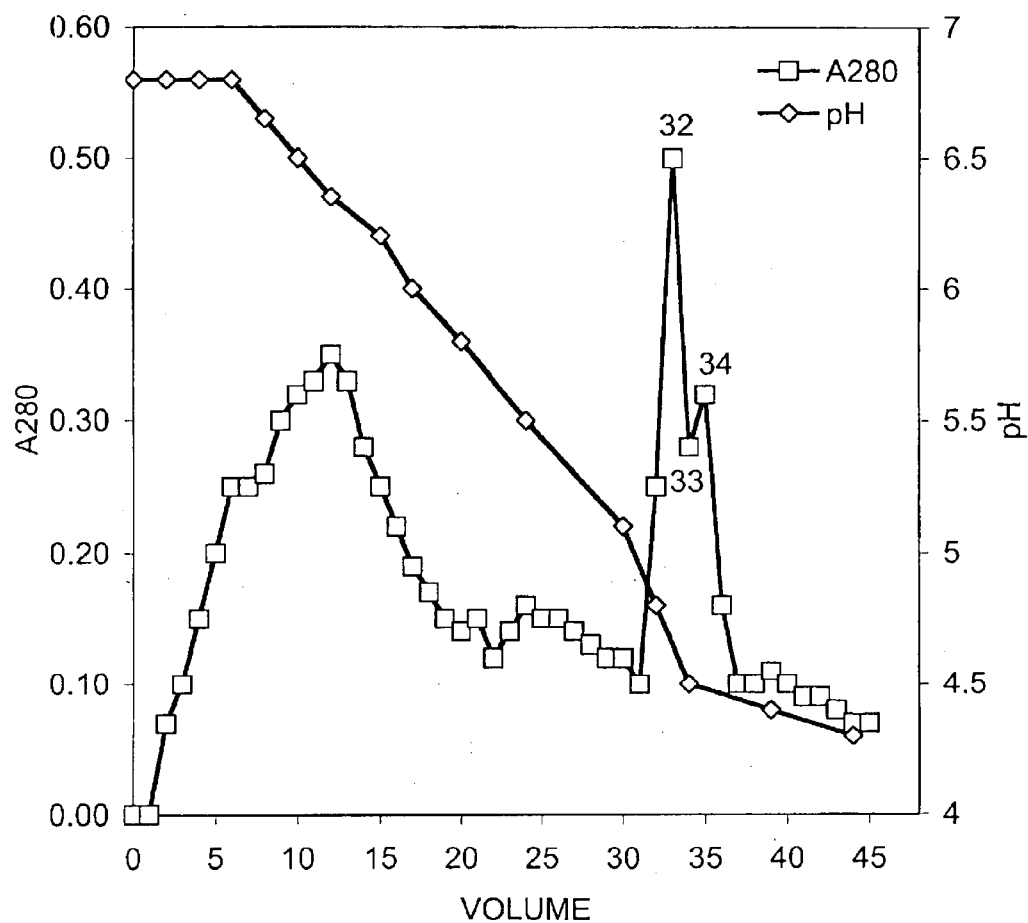
FIG. 22 is a graph illustrating chromatofocusing of isomerase activity from *P. acnes* ATCC 6919.
Figures 23A, 23B:
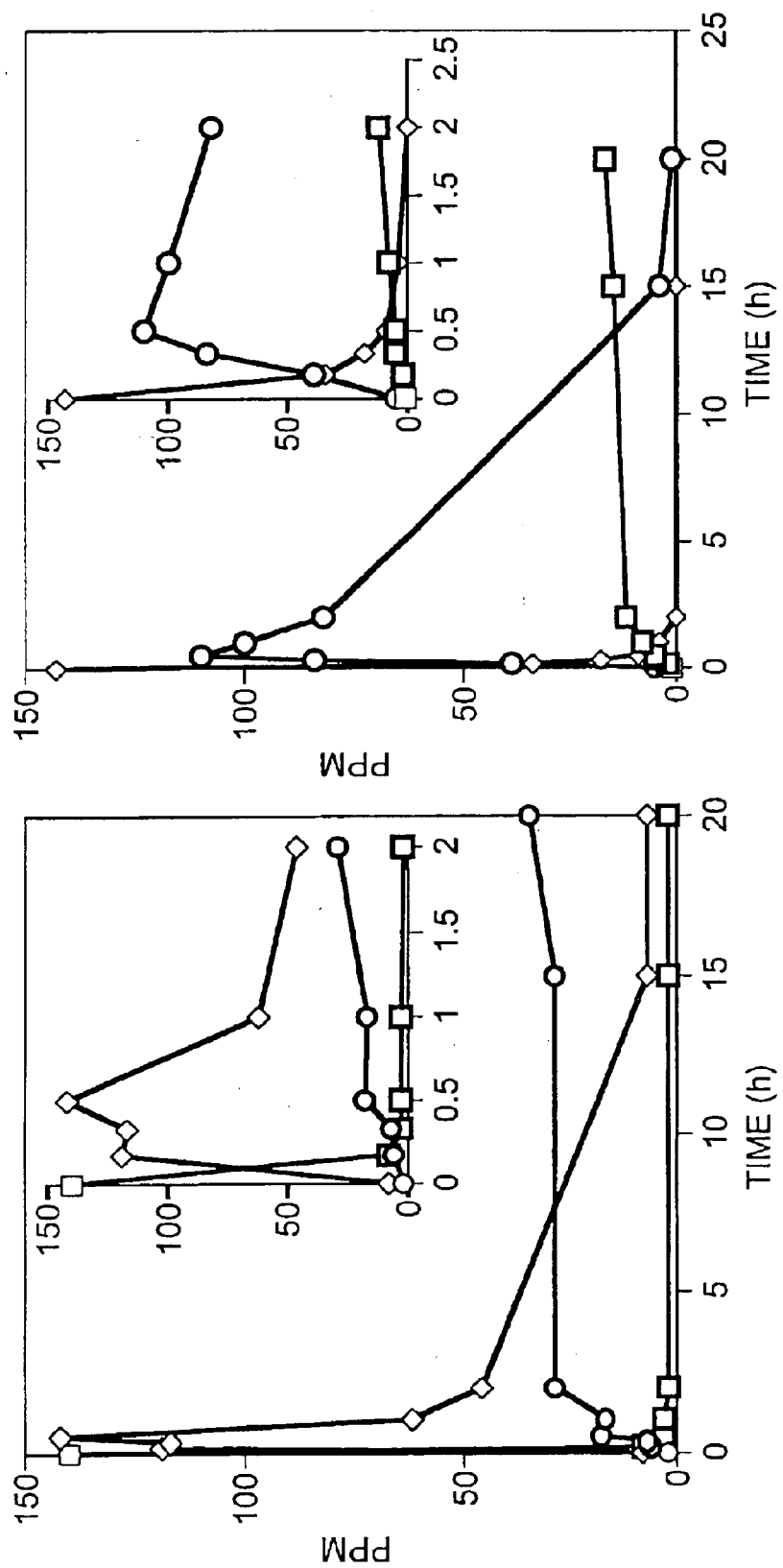
FIG. 23A is a graph showing a time course of CLA formation by *C. sporogenes* ATCC 25762 under aerobic conditions at room temperature.
FIG. 23B is a graph showing a time course of CLA formation by *C. sporogenes* ATCC 25762 under anaerobic conditions at room temperature.
Figures 23C, 23D:
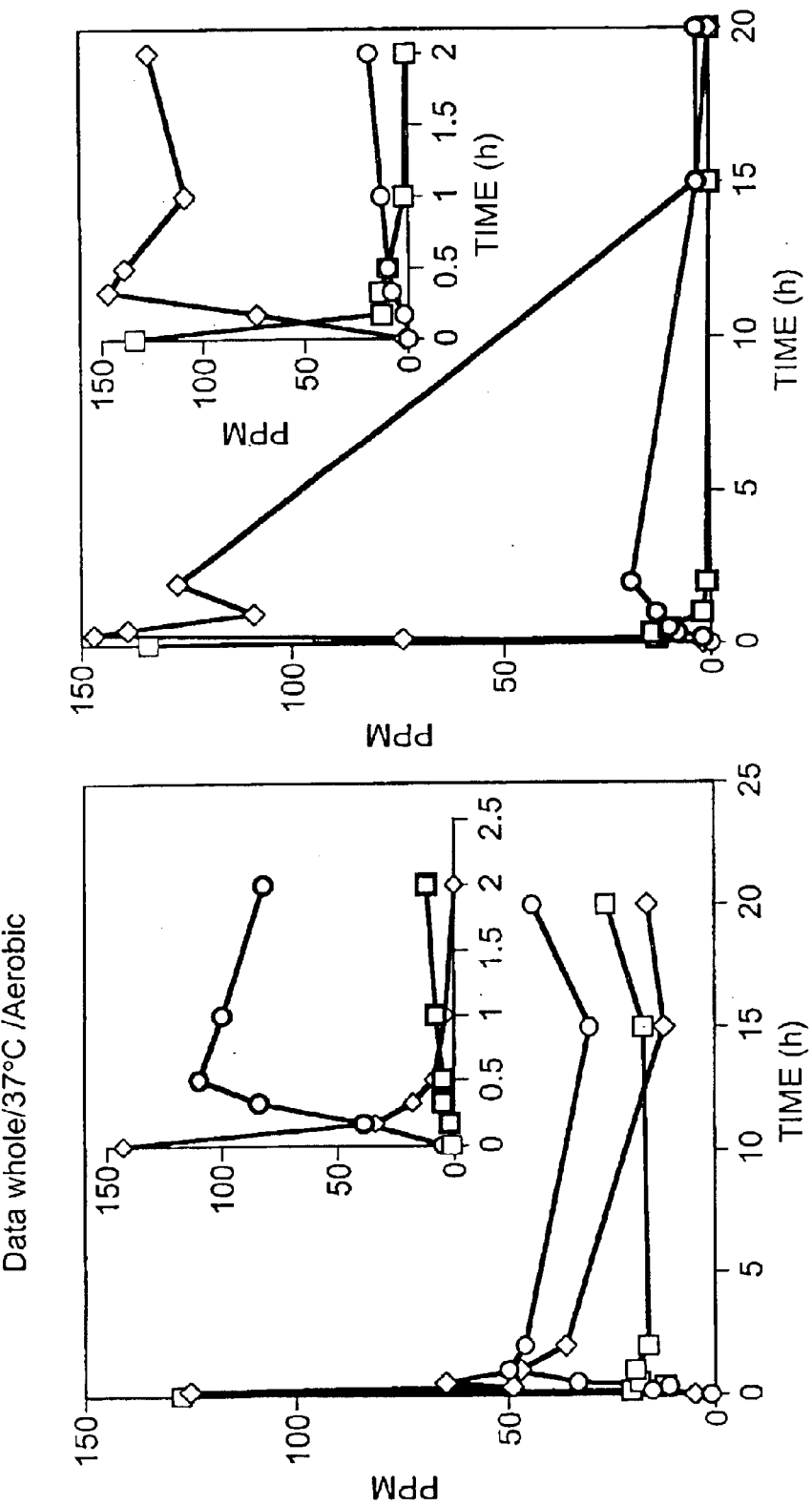
FIG. 23C is a graph showing a time course of CLA formation by *C. sporogenes* ATCC 25762 under aerobic conditions at 37° C.
FIG. 23D is a graph showing a time course of CLA formation by *C. sporogenes* ATCC 25762 under anaerobic conditions at 37° C.

Following HIC chromatography, a single fraction containing high isomerase activity was applied to a Pharmacia MonoP chromatofocusing column equilibrated with 20 mM bis-Tris (pH 6.5). The pH gradient was formed using 10% Polybuffer 74 (pH 4.0). Results are shown in FIG. 22. The isomerase activity eluted in a sharp peak around pH 4.5. The three fractions containing activity were examined for purity by SDS PAGE. Fraction 32 appeared on 12.5% and 20% gels as a single protein band with a mass of 50 kDa.

This material was submitted for amino acid sequencing. After running the sample on a SDS PAGE gel, the single band was transferred and N-terminal sequencing performed at the UW Medical College of Wisconsin. Surprisingly, several signals were obtained, indicating the presence of multiple peptides or that the N-terminal portion of the peptide was highly degraded (unlikely) in this apparent single band. Subsequent analysis of isomerase purified further (described below) determined that the N-terminus of the protein was blocked.

To further modify the purification scheme to obtain pure isomerase, the protocols previously used were revised and improved to enhance the purification. As before, soluble crude extract was prepared by cell disruption. This material was fractionated using DEAE chromatography. Fractions from several runs containing significant isomerase activity were pooled, dialyzed, and reapplied to the same column. The active fractions were pooled, made 1 molar in $(NH_4)_2SO_4$, and applied to a phenyl hydrophobic column in several runs. Active fractions were concentrated, if necessary, and analyzed by SDS PAGE chromatography. Fractions having high isomerase activity exhibited a large number of protein bands at this stage. Selected fractions from the HIC column were pooled, concentrated, dialyzed, and applied to a chromatofocusing column. Protein elution was accomplished with a shallower pH gradient than was previously used, from 5.5 to 4.0. The isomerase activity eluted as a sharp peak at about pH 4.2. Active fractions were examined for purity by SDS PAGE. At this point, several fractions appear to contain a single band approximately 50 kDa in size (data not shown). This material is currently being carefully checked for homogeneity. Other active fractions exhibited three to four additional bands. These fractions will be applied to a gel filtration column if further purification is required.

N-terminal sequencing of the P. acnes linoleate isomerase has been completed. The N-terminal amino acid is blocked, and therefore, N-terminal sequence cannot be determined directly. After fragmentation with protease, internal fragments will be chromatographically separated and the amino acid sequence will be determined. Upon obtaining the sequence, the entire linoleate isomerase nucleic acid and amino acid sequence will be derived using methods described for the L. reuteri linoleate isomerase in Example 5, and as described below.

In preparation for cloning the 10,12 linoleate isomerase gene from Proprionibacterium acnes, a genomic DNA library is being created. Using a modified protocol for DNA isolation from Gram-positive bacteria, genomic DNA of good quality was isolated from P. acnes. After small-scale tests, genomic DNA was partially digested with Sau3AI, partially filled with dGTP and DATP, size selected by electrophoresis through agarose gel, and purified from agarose gel by electroelution. This purified DNA digest will be ligated to XhoI half-site arm of the BlueStar phage vector, packaged and plated. The quality of the library (titer and percentage of recombinant phage) will be tested. Oligonucleotide probes will be created based on the determination of the internal fragment sequences of the P. acnes linoleate isomerase and will be used to screen the library and isolate one or more clones for sequence analysis.

Example 10

The following example describes the purification and characterization of a linoleate isomerase from Clostridium sporogenes.

Previous work by the present inventors and by others has shown that C. sporogenes is capable of converting significant amounts of linoleic acid to CLA. The linoleate isomerase from C. sporogenes appears to have activity levels and characteristics most similar to that of L. reuteri PYR8. The following experiments describe the purification and characterization of the linoleate isomerase from this microorganism, with the goal to clone this isomerase gene, as has been described for L. reuteri in Example 5. The cloned C. sporogenes isomerase gene activity and functionality will then be compared to the recombinant L. reuteri activity.

C. sporogenes ATCC 25762 was grown in a Brain Heart Infusion Broth (BHI) medium under anaerobic conditions. Bacterial growth was measured with a spectrophotometer at 600 nm. When cells were grown at 37° C., pH 7.5, stationary phase was reached after 6 hours incubation. Further incubation resulted in rapid lysis of the culture. Cultures were harvested, therefore, after about 6 hours growth. The cell pellet was washed with 0. 1 M Tris, pH 6.0, containing 15 mM NaCl.

Biological transformation of CLA was performed by resuspending harvested cells in fresh growth medium containing 200 ppm linoleic acid. After incubation, fatty acids were extracted with hexane and analyzed by gas chromatography using an isothermal program at 215° C. for 14 minutes. FIG. 23A–D shows a time course of biotransformation of linoleic acid by *C. sporogenes*. Resuspended cells were grown under aerobic (FIGS. 23A & C) or anaerobic (B & D) conditions at room temperature (A & B) or at 37° C. (C & D). A rapid production of c9, t11-CLA with a simultaneous decrease in linoleic acid was observed within 30 minutes under all conditions tested. Upon further incubation, t9, t11-CLA accumulated at the expense of c9, t11-CLA. Upon extended incubation (15–20 hours), c9, t11-CLA disappeared. Apparently the CLA was metabolized further. Similar amounts of CLA were formed under aerobic and anaerobic conditions.

Figure 24:
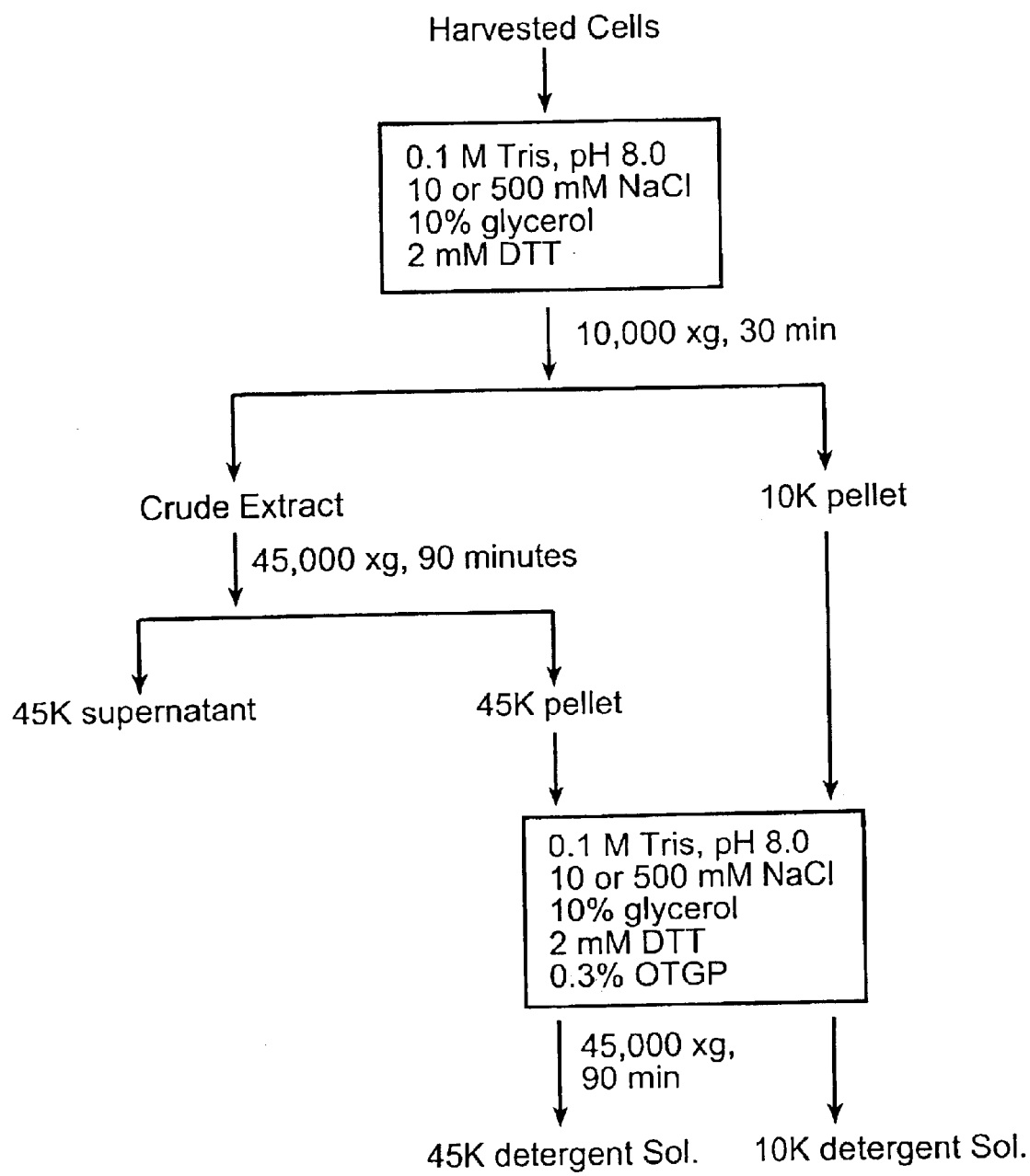
FIG. 24 is a flow diagram showing an extraction protocol for *C. sporogenes* ATCC 25762.

The cells were extracted as described in FIG. 24 to give four principal fractions. Tables 1 and 2 show the distribution of isomerase activity and protein concentration in fractions which were prepared with low salt (10 mm NaCl) from frozen cells and with high salt (500 mM NaCl) from fresh cells, respectively. Enzyme activity was detected in all fractions. The highest activity was found in the 45 k/0.3% OTGP soluble fraction. It has been reported that detergents require high concentration of salt for effective solubilization of membrane proteins. Addition of NaCl in extract buffer resulted in increasing specific activity (Table 2), indicating the effectiveness of high salt. The specific activity was at least 50-fold higher in high salt detergent soluble fractions (Table 3) than in low salt detergent soluble fractions (Table 2). Conditions under which the active cultures are stored could also affect activity. These results suggested that the *C. sporogenes* linoleate isomerase has characteristics similar to the *L. reuteri* PYR8 membrane-associated enzyme.

TABLE 2

Linoleate Isomerase Activity - Low Salt Extracts of Frozen Cells

| Fraction | Protein (mg/ml) | Total Protein (mg) | $OD_{234}$ | Specific Activity ($OD_{234}$/60 min/mg protein) |
|---|---|---|---|---|
| Crude Extract | 6.8 | 408 | 0.26 ± 0.01 | 0.38 |
| 45K Supernatant | 4.8 | 288 | 0.12 ± 0.01 | 0.25 |
| 45K OTGP Soluble | 1.2 | 30 | 0.05 ± 0.00 | 0.41 |
| 10K OTGP Soluble | 2.9 | 73 | 0.05 ± 0.01 | 0.17 |

TABLE 3

Linoleate Isomerase Activity - High Salt Extracts of Fresh Cells

| Fraction | Protein (mg/ml) | Total Protein (mg) | $OD_{234}$ | Specific Activity ($OD_{234}$/60 min/mg protein) |
|---|---|---|---|---|
| Crude Extract | 6.0 | 390 | 0.66 ± 0.02 | 1.10 |
| 45K Supernatant | 6.0 | 390 | 0.31 ± 0.02 | 0.51 |
| 45K OTGP Soluble | 0.8 | 20 | 0.16 ± 0.01 | 20.0 |
| 10K OTGP Soluble | 2.0 | 44 | 0.25 ± 0.01 | 12.5 |

Figure 25:
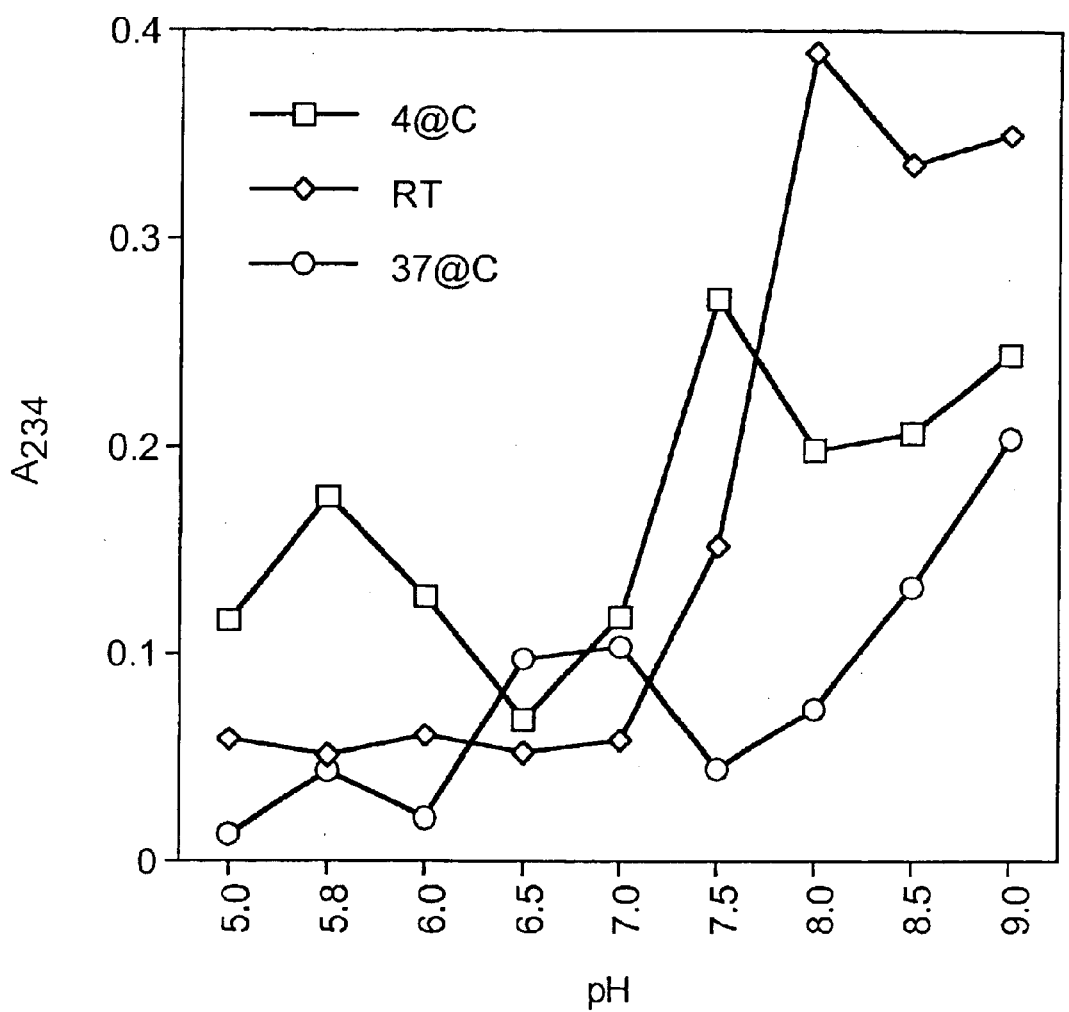
FIG. 25 is a line graph showing linoleate isomerase optimum pH and temperature in *C. sporogenes* ATCC 25762.

Temperature optimization with crude extracts was carried out at 4° C., room temperature (~25° C.) and 37° C. The best temperature for the isomerase activity was room temperature (FIG. 25). The isomerase activity decreased to 73% of optimum at 4° C. and 63% of optimum at 37° C. The optimum pH was monitored by adjusting the pH from 5.0 to 9.0 using the 0.1M Tris buffer with 10 mM NaCl, 1 mM DTT and 40 ppm linoleic acid. The optimum pH was found to be 7.5, 8.0 and 9.0 for incubating at 4° C., room temperature and 37° C., respectively (FIG. 25).

Figure 26:
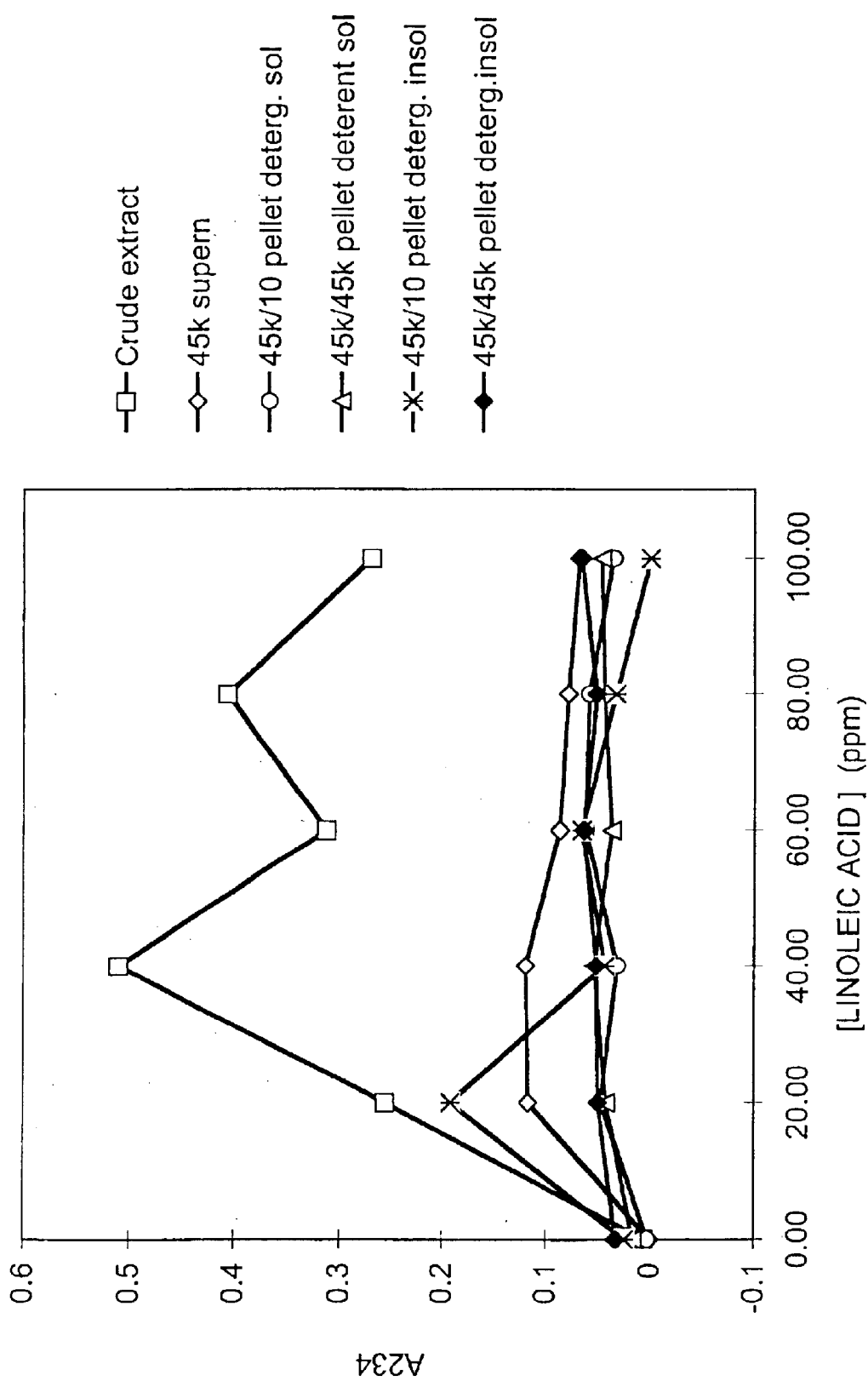
FIG. 26 is a line graph showing optimum linoleic acid concentration for *C. sporogenes* ATCC 25762 linoleate isomerase.
Figure 27:
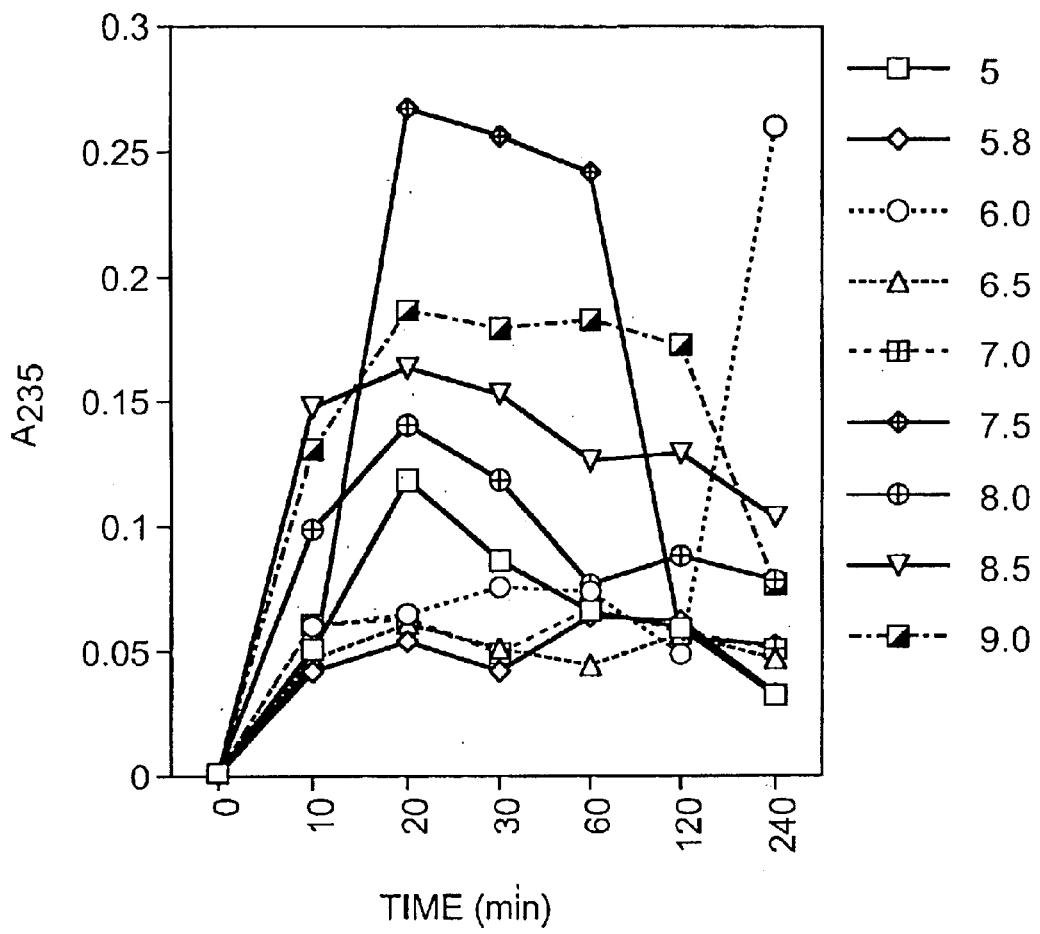
FIG. 27 is a graph showing the time course for CLA formation by *C. sporogenes* ATCC 25762 linoleate isomerase.

The concentration of linoleic acid was tested from 0 to 100 ppm (FIG. 26). The optimum concentration for linoleic add was determined to be 40 ppm. A time course study indicated that the activity responded linearly within 20 minutes and showed a slight decrease upon 60 minutes incubation at optimum pH, temperature and substrate concentration (FIG. 27).

Figure 28:
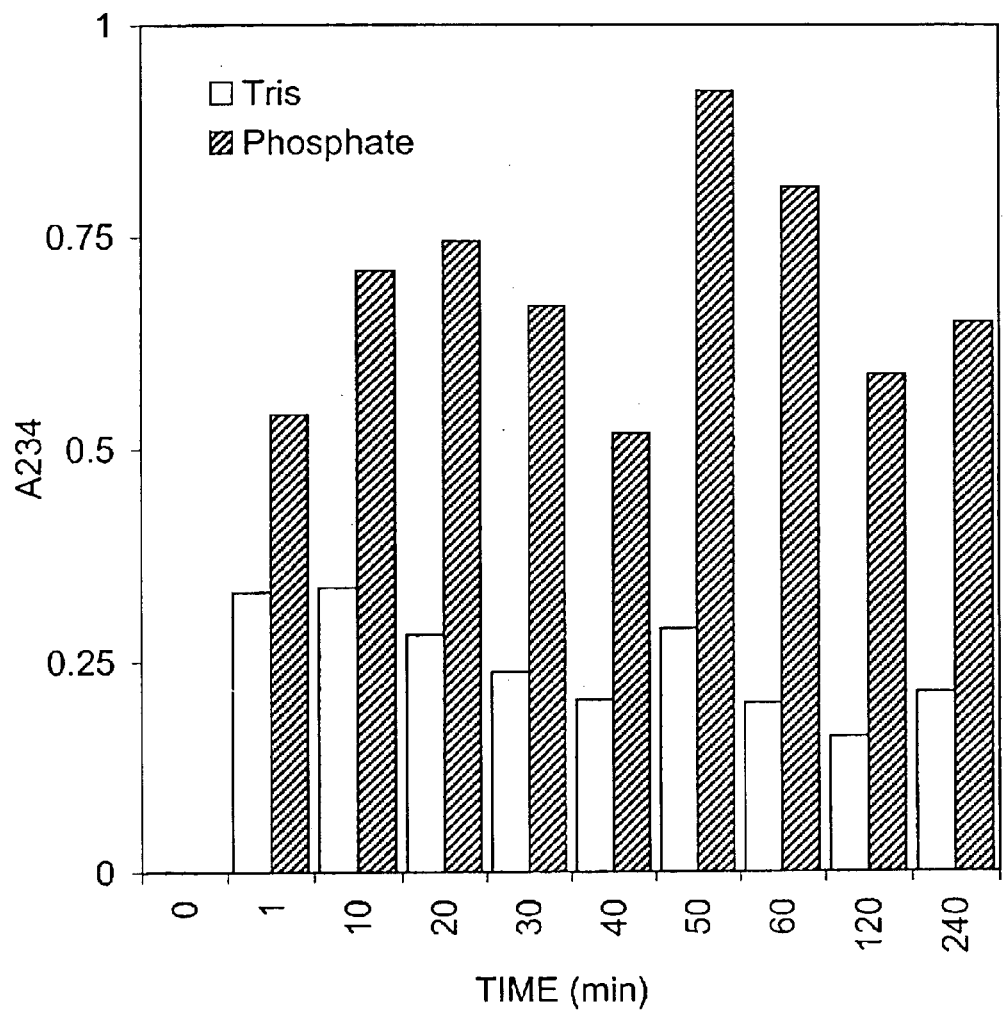
FIG. 28 is a bar graph illustrating the stability of *C. sporogenes* ATCC 25762 linoleate isomerase in Tris and phosphate buffers.

The *C. sporogenes* isomerase was alternatively extracted by sonication in 0.1 M Tris, pH7.5, 10 mM NaCl, 2 mM DTT and 10% glycerol. This extraction was of higher efficiency (about 20%) than that by French press. This is different from the isomerase isolated from *L. reuteri*, wherein it was observed that sonication resulted in a total loss of activity. Isomerase activity was higher in phosphate buffer, pH 7.5, than in Tris buffer, pH 7.5 (FIG. 28). The enzyme was most stable in phosphate buffer.

The detergent soluble fraction was further purified by Method A, B or C, infra.

Method A

Figure 29:
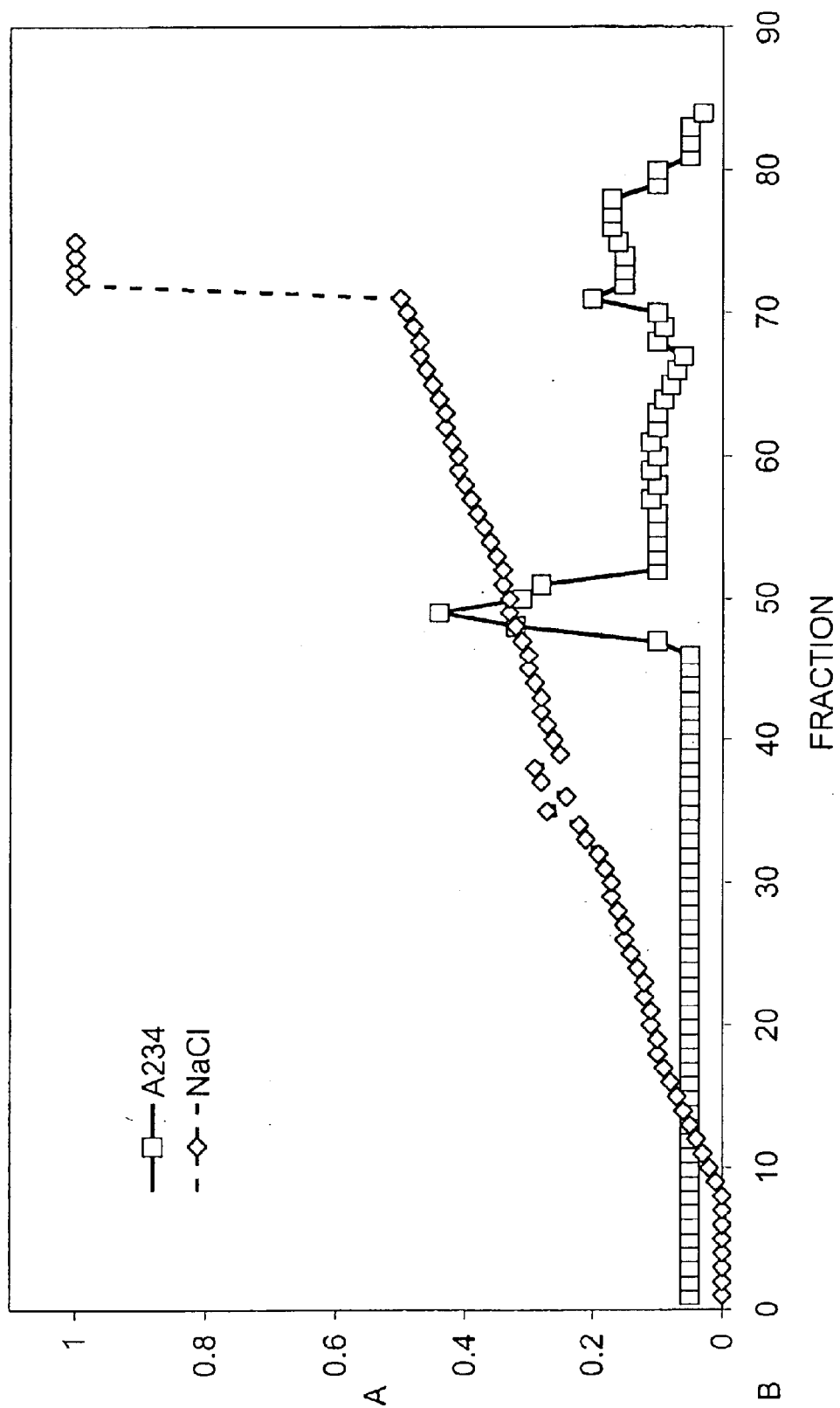
FIG. 29 is an elution profile of fresh *C. sporogenes* ATCC 25762 linoleate isomerase extracts from DEAE-5PW.

Experimental conditions for purification of the isomerase by DEAE-5PW chromatography have been established. Under these conditions, 75% of the isomerase was recovered. FIG. 29 gives an overview of the purification of the isomerase from OTGP solubilized protein. Three experiments were performed with similar results: the *C. sporogenes* isomerase eluted from the column by 0.5 M NaCl. The peak fractions (#48 to #51) contained 60% of the isomerase loaded on the column, resulting in a 6-fold purification to an average specific activity of 32. The column was eluted further with 1M NaCl, and putative enzyme activity was detected by UV analysis (linoleic acid (LA) was apparently converted into products with spectra identical to CLA). However, analysis of these fractions by GC showed that the major product of the conversion had a retention time of 13 minutes, while the retention time of c9, t11-CLA is about 10 minutes. Although this peak was minor as compared to the peak eluted by 0.5 M NaCl, this data suggested that *C. sporogenes* cells may have the ability to produce other isomers of CLA. It was observed that a freshly prepared extract should be used to achieve a high recovery of isomerase activity by ion-exchange chromatography, because the detergent solubilized protein tended to lose activity or it precipitated after storage at 4° C. for more than 3 days (data not shown).

A rapid spectrophotometric assay for CLA, measuring absorbance at $OD_{234}$ (detects conjugated fatty acid bonds as well as other UV absorbing compounds), was used to estimate CLA concentration in column eluate fractions. It was important to confirm that the $OD_{234}$ absorbing material was CLA before attempting further purification. Gas chromatography was used for this purpose. Comparison of the $OD_{234}$ data with the result obtained by gas chromatography showed good correlation, indicating that the "active" fractions collected contained the desired isomerase activity.

Isomerase was partially purified on DEAE with acceptable minimal loss of activity as described above. However, the activity of pooled enzyme fractions decreased by 50% after overnight storage at 4° C. In some experiments, no activity was detected after DEAE purification. Therefore, it would be important to maintain the enzyme activity to continue purification.

It was demonstrated that the *C. sporogenes* linoleate isomerase is a membrane protein. The detergent, octyl-thioglucopyranoside (OTGP), has been used successfully to solubilize isomerase. Unfortunately, OPTG (and the solubilized enzyme) precipitated slowly during purification at 4° C. A nondenaturing detergent, Triton X-100 with a high concentration of salt, is commonly used to distinguish between peripheral and integral membrane proteins. No significant difference was found in the efficiency of the solubilization between 1% Triton X-100 and 0.3% OPTG. Less total protein was solubilized with a mixture of 0.1% Triton X-100 and 0.3% OPTG. The efficiency of solubilization by 1 M NaCl alone was very low, indicating that the isomerase is an integral membrane protein.

Method B

Figure 30:
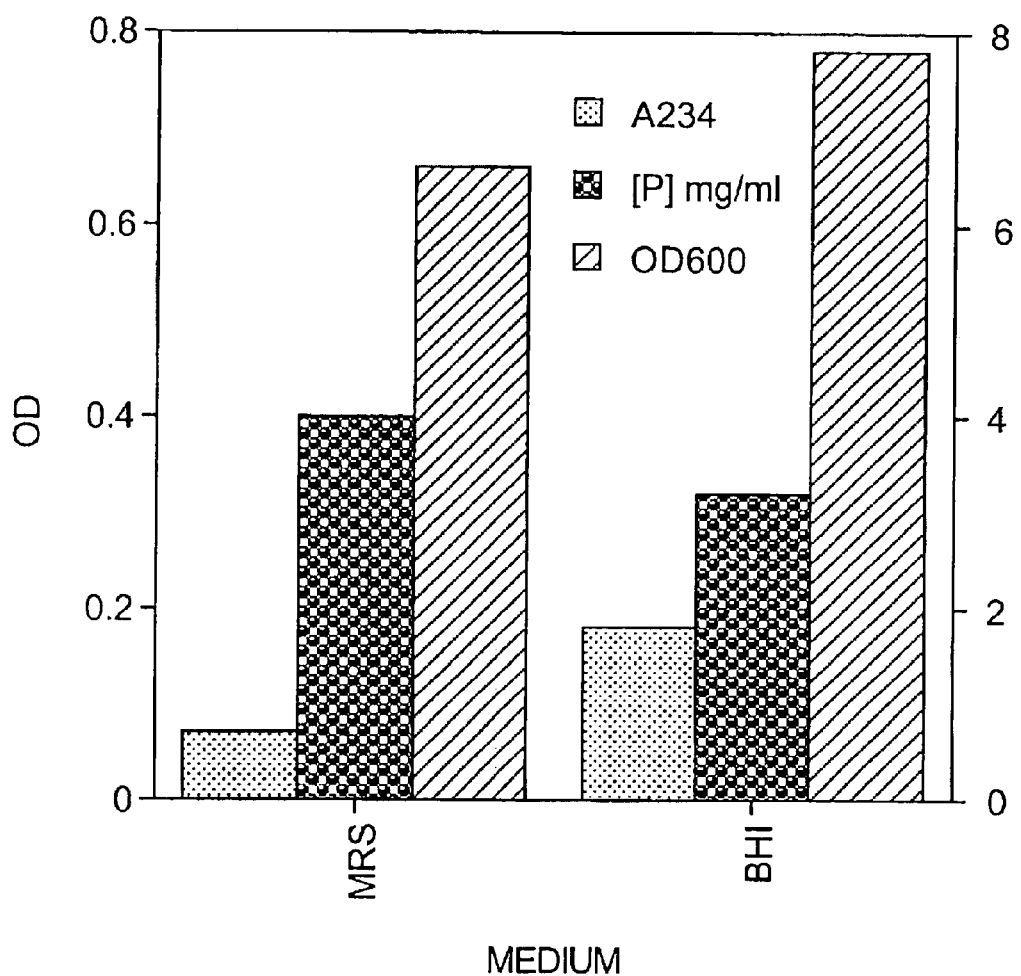
FIG. 30 is a bar graph demonstrating the effect of culture medium on *C. sporogenes* ATCC 25762 growth and linoleate isomerase activity.

It was clearly necessary to improve the activity and stability of the *C. sporogenes* isomerase. Two different media, BHI and MRS, were tested. Results are shown in FIG. 30. At pH 7.0, less isomerase was produced in MRS medium, although a higher total protein was obtained. There is no difference in stability of isomerase produced in either medium. Protease inhibitors, PMSF (0.1–1.0 mM), iodoacetamide (1 mM) and pepstatin A were tested for their effects on the stability of isomerase. None provided measurable benefit.

Figure 31:
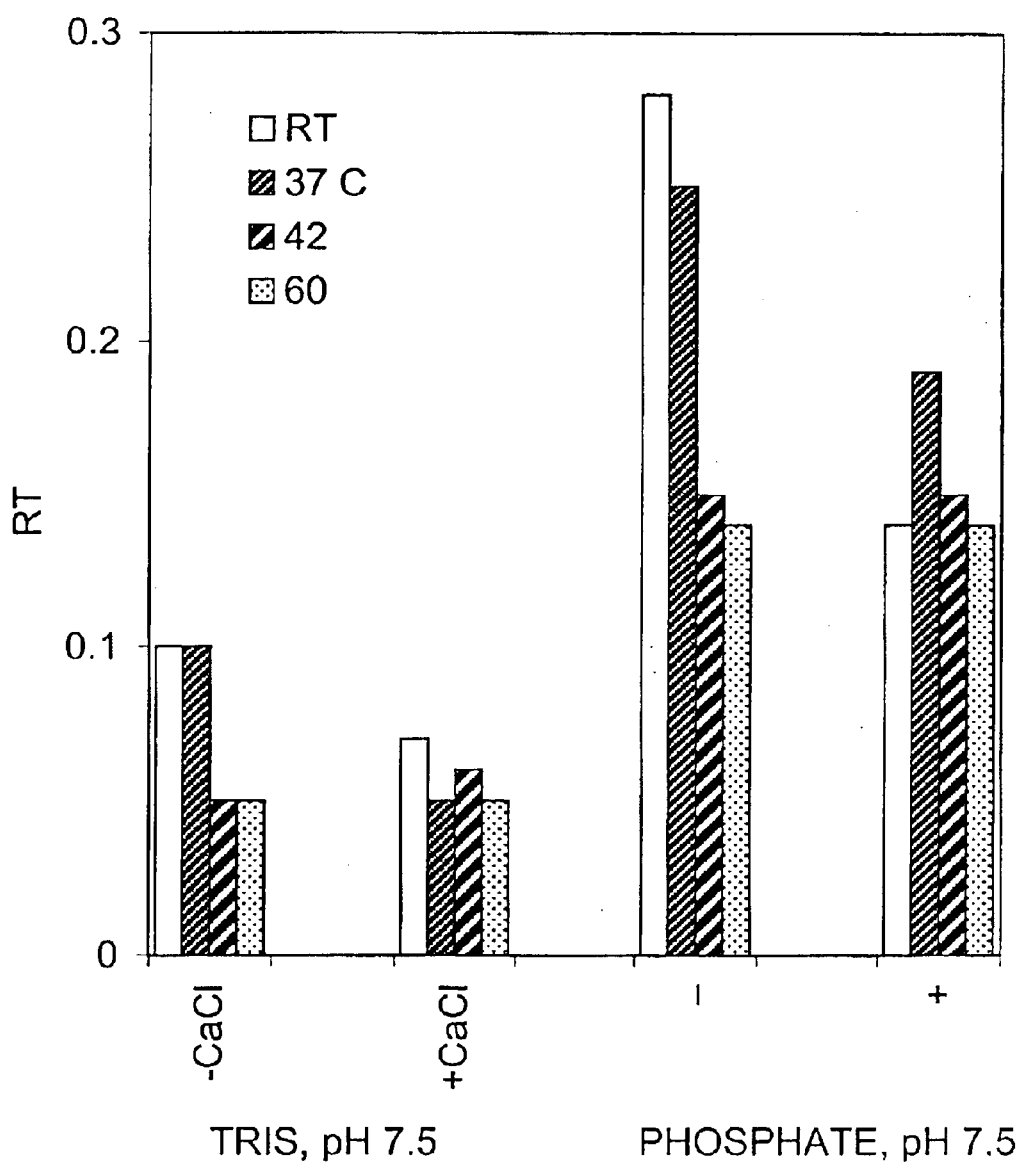
FIG. 31 is a bar graph showing the effect of $CaCl_2$ on *C. sporogenes* ATCC 25762 linoleate isomerase activity.

It has been reported that solubilization in the presence of lysophosphatidylcholine (LPC) allows higher detergent concentrations to be used, thus allowing more complete membrane protein solubilization. $CaCl_2$ can activate enzymes, such as some nucleases. Added $CaCl_2$ plus LPC has been demonstrated to stabilize detergent solubilized sodium channel membrane proteins. None of these positive effects was observed on the linoleate isomerase. Moreover, $CaCl_2$ decreased the enzyme activity in both Tris and phosphate buffer systems. At temperatures higher than 37° C., $CaCl_2$ had no effect on the activity, but the isomerase activity was reduced to 50% at the temperatures of 42° C. and 60° C. (FIG. 31).

Figure 32:
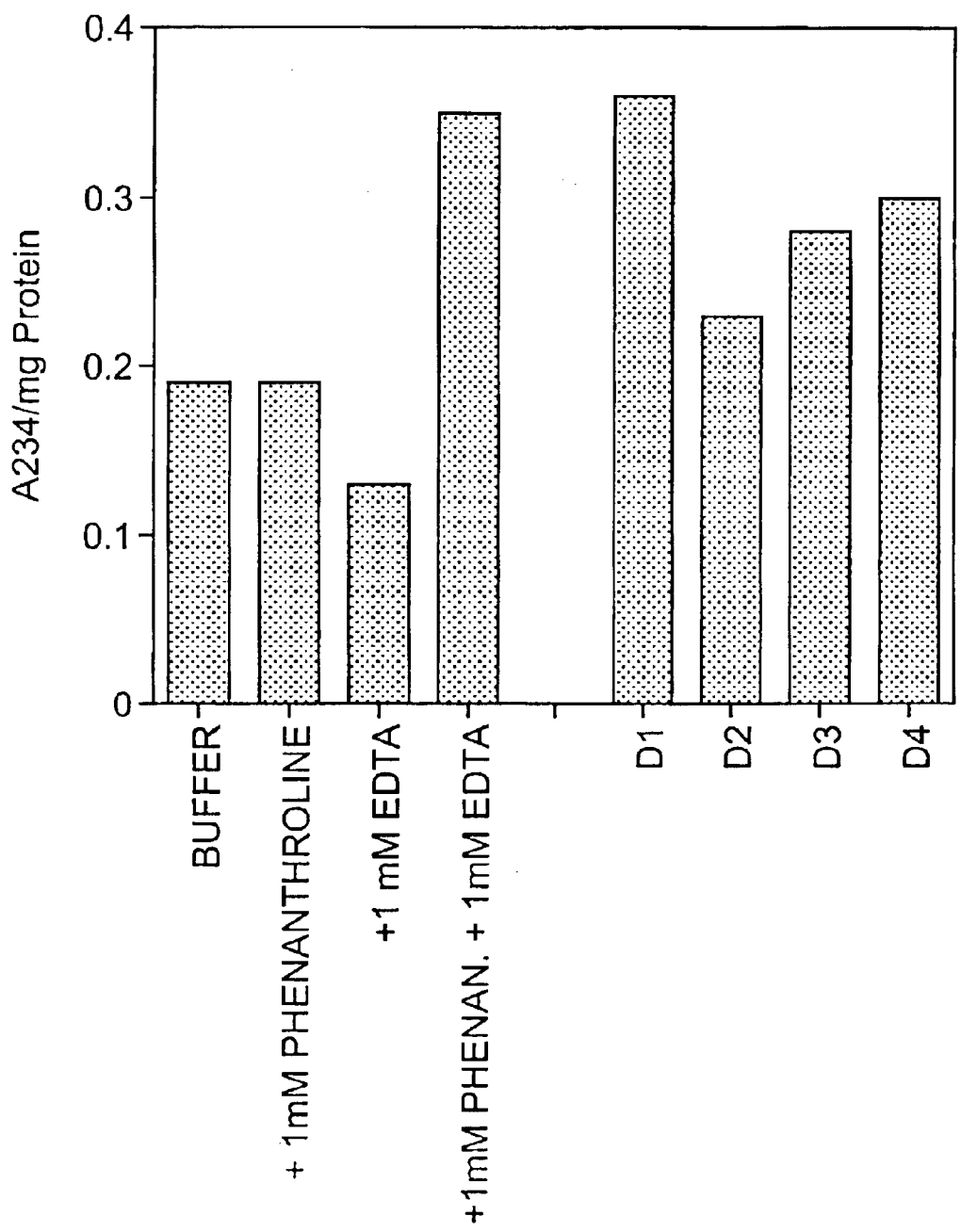
FIG. 32 is a bar graph showing the effect of chelating agents on *C. sporogenes* ATCC 25762.
Figure 33:
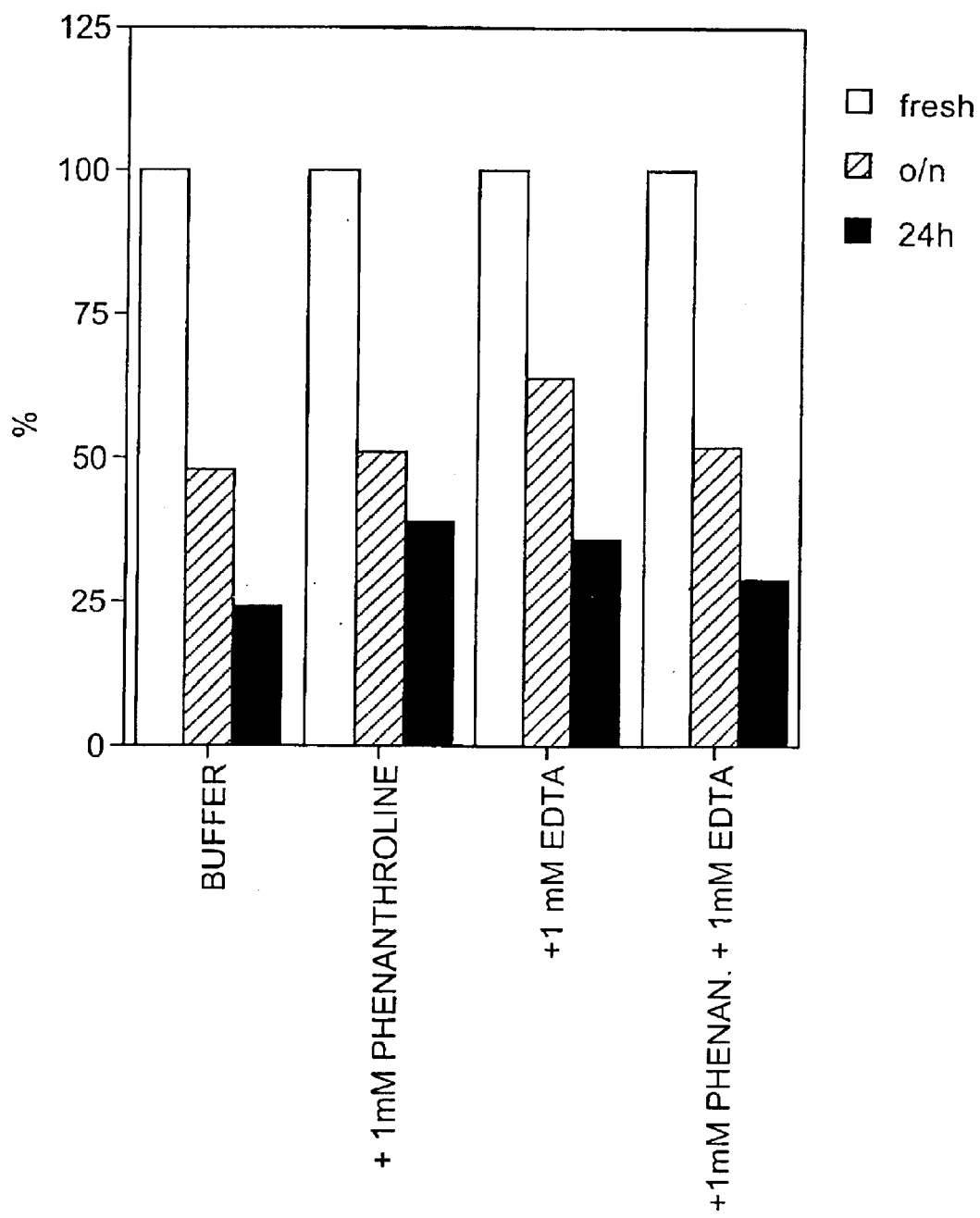
FIG. 33 is a bar graph showing the effect of chelating agents on stability of linoleate isomerase.

FIG. 32 shows the effect of the iron-chelating agents, phenanthroline and EDTA, on the enzyme activity and stability. It seems that the enzyme in crude extracts was protected by phenanthroline. This protection was more effective when 1 mM of phenanthroline was combined with 1 mM EDTA, although addition of 1 mM EDTA had a negative effect. In contrast, the addition of iron-chelating compounds to detergent buffer resulted in a loss of activity during the enzyme preparation, but a slight increase in stability (FIG. 33).

Prior to efforts to further purify the 9,11-linoleic acid isomerase from *C. sporogenes*, endeavors were made to increase the stability of the enzyme in crude extracts and in the detergent soluble fraction to be able to complete the procedures necessary for purification.

Figure 34:
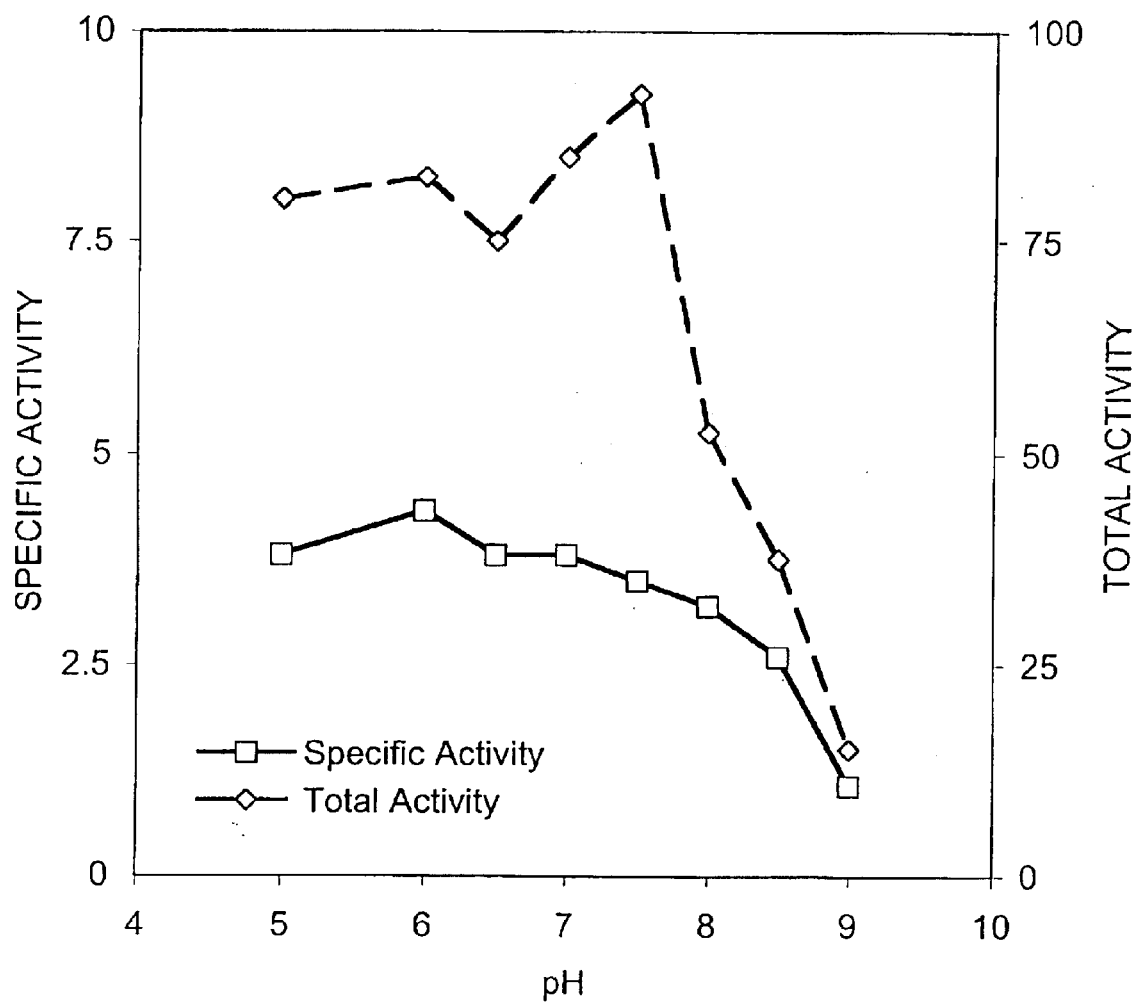
FIG. 34 is a line graph illustrating the effect of pH on extraction efficiency of linoleate isomerase in *C. sporogenes* ATCC 25762.
Figure 35:
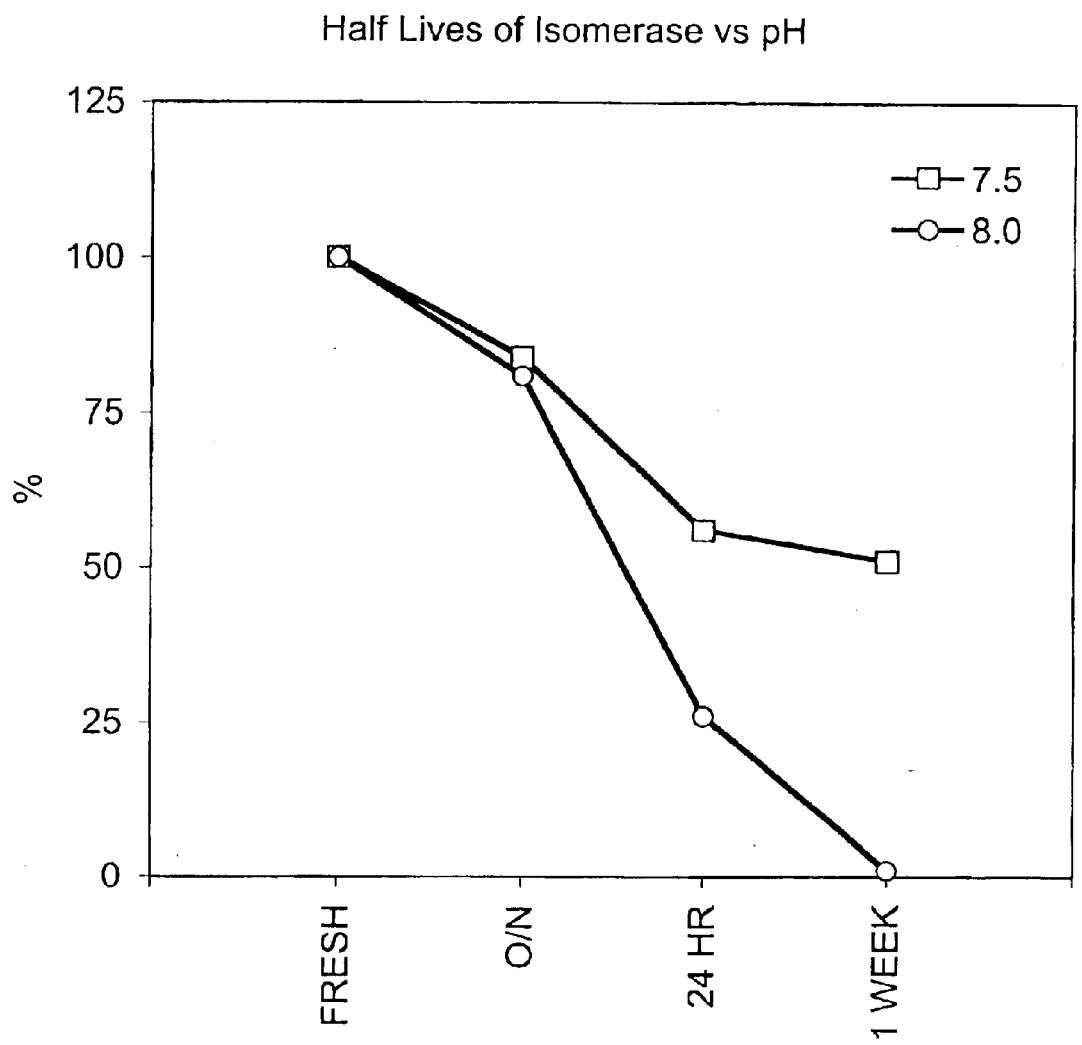
FIG. 35 is a line graph demonstrating the half lives of linoleate isomerase in *C. sporogenes* ATCC 25762 versus pH.

The effect of pH and type of buffer used during enzyme extraction, on extraction efficiency and on enzyme stability were examined. Crude extracts were prepared with 0.1 M Tris buffer at pH 5.0–9.0. The pH during extraction had a strong impact on both extraction efficiency and enzyme stability. The optimum pH for the extraction of the isomerase was 7.5 (FIG. 34), and at this pH, the half-life of isomerase was extended from one day at pH 8.0 to one week (FIG. 35).

Figure 36:
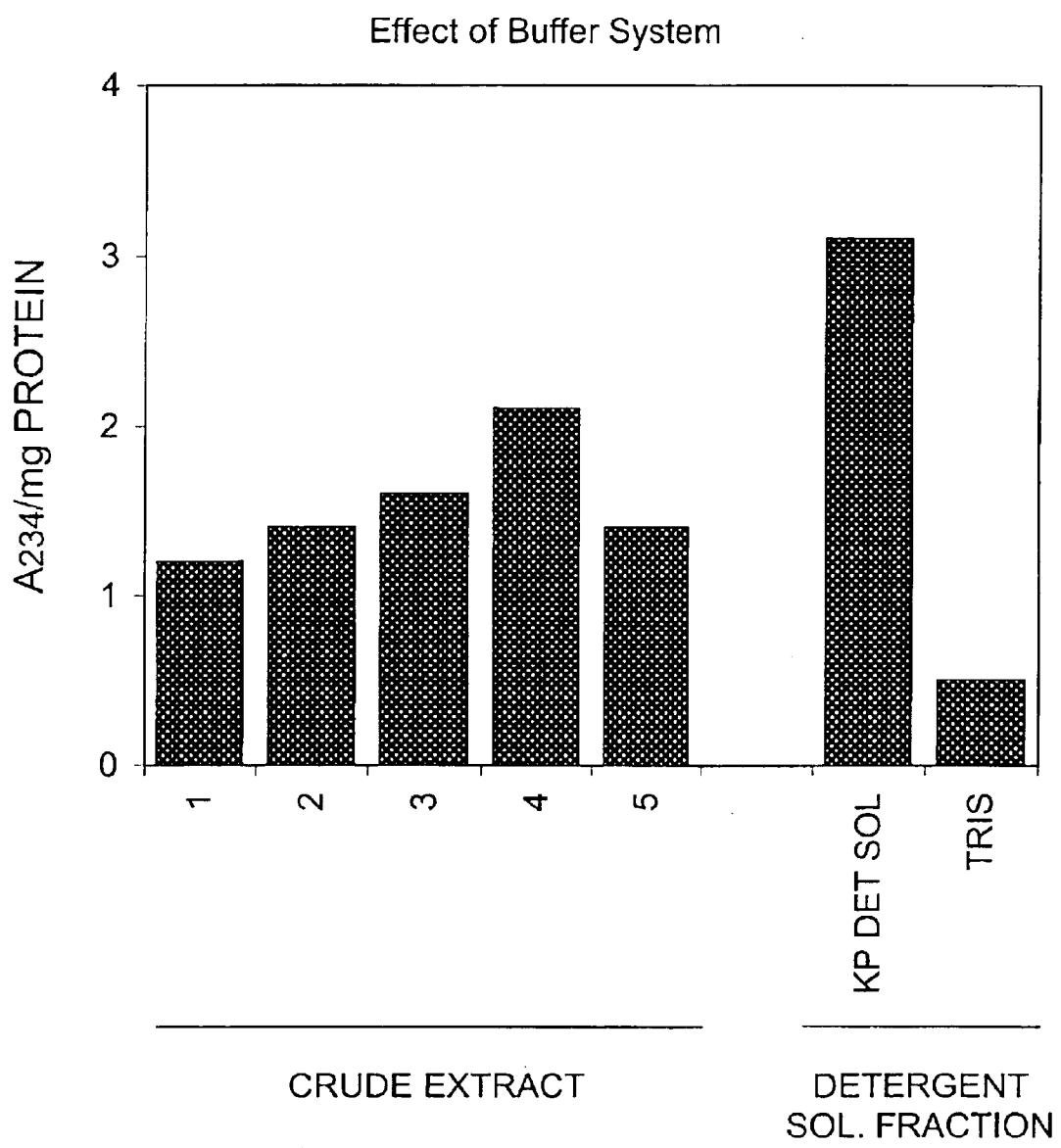
FIG. 36 is a bar graph showing the effect of buffer system on the activity of linoleate isomerase in *C. sporogenes* ATCC 25762.
Figure 37:
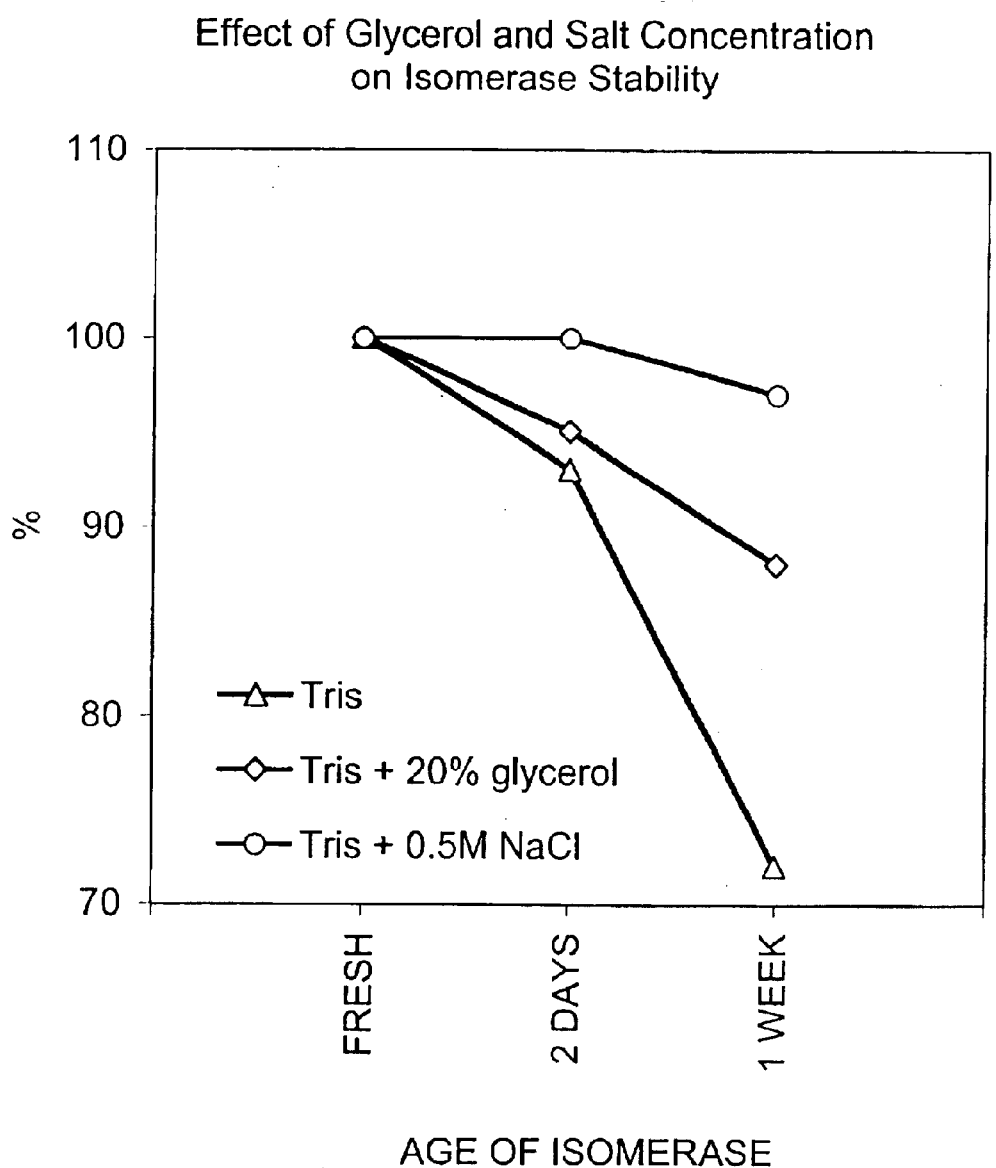
FIG. 37 is a line graph illustrating the effect of glycerol and salt concentration on the stability of crude extracts of linoleate isomerase in *C. sporogenes* ATCC 25762.

The effect of the type of buffer was also significant. Tris buffer, potassium phosphate buffer, and Hepes buffer were compared, and the results are shown in FIG. 36. Phosphate buffer was the most effective in extraction and solubilization of the isomerase. This buffer produced a distinct increase in the activity obtained. In crude extracts, activity was about double that obtained with Tris, and in detergent soluble fractions a four- to seven-fold increase was measured. Further improvements (FIG. 37) were obtained by increasing the NaCl (20% increase in activity) and glycerol concentrations (30% increase).

Figure 38:
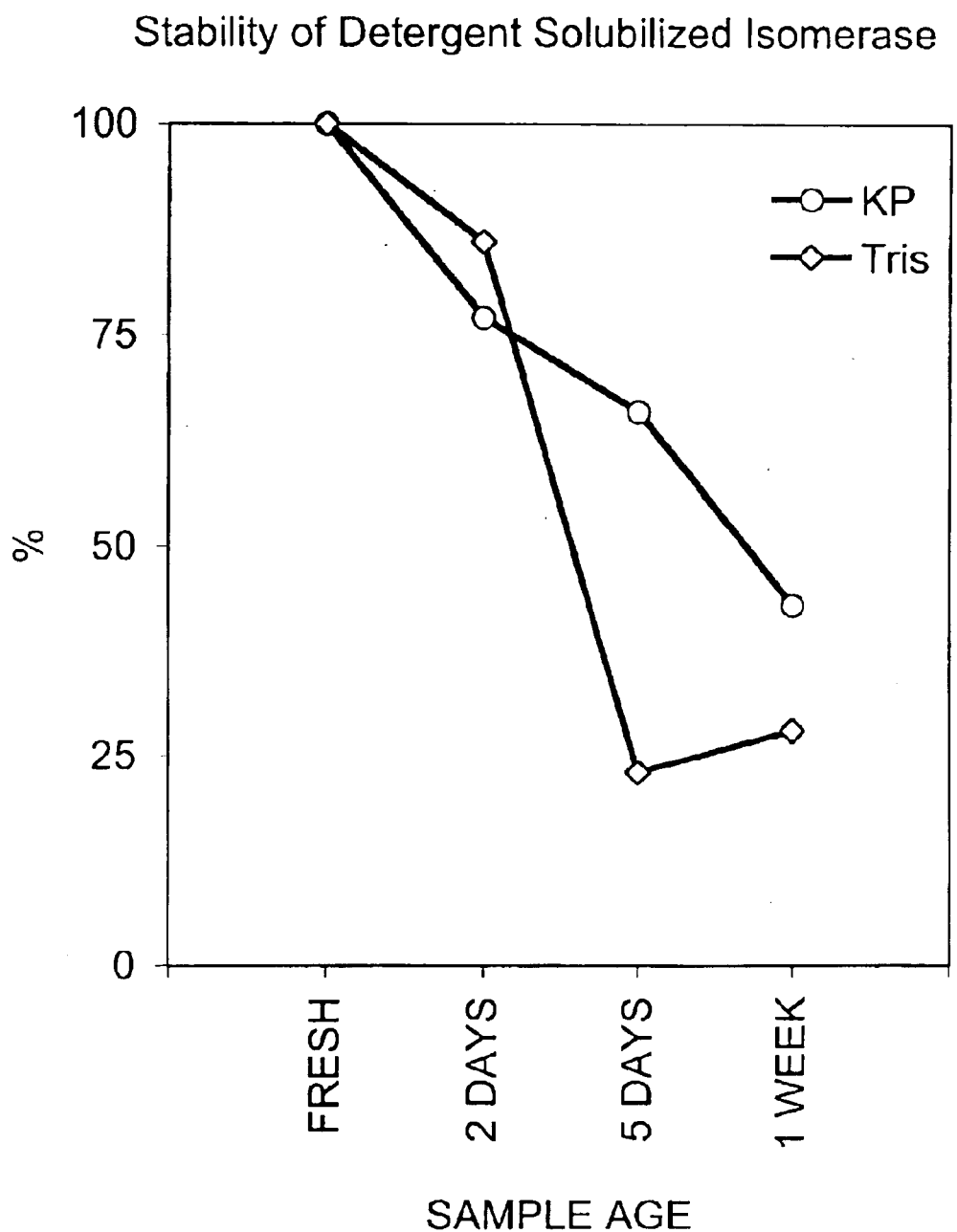
FIG. 38 is a line graph showing the stability of detergent solubilized linoleate isomerase in *C. sporogenes* ATCC 25762.

The enzyme stability was compared at pH 7.5. In general, the isomerase was more stable in crude extracts than in detergent solubilized fractions (FIG. 38). A half-life of 10, 11 and 13 days was measured in Tris, phosphate and Hepes crude extracts, respectively. Increasing glycerol and salt concentration provided major improvements on stability, resulting in near full retention of activity for one-week. However, half-life of detergent solubilized isomerase was only three and six days in Tris and phosphate buffer, respectively.

Figure 39:
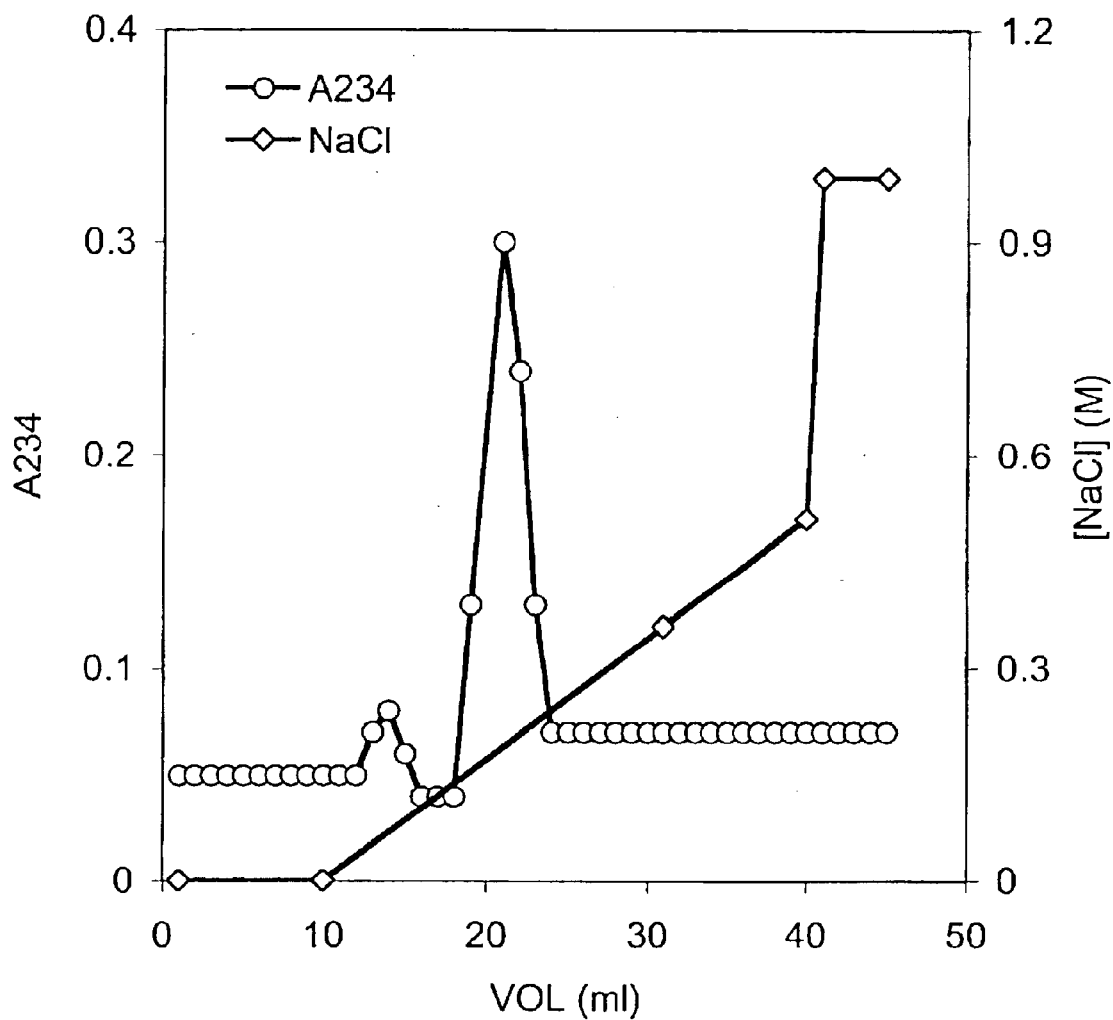
FIG. 39 is an elution profile of *C. sporogenes* ATCC 25762 linoleate isomerase on DEAE Mono Q.

A small-scale purification was performed using a Pharmacia DEAE Mono Q column with enzyme solubilized with 0.3% octyl-thioglucopyranoside (OTGP), as described above, and with phosphate buffer replacing the previously used Tris. A single peak of activity, eluting at approximately 250 mM NaCl, was obtained (FIG. 39). The specific activity after this step increased 2.5 fold. This result was reproducible and repeatable. SDS-PAGE analysis of the protein from this column showed a band corresponding to a molecular weight of approximately 70 kDa (data not shown). The molecular mass is similar to that of the 9,11 isomerase of *L. reuteri*, suggesting that the two isomerases may have similar characteristics.

OTGP has been used successfully to solubilize the isomerase. However, the detergent (and the solubilized enzyme) slowly precipitates at 4° C. This precipitation results in more than 50% loss of activity after desalting of the enzyme solution by dialysis, but more importantly, it clogs the ion exchange columns, rendering them unusable.

Therefore, detergents that could efficiently solubilize the isomerase while avoiding the precipitation problem were sought. Triton X-100 has a good performance as solubilizing agent for the isomerase, and the amount of protein solubilized increased with increasing Triton X-100 concentrations. Isomerase extraction was also enhanced at high salt concentration (500 mM NaCl). However, it was determined that enzyme activity was completely lost when the solution was dialyzed before ion exchange. The use of low salt concentration resulted in lower protein extraction from the membrane pellet, but similar enzyme activity and eliminates the requirement for the desalting step.

Extraction efficiency similar to that obtained with OTGP has been achieved using 2% Triton X-100 in 50 mM phosphate buffer. A comparison of soluble protein and specific activity in the two detergent systems is shown in Table 4. The enzyme stability is reduced in Triton with respect to OTGP, which is one remaining disadvantage of this new detergent system. However, the conditions would still give a workable time frame to purify the enzyme by multiple steps of chromatography. The continued purification scheme for the isomerase is DEAE chromatography, followed by chromatofocusing, as has been done for the isomerases described in Examples 5 and 9.

TABLE 4

Preparation of *C. sporogenes* 9,11 Isomerase Extracts with OTGP and Triton X-100

| Sample | Enzyme Activity (A234) | Protein (mg/ml) | Specific Activity (A234/mg) |
|---|---|---|---|
| Crude Extract | 0.84 | 7.6 | 1.10 |
| 45K Soluble | 0.12 | 6.6 | 0.18 |
| 0.3% OTGP Soluble | 0.40 | 3.3 | 1.22 |
| 2% Triton - 50 mM NaCl | 0.42 | 2.8 | 1.50 |

A third nonionic detergent, octyl glucoside (OG) was tested for its ability to solubilize the *C. sporogenes* linoleate isomerase. OG effectively solubilized the isomerase and the activity of the solubilized enzyme was stable. OG at 1.5% (2×critical micelle concentration) produced an isomerase specific activity about 20% higher than that of OTGP solubilized isomerase. No precipitation was observed in the solubilized membrane protein sample after dialysis.

Method C

While OG can be used to solubilize linoleate isomerase, this detergent is too expensive to use in large-scale isomerase purification. The protocol to solubilize linoleate isomerase was modified to initially solubilize isomerase with OG, and then keep the enzyme solubilized with OTGP. The membrane fraction was solubilized with 1.5% OG in 50 mM potassium phosphate buffer at 15° C. OG solubilized proteins were dialyzed against 20 mM potassium phosphate buffer, pH 7.5, 10 mM NaCl, 2mM dithiothreitol and 0.3% OTGP. After centrifugation at 45,000 g for 30 minutes, the solubilized proteins were applied to a DEAE-5PW column, equilibrated with low salt buffer (20 mM bis-Tris, pH7.5, 10 mM NaCl, 0.3% OTGP, 1 mM dithiothreitol, 1 mM EDTA and 1 µM pepstatin A) and eluted with a linear gradient of NaCl from 0 to 0.5 M at 16° C.

Figure 40:
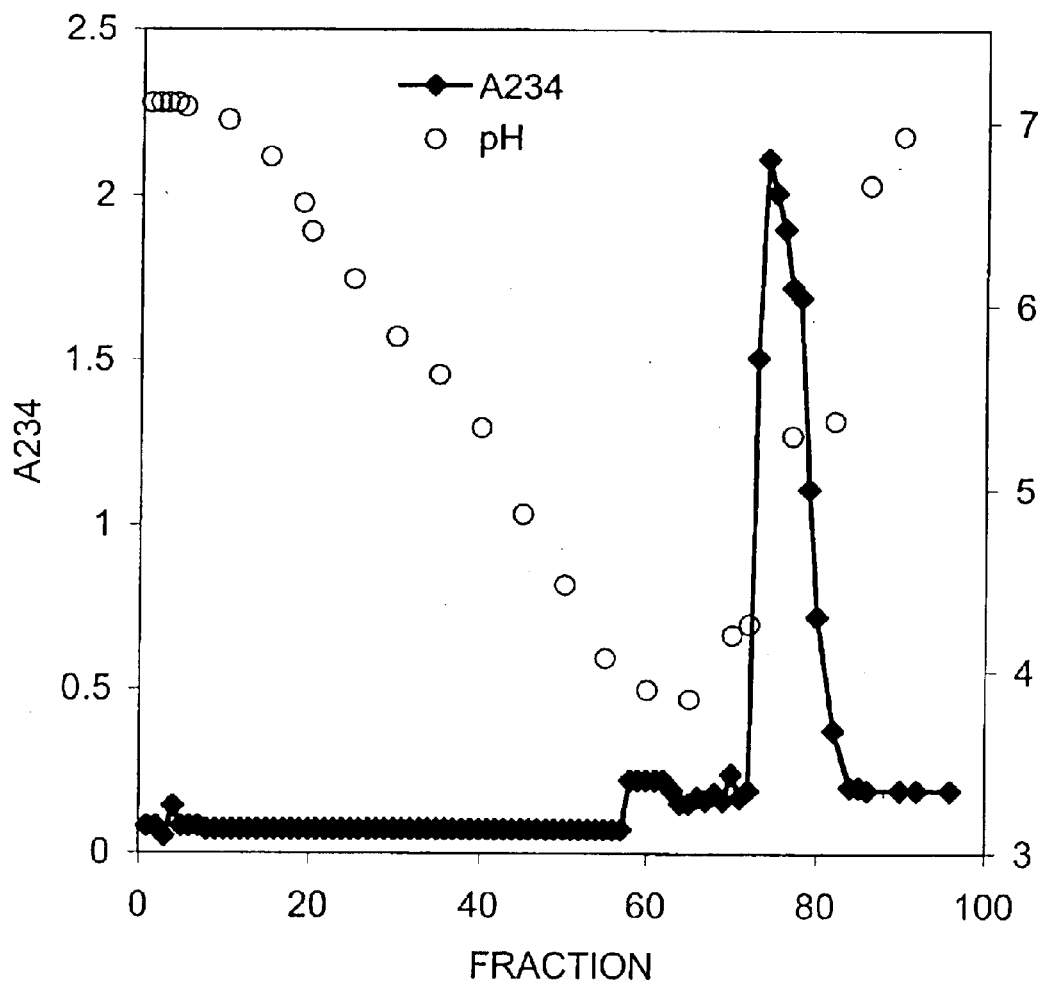
FIG. 40 is an elution profile of *C. sporogenes* ATCC 25762 detergent solubilized linoleate isomerase on DEAE-5PW column.

The DEAE-5PW column chromatography achieved a 4-fold purification. Two distinct peaks of isomerase activity were revealed (FIG. 40). Peak II, which eluted at higher ionic strength, was observed in all previous DEAE chromatography experiments. Peak I, which was eluted at lower ionic strength (0.18M NaCl), was observed for the first time. Both peaks catalyzed isomerization of linoleic acid to c9, t11-CLA, as determined by GC analysis of methyl ester products. Peak II was chosen for further purification.

Figure 41:
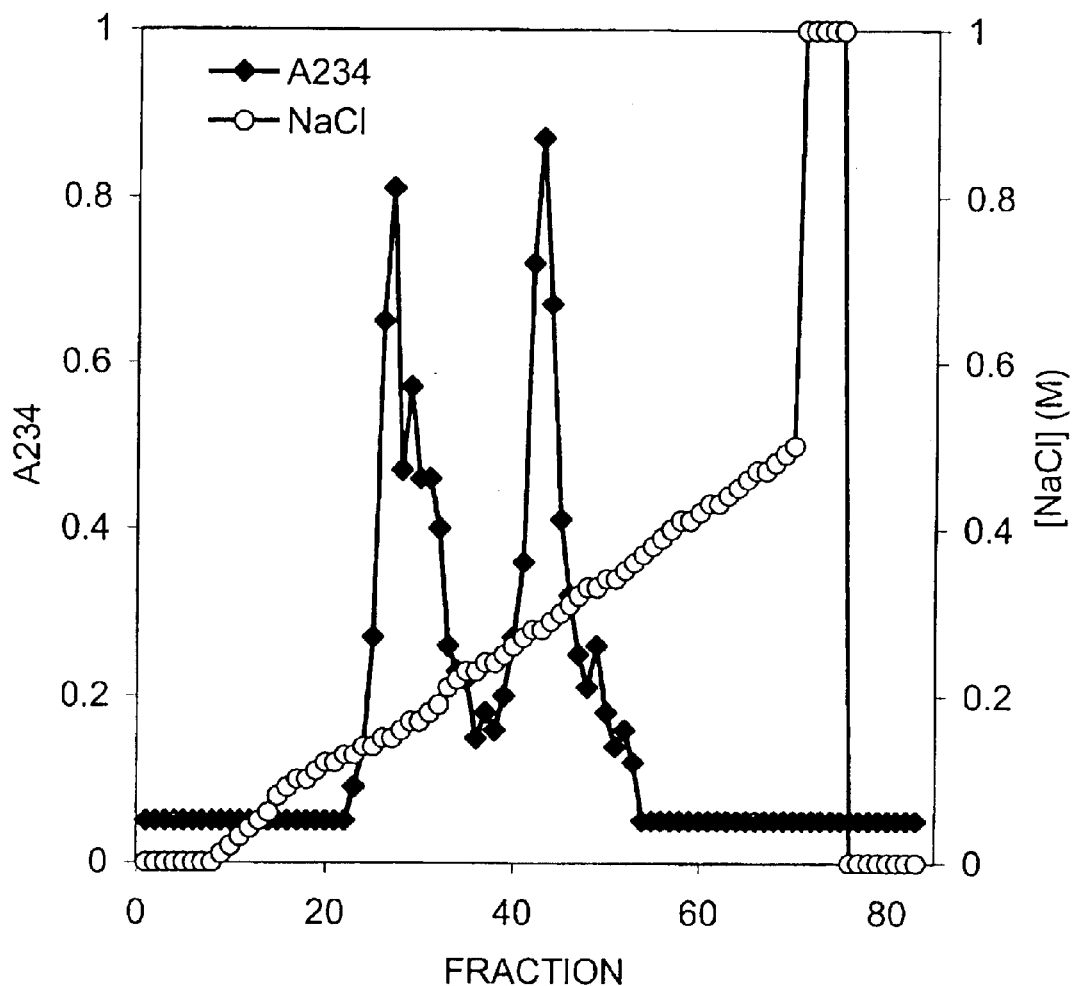
FIG. 41 is an elution profile showing separation of partially purified *C. sporogenes* ATCC 25762 linoleate isomerase by chromatofocusing.

Active fractions (fraction 43–47) from DEAE peak II were pooled, concentrated and dialyzed against 25 mM bis-Tris, pH 7.1 containing 0.3% OTGP, and then loaded on a Mono-p chromatofocusing gel column. Elution was carried out with 100 ml of 10% polybuffer74, lowering the final pH to 3.5. The isomerase activity was retained on the column. Following completion of the polybuffer74 gradient, the isomerase activity was eluted with 1 M NaCl in 50 mM bis-Tris, pH 7.1 (FIG. 41). This chromatofocusing step achieved another 2 to 6 fold purification (Table 5). Examinations by SDS PAGE of chromatofocusing fractions possessing enzymatic activity revealed two major bands.

TABLE 5

Summary of chromatofocusing

| Fraction | A234 | [P] (mg/ml) | Specific Activity | Fold |
|---|---|---|---|---|
| A/S* | 1.76 | 0.97 | 9 | 1 |
| F73 | 1.51 | 0.35 | 22 | 2 |
| F74 | 2.11 | 0.66 | 16 | 2 |

TABLE 5-continued

Summary of chromatofocusing

| Fraction | A234 | [P] (mg/ml) | Specific Activity | Fold |
|---|---|---|---|---|
| F75 | 2.01 | 0.26 | 39 | 4 |
| F76 | 1.90 | 0.18 | 53 | 6 |
| F77 | 1.72 | 0.26 | 33 | 4 |
| F78 | 1.69 | 0.21 | 40 | 4 |
| F79 | 1.11 | 0.29 | 19 | 2 |
| F80 | 0.72 | 0.18 | 20 | 2 |
| F82 | 0.37 | 0.07 | 26 | 2 |

Total loading: A234 = 88
Fractions: A235 = 75
Recovering = 85%
*A/S: Applied Sample This protocol can be used to purify sufficient *C. sporogenes* linoleate isomerase protein to determine the N-terminal sequence for the isomerase, and to subsequently clone and sequence the entire enzyme, as described for the *L. reuteri* linoleate isomerase described above.

Example 11

The following example describes the optimization of growth conditions for *L. reuteri* PYR8.

Fermentation work was concentrated on the optimization of growth conditions for *L. reuteri* PYR8. A fermentation medium that could consistently support cell growth well and isomerase production, thus eliminating the variability previously observed was pursued.

Working with MRS medium, it was determined that the linoleate isomerase activity was variable, mainly due to the medium composition and sterilization procedures that had some effect on cell growth. The number of inoculum stages and the inoculum size did not affect final cell concentration. Mixed versus static growth, suspected to affect the gas balance in the medium, did not appear to be a significant variable. Given the medium richness, toxic concentrations of some compounds were suspected as a possible reason for the variability. However, it was determined that different dilutions of MRS resulted in proportional lower cell densities (data not shown) indicating a nutritional limitation in the medium. Additionally, high variability was observed when using two batches of the same medium.

Experiments performed in one and ten-liter fermentors indicated that a different medium (AV) with composition similar to MRS, but with higher yeast extract, peptone and acetate concentration, and without beef extract, gave consistently better results in fermentors than MRS with respect to both cell growth and isomerase activity. We adopted this medium as our base medium for further work. Its composition is shown in Table 6.

TABLE 6

Composition of AV Medium

| Component | Concentration |
|---|---|
| Yeast Extract | 10 g/l |
| Proteose Peptone #3 (Difco) | 20 g/l |
| Sodium Acetate | 10 g/l |
| Glucose | 20 g/l |
| Tween 80 | 1 ml/l |

TABLE 6-continued

Composition of AV Medium

| Component | Concentration |
|---|---|
| MgSO4 | 0.028 g/l |
| MnSO4.2H2O | 0.012 g/l |
| FeSO4.7H2O | 0.0034 g/l |
| Vitamin Mixture | 10 ml/l |

The vitamin mixture contained riboflavin, pantothenic acid, pyridoxal, nicotinic acid, folic acid, choline chloride, biotin and thiamine.

A full factorial experiment was run in bottles, dividing this medium into seven categories (yeast extract, peptone, acetate, glucose, Tween 80, salts and vitamins), and studying the impact of two concentrations of the components in each category as follows: 2.5 and 10 g/l yeast extract, 10 and 20 g/11 peptone, 10 and 20 g/l glucose, 5 and 10 g/l acetate, 0.5 and 1 ml/l Tween 80, 0.5× and 1× salts concentration and no addition vs. addition of vitamins. This study demonstrated clearly that yeast extract concentration had the most significant impact on growth, followed by glucose and the combined effect of glucose and yeast extract. Peptone effect was marginal and the other components did not affect growth. The concentration of Tween 80 seemed to affect isomerase activity, as measured by conversion of linoleic acid to CLA.

Difco yeast extract was successfully replaced by KAT east extract, and several industrial type nitrogen sources were tested as replacements for Peptone #3. These are summarized in Table 7.

TABLE 7

Nitrogen Sources Evaluated as Medium Components

| Nitrogen Source Name | Type | Manufacturer |
|---|---|---|
| N-Z-Amine A | Enzyme Hydrolysate of Casein | Quest |
| N-Z-Amine YT | Enzyme Hydrolysate of Casein | Quest |
| Pepticase | Enzyme Hydrolysate of Casein | Quest |
| Amicase | Acid Hydrolysate of Casein | Quest |
| Edamin K | Enzyme Hydrolysate of Lactalbumin | Quest |
| Amisoy | Acid Hydrolysate of Soy | Quest |
| Hy-soy | Enzyme Hydrolysate of Soy | Quest |
| Primatone RL | Enzyme Hydrolysate of Meat | Quest |
| Primatone HS | Enzyme Hydrolysate of Meat | Quest |
| Primagen | Enzyme Hydrolysate of Animal Tissue | Quest |
| Pancase | Pancreatic Digest of Casein | Red Star |
| Amberferm 2000 | Proteolyzed Dairy Protein | Red Star |
| Amberferm 2234 | Proteolyzed Dairy Protein | Red Star |
| Amberferm 4000 | Acid Hydrolyzed Vegetable Protein | Red Star |
| Amberferm 4002 | Acid Hydrolyzed Vegetable Protein Blend | Red Star |
| Amberferm 4015G | Enzyme Hydrolyzed Soy Protein | Red Star |
| Amberferm 4016 | Enzyme Hydrolyzed Soy | Red Star |
| Whey Protein Concentrate | Corn Steep Liquor | Roquette |
| Nutrisoy Soy Flour | Hydrolyze in the Lab with Neutrase | ADM |
| Nutrisoy Soy Flour with Added Oils | Hydrolyze in the Lab with Neutrase | ADM |
| Pharmamedia | Cottonseed Flour | Traders |

Most of these nitrogen sources supported growth of *L. reuteri* PYR8, but isomerase activity was not always detected. The most promising ones, N-Z-Amine A, Amberferm 2234, Amberferm 4015, Amisoy and Hy-Soy were further tested in fermentors. Hy-soy was determined not just to be a good replacement for peptone, but to actually improve growth over peptone.

Lactose, fructose and galactose were compared to glucose as possible carbon sources. The organism did not grow on fructose and lactose, and galactose did not offer any advantage over glucose.

Fermentations performed with peptone and increasing levels of yeast extract up to 20 g/l indicated that yeast extract concentrations above 10 g/l were still beneficial. Further optimization proceeded with a full factorial experiment in fermentors where the effects two levels of yeast extract (20 and 30 g/l), Hy-Soy (10 and 20 g/l) and glucose (20 and 30 g/l) were compared. pH control at 4.8 was adopted to avoid low pH inhibition due to the higher acid production from the higher glucose concentrations. The growth results from these fermentations showed that even though there was not a statistically significant difference between conditions, higher yeast extract fermentors resulted in slightly higher optical density (data not shown). The culture in the medium with high level of the three components grew faster and reached a higher cell density.

The medium with 30 g/l yeast extract, 10 g/l Hy-Soy and 30 g/l glucose was chosen for further optimizations steps.

The effects of growth temperature and Tween 80 concentration were studied. Fermentations were performed at 11 and 1.5 ml/l Tween 80 and 37° C., 40° C. and 43° C. Medium with Hy-Soy at 20 g/l was also compared at 37° C. and 43° C. The growth and conversion results indicated clearly that higher temperatures were beneficial for growth and isomerase activity (data not shown). The increase in Tween 80 concentration did not seem to impact linoleic acid conversion significantly, although a higher conversion rate was observed at 43° C. with higher Tween 80 concentration.

A temperature of 40° C. was adopted as the preferred growth temperature and the medium containing 30 g/l yeast extract, 10 g/l Hy-Soy, 30 g/l glucose and 1.5 ml/l Tween, as the new base medium. In another set of fermentations, the reproducibility of the process was tested in triplicate fermentors. Higher concentrations of yeast extract, Hy-Soy and glucose were also compared at 40° C. The results showed that good reproducibility can be obtained with this medium and growing conditions, with respect to final cell density and isomerase activity (data not shown). Further increases in the concentrations of the main components favored cell growth. An optical density above 10 units was obtained with 40 g/l yeast extract, 20 g/l Hy-Soy and 40 g/l glucose. The specific enzyme activity and activity per cell was similar under all these different conditions. Therefore, an increase in cell density resulted in increased isomerase activity.

The medium with 30 g/l yeast extract, 10 g/l Hy-Soy and 30 g/l glucose plus the additional components of the AV medium described above, resulted in cell densities (measured by OD and DCW) twice as high as those obtained with MRS, and a much more reliable performance. With these conditions, the fermentation performed consistently better in fermentors than in static bottles. The cultures were harvested at 24 and 30 hours to determine isomerase activity as a function of culture age. No difference was found in the rate of conversion of linoleic acid to CLA between cells of different age for any of the media tested. The shorter fermentation time is due to the faster growth in this medium and at the higher temperature. At 24 hours, the culture had already reached stationary phase.

Several substances were tested as possible inducers of the 9,11 linoleate isomerase. The materials tested included: lauric acid, myristic acid, palmitic acid, palmitoleic acid, oleic acid, linoleic acid, linolenic acid, oleic acid stearyl ester, linoleyl alcohol, linoleic acid methyl ester, linoleic acid ethyl ester, stearic acid and linoleic acid methyl ester. They were added to the growth medium at a 100 mg/l level. No positive effect was found with any of the compounds, and some of them were detrimental to the expression and/or activity of the isomerase. The determination of the existence of a positive effect may be obscured by the required presence of Tween 80, which may be an inducer in itself, but which cannot be eliminated because it is required for growth.

Example 12

The following example describes the determination of conditions to improve enzyme stability and performance and on testing the limitations of the biotransformation process. Whole cells of L. reuteri PYR8 were used in all biotransformation experiments described below.

One aspect of the preservation of the enzyme activity is the handling of the cells immediately after harvesting and the determination of suitable storage conditions. The preservation of activity in cells maintained in different buffers was investigated, and it was determined that reduced buffers such as TKM/EDTA/NaCl (50 mM Tris.HCl, 25 mM KCl, 5 mM $MgCl_2$, 1.25 mM EDTA, 0.1 mM NaCl, pH 7.5) with 20 mM cysteine or 20 mM DTT preserved isomerase activity much better than other buffers or culture medium. Cells maintained in 100 mM Bis-Tris pH 5.8 with 10 mM NaCl, 10% glycerol and 2 mM DTT (breakage buffer) did not lose any activity in 48 hours. It was also determined that the biotransformation rate measured in this buffer was very similar to that measured in the culture medium (MRS) which had been used as the preferred medium to perform the reaction.

Isomerase activity could also be preserved by freezing the cell paste. The cell paste was frozen immediately after harvesting with and without washing with either MRS or breakage buffer. No differences were observed. Some interesting results were also obtained when the cells were directly preserved in the culture broth with or without harvesting. A comparison was made between activity in cells immediately after harvest, cells that were harvested and maintained as a cell paste (no washing) at 4° C. for 24 hours, cells that were kept without harvesting in the culture broth at 4° C. for 24 hours, and cells from culture broth that were kept at room temperature for 24 hours. The conversion of linoleic acid to CLA was very similar in every case, with only a slight decrease observed in those cells that had been maintained at room temperature for a day.

In another experiment, the isomerase activity was followed in cells that were handled in different ways after harvesting. Cells were resuspended in either MRS, breakage buffer or culture supernatant (pH adjusted to 5.8). Isomerase activity, compared as conversion of 1000 ppm linoleic acid, was measured in the cells immediately after harvesting, after being held for 24 hours at 4° C. and after a four hour period at 22° C. followed by 20 hours at 4° C. The results from these different experiments indicated that the enzyme activity is better preserved when the cells are maintained under strictly non-growing conditions (data not shown). In several repeat experiments, cells resuspended in MRS gave more variable results than cells resuspended in breakage buffer. When cells in MRS were kept at room temperature, the deterioration was even more marked. Breakage buffer was selected as the medium of choice to perform the biotransformation because of the better enzyme stability. Cells can also be preserved prior to harvesting in the culture broth at the low pH reached at the end of the fermentation.

Another aspect of the biotransformation investigated was the possible presence of mass transfer limitations between the oil, the water phase and the membrane bound enzyme. Experiments were done using different methods of addition of the linoleic acid and performing the isomerization reaction in stirred jars at different agitation rates.

Linoleic acid was added as 99% LA, dissolved in propyleneglycol (100 mg/ml solution) or emulsified with 0.5, 5 or 30% lecithin. The emulsion was prepared by blending the linoleic acid and the lecithin with the reaction medium before the addition of the cells. Linoleic acid was added at 1000 and 2000 ppm. The results indicated that there was no significant difference between adding the pure acid or the propyleneglycol solution, and that the reaction was slightly faster with both than when the acid was emulsified with lecithin (data not shown). High levels of lecithin seemed to negatively affect the final conversion.

Two biotransformation reactions were performed in stirred jars with 300 ml of reaction medium. Cells were concentrated 10-fold with respect to the original culture density. The reaction was run between 6° C. and 8° C., in MRS, and linoleic acid was added dissolved in propyleneglycol. 1000 ppm were added at time 0 and another 1000 ppm at two hours. Agitation was kept at 200 rpm in one reactor and 1000 rpm in the other. Results showed that no significant difference was found between the two conditions. These experiments indicated that mass transfer limitations are not a major problem when working with this enzyme.

The effect of substrate and product on the enzyme performance was also investigated, as well as the possibility of recycling the cells. The effect of CLA on the reaction was studied by adding different concentrations of either a mixture of isomers (Sigma material, approximately 41% 9,11 isomer and 48% 10,12 CLA), or just 9,11 CLA (Matreya material, approximately 77% 9,11 CLA). Concentrations from 500 to 3000 ppm were tested. Some experiments were also performed recycling the broth from a previous biotransformation reaction with L. reuteri PYR8, resulting in an initial CLA concentration around 700 ppm. In every case, 1000 ppm linoleic acid were added. With both the Sigma and the Matreya CLA, the reaction was completely inhibited even at the lowest concentration tested, and linoleic acid and CLA remained constant over the four-hour period that the reaction was followed. In the same period, almost complete conversion of the linoleic acid was obtained in the control without exogenous CLA. However, the effect was not detected when the CLA present came from recycled reaction broth. In this case, there was no difference in conversion rate between no CLA presence and 700 ppm. The results may indicate that some of the impurities present in the chemically produced CLA may be stronger inhibitors of the 9,11 isomerase than the product itself.

Three separate experiments were performed where the cells were recycled after a first biotransformation step. In the first experiment, a biotransformation step with 1000 ppm linoleic acid was completed in three hours in both MRS and breakage buffer. 98–99% of the linoleic acid was isomerized to 9,11 CLA. Cells were recovered by centrifugation, resuspended in the same medium, 1000 ppm linoleic acid were added, and the reaction proceeded for another three hours. Very good conversions were obtained in every case (data not shown).

In the second experiment, cell recycle was studied with cells that have performed the biotransformation at different levels of linoleic acid. Cells were harvested, resuspended in breakage buffer at a 10-fold concentration, and linoleic acid was added at 1000, 1500, 2000, 2500 and 3000 ppm level. Given the higher linoleic acid concentration, the reaction was allowed to proceed for six hours. At that time, the cells were recovered by centrifugation, washed with buffer to remove (at least partially) non reacted linoleic acid and CLA, and to place all the cells under comparable conditions. 1000 ppm linoleic acid were added and the reaction was followed for four hours. The conversions and CLA concentrations obtained during the first stage indicated that with cells with good activity, no substrate inhibition was detected up to 3000 ppm linoleic acid. The reactions at higher linoleic acid did not reach completion in seven hours, but the rate of formation of CLA was very similar at the different substrate concentrations. However, when the cells were recycled and supplied with linoleic acid in a second stage, the reaction did not take place and isomerase activity was not detected in any of the cells, regardless of the linoleic acid level to which they had been exposed. Cells from the same lot that were not exposed to linoleic acid maintained full activity after 24 hours.

These results prompted the need to investigate the length of exposure to the reaction mix in relation to the loss of activity observed. Since it was clear that the activity was not lost in cells which had not performed the reaction, either the substrate, or more likely the product, might interact with the enzyme and affect its activity.

In the third recycle experiment, cells were concentrated as usual and the reaction was started at 2000 ppm. Aliquots were taken while the reaction proceeded, every two hours up to eight hours with one final sample at 25 hours. The cells from each aliquot were recovered by centrifugation and resuspended in buffer. 1000 ppm linoleic acid was added. The reaction was then followed for three hours. The results clearly indicated that the activity was slowly being lost in the cells. The reaction slowed down over time in the first stage and the activity was not recovered when the cells were placed in fresh reaction medium. While cells recycled after two hours had very good activity and could quickly transform the 1000 ppm linoleic acid to CLA, cells recycled after eight hours had no activity. Once again, full activity was preserved in the control (no reaction) after 25 hours.

This experiment provided a clear demonstration that the enzyme is either inactivated or becomes inaccessible to the substrate during the reaction. The reason is not clear, but an interaction with the product is suggested, as the activity seems to be lost as the product accumulates. It is not clear at this time the nature of this interaction or if it is directly related to the enzyme or the physical conditions of the cells. Studies will be required with immobilized enzyme to better understand this effect.

Example 13

The following example describes a preferred biotransformation protocol.

Cells of *Lactobacillus reuteri* (or another organism carrying the linoleate isomerase gene) are grown in modified AV medium with 40 g/l yeast extract, 20 g/l Hy-soy and 40 g/l glucose (or other appropriate medium for other organisms) to a cell density of about 3–4 g/l dry cell weight. When the cells reach stationary phase, they are harvested and resuspended in breakage buffer at a concentration between 5 and 20 g dry cell weight per liter. The biotransformation reaction should be preferably carried out at a temperature between 4° C. and 8° C. to maintain the enzyme activity. The linoleic acid can be added as a 99% oil, as a component of another oil, as an oil phase, or dissolved in a cosolvent such as propylene glycol. It can be added at concentrations between 0.5 and 4 g/l. The addition should preferably be done in several steps of smaller amounts. To obtain higher CLA concentrations, it is also possible to add the cells in successive steps while the reaction proceeds. Under these conditions, and at these linoleic acid concentrations, conversion of linoleic acid to CLA between 80% and 100% is expected within 2 to 8 hours.

Example 14

The following example describes the biotransformation of linoleic acid to 10,12 CLA with *P. acnes* whole cells.

The objective of these studies was to begin the characterization of the behavior of the 10,12 linoleic acid isomerase and to determine the conditions to enhance its performance.

*P. acnes* is a strict anaerobe for which growth in the medium currently used is very poor. Some previous experiments suggested that *P. acnes* was able to further metabolize 10,12 CLA. The new experiments also indicated this to be the case, but it seems to be a slow process which may depend on the conditions of the reaction. It must be noted that with the current cell concentration achieved in the culture, and the same bioconversion protocol used in the production of the 9,11 CLA isomer (10-fold concentration of the cells, resuspension in buffer, addition of linoleic acid dissolved in propyleneglycol), the reaction proceeds at a much lower rate than that of the 9,11 isomerase, and much lower conversions are achieved.

The reaction was compared in culture medium vs. breakage buffer, at different temperatures and in the presence and absence of air. Temperature had a strong effect on the reaction rate. The reaction proceed very slowly at 4° C. and the rate increased with temperature, from room temperature to 37° C. No significant difference in conversion was found between the use of growth medium or a buffer, or the presence or absence of oxygen during the time frame allowed for the reaction to proceed (30 hours) (data not shown).

Further experiments with different cell and substrate concentrations had shown an apparent decrease in the CLA concentration when the reaction proceeded more than 48 hours, while the formation of CLA from linoleic acid seemed to stop at that time.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An isolated linoleate isomerase from a bacterium selected from the group consisting of Lactobacillus, Clostridium, Propionibacterium, Butyrivibrio, and Eubacterium having characteristics comprising:
   a. a molecular weight of between about 50 kDa and about 70 kDa;
   b. an optimum pH of from about 6.8 to about 9.0; and,
   c. a $K_m$ of at least about 8.1 μM for linoleic acid at pH 7.5 and at a temperature of about 20° C.,
      wherein said isolated linoleate isomerase has been isolated from a cell as a soluble or solubilized enzyme preparation, and wherein said isolated linoleate isomerase has linoleate isomerase enzymatic activity.

2. The linoleate isomerase of claim 1, wherein said linoleate isomerase is selected from the group consisting of *Lactobacillus reuteri*, *Clostridium sporogenes*, *Propionibacterium acnes*, *Butyrivibrio fibrisolvens*, *Propionibacterium acidipropionici*, *Propionibacterium freudenreichii* and *Eubacterium lentum* linoleate isomerases.

3. The linoleate isomerase of claim 1, wherein said linoleate isomerase is a *Lactobacillus reuteri* linoleate isomerase.

4. The linoleate isomerase of claim 1, wherein said linoleate isomerase is a *Clostridium sporogenes* linoleate isomerase.

5. The linoleate isomerase of claim 1, wherein said linoleate isomerase is a *Propionibacterium acnes* linoleate isomerase.

6. The linoleate isomerase of claim 1, wherein said linoleate isomerase converts linoleic acid and linolenic acid to CLA (conjugated linoleic acid or conjugated linolenic acid).

7. The linoleate isomerase of claim 1, wherein said linoleate isomerase converts linoleic acid and linolenic acid to (cis, trans)-9,11-linoleic acid.

8. The linoleate isomerase of claim 7, wherein said linoleate isomerase is about 67 kDa.

9. The linoleate isomerase of claim 1, wherein said linoleate isomerase converts linoleic acid and linolenic acid to (trans, cis)-10,12-linoleic acid.

10. The linoleate isomerase of claim 9, wherein said linoleate isomerase is about 50 kDa.

11. The linoleate isomerase of claim 9, wherein said linoleate isomerase has a pH optimum of about 6.8.

12. The linoleate isomerase of claim 1, wherein said linoleate isomerase has a Km of about 8.1 μM for linoleic acid; a pH optimum of about 7.5; and a Ki of about 80 μM for oleic acid.

13. The linoleate isomerase of claim 1, wherein the initial velocity of said linoleate isomerase decreases at about 60 μM linoleic acid.

14. The linoleate isomerase of claim 1, wherein said linoleate isomerase is a membrane enzyme.

15. The linoleate isomerase of claim 1, wherein said linoleate isomerase is a soluble enzyme.

16. The linoleate isomerase of claim 1, wherein said linoleate isomerase is bound to a solid support.

17. The linoleate isomerase of claim 16, wherein said solid support is selected from the group consisting of organic supports, biopolymer supports and inorganic supports.

18. The isolated bacterial linoleate isomerase of claim 1, wherein said linoleate isomerase has characteristics comprising:

a molecular weight of about 50 kD;

b. an optimum pH of about 6.8 at room temperature;

c. a $K_m$ of at least about 8.1 $\mu$M for linoleic acid at pH 7.5 and at a temperature of about 20° C.; and, d. converts linoleic acid and linolenic acid to (trans, cis)-10,12-linoleic acid.

19. The isolated linoleate isomerase of claim 1, wherein said isolated linoleate isomerase has been isolated by detergent solubilization.

20. The isolated linoleate isomerase of claim 1, wherein said isolated linoleate isomerase has at least about a 6-fold increase in enzyme activity as compared to a crude extract having linoleate isomerase activity.

21. The isolated linoleate isomerase of claim 1, wherein said isolated linoleate isomerase has been isolated by DEAE ion exchange chromatography.

22. The isolated linoleate isomerase of claim 1, wherein said isolated linoleate isomerase has been isolated by chromatofocusing methods.

23. The isolated linoleate isomerase of claim 1, wherein said isolated linoleate isomerase has been produced recombinantly.

24. The isolated linoleate isomerase of claim 1, wherein said isolated linoleate isomerase is of a purity to appear as a single band on an SDS-PAGE gel.

25. The isolated linoleate isomerase of claim 1, wherein said isolated linoleate isomerase is of a purity to elute from a chromatography column and appear as a single band on an SDS-PAGE gel.

26. The isolated linoleate isomerase of claim 1, wherein said isolated linoleate isomerase is of a purity to determine the N-terminal amino acid sequence of said isomerase.

27. A composition comprising the isolated linoleate isomerase of claim 1, and a lipid material.

28. An isolated linoleate isomerase comprising an amino acid sequence selected from the group consisting of:

a. an amino acid sequence selected from the group consisting of SEQ ID NO:9, SEQ ID NO:11 and SEQ ID NO:18; and b. an amino acid sequence that is at least 90% identical to an amino acid sequence selected from the group consisting of SEQ ID NO:9, SEQ ID NO:11 and SEQ ID NO:18;

wherein said isolated linoleate isomerase has linoleate isomerase enzymatic activity.

29. The linoleate isomerase of claim 28, wherein said linoleate isomerase comprises an amino acid sequence selected from the group consisting of SEQ ID NO:9, SEQ ID NO:11, SEQ ID NO:18.

30. The linoleate isomerase of claim 28, wherein said linoleate isomerase comprises the amino acid sequence SEQ ID NO:18.

31. The linoleate isomerase of claim 28, wherein said linoleate isomerase is bound to a solid support.

32. An isolated linoleate isomerase comprising an amino acid sequence selected from the group consisting of:

a. an amino acid sequence selected from the group consisting of: SEQ ID NO: 9, SEQ ID NO:11, SEQ ID NO:18; and b. enzymatically active fragments of said amino acid sequence of (a);

wherein said isolated linoleate isomerase has linoleate isomerase enzymatic activity.

33. The linoleate isomerase of claim 32, wherein said linoleate isomerase is bound to a solid support.

34. A method for producing CLA (conjugated linoleic acid or conjugated linolenic acid), comprising contacting an oil, said oil comprising a compound selected from the group consisting of linoleic acid and linolenic acid, with an isolated linoleate isomerase of claim 1 to convert at least a portion of said compound to CLA.

35. The method of claim 34, wherein said compound is in the form of a triglyceride and wherein said method further comprises contacting said oil with a hydrolysis enzyme to convert at least a portion of said triglyceride to free fatty acids.

36. The method of claim 35, wherein said hydrolysis enzyme is selected from the group consisting of lipases, phospholipases and esterases.

37. The method of claim 34, further comprising the step of recovering said CLA.

38. The method of claim 34, wherein said CLA is (cis, trans)-9,11-linoleic acid.

39. The method of claim 34, wherein said CLA is (trans, cis)-10,12-linoleic acid.

40. The method of claim 34, wherein said oil is selected from the group consisting of sunflower oil, safflower oil, corn oil, linseed oil, palm oil, rapeseed oil, sardine oil, herring oil, mustard seed oil, peanut oil, sesame oil, perilla oil, cottonseed oil, soybean oil, dehydrated castor oil and walnut oil.

41. The method of claim 34, wherein said linoleate isomerase has a Km of about 8.1 $\mu$M for linoleic acid; a pH optimum of about 7.5; and a Ki of about 80 $\mu$M for oleic acid.

42. The method of claim 34, wherein said linoleate isomerase comprises an amino acid sequence with at least about 90% identity with the amino acid sequence selected from the group consisting of SEQ ID NO:9, SEQ ID NO:11 and SEQ ID NO:18.

43. The method of claim 34, wherein said linoleate isomerase comprises an amino acid sequence selected from the group consisting of SEQ ID NO:9, SEQ ID NO:11 and SEQ ID NO:18.

44. The method of claim 34, wherein said linoleate isomerase comprises an amino acid sequence of SEQ ID NO:18.

45. The method of claim 34, wherein said linoleate isomerase is bound to a solid support.

46. The method of claim 45, wherein said solid support is selected from the group consisting of organic supports, biopolymer supports and inorganic supports.

47. A method for producing CLA, comprising contacting an oil, said oil comprising a compound selected from the group consisting of linoleic acid and linolenic acid, with an isolated linoleate isomerase of claim 28, to convert at least a portion of said compound to CLA.

* * * * *

SEQUENCE LISTING

<160> NUMBER OF SEQ ID NOS: 41

<210> SEQ ID NO 1
<211> LENGTH: 35
<212> TYPE: PRT
<213> ORGANISM: Lactobacillus reuteri
<220> FEATURE:
<221> NAME/KEY: UNSURE
<222> LOCATION: (30)

<400> SEQUENCE: 1

Met Tyr Tyr Ser Asn Gly Asn Tyr Glu Ala Phe Ala Arg Pro Lys Lys
 1               5                  10                  15

Pro Ala Gly Val Asp Lys Lys His Ala Tyr Ile Val Gly Xaa Gly Leu
            20                  25                  30

Ala Ser Leu
        35

<210> SEQ ID NO 2
<211> LENGTH: 29
<212> TYPE: DNA
<213> ORGANISM: Lactobacillus reuteri
<220> FEATURE:
<221> NAME/KEY: misc_feature
<222> LOCATION: (1)..(29)
<223> OTHER INFORMATION: PRIMER
<220> FEATURE:
<221> NAME/KEY: misc_feature
<222> LOCATION: (21)
<223> OTHER INFORMATION: n = g, a, c, or t
<220> FEATURE:
<221> NAME/KEY: misc_feature
<222> LOCATION: (27)
<223> OTHER INFORMATION: n = g, a, c, or t

<400> SEQUENCE: 2
cgtgaattca tgtaytayws naayggnaa                                        29

<210> SEQ ID NO 3
<211> LENGTH: 27
<212> TYPE: DNA
<213> ORGANISM: Lactobacillus reuteri
<220> FEATURE:
<221> NAME/KEY: misc_feature
<222> LOCATION: (1)..(27)
<223> OTHER INFORMATION: PRIMER
<220> FEATURE:
<221> NAME/KEY: misc_feature
<222> LOCATION: (10)
<223> OTHER INFORMATION: n = g, a, c, or t
<220> FEATURE:
<221> NAME/KEY: misc_feature
<222> LOCATION: (19)
<223> OTHER INFORMATION: n = g, a, c, or t

<400> SEQUENCE: 3
actggatccn acdatratng crtgytt                                          27

<210> SEQ ID NO 4
<211> LENGTH: 87
<212> TYPE: DNA
<213> ORGANISM: Lactobacillus reuteri
<220> FEATURE:
<221> NAME/KEY: CDS
<222> LOCATION: (1)..(87)

<400> SEQUENCE: 4

```
atg tat tat tcg aac gga aat tat gaa gcc ttt gct cga cca aag aag      48
Met Tyr Tyr Ser Asn Gly Asn Tyr Glu Ala Phe Ala Arg Pro Lys Lys
 1               5                  10                  15 cct gct ggc gtt gat aag aaa cac gcc tac ata gtc gga                  87
Pro Ala Gly Val Asp Lys Lys His Ala Tyr Ile Val Gly
             20                  25
```

<210> SEQ ID NO 5
<211> LENGTH: 29
<212> TYPE: PRT
<213> ORGANISM: Lactobacillus reuteri

<400> SEQUENCE: 5

```
Met Tyr Tyr Ser Asn Gly Asn Tyr Glu Ala Phe Ala Arg Pro Lys Lys
 1               5                  10                  15

Pro Ala Gly Val Asp Lys Lys His Ala Tyr Ile Val Gly
             20                  25
```

<210> SEQ ID NO 6
<211> LENGTH: 17
<212> TYPE: DNA
<213> ORGANISM: Lactobacillus reuteri
<220> FEATURE:
<221> NAME/KEY: misc_feature
<222> LOCATION: (1)..(17)
<223> OTHER INFORMATION: PRIMER

<400> SEQUENCE: 6
ggtcgagcaa aggcttc                                                   17

<210> SEQ ID NO 7
<211> LENGTH: 17
<212> TYPE: DNA
<213> ORGANISM: Lactobacillus reuteri
<220> FEATURE:
<221> NAME/KEY: misc_feature
<222> LOCATION: (1)..(17)
<223> OTHER INFORMATION: PRIMER

<400> SEQUENCE: 7
aagcctgctg gcgttga                                                   17

<210> SEQ ID NO 8
<211> LENGTH: 596
<212> TYPE: DNA
<213> ORGANISM: Lactobacillus reuteri
<220> FEATURE:
<221> NAME/KEY: CDS
<222> LOCATION: (122)..(595)

<400> SEQUENCE: 8
aaaaattatt tagaattaat ttataagttc attgtgttta ataaaattga cactttcaac    60
cgctttcact aaaattaagg tagttatgat gcacttgttt actgagaagg gagtcgtcaa   120

```
a atg tat tat tca aac ggg aat tat gaa gcc ttt gct cga cca aag aag  169
  Met Tyr Tyr Ser Asn Gly Asn Tyr Glu Ala Phe Ala Arg Pro Lys Lys
   1               5                  10                  15 cct gct ggc gtt gat aag aaa cat gcc tac att gtc ggt ggt ggt tta    217
Pro Ala Gly Val Asp Lys Lys His Ala Tyr Ile Val Gly Gly Gly Leu
             20                  25                  30 gct ggt tta tcg gcc gcc gtg ttt tta att cgt gat gcc caa atg ccg    265
Ala Gly Leu Ser Ala Ala Val Phe Leu Ile Arg Asp Ala Gln Met Pro
         35                  40                  45 ggt gag aat atc cat att tta gag gaa tta ccg gtt gcc ggt ggt tct    313
Gly Glu Asn Ile His Ile Leu Glu Glu Leu Pro Val Ala Gly Gly Ser
     50                  55                  60
```

```
ctt gat ggt gaa gat cgt cct gga att ggt ttt gtt act cgt gga ggc     361
Leu Asp Gly Glu Asp Arg Pro Gly Ile Gly Phe Val Thr Arg Gly Gly
 65                  70                  75                  80 cgg gaa atg gag aac cat ttc gag tgt atg tgg gac atg tat cgt tca     409
Arg Glu Met Glu Asn His Phe Glu Cys Met Trp Asp Met Tyr Arg Ser
                 85                  90                  95 att cca tca ctt gaa atc cca ggt gct tcc tac ctt gat gaa tac tac     457
Ile Pro Ser Leu Glu Ile Pro Gly Ala Ser Tyr Leu Asp Glu Tyr Tyr
             100                 105                 110 tgg tta gat aag gaa gat cca aac agt tct aat tgt cgt tta acc tat     505
Trp Leu Asp Lys Glu Asp Pro Asn Ser Ser Asn Cys Arg Leu Thr Tyr
         115                 120                 125 aag cgg gga aat gaa gtt cca tcg gac ggt aaa tat ggt tta agt aaa     553
Lys Arg Gly Asn Glu Val Pro Ser Asp Gly Lys Tyr Gly Leu Ser Lys
     130                 135                 140 aag gca atc aaa gag ctg act aag cta att atg acc cct aaa g           596
Lys Ala Ile Lys Glu Leu Thr Lys Leu Ile Met Thr Pro Lys
145                 150                 155
```

<210> SEQ ID NO 9
<211> LENGTH: 158
<212> TYPE: PRT
<213> ORGANISM: Lactobacillus reuteri

<400> SEQUENCE: 9

```
Met Tyr Tyr Ser Asn Gly Asn Tyr Glu Ala Phe Ala Arg Pro Lys Lys
 1               5                  10                  15

Pro Ala Gly Val Asp Lys Lys His Ala Tyr Ile Val Gly Gly Gly Leu
                20                  25                  30

Ala Gly Leu Ser Ala Ala Val Phe Leu Ile Arg Asp Ala Gln Met Pro
            35                  40                  45

Gly Glu Asn Ile His Ile Leu Glu Glu Leu Pro Val Ala Gly Gly Ser
        50                  55                  60

Leu Asp Gly Glu Asp Arg Pro Gly Ile Gly Phe Val Thr Arg Gly Gly
 65                 70                  75                  80

Arg Glu Met Glu Asn His Phe Glu Cys Met Trp Asp Met Tyr Arg Ser
                 85                  90                  95

Ile Pro Ser Leu Glu Ile Pro Gly Ala Ser Tyr Leu Asp Glu Tyr Tyr
            100                 105                 110

Trp Leu Asp Lys Glu Asp Pro Asn Ser Ser Asn Cys Arg Leu Thr Tyr
        115                 120                 125

Lys Arg Gly Asn Glu Val Pro Ser Asp Gly Lys Tyr Gly Leu Ser Lys
    130                 135                 140

Lys Ala Ile Lys Glu Leu Thr Lys Leu Ile Met Thr Pro Lys
145                 150                 155
```

<210> SEQ ID NO 10
<211> LENGTH: 1709
<212> TYPE: DNA
<213> ORGANISM: Lactobacillus reuteri

<400> SEQUENCE: 10

```
cggaaggcat caaatccca atgaattccc accaaactta gtgcataggg caagaagggt      60
gtcccgcgat tggtatgcat ggattggaac ccgcctttaa gattaatgcg cctgaaggaa    120
gccagctggt cgccaatccg tagcaccatt ccctgggcaa ttcggctttt atattgaccg    180
agttgtcctg tttaaccagg catcaccttg ccacgcccct ccttgacggt caagatgatt    240
```

```
tacagcatag ggtgcacttg caatcttagc gttaagattt gtttggttat tattgataat    300
aaacgcaccg gctttgttcc aggtaattga aatgccaagt tgttggcgaa cagccggagt    360
taagactgaa ttagcctgtt cctgagttgg cggtaatgtt ttttgatcg ttgtgactgg     420
ttttcttcca ataagcaatt ttactaatat ggtttaacga agcatttgtt agctgaggtt    480
gctggataac tccagtaact actaataaac cagcaagagc aaataaaagg tgatagaggc    540
gtttcttaag tttcataaat tcactccatt tctaataatt ccaaagtcta ttttactagt    600
ttgaacatac gtttggaata attatttaga attaattat aagttcattg tgtttaataa     660
aattgacact ttcaaccgct ttcactaaaa ttaaggtagt tatgatgcac ttgtttactg    720
agaagggagt cgtcaaaatg tattattcaa acgggaatta tgaagccttt gctcgaccaa    780
agaagcctgc tggcgttgat aagaaacatg cctacattgt cggtggtggt ttagctggtt    840
tatcggccgc cgtgttttta attcgtgatg cccaaatgcc gggtgagaat atccatattt    900
tagaggaatt accggttgcc ggtggttctc ttgatggtga agatcgtcct ggaattggtt    960
ttgttactcg tggaggccgg gaaatggaga accatttcga gtgtatgtgg gacatgtatc   1020
gttcaattcc atcacttgaa atcccaggtg cttcctacct tgatgaatac tactggttag   1080
ataaggaaga tccaaacagt tctaattgtc gtttaaccta taagcgggga atgaagttc    1140
catcggacgg taaatatggt ttaagtaaaa aggcaatcaa agagctgact aagctaatta   1200
tgaccctga agaaaattg ggaagggaga ctattggtga atacttctct gatgatttct     1260
ttgaaagcaa tttctggatt tattggtcaa caatgtttgc gtttgaacgg tggcactctc   1320
tagctgaaat gcgtcgttat atgatgcggt ttattcacca tattgatggt ttaccggatt   1380
tcactgcact gaagtttaat aagtataacc aatatgaatc aatgaccaag ccgctattgg   1440
cctacctgaa agatcatcat gtcaagattg agtacgatac ccaggtaaag aatgttattg   1500
ttgatactca tgggcggcaa aagcacgcta agcgaatctt attaactcaa gccggtaaag   1560
ataaagttgt tgagttaacg gacaatgacc ttgtctttgt cacaaacggt tcaattacag   1620
aaagttctac ttacggcagt caccatcaag ccagctcgac caacgcagca cttggtgggt   1680
agttggaaac tgtgggaaaa ccttgctcc                                     1709
```

<210> SEQ ID NO 11
<211> LENGTH: 324
<212> TYPE: PRT
<213> ORGANISM: Lactobacillus reuteri
<220> FEATURE:
<221> NAME/KEY: UNSURE
<222> LOCATION: (315)

<400> SEQUENCE: 11

Met Tyr Tyr Ser Asn Gly Asn Tyr Glu Ala Phe Ala Arg Pro Lys Lys
 1               5                  10                  15

Pro Ala Gly Val Asp Lys Lys His Ala Tyr Ile Val Gly Gly Gly Leu
             20                  25                  30

Ala Gly Leu Ser Ala Ala Val Phe Leu Ile Arg Asp Ala Gln Met Pro
         35                  40                  45

Gly Glu Asn Ile His Ile Leu Glu Glu Leu Pro Val Ala Gly Gly Ser
     50                  55                  60

Leu Asp Gly Glu Asp Arg Pro Gly Ile Gly Phe Val Thr Arg Gly Gly
 65                  70                  75                  80

Arg Glu Met Glu Asn His Phe Glu Cys Met Trp Asp Met Tyr Arg Ser
                 85                  90                  95

```
Ile Pro Ser Leu Glu Ile Pro Gly Ala Ser Tyr Leu Asp Glu Tyr Tyr
            100                 105                 110
Trp Leu Asp Lys Glu Asp Pro Asn Ser Ser Asn Cys Arg Leu Thr Tyr
            115                 120                 125
Lys Arg Gly Asn Glu Val Pro Ser Asp Gly Lys Tyr Gly Leu Ser Lys
130                 135                 140
Lys Ala Ile Lys Glu Leu Thr Lys Leu Ile Met Thr Pro Glu Glu Lys
145                 150                 155                 160
Leu Gly Arg Glu Thr Ile Gly Glu Tyr Phe Ser Asp Asp Phe Phe Glu
                165                 170                 175
Ser Asn Phe Trp Ile Tyr Trp Ser Thr Met Phe Ala Phe Glu Arg Trp
            180                 185                 190
His Ser Leu Ala Glu Met Arg Arg Tyr Met Met Arg Phe Ile His His
            195                 200                 205
Ile Asp Gly Leu Pro Asp Phe Thr Ala Leu Lys Phe Asn Lys Tyr Asn
210                 215                 220
Gln Tyr Glu Ser Met Thr Lys Pro Leu Leu Ala Tyr Leu Lys Asp His
225                 230                 235                 240
His Val Lys Ile Glu Tyr Asp Thr Gln Val Lys Asn Val Ile Val Asp
                245                 250                 255
Thr His Gly Arg Gln Lys His Ala Lys Arg Ile Leu Leu Thr Gln Ala
                260                 265                 270
Gly Lys Asp Lys Val Val Glu Leu Thr Asp Asn Asp Leu Val Phe Val
            275                 280                 285
Thr Asn Gly Ser Ile Thr Glu Ser Ser Thr Tyr Gly Ser His His Gln
            290                 295                 300
Ala Ser Ser Thr Asn Ala Ala Leu Gly Gly Xaa Leu Glu Thr Val Gly
305                 310                 315                 320
Lys Pro Cys Ser

<210> SEQ ID NO 12
<211> LENGTH: 17
<212> TYPE: DNA
<213> ORGANISM: Lactobacillus reuteri
<220> FEATURE:
<221> NAME/KEY: misc_feature
<222> LOCATION: (1)..(17)
<223> OTHER INFORMATION: PRIMER

<400> SEQUENCE: 12
ccaattccag gacgatc                                                17

<210> SEQ ID NO 13
<211> LENGTH: 19
<212> TYPE: DNA
<213> ORGANISM: Lactobacillus reuteri
<220> FEATURE:
<221> NAME/KEY: misc_feature
<222> LOCATION: (1)..(19)
<223> OTHER INFORMATION: PRIMER

<400> SEQUENCE: 13
acatgtatcg ttcaattcc                                              19

<210> SEQ ID NO 14
<211> LENGTH: 1165
<212> TYPE: DNA
<213> ORGANISM: Lactobacillus reuteri
```

```
<400> SEQUENCE: 14
aagcctgctg gcgttgataa gaaacatgcc tacattgtcg gtggtggttt agctggttta      60
tcggccgccg tgttttaat  tcgtgatgcc caaatgccgg gtgagaatat ccatatttta     120
gaggaattac cggttgaata attaatggta atgtttcttt ggacattcgg aacaaagaca     180
ttgtattcta gagaaccatc actagattta gcttcgatat gagcacctgc cggaacgata     240
ttattaccgt cataaatatt ggtaactcgg tagcgaactt gcttattctg atctaatgct     300
tttctcacca gaccttcgta gtaattttgc cctgttgagt tcttacttcg tgcttcattt     360
gcccaggcag tttgcgtggc aatattagat ggatttgatt cggatgcatc aaatccatga     420
atacccacca actagtgcat agggcaagaa ggtgtccgcg atcgtatgca tgattgtacc     480
cgcctttaag attatgcgcc tgaaaggaag ccagctggtc gccaatccgt agcaccattc     540
cctgggcaat tcggctttta tattgaccga gttgtcctgt taaccaggc  atcaccttgc     600
cacgcccttc cttgacggtc aagatgattt acagcatagg gtgcacttgc aatcttagcg     660
ttaagatttg tttggttatt attgataata acgcaccgg  ctttgttcca ggtaattgaa     720
atgccaagtt gttggcgaac agccggagtt aagactgaat tagcctgttc ctgagttggc     780
ggtaatgttt ttttgatcgt tgtgactggt tttcttccaa taagcaattt tactaatatg     840
gtttaacgaa gcatttgtta gctgaggttg ctggataact ccagtaacta ctaataaacc     900
agcaagagca aataaaaggt gatagaggcg tttcttaagt ttcataaatt cactccattt     960
ctaataattc caaagtctat tttactagtt tgaacatacg tttggaataa ttatttagaa    1020
ttaatttata agttcattgt gtttaataaa attgacactt caaccgctt  tcactaaaat    1080
taaggtagtt atgatgcact tgtttactga agggagtc  gtcaaaatgt attattcaaa    1140
cgggaattat gaagcctttg ctcga                                          1165

<210> SEQ ID NO 15
<211> LENGTH: 2319
<212> TYPE: DNA
<213> ORGANISM: Lactobacillus reuteri

<400> SEQUENCE: 15
ccaattccag gacgatcttc accatcaaga gaaccaccgg caaccggtcc cttaccgcta      60
tcctgatctt tctttccttc ctcaacttgc ttttgagctg cctttactag gttcatagta     120
aagaagggct tcaatactgg cttaaaatcc tttttaaagt ggtcagtaag gttttggtat     180
aagcggacat cattgtcaaa taccaatact tcttcaaatt gatttcggtg agcatcaaat     240
gaagcttcgt ctaaatctac actcccaaga atcacacggg aatcatgagt agttgaacta     300
cttaacaagt aaaacttaga atggataacc tgagtaggcg cgattgatac gcgaaaaaga     360
ttatttaaga cgttcgtttg gttgtcactg gttaacgctg agaagagttt agcagcttct     420
ttatttgctg aactaaggag agcattggta agtgcaacct ttgtcaccat ctcatcagca     480
cttaattcac tagttgattg ggagcttaac gctacattaa tactgataaa attactaagg     540
tatttattaa tgaagtcagc agtaatttc  ccagttactg cgattaactg atcgtatttt     600
tgtgaatcaa ataattgatg gatctttaat ggtggtgttt cttgaccatc aaaaacaata     660
tgaattttc  ttataccagc agtttctgtc atgaccataa tcctttacta tcaataaata     720
tattagtttt attttcgact atttaatccc tttttgcaag tggttccccg ataagctata     780
taaaaaaaga agccggaaat ttccagcttc tttcatcttt atagtaagtg ctgttgctcc     840
attaattcac caatccacgt tccttggagt ttctttaata atggcttttc aacaatcttt     900
```

-continued

```
ggaattggca agtccatgtc ttttaacggc ttcttatcat tcatgtaata cattgcccgc      960
attaactctc gaagatcata aatagagtta aagacttctg gaactcccg atcaacatct     1020
aatagagtgt agacggcttc cattgcggtc cgtactgaat attccgtggt aaatacggta    1080
tctcgacttg gagattcagc aaagttacca ataaatgcca agttagcgga tccttctgga   1140
acaacgtctg gacggtcgcc cttaactcgt ggcataaagt agctagtgat aaatggcata   1200
tatactggaa cagtattaat tgaactctcc ttagccaaat cgtcaattaa cggcttctgg   1260
aaccccaga tggatagcca ttcttagta atctcttcac cagtacaatc aacgatccgt     1320
ttcttaatat agtttccctt tgtattagag tacagaccgt aaatccaaac aatggtttca   1380
tttttctttt gtttcttgaa gtgcggttga cggtgaattg tccaggaaag catccaatta   1440
gagtcagtga ccgtaatgat tccaccagta ttaactttgc catcatggag atctcgcttg   1500
gttaagcgtt caatgtatgg ttcaacttgc gggttcttaa cggttgcagt agcggaaatg   1560
aaccagcttc tccctggaag attcttgcaa agacatcag gatgaccaaa atcagctgac    1620
tgccgagcaa ggttttccca cagtttccaa ctaccaccaa gtgctgcgtt ggtcgagctg   1680
cttgatggtg actgccgtaa gtagaacttt ctgtaattga accgtttgtg acaaagacaa   1740
ggtcattgtc cgtaactca acaactttat ctttaccggc ttgagttaat aagattcgct    1800
tagcgtgctt tgccgccca tgagtatcaa caataacatt ctttacctgg gtatcgtact    1860
caatcttgac atgatgatct ttcaggtagg ccaatagcgg cttggtcatt gattcatatt   1920
ggttatactt attaaacttc agtgcagtga atccggtaa accatcaata tggtgaataa    1980
accgcatcat ataacgacgc atttcagcta gagagtgcca ccgttcaaac gcaaacattg   2040
ttgaccaata aatccagaaa ttgctttcaa agaaatcatc agagaagtat tcaccaatag   2100
tctcccttcc caatttttct tcaggggtca taattagctt agtcagctct ttgattgcct   2160
ttttacttaa accatatta ccgtccgatg gaacttcatt tccccgctta taggttaaac    2220
gacaattaga actgtttgga tcttccttat ctaaccagta gtattcatca aggtaggaag   2280
cacctgggat ttcaagtgat ggaattgaac gatacatgt                           2319
```

<210> SEQ ID NO 16
<211> LENGTH: 3551
<212> TYPE: DNA
<213> ORGANISM: Lactobacillus reuteri

<400> SEQUENCE: 16

```
accggttgaa taattaatgg taatgtttct ttggacattc ggaacaaaga cattgtattc     60
tagagaacca tcactagatt tagcttcgat atgagcacct gccggaacga tattattacc   120
gtcataaata ttggtaactc ggtagcgaac ttgcttattc tgatctaatg cttttctcac   180
cagaccttcg tagtaatttt gccctgttga gttcttactt cgtgcttcat ttgcccaggc   240
agtttgcgtg gcaatattag atggatttga ttcggatgca tcaaatccat gaataccacc   300
aactagtgca taggcaagaa ggtgtccgcg atcgtatgca tgattgtacc cgcctttaag   360
attatgcgcc tgaaaggaag ccagctggtc gccaatccgt agcaccattc cctgtggcaa   420
atttcggctt ttatattgac cgagttgtcc tgtttaacca ggcatcacct tgccacgccc   480
ttccttgacg gtcaagatga tttacagcat agggtgcact tgcaatctta gcgttaagat   540
ttgtttggtt attattgata ataaacgcac cggcttgtt ccaggtaatt gaatgccaa     600
gttgttggcg aacagccgga gttaagactg aattagcctg ttcctgagtt ggcggtaatg   660
```

| | |
|---|---|
| ttttttttgat cgttgtgact ggttttcttc caataagcaa ttttactaat atggtttaac | 720 |
| gaagcatttg ttagctgagg ttgctggata actccagtaa ctactaataa accagcaaga | 780 |
| gcaaataaaa ggtgatagag gcgtttctta agtttcataa attcactcca tttctaataa | 840 |
| ttccaaagtc tattttacta gtttgaacat acgtttggaa taattattta gaattaattt | 900 |
| ataagttcat tgtgtttaat aaaattgaca ctttcaaccg ctttcactaa aattaaggta | 960 |
| gttatgatgc acttgtttac tgagaaggga gtcgtcaaaa tgtattattc aaacgggaat | 1020 |
| tatgaagcct ttgctcgacc aaagaagcct gctggcgttg ataagaaaca tgcctacatt | 1080 |
| gtcggtggtg gtttagctgg tttatcggcc gccgtgtttt taattcgtga tgcccaaatg | 1140 |
| ccgggtgaga atatccatat tttagaggaa ttaccggttg ccgtggttc tcttgatggt | 1200 |
| gaagatcgtc ctggaattgg ttttgttact cgtggaggcc gggaaatgga gaaccatttc | 1260 |
| gagtgtatgt gggacatgta tcgttcaatt ccatcacttg aaatcccagg tgcttcctac | 1320 |
| cttgatgaat actactggtt agataaggaa gatccaaaca gttctaattg tcgtttaacc | 1380 |
| tataagcggg gaaatgaagt tccatcggac ggtaaatatg gtttaagtaa aaaggcaatc | 1440 |
| aaagagctga ctaagctaat tatgaccect gaagaaaaat tgggaaggga gactattggt | 1500 |
| gaatacttct ctgatgattt ctttgaaagc aatttctgga tttattggtc aacaatgttt | 1560 |
| gcgtttgaac ggtggcactc tctagctgaa atgcgtcgtt atatgatgcg gtttattcac | 1620 |
| catattgatg gttaccggaa tttcactgca ctgaagttta ataagtataa ccaatatgaa | 1680 |
| tcaatgacca agccgctatt ggcctacctg aaagatcatc atgtcaagat tgagtacgat | 1740 |
| acccaggtaa agaatgttat tgttgatact catgggcggc aaaagcacgc taagcgaatc | 1800 |
| ttattaactc aagccggtaa agataaagtt gttgagttaa cggacaatga ccttgtcttt | 1860 |
| gtcacaaacg gttcaattac agaaagttct acttacggca gtcaccatca agcagctcga | 1920 |
| ccaacgcaag cacttggtgg tagttggaaa ctgtgggaaa accttgctcg gcagtcagct | 1980 |
| gattttggtc atcctgatgt cttttgcaag aatcttccag ggagaagctg gttcatttcc | 2040 |
| gctactgcaa ccgttaagaa cccgcaagtt gaaccataca ttgaacgctt aaccaagcga | 2100 |
| gatctccatg atggcaaagt taatactggt ggaatcatta cggtcactga ctctaattgg | 2160 |
| atgctttcct ggacaattca ccgtcaaccg cacttcaaga aacaaaagaa aaatgaaacc | 2220 |
| attgtttgga tttacggtct gtactctaat acaaagggaa actatattaa gaaacggatc | 2280 |
| gttgattgta ctggtgaaga gattactaaa gaatggctat ccatctgggg gttccagaag | 2340 |
| ccgttaattg acgatttggc taaggagagt tcaattaata ctgttccagt atatatgcca | 2400 |
| tttatcacta gctactttat gccacgagtt aagggcgacc gtccagacgt tgttccagaa | 2460 |
| ggatccgcta acttggcatt tattggtaac tttgctgaat ctccaagtcg agataccgta | 2520 |
| tttaccacgg aatattcagt acggaccgca atggaagccg tctacactct attagatgtt | 2580 |
| gatcggggag ttccagaagt ctttaactct atttatgatc ttcgagagtt aatgcgggca | 2640 |
| atgtattaca tgaatgataa gaagccgtta aaagacatgg acttgccaat tccaaagatt | 2700 |
| gttgaaaagc cattattaaa gaaactccaa ggaacgtgga ttggtgaatt aatggagcaa | 2760 |
| cagcacttac tataaagatg aaagaagctg gaaatttccg gcttctttt ttatatagct | 2820 |
| tatcggggaa ccacttgcaa aaagggatta aatagtcgaa aataaaacta atatatttat | 2880 |
| tgatagtaaa ggattatggt catgacagaa actgctggta taagaaaaat tcatattgtt | 2940 |
| tttgatggtc aagaaacacc accattaaag atccatcaat tatttgattc acaaaaatac | 3000 |
| gatcagttaa tcgcagtaac tgggaaaatt actgctgact tcattaataa ataccttagt | 3060 |

-continued

```
aattttatca gtattaatgt agcgttaagc tcccaatcaa ctagtgaatt aagtgctgat    3120
gagatggtga caaggttgc acttaccaat gctctcctta gttcagcaaa taaagaagct    3180
gctaaactct tctcagcgtt aaccagtgac aaccaaacga acgtcttaaa taatcttttt    3240
cgcgtatcaa tcgcgcctac tcaggttatc cattctaagt tttacttgtt aagtagttca    3300
actactcatg attcccgtgt gattcttggg agtgtagatt tagacgaagc ttcatttgat    3360
gctcaccgaa atcaatttga agaagtattg gtatttgaca atgatgtccg cttataccaa    3420
aaccttactg accactttaa aaaggatttt aagccagtat tgaagccctt ctttactatg    3480
aacctagtaa aggcagctca aaagcaagtt gaggaaggaa agaaagatca ggatagcggt    3540
aagggaccgg t                                                         3551
```

<210> SEQ ID NO 17
<211> LENGTH: 1776
<212> TYPE: DNA
<213> ORGANISM: Lactobacillus reuteri
<220> FEATURE:
<221> NAME/KEY: CDS
<222> LOCATION: (1)..(1776)

<400> SEQUENCE: 17

```
atg tat tat tca aac ggg aat tat gaa gcc ttt gct cga cca aag aag      48
Met Tyr Tyr Ser Asn Gly Asn Tyr Glu Ala Phe Ala Arg Pro Lys Lys
 1               5                  10                  15 cct gct ggc gtt gat aag aaa cat gcc tac att gtc ggt ggt gtt tta     96
Pro Ala Gly Val Asp Lys Lys His Ala Tyr Ile Val Gly Gly Gly Leu
             20                  25                  30 gct ggt tta tcg gcc gcc gtg ttt tta att cgt gat gcc caa atg ccg    144
Ala Gly Leu Ser Ala Ala Val Phe Leu Ile Arg Asp Ala Gln Met Pro
         35                  40                  45 ggt gag aat atc cat att tta gag gaa tta ccg gtt gcc ggt ggt tct    192
Gly Glu Asn Ile His Ile Leu Glu Glu Leu Pro Val Ala Gly Gly Ser
     50                  55                  60 ctt gat ggt gaa gat cgt cct gga att ggt ttt gtt act cgt gga ggc    240
Leu Asp Gly Glu Asp Arg Pro Gly Ile Gly Phe Val Thr Arg Gly Gly
 65                  70                  75                  80 cgg gaa atg gag aac cat ttc gag tgt atg tgg gac atg tat cgt tca    288
Arg Glu Met Glu Asn His Phe Glu Cys Met Trp Asp Met Tyr Arg Ser
                 85                  90                  95 att cca tca ctt gaa atc cca ggt gct tcc tac ctt gat gaa tac tac    336
Ile Pro Ser Leu Glu Ile Pro Gly Ala Ser Tyr Leu Asp Glu Tyr Tyr
            100                 105                 110 tgg tta gat aag gaa gat cca aac agt tct aat tgt cgt tta acc tat    384
Trp Leu Asp Lys Glu Asp Pro Asn Ser Ser Asn Cys Arg Leu Thr Tyr
        115                 120                 125 aag cgg gga aat gaa gtt cca tcg gac ggt aaa tat ggt tta agt aaa    432
Lys Arg Gly Asn Glu Val Pro Ser Asp Gly Lys Tyr Gly Leu Ser Lys
    130                 135                 140 aag gca atc aaa gag ctg act aag cta att atg acc cct gaa gaa aaa    480
Lys Ala Ile Lys Glu Leu Thr Lys Leu Ile Met Thr Pro Glu Glu Lys
145                 150                 155                 160 ttg gga agg gag act att ggt gaa tac ttc tct gat gat ttc ttt gaa    528
Leu Gly Arg Glu Thr Ile Gly Glu Tyr Phe Ser Asp Asp Phe Phe Glu
                165                 170                 175 agc aat ttc tgg att tat tgg tca aca atg ttt gcg ttt gaa cgg tgg    576
Ser Asn Phe Trp Ile Tyr Trp Ser Thr Met Phe Ala Phe Glu Arg Trp
            180                 185                 190 cac tct cta gct gaa atg cgt cgt tat atg atg cgg ttt att cac cat    624
```

```
His Ser Leu Ala Glu Met Arg Arg Tyr Met Met Arg Phe Ile His His
            195                 200                 205 att gat ggt tta ccg gat ttc act gca ctg aag ttt aat aag tat aac      672
Ile Asp Gly Leu Pro Asp Phe Thr Ala Leu Lys Phe Asn Lys Tyr Asn
        210                 215                 220 caa tat gaa tca atg acc aag ccg cta ttg gcc tac ctg aaa gat cat      720
Gln Tyr Glu Ser Met Thr Lys Pro Leu Leu Ala Tyr Leu Lys Asp His
225                 230                 235                 240 cat gtc aag att gag tac gat acc cag gta aag aat gtt att gtt gat      768
His Val Lys Ile Glu Tyr Asp Thr Gln Val Lys Asn Val Ile Val Asp
                245                 250                 255 act cat ggg cgg caa aag cac gct aag cga atc tta tta act caa gcc      816
Thr His Gly Arg Gln Lys His Ala Lys Arg Ile Leu Leu Thr Gln Ala
            260                 265                 270 ggt aaa gat aaa gtt gtt gag tta acg gac aat gac ctt gtc ttt gtc      864
Gly Lys Asp Lys Val Val Glu Leu Thr Asp Asn Asp Leu Val Phe Val
        275                 280                 285 aca aac ggt tca att aca gaa agt tct act tac ggc agt cac cat caa      912
Thr Asn Gly Ser Ile Thr Glu Ser Ser Thr Tyr Gly Ser His His Gln
290                 295                 300 gca gct cga cca acg caa gca ctt ggt ggt agt tgg aaa ctg tgg gaa      960
Ala Ala Arg Pro Thr Gln Ala Leu Gly Gly Ser Trp Lys Leu Trp Glu
305                 310                 315                 320 aac ctt gct cgg cag tca gct gat ttt ggt cat cct gat gtc ttt tgc     1008
Asn Leu Ala Arg Gln Ser Ala Asp Phe Gly His Pro Asp Val Phe Cys
                325                 330                 335 aag aat ctt cca ggg aga agc tgg ttc att tcc gct act gca acc gtt     1056
Lys Asn Leu Pro Gly Arg Ser Trp Phe Ile Ser Ala Thr Ala Thr Val
            340                 345                 350 aag aac ccg caa gtt gaa cca tac att gaa cgc tta acc aag cga gat     1104
Lys Asn Pro Gln Val Glu Pro Tyr Ile Glu Arg Leu Thr Lys Arg Asp
        355                 360                 365 ctc cat gat ggc aaa gtt aat act ggt gga atc att acg gtc act gac     1152
Leu His Asp Gly Lys Val Asn Thr Gly Gly Ile Ile Thr Val Thr Asp
370                 375                 380 tct aat tgg atg ctt tcc tgg aca att cac cgt caa ccg cac ttc aag     1200
Ser Asn Trp Met Leu Ser Trp Thr Ile His Arg Gln Pro His Phe Lys
385                 390                 395                 400 aaa caa aag aaa aat gaa acc att gtt tgg att tac ggt ctg tac tct     1248
Lys Gln Lys Lys Asn Glu Thr Ile Val Trp Ile Tyr Gly Leu Tyr Ser
                405                 410                 415 aat aca aag gga aac tat att aag aaa cgg atc gtt gat tgt act ggt     1296
Asn Thr Lys Gly Asn Tyr Ile Lys Lys Arg Ile Val Asp Cys Thr Gly
            420                 425                 430 gaa gag att act aaa gaa tgg cta tcc atc tgg ggg ttc cag aag ccg     1344
Glu Glu Ile Thr Lys Glu Trp Leu Ser Ile Trp Gly Phe Gln Lys Pro
        435                 440                 445 tta att gac gat ttg gct aag gag agt tca att aat act gtt cca gta     1392
Leu Ile Asp Asp Leu Ala Lys Glu Ser Ser Ile Asn Thr Val Pro Val
450                 455                 460 tat atg cca ttt atc act agc tac ttt atg cca cga gtt aag ggc gac     1440
Tyr Met Pro Phe Ile Thr Ser Tyr Phe Met Pro Arg Val Lys Gly Asp
465                 470                 475                 480 cgt cca gac gtt gtt cca gaa gga tcc gct aac ttg gca ttt att ggt     1488
Arg Pro Asp Val Val Pro Glu Gly Ser Ala Asn Leu Ala Phe Ile Gly
                485                 490                 495 aac ttt gct gaa tct cca agt cga gat acc gta ttt acc acg gaa tat     1536
Asn Phe Ala Glu Ser Pro Ser Arg Asp Thr Val Phe Thr Thr Glu Tyr
            500                 505                 510
```

```
tca gta cgg acc gca atg gaa gcc gtc tac act cta tta gat gtt gat       1584
Ser Val Arg Thr Ala Met Glu Ala Val Tyr Thr Leu Leu Asp Val Asp
        515                 520                 525 cgg gga gtt cca gaa gtc ttt aac tct att tat gat ctt cga gag tta       1632
Arg Gly Val Pro Glu Val Phe Asn Ser Ile Tyr Asp Leu Arg Glu Leu
530                 535                 540 atg cgg gca atg tat tac atg aat gat aag aag ccg tta aaa gac atg       1680
Met Arg Ala Met Tyr Tyr Met Asn Asp Lys Lys Pro Leu Lys Asp Met
545                 550                 555                 560 gac ttg cca att cca aag att gtt gaa aag cca tta tta aag aaa ctc       1728
Asp Leu Pro Ile Pro Lys Ile Val Glu Lys Pro Leu Leu Lys Lys Leu
                565                 570                 575 caa gga acg tgg att ggt gaa tta atg gag caa cag cac tta cta taa       1776
Gln Gly Thr Trp Ile Gly Glu Leu Met Glu Gln Gln His Leu Leu
            580                 585                 590

<210> SEQ ID NO 18
<211> LENGTH: 591
<212> TYPE: PRT
<213> ORGANISM: Lactobacillus reuteri

<400> SEQUENCE: 18

Met Tyr Tyr Ser Asn Gly Asn Tyr Glu Ala Phe Ala Arg Pro Lys Lys
  1               5                  10                  15

Pro Ala Gly Val Asp Lys Lys His Ala Tyr Ile Val Gly Gly Gly Leu
             20                  25                  30

Ala Gly Leu Ser Ala Ala Val Phe Leu Ile Arg Asp Ala Gln Met Pro
         35                  40                  45

Gly Glu Asn Ile His Ile Leu Glu Glu Leu Pro Val Ala Gly Gly Ser
     50                  55                  60

Leu Asp Gly Glu Asp Arg Pro Gly Ile Gly Phe Val Thr Arg Gly Gly
 65                  70                  75                  80

Arg Glu Met Glu Asn His Phe Glu Cys Met Trp Asp Met Tyr Arg Ser
                 85                  90                  95

Ile Pro Ser Leu Glu Ile Pro Gly Ala Ser Tyr Leu Asp Glu Tyr Tyr
            100                 105                 110

Trp Leu Asp Lys Glu Asp Pro Asn Ser Ser Asn Cys Arg Leu Thr Tyr
        115                 120                 125

Lys Arg Gly Asn Glu Val Pro Ser Asp Gly Lys Tyr Gly Leu Ser Lys
    130                 135                 140

Lys Ala Ile Lys Glu Leu Thr Lys Leu Ile Met Thr Pro Glu Glu Lys
145                 150                 155                 160

Leu Gly Arg Glu Thr Ile Gly Glu Tyr Phe Ser Asp Asp Phe Phe Glu
                165                 170                 175

Ser Asn Phe Trp Ile Tyr Trp Ser Thr Met Phe Ala Phe Glu Arg Trp
            180                 185                 190

His Ser Leu Ala Glu Met Arg Arg Tyr Met Met Arg Phe Ile His His
        195                 200                 205

Ile Asp Gly Leu Pro Asp Phe Thr Ala Leu Lys Phe Asn Lys Tyr Asn
    210                 215                 220

Gln Tyr Glu Ser Met Thr Lys Pro Leu Leu Ala Tyr Leu Lys Asp His
225                 230                 235                 240

His Val Lys Ile Glu Tyr Asp Thr Gln Val Lys Asn Val Ile Val Asp
                245                 250                 255

Thr His Gly Arg Gln Lys His Ala Lys Arg Ile Leu Leu Thr Gln Ala
            260                 265                 270
```

```
Gly Lys Asp Lys Val Val Glu Leu Thr Asp Asn Asp Leu Val Phe Val
            275                 280                 285

Thr Asn Gly Ser Ile Thr Glu Ser Ser Thr Tyr Gly Ser His His Gln
        290                 295                 300

Ala Ala Arg Pro Thr Gln Ala Leu Gly Gly Ser Trp Lys Leu Trp Glu
305                 310                 315                 320

Asn Leu Ala Arg Gln Ser Ala Asp Phe Gly His Pro Asp Val Phe Cys
                325                 330                 335

Lys Asn Leu Pro Gly Arg Ser Trp Phe Ile Ser Ala Thr Ala Thr Val
            340                 345                 350

Lys Asn Pro Gln Val Glu Pro Tyr Ile Glu Arg Leu Thr Lys Arg Asp
        355                 360                 365

Leu His Asp Gly Lys Val Asn Thr Gly Gly Ile Ile Thr Val Thr Asp
    370                 375                 380

Ser Asn Trp Met Leu Ser Trp Thr Ile His Arg Gln Pro His Phe Lys
385                 390                 395                 400

Lys Gln Lys Lys Asn Glu Thr Ile Val Trp Ile Tyr Gly Leu Tyr Ser
                405                 410                 415

Asn Thr Lys Gly Asn Tyr Ile Lys Lys Arg Ile Val Asp Cys Thr Gly
            420                 425                 430

Glu Glu Ile Thr Lys Glu Trp Leu Ser Ile Trp Gly Phe Gln Lys Pro
        435                 440                 445

Leu Ile Asp Asp Leu Ala Lys Glu Ser Ser Ile Asn Thr Val Pro Val
    450                 455                 460

Tyr Met Pro Phe Ile Thr Ser Tyr Phe Met Pro Arg Val Lys Gly Asp
465                 470                 475                 480

Arg Pro Asp Val Val Pro Glu Gly Ser Ala Asn Leu Ala Phe Ile Gly
                485                 490                 495

Asn Phe Ala Glu Ser Pro Ser Arg Asp Thr Val Phe Thr Thr Glu Tyr
            500                 505                 510

Ser Val Arg Thr Ala Met Glu Ala Val Tyr Thr Leu Leu Asp Val Asp
        515                 520                 525

Arg Gly Val Pro Glu Val Phe Asn Ser Ile Tyr Asp Leu Arg Glu Leu
    530                 535                 540

Met Arg Ala Met Tyr Tyr Met Asn Asp Lys Lys Pro Leu Lys Asp Met
545                 550                 555                 560

Asp Leu Pro Ile Pro Lys Ile Val Glu Lys Pro Leu Leu Lys Lys Leu
                565                 570                 575

Gln Gly Thr Trp Ile Gly Glu Leu Met Glu Gln Gln His Leu Leu
            580                 585                 590

<210> SEQ ID NO 19
<211> LENGTH: 656
<212> TYPE: DNA
<213> ORGANISM: Lactobacillus reuteri
<220> FEATURE:
<221> NAME/KEY: CDS
<222> LOCATION: (1)..(654)

<400> SEQUENCE: 19 atg gtc atg aca gaa act gct ggt ata aga aaa att cat att gtt ttt    48
Met Val Met Thr Glu Thr Ala Gly Ile Arg Lys Ile His Ile Val Phe
  1               5                  10                  15 gat ggt caa gaa aca cca cca tta aag atc cat caa tta ttt gat tca    96
Asp Gly Gln Glu Thr Pro Pro Leu Lys Ile His Gln Leu Phe Asp Ser
             20                  25                  30
```

```
caa aaa tac gat cag tta atc gca gta act ggg aaa att act gct gac        144
Gln Lys Tyr Asp Gln Leu Ile Ala Val Thr Gly Lys Ile Thr Ala Asp
         35                  40                  45 ttc att aat aaa tac ctt agt aat ttt atc agt att aat gta gcg tta        192
Phe Ile Asn Lys Tyr Leu Ser Asn Phe Ile Ser Ile Asn Val Ala Leu
 50                  55                  60 agc tcc caa tca act agt gaa tta agt gct gat gag atg gtg aca aag        240
Ser Ser Gln Ser Thr Ser Glu Leu Ser Ala Asp Glu Met Val Thr Lys
 65                  70                  75                  80 gtt gca ctt acc aat gct ctc ctt agt tca gca aat aaa gaa gct gct        288
Val Ala Leu Thr Asn Ala Leu Leu Ser Ser Ala Asn Lys Glu Ala Ala
                 85                  90                  95 aaa ctc ttc tca gcg tta acc agt gac aac caa acg aac gtc tta aat        336
Lys Leu Phe Ser Ala Leu Thr Ser Asp Asn Gln Thr Asn Val Leu Asn
             100                 105                 110 aat ctt ttt cgc gta tca atc gcg cct act cag gtt atc cat tct aag        384
Asn Leu Phe Arg Val Ser Ile Ala Pro Thr Gln Val Ile His Ser Lys
         115                 120                 125 ttt tac ttg tta agt agt tca act act cat gat tcc cgt gtg att ctt        432
Phe Tyr Leu Leu Ser Ser Ser Thr Thr His Asp Ser Arg Val Ile Leu
130                 135                 140 ggg agt gta gat tta gac gaa gct tca ttt gat gct cac cga aat caa        480
Gly Ser Val Asp Leu Asp Glu Ala Ser Phe Asp Ala His Arg Asn Gln
145                 150                 155                 160 ttt gaa gaa gta ttg gta ttt gac aat gat gtc cgc tta tac caa aac        528
Phe Glu Glu Val Leu Val Phe Asp Asn Asp Val Arg Leu Tyr Gln Asn
                165                 170                 175 ctt act gac cac ttt aaa aag gat ttt aag cca gta ttg aag ccc ttc        576
Leu Thr Asp His Phe Lys Lys Asp Phe Lys Pro Val Leu Lys Pro Phe
            180                 185                 190 ttt act atg aac cta gta aag gca gct caa aag caa gtt gag gaa gga        624
Phe Thr Met Asn Leu Val Lys Ala Ala Gln Lys Gln Val Glu Glu Gly
        195                 200                 205 aag aaa gat cag gat agc ggt aag gga ccg gt                             656
Lys Lys Asp Gln Asp Ser Gly Lys Gly Pro
    210                 215

<210> SEQ ID NO 20
<211> LENGTH: 218
<212> TYPE: PRT
<213> ORGANISM: Lactobacillus reuteri

<400> SEQUENCE: 20

Met Val Met Thr Glu Thr Ala Gly Ile Arg Lys Ile His Ile Val Phe
 1               5                  10                  15

Asp Gly Gln Glu Thr Pro Pro Leu Lys Ile His Gln Leu Phe Asp Ser
                 20                  25                  30

Gln Lys Tyr Asp Gln Leu Ile Ala Val Thr Gly Lys Ile Thr Ala Asp
         35                  40                  45

Phe Ile Asn Lys Tyr Leu Ser Asn Phe Ile Ser Ile Asn Val Ala Leu
 50                  55                  60

Ser Ser Gln Ser Thr Ser Glu Leu Ser Ala Asp Glu Met Val Thr Lys
 65                  70                  75                  80

Val Ala Leu Thr Asn Ala Leu Leu Ser Ser Ala Asn Lys Glu Ala Ala
                 85                  90                  95

Lys Leu Phe Ser Ala Leu Thr Ser Asp Asn Gln Thr Asn Val Leu Asn
            100                 105                 110

Asn Leu Phe Arg Val Ser Ile Ala Pro Thr Gln Val Ile His Ser Lys
         115                 120                 125
```

```
Phe Tyr Leu Leu Ser Ser Thr Thr His Asp Ser Arg Val Ile Leu
    130                 135                 140

Gly Ser Val Asp Leu Asp Glu Ala Ser Phe Asp Ala His Arg Asn Gln
145                 150                 155                 160

Phe Glu Glu Val Leu Val Phe Asp Asn Asp Val Arg Leu Tyr Gln Asn
                165                 170                 175

Leu Thr Asp His Phe Lys Lys Asp Phe Lys Pro Val Leu Lys Pro Phe
            180                 185                 190

Phe Thr Met Asn Leu Val Lys Ala Ala Gln Lys Gln Val Glu Glu Gly
        195                 200                 205

Lys Lys Asp Gln Asp Ser Gly Lys Gly Pro
    210                 215
```

<210> SEQ ID NO 21
<211> LENGTH: 726
<212> TYPE: DNA
<213> ORGANISM: Lactobacillus reuteri
<220> FEATURE:
<221> NAME/KEY: CDS
<222> LOCATION: (1)..(726)
<220> FEATURE:
<221> NAME/KEY: unsure
<222> LOCATION: (12)
<220> FEATURE:
<221> NAME/KEY: unsure
<222> LOCATION: (297)
<220> FEATURE:
<221> NAME/KEY: misc_feature
<222> LOCATION: (10)..(12)
<223> OTHER INFORMATION: Xaa = Tyr or stop
<220> FEATURE:
<221> NAME/KEY: misc_feature
<222> LOCATION: (295)..(297)
<223> OTHER INFORMATION: Xaa = Tyr or stop

<400> SEQUENCE: 21

```
atg ctt cgt tan acc ata tta gta aaa ttg ctt att gga aga aaa cca        48
Met Leu Arg Xaa Thr Ile Leu Val Lys Leu Leu Ile Gly Arg Lys Pro
  1               5                  10                  15 gtc aca acg atc aaa aaa aca tta ccg cca act cag gaa cag gct aat        96
Val Thr Thr Ile Lys Lys Thr Leu Pro Pro Thr Gln Glu Gln Ala Asn
             20                  25                  30 tca gtc tta act ccg gct gtt cgc caa caa ctt ggc att tca att acc       144
Ser Val Leu Thr Pro Ala Val Arg Gln Gln Leu Gly Ile Ser Ile Thr
         35                  40                  45 tgg aac aaa gcc ggt gcg ttt att atc aat aat aac caa aca aat ctt       192
Trp Asn Lys Ala Gly Ala Phe Ile Ile Asn Asn Asn Gln Thr Asn Leu
     50                  55                  60 aac gct aag att gca agt gca ccc tat gct gta aat cat ctt gac cgt       240
Asn Ala Lys Ile Ala Ser Ala Pro Tyr Ala Val Asn His Leu Asp Arg
 65                  70                  75                  80 caa gga agg gcg tgg caa ggt gat gcc tgg tta aac agg aca act cgg       288
Gln Gly Arg Ala Trp Gln Gly Asp Ala Trp Leu Asn Arg Thr Thr Arg
                 85                  90                  95 tca ata tan aag ccg aaa ttt gcc aca ggg aat ggt gct acg gat tgg       336
Ser Ile Xaa Lys Pro Lys Phe Ala Thr Gly Asn Gly Ala Thr Asp Trp
            100                 105                 110 cga cca gct ggc ttc ctt cag gcg cat aat ctt aaa ggc ggg tac aat       384
Arg Pro Ala Gly Phe Leu Gln Ala His Asn Leu Lys Gly Gly Tyr Asn
        115                 120                 125 cat gca tac gat cgc gga cac ctt ctt gcc tat gca cta gtt ggt ggt       432
His Ala Tyr Asp Arg Gly His Leu Leu Ala Tyr Ala Leu Val Gly Gly
    130                 135                 140
```

-continued

```
att cat gga ttt gat gca tcc gaa tca aat cca tct aat att gcc acg    480
Ile His Gly Phe Asp Ala Ser Glu Ser Asn Pro Ser Asn Ile Ala Thr
145                 150                 155                 160 caa act gcc tgg gca aat gaa gca cga agt aag aac tca aca ggg caa    528
Gln Thr Ala Trp Ala Asn Glu Ala Arg Ser Lys Asn Ser Thr Gly Gln
                165                 170                 175 aat tac tac gaa ggt ctg gtg aga aaa gca tta gat cag aat aag caa    576
Asn Tyr Tyr Glu Gly Leu Val Arg Lys Ala Leu Asp Gln Asn Lys Gln
            180                 185                 190 gtt cgc tac cga gtt acc aat att tat gac ggt aat aat atc gtt ccg    624
Val Arg Tyr Arg Val Thr Asn Ile Tyr Asp Gly Asn Asn Ile Val Pro
        195                 200                 205 gca ggt gct cat atc gaa gct aaa tct agt gat ggt tct cta gaa tac    672
Ala Gly Ala His Ile Glu Ala Lys Ser Ser Asp Gly Ser Leu Glu Tyr
    210                 215                 220 aat gtc ttt gtt ccg aat gtc caa aga aac att acc att aat tat tca    720
Asn Val Phe Val Pro Asn Val Gln Arg Asn Ile Thr Ile Asn Tyr Ser
225                 230                 235                 240 acc ggt                                                             726
Thr Gly
```

<210> SEQ ID NO 22
<211> LENGTH: 242
<212> TYPE: PRT
<213> ORGANISM: Lactobacillus reuteri
<220> FEATURE:
<221> NAME/KEY: misc_feature
<222> LOCATION: 4
<223> OTHER INFORMATION: Xaa = Tyr or stop
<220> FEATURE:
<221> NAME/KEY: misc_feature
<222> LOCATION: 99
<223> OTHER INFORMATION: Xaa = Tyr or stop

<400> SEQUENCE: 22

```
Met Leu Arg Xaa Thr Ile Leu Val Lys Leu Leu Ile Gly Arg Lys Pro
1               5                   10                  15

Val Thr Thr Ile Lys Lys Thr Leu Pro Pro Thr Gln Glu Gln Ala Asn
            20                  25                  30

Ser Val Leu Thr Pro Ala Val Arg Gln Gln Leu Gly Ile Ser Ile Thr
        35                  40                  45

Trp Asn Lys Ala Gly Ala Phe Ile Ile Asn Asn Asn Gln Thr Asn Leu
    50                  55                  60

Asn Ala Lys Ile Ala Ser Ala Pro Tyr Ala Val Asn His Leu Asp Arg
65                  70                  75                  80

Gln Gly Arg Ala Trp Gln Gly Asp Ala Trp Leu Asn Arg Thr Arg
                85                  90                  95

Ser Ile Xaa Lys Pro Lys Phe Ala Thr Gly Asn Gly Ala Thr Asp Trp
            100                 105                 110

Arg Pro Ala Gly Phe Leu Gln Ala His Asn Leu Lys Gly Gly Tyr Asn
        115                 120                 125

His Ala Tyr Asp Arg Gly His Leu Leu Ala Tyr Ala Leu Val Gly Gly
    130                 135                 140

Ile His Gly Phe Asp Ala Ser Glu Ser Asn Pro Ser Asn Ile Ala Thr
145                 150                 155                 160

Gln Thr Ala Trp Ala Asn Glu Ala Arg Ser Lys Asn Ser Thr Gly Gln
                165                 170                 175

Asn Tyr Tyr Glu Gly Leu Val Arg Lys Ala Leu Asp Gln Asn Lys Gln
            180                 185                 190
```

```
Val Arg Tyr Arg Val Thr Asn Ile Tyr Asp Gly Asn Asn Ile Val Pro
        195                 200                 205

Ala Gly Ala His Ile Glu Ala Lys Ser Ser Asp Gly Ser Leu Glu Tyr
    210                 215                 220

Asn Val Phe Val Pro Asn Val Gln Arg Asn Ile Thr Ile Asn Tyr Ser
225                 230                 235                 240

Thr Gly

<210> SEQ ID NO 23
<211> LENGTH: 18
<212> TYPE: DNA
<213> ORGANISM: Lactobacillus reuteri
<220> FEATURE:
<221> NAME/KEY: misc_feature
<222> LOCATION: (1)..(18)
<223> OTHER INFORMATION: PRIMER

<400> SEQUENCE: 23
aatctagtga tggttctc                                              18

<210> SEQ ID NO 24
<211> LENGTH: 18
<212> TYPE: DNA
<213> ORGANISM: Lactobacillus reuteri
<220> FEATURE:
<221> NAME/KEY: misc_feature
<222> LOCATION: (1)..(18)
<223> OTHER INFORMATION: PRIMER

<400> SEQUENCE: 24
caagttgagg aaggaaag                                              18

<210> SEQ ID NO 25
<211> LENGTH: 3684
<212> TYPE: DNA
<213> ORGANISM: Lactobacillus reuteri

<400> SEQUENCE: 25
caagttgagg aaggaaagaa agatcaggat agcggtaagg gaccggttat ccttgataat    60
gaaacaacag ataagatcgc tgaaacagac atggtggatc tgttgaagca tgaccttcag   120
catgatattg accataatct tgttcctgaa atgatcacaa agtcaatgcg tgatattacc   180
ataaatcgtt ctcaagcaaa ggagaaaatt gctaagcagg ttaagcaaca tgatacgatt   240
tatactttgc aaaaagaagc ggtctctcct cgggcagcta agccaaaact aaagactcga   300
gaaaaaatta ccaagcaggt tcaggatgct ttgatcagtg aatgtcacc acagcaacgg   360 gatgctgaga aaagtacac gacttttctg tacgatcggc caatggaacg aaacattgcg   420
aataacaata gtggcctata cgttcctaat gatacgggaa ctcacccaat cccatttggt   480
aaaattgcaa ctatttctga aattcgtgac ggtttaaaga gcattgatgc tgttatgaag   540
ggctatcagc agtttgtcgt tgattatgat gctgactacg ggaagcggtt ctttgaagca   600
attttgtata gttttactgc accgttttta tgggaaattc gttctaaagc tagcctgaac   660
cctgaagatg ggaatgatgt tcctaatttc ctaatcctag gggcaacggc tggttccgga   720
aagtctaccc ttcttcggat tattaatcag ctcacgtgga cactgatcg ctcgttgatt   780 gactttggaa cgatctaccc gtcgcaaaact cctcaaaaga aggcaaagac tgttgaggcg   840
atggaacatt atatgaaact tggtagttca tacccggttt tgttagatga aattgaaccg   900
tacttcttcc agcaagatca atatagtcga ctggagttct ggtttgctat gattaaggtt   960
```

```
gttacgatta ttgcaatgat tattcttggt ttactggtta tcgttcttgg gttaggtaat  1020
aactggcacc cagttgggat ttctaatttg tggtctcatg gcggattctt taccggtggc  1080
tttatgggct ttatgttctc gctatctgtg attgctggtc cttatcaggg aattgagtta  1140
ttgggaatca ctgctggtga agctgaatca ccacgtcatg cgattgtgaa atcagttaag  1200
tccgttatct ggcggatctt aatcttctat attggtgcaa ttttcgtcat tgtttctatt  1260
tacccatgga acgaattgaa gtccgttggc tcaccattcg ttgaaaccttc acgaaggtt  1320
ggaattactg gagcagccgg aatcattaac tttgttgttt tgacggcagc tctttctgga  1380
gctaactctg gaatttacag tgctagtcgg atgttgttca agctttctgt tgatggggaa  1440
gtaccaaagt tctttagtaa gctttccaag cgcgttgttc ctaatgttgc aatcctcacg  1500
atttcttcct ggatcttcct tggctttgta attaatgaat taatgtcgat ttttagttct  1560
gctgctcaaa atattttcgt cattgtatat agttccagtg ttcttccagg atggtacca   1620
tggtttatca ttctcttgtc agaacttcac ttcagaaaag aacaccctga acagcttaaa  1680
gatcatccat tcaagatgcc gctttacccg gcttataact actttagttt gattgccttg  1740
actgtgatct tgatcttcat gttctttaac ccagatactc gagtttcagt atcagttggt  1800
gttatcttct tgattatcat gagtattatt tatcgtgttc gtgttcatga aggaaaagaa  1860
aagtaaatat atagctaaag cagctttgta aatcctgcgt acaataccc  ttagggttga  1920
cactttaaat aataaagtg tgaatcctag ggggtgtttt gcattgtaag ttattcaact   1980
attgaaaagc ttaaattact tcatgattat cagaaatcgg attatggttt aacggtgtac  2040
tccgattacc atggtgtccg accagcaaac atgagtaagt ggattaagca attcctactc  2100
gctggattgg cgggattaat tagacctaag cataatcaga agtactcatt agagactaag  2160
ttaactgctg taaaagctta tctttctggc aagtatacta atcaagcaat tctccagcag  2220
tatcaaatta gaaatatttc tcaactacat caatggggtta tcagttacaa taatgacaaa  2280
ctccgagtta atcagacaac gagaaagcga gtcagaaaaa tgggacgaaa agtaaccttt  2340
gatgaaaaga ggcagattgt ccgatggaca attgaacata acaataacta taaagcggct  2400
gcagagaagt atgatattag ttaccaacga gtttattctt gggtacggaa gtaccgagta  2460
aatagcgact gggaagtact aaaagataac cgtgggcgta ataaaggaaa agagcccact  2520
aatgaactag aaaaactaag gaaacgagtt cgtgagctag aagatcgtga ccgtgaacgg  2580
gagctgcaaa tcgctttcgc aaaaaaatta gtcgaaatac gcaatcggga ggtgaaacga  2640
ccggacgata tcaagcgatt caagaaatga acaatgaagg ttattccatt agtgaattgg  2700
ccaaggtcgc tggaattact agacaggctt actacaaatg gttgaaacat gaaccgacta  2760
aatatgagat tgaagaatcg gagattctcc aattgattaa acagttagaa aatgaacata  2820
agcaaagcgt tggttatgac aaaatgacta ggttaatcaa gttaagtcag cagatctctt  2880
ataccgttaa taagaaacga gtcattcgta ttatgaaagg ccatagtatc aaggccgact  2940
atcgtcagcc aaccgacaaa cgtattcaag cccagcaaac ttatgaagct gaaaatattc  3000
ttaaccgaca atttgaccaa actgcagcta accagtttg  ggttacggat acgacggaac  3060
tgaattacgg aatctggctt aataaagttc gtctacatat agtattagat ttatatggtc  3120
aatacccagt aagctggtta attacaccta cagaaaccgc tgaaggagta gttcaagtgt  3180
tcgagcaagc acggatgaaa gaaggagcac tagctccgtt aattcatact gatcgtggtg  3240
cggcgtatac ttccaaagca tttaatcagt atttagtagt taatggtgcc caacacagtt  3300
```

-continued

| | |
|---|---|
| attcagcacc agggacaccg gctgacaatg ccgtaataga acattggtgg gcagatttta | 3360 |
| aggctatttg gatcgcacat ctacctaaag cacaaacatt attagaacta gaagaacaag | 3420 |
| ttagagaagg aattacctat ttcactgaaa aatttatctc agcgaagaga atgaccttta | 3480 |
| ccgcagcgga ataccgcttt ggcaaggcca actaatttt attatttaat gtgtaaactt | 3540 |
| gacagggcac agtaccctgt tgagggact cacaaagct gctttttag ttttgtttta | 3600 |
| ctgcaccggt tgaataatta atggtaatgt ttctttggac attcggaaca aagacattgt | 3660 |
| attctagaga accatcacta gatt | 3684 |

<210> SEQ ID NO 26
<211> LENGTH: 7113
<212> TYPE: DNA
<213> ORGANISM: Lactobacillus reuteri
<220> FEATURE:
<221> NAME/KEY: unsure
<222> LOCATION: (3109)
<220> FEATURE:
<221> NAME/KEY: unsure
<222> LOCATION: (3394)

<400> SEQUENCE: 26

| | |
|---|---|
| gtcgactgga gttctggttt gctatgatta aggttgttac gattattgca atgattattc | 60 |
| ttggtttact ggttatcgtt cttgggttag gtaataactg gcacccagtt gggatttcta | 120 |
| atttgtggtc tcatggcgga ttctttaccg gtggctttat gggctttatg ttctcgctat | 180 |
| ctgtgattgc tggttcttat cagggaattg agttattggg aatcactgct ggtgaagctg | 240 |
| aatcaccacg tcatgcgatt gtgaaatcag ttaagtccgt tatctggcgg atcttaatct | 300 |
| tctatattgg tgcaattttc gtcattgttt ctatttaccc atggaacgaa ttgaagtccg | 360 |
| ttggctcacc attcgttgaa accttcacga aggttggaat tactggagca gccggaatca | 420 |
| ttaactttgt tgttttgacg gcagctcttt ctggagctaa ctctgaatt tacagtgcta | 480 |
| gtcggatgtt gttcaagctt tctgttgatg gggaagtacc aaagttcttt agtaagcttt | 540 |
| ccaagcgcgt tgttcctaat gttgcaatcc tcacgatttc ttcctggatc ttccttggct | 600 |
| ttgtaattaa tgaattaatg tcgattttta gttctgctgc tcaaaatatt ttcgtcattg | 660 |
| tatatagttc cagtgttctt ccagggatgg taccatggtt tatcattctc ttgtcagaac | 720 |
| ttcacttcag aaaagaacac cctgaacagc ttaaagatca tccattcaag atgccgcttt | 780 |
| acccggctta taactacttt agtttgattg ccttgactgt gatcttgatc ttcatgttct | 840 |
| ttaacccaga tactcgagtt tcagtatcag ttggtgttat cttcttgatt atcatgagta | 900 |
| ttatttatcg tgttcgtgtt catgaaggaa agaaaagta aatatatagc taaagcagct | 960 |
| ttgtaaatcc tgcgtacaat accccttagg gttgacactt taaataataa aagtgtgaat | 1020 |
| cctagggggt gttttgcatt gtaagttatt caactattga aaagcttaaa ttacttcatg | 1080 |
| attatcagaa atcggattat ggtttaacgg tgtactccga ttaccatggt gtccgaccag | 1140 |
| caaacatgag taagtggatt aagcaattcc tactcgctgg attggcggga ttaattagac | 1200 |
| ctaagcataa tcagaagtac tcattagaga ctaagttaac tgctgtaaaa gcttatcttt | 1260 |
| ctggcaagta tactaatcaa gcaattctcc agcagtatca aattagaaat atttctcaac | 1320 |
| tacatcaatg ggttatcagt tacaataatg acaaactccg agttaatcag acaacgagaa | 1380 |
| agcgagtcag aaaaatggga cgaaaagtaa cctttgatga aaagaggcag attgtccgat | 1440 |
| ggacaattga acataacaat aactataaag cggctgcaga gaagtatgat attagttacc | 1500 |
| aacgagttta ttcttgggta cggaagtacc gagtaaatag cgactgggaa gtactaaaag | 1560 |

```
ataaccgtgg gcgtaataaa ggaaaagagc ccactaatga actagaaaaa ctaaggaaac    1620
gagttcgtga gctagaagat cgtgaccgtg aacgggagct gcaaatcgct ttcgcaaaaa    1680
aattagtcga aatacgcaat cgggaggtga aacgaccgga cgatatcaag cgattcaaga    1740
aatgaacaat gaaggttatt ccattagtga attggccaag gtcgctggaa ttactagaca    1800
ggcttactac aaatggttga aacatgaacc gactaaatat gagattgaag aatcggagat    1860
tctccaattg attaaacagt tagaaaatga acataagcaa agcgttggtt atgacaaaat    1920
gactaggtta atcaagttaa gtcagcagat ctcttatacc gttaataaga aacgagtcat    1980
tcgtattatg aaaggccata gtatcaaggc cgactatcgt cagccaaccg acaaacgtat    2040
tcaagcccag caaacttatg aagctgaaaa tattcttaac cgacaatttg accaaactgc    2100
agctaaccaa gtttgggtta cggatacgac ggaactgaat tacggaatct ggcttaataa    2160
agttcgtcta catatagtat tagatttata tggtcaatac ccagtaagct ggttaattac    2220
acctacagaa accgctgaag gagtagttca agtgttcgag caagcacgga tgaaagaagg    2280
agcactagct ccgttaattc atactgatcg tggtgcggcg tatacttcca aagcatttaa    2340
tcagtattta gtagttaatg gtgcccaaca cagttattca gcaccaggga caccggctga    2400
caatgccgta atagaacatt ggtgggcaga ttttaaggct atttggatcg cacatctacc    2460
taaagcacaa acattattag aactagaaga acaagttaga gaaggaatta cctatttcac    2520
tgaaaaattt atctcagcga agagaaatga ccttaccgca gcggaatacc gctttggcaa    2580
ggccaactaa ttttttattat ttaatgtgta aacttgacag ggcacagtac cctgtttgag    2640
gggactcaca aagctgcttt tttagttttg ttttactgca ccggttgaat aattaatggt    2700
aatgtttctt tggacattcg gaacaaagac attgtattct agagaaccat cactagattt    2760
agcttcgata tgagcacctg ccggaacgat attattaccg tcataaatat tggtaactcg    2820
gtagcgaact tgcttattct gatctaatgc ttttctcacc agaccttcgt agtaattttg    2880
ccctgttgag ttcttacttc gtgcttcatt tgcccaggca gtttgcgtgg caatattaga    2940
tggatttgat tcggatgcat caaatccatg aataccacca actagtgcat aggcaagaag    3000
gtgtccgcga tcgtatgcat gattgtaccc gcctttaaga ttatgcgcct gaaggaagcc    3060
agctggtcgc caatccgtag caccattccc tgtggcaaat ttcggcttnt atattgaccg    3120
agttgtcctg tttaaccagg catcaccttg ccacgccctt ccttgacggt caagatgatt    3180
tacagcatag ggtgcacttg caatcttagc gttaagattt gtttggttat tattgataat    3240
aaacgcaccg gctttgttcc aggtaattga aatgccaagt tgttggcgaa cagccggagt    3300
taagactgaa ttagcctgtt cctgagttgg cggtaatgtt tttttgatcg ttgtgactgg    3360
ttttcttcca ataagcaatt ttactaatat ggtntaacga agcatttgtt agctgaggtt    3420
gctggataac tccagtaact actaataaac cagcaagagc aaataaaagg tgatagaggc    3480
gtttcttaag tttcataaat tcactccatt tctaataatt ccaaagtcta ttttactagt    3540
ttgaacatac gtttggaata attatttaga attaatttat aagttcattg tgtttaataa    3600
aattgacact ttcaaccgct ttcactaaaa ttaaggtagt tatgatgcac ttgtttactg    3660
agaagggagt cgtcaaaatg tattattcaa acgggaatta tgaagccttt gctcgaccaa    3720
agaagcctgc tggcgttgat aagaaacatg cctacattgt cggtggtggt ttagctggtt    3780
tatcggccgc cgtgttttta attcgtgatg cccaaatgcc gggtgagaat atccatattt    3840
tagaggaatt accggttgcc ggtggttctc ttgatggtga agatcgtcct ggaattggtt    3900
```

```
ttgttactcg tggaggccgg gaaatggaga accatttcga gtgtatgtgg gacatgtatc   3960
gttcaattcc atcacttgaa atcccaggtg cttcctacct tgatgaatac tactggttag   4020
ataaggaaga tccaaacagt tctaattgtc gtttaaccta aagcggggga aatgaagttc   4080
catcggacgg taaatatggt ttaagtaaaa aggcaatcaa agagctgact aagctaatta   4140
tgacccctga agaaaaattg ggaagggaga ctattggtga atacttctct gatgatttct   4200
ttgaaagcaa tttctggatt tattggtcaa caatgtttgc gtttgaacgg tggcactctc   4260
tagctgaaat gcgtcgttat atgatgcggt ttattcacca tattgatggt ttaccggatt   4320
tcactgcact gaagtttaat aagtataacc aatatgaatc aatgaccaag ccgctattgg   4380
cctacctgaa agatcatcat gtcaagattg agtacgatac ccaggtaaag aatgttattg   4440
ttgatactca tgggcggcaa aagcacgcta agcgaatctt attaactcaa gccggtaaag   4500
ataaagttgt tgagttaacg gacaatgacc ttgtctttgt cacaaacggt tcaattacag   4560
aaagttctac ttacggcagt caccatcaag cagctcgacc aacgcaagca cttggtggta   4620
gttggaaact gtgggaaaac cttgctcggc agtcagctga ttttggtcat cctgatgtct   4680
tttgcaagaa tcttccaggg agaagctggt tcatttccgc tactgcaacc gttaagaacc   4740
cgcaagttga accatacatt gaacgcttaa ccaagcgaga tctccatgat ggcaaagtta   4800
atactggtgg aatcattacg gtcactgact ctaattggat gctttcctgg acaattcacc   4860
gtcaaccgca cttcaagaaa caaagaaaa atgaaaccat tgtttggatt tacggtctgt   4920
actctaatac aaagggaaac tatattaaga aacggatcgt tgattgtact ggtgaagaga   4980
ttactaaaga atggctatcc atctgggggt tccagaagcc gttaattgac gatttggcta   5040
aggagagttc aattaatact gttccagtat atatgccatt tatcactagc tactttatgc   5100
cacgagttaa gggcgaccgt ccagacgttg ttccagaagg atccgctaac ttggcattta   5160
ttggtaactt tgctgaatct ccaagtcgag ataccgtatt taccacggaa tattcagtac   5220
ggaccgcaat ggaagccgtc tacactctat tagatgttga tcgggagtt ccagaagtct   5280 ttaactctat ttatgatctt cgagagttaa tgcgggcaat gtattacatg aatgataaga   5340
agccgttaaa agacatggac ttgccaattc caaagattgt tgaaaagcca ttattaaaga   5400
aactccaagg aacgtggatt ggtgaattaa tggagcaaca gcacttacta taagatgaa   5460 agaagctgga aatttccggc ttcttttttt atatagctta tcggggaacc acttgcaaaa   5520
agggattaaa tagtcgaaaa taaaactaat atatttattg atagtaaagg attatggtca   5580
tgacagaaac tgctggtata agaaaaattc atattgtttt tgatggtcaa gaaacaccac   5640
cattaaagat ccatcaatta tttgattcac aaaaatacga tcagttaatc gcagtaactg   5700
ggaaaattac tgctgacttc attaataaat accttagtaa ttttatcagt attaatgtag   5760
cgttaagctc ccaatcaact agtgaattaa gtgctgatga gatggtgaca aaggttgcac   5820
ttaccaatgc tctccttagt tcagcaaata agaagctgc taaactcttc tcagcgttaa   5880
ccagtgacaa ccaaacgaac gtcttaaata atcttttttcg cgtatcaatc gcgcctactc   5940
aggttatcca ttcaagtttt acttgttaa gtagttcaac tactcatgat tcccgtgtga   6000
ttcttgggag tgtagattta gacgaagctt catttgatgc tcaccgaaat caatttgaag   6060
aagtattggt atttgacaat gatgtccgct tataccaaaa ccttactgac cactttaaaa   6120
aggattttaa gccagtattg aagcccttct ttactatgaa cctagtaaag gcagctcaaa   6180
agcaagttga ggaaggaaag aaagatcagg atagcggtaa gggaccggtt atccttgata   6240
atgaaacaac agataagatc gctgaaacag acatggtgga tctgttgaag catgaccttc   6300
```

```
agcatgatat tgaccataat cttgttcctg aaatgatcac aaagtcaatg cgtgatatta    6360
ccataaatcg ttctcaagca aaggagaaaa ttgctaagca ggttaagcaa catgatacga    6420
tttatacttt gcaaaagaa gcggtctctc ctcgggcagc taagccaaaa ctaaagactc     6480
gagaaaaaat taccaagcag gttcaggatg ctttgatcag tggaatgtca ccacagcaac    6540
gggatgctga gaaaaagtac acgacttttc tgtacgatcg gccaatggaa cgaaacattg    6600
cgaataacaa tagtggccta tacgttccta atgatacggg aactcaccca atcccatttg    6660
gtaaaattgc aactatttct gaaattcgtg acggtttaaa gagcattgat gctgttatga    6720
agggctatca gcagtttgtc gttgattatg atgctgacta cgggaagcgg ttctttgaag    6780
caattttgta tagtttact gcaccgtttt tatgggaaat tcgttctaaa gctagcctga     6840
accctgaaga tgggaatgat gttcctaatt tcctaatcct aggggcaacg gctggttccg    6900
gaaagtctac ccttcttcgg attattaatc agctcacgtg gaacactgat cgctcgttga    6960
ttgactttgg aacgatctac ccgtcgcaaa ctcctcaaaa gaaggcaaag actgttgagg    7020
cgatggaaca ttatatgaaa cttggtagtt catacccggt tttgttagat gaaattgaac    7080
cgtacttctt ccagcaagat caatatagtc gac                                 7113

<210> SEQ ID NO 27
<211> LENGTH: 941
<212> TYPE: DNA
<213> ORGANISM: Lactobacillus reuteri
<220> FEATURE:
<221> NAME/KEY: CDS
<222> LOCATION: (3)..(941)

<400> SEQUENCE: 27 gt cga ctg gag ttc tgg ttt gct atg att aag gtt gtt acg att att         47
   Arg Leu Glu Phe Trp Phe Ala Met Ile Lys Val Val Thr Ile Ile
    1               5                  10                  15 gca atg att att ctt ggt tta ctg gtt atc gtt ctt ggg tta ggt aat        95
Ala Met Ile Ile Leu Gly Leu Leu Val Ile Val Leu Gly Leu Gly Asn
             20                  25                  30 aac tgg cac cca gtt ggg att tct aat ttg tgg tct cat ggc gga ttc       143
Asn Trp His Pro Val Gly Ile Ser Asn Leu Trp Ser His Gly Gly Phe
         35                  40                  45 ttt acc ggt ggc ttt atg ggc ttt atg ttc tcg cta tct gtg att gct       191
Phe Thr Gly Gly Phe Met Gly Phe Met Phe Ser Leu Ser Val Ile Ala
     50                  55                  60 ggt tct tat cag gga att gag tta ttg gga atc act gct ggt gaa gct       239
Gly Ser Tyr Gln Gly Ile Glu Leu Leu Gly Ile Thr Ala Gly Glu Ala
 65                  70                  75 gaa tca cca cgt cat gcg att gtg aaa tca gtt aag tcc gtt atc tgg       287
Glu Ser Pro Arg His Ala Ile Val Lys Ser Val Lys Ser Val Ile Trp
             80                  85                  90                  95 cgg atc tta atc ttc tat att ggt gca att ttc gtc att gtt tct att       335
Arg Ile Leu Ile Phe Tyr Ile Gly Ala Ile Phe Val Ile Val Ser Ile
                100                 105                 110 tac cca tgg aac gaa ttg aag tcc gtt ggc tca cca ttc gtt gaa acc       383
Tyr Pro Trp Asn Glu Leu Lys Ser Val Gly Ser Pro Phe Val Glu Thr
            115                 120                 125 ttc acg aag gtt gga att act gga gca gcc gga atc att aac ttt gtt       431
Phe Thr Lys Val Gly Ile Thr Gly Ala Ala Gly Ile Ile Asn Phe Val
        130                 135                 140 gtt ttg acg gca gct ctt tct gga gct aac tct gga att tac agt gct       479
Val Leu Thr Ala Ala Leu Ser Gly Ala Asn Ser Gly Ile Tyr Ser Ala
    145                 150                 155
```

```
agt cgg atg ttg ttc aag ctt tct gtt gat ggg gaa gta cca aag ttc      527
Ser Arg Met Leu Phe Lys Leu Ser Val Asp Gly Glu Val Pro Lys Phe
160             165                 170                 175 ttt agt aag ctt tcc aag cgc gtt gtt cct aat gtt gca atc ctc acg      575
Phe Ser Lys Leu Ser Lys Arg Val Val Pro Asn Val Ala Ile Leu Thr
        180                 185                 190 att tct tcc tgg atc ttc ctt ggc ttt gta att aat gaa tta atg tcg      623
Ile Ser Ser Trp Ile Phe Leu Gly Phe Val Ile Asn Glu Leu Met Ser
            195                 200                 205 att ttt agt tct gct gct caa aat att ttc gtc att gta tat agt tcc      671
Ile Phe Ser Ser Ala Ala Gln Asn Ile Phe Val Ile Val Tyr Ser Ser
                210                 215                 220 agt gtt ctt cca ggg atg gta cca tgg ttt atc att ctc ttg tca gaa      719
Ser Val Leu Pro Gly Met Val Pro Trp Phe Ile Ile Leu Leu Ser Glu
225                 230                 235 ctt cac ttc aga aaa gaa cac cct gaa cag ctt aaa gat cat cca ttc      767
Leu His Phe Arg Lys Glu His Pro Glu Gln Leu Lys Asp His Pro Phe
240                 245                 250                 255 aag atg ccg ctt tac ccg gct tat aac tac ttt agt ttg att gcc ttg      815
Lys Met Pro Leu Tyr Pro Ala Tyr Asn Tyr Phe Ser Leu Ile Ala Leu
                260                 265                 270 act gtg atc ttg atc ttc atg ttc ttt aac cca gat act cga gtt tca      863
Thr Val Ile Leu Ile Phe Met Phe Phe Asn Pro Asp Thr Arg Val Ser
            275                 280                 285 gta tca gtt ggt gtt atc ttc ttg atc atc atg agt att att tat cgt      911
Val Ser Val Gly Val Ile Phe Leu Ile Ile Met Ser Ile Ile Tyr Arg
                290                 295                 300 gtt cgt gtt cat gaa gga aaa gaa aag taa                              941
Val Arg Val His Glu Gly Lys Glu Lys
305                 310

<210> SEQ ID NO 28
<211> LENGTH: 312
<212> TYPE: PRT
<213> ORGANISM: Lactobacillus reuteri

<400> SEQUENCE: 28

Arg Leu Glu Phe Trp Phe Ala Met Ile Lys Val Val Thr Ile Ile Ala
1               5                   10                  15

Met Ile Ile Leu Gly Leu Leu Val Ile Val Leu Gly Leu Gly Asn Asn
            20                  25                  30

Trp His Pro Val Gly Ile Ser Asn Leu Trp Ser His Gly Gly Phe Phe
        35                  40                  45

Thr Gly Gly Phe Met Gly Phe Met Phe Ser Leu Ser Val Ile Ala Gly
    50                  55                  60

Ser Tyr Gln Gly Ile Glu Leu Leu Gly Ile Thr Ala Gly Glu Ala Glu
65                  70                  75                  80

Ser Pro Arg His Ala Ile Val Lys Ser Val Lys Ser Val Ile Trp Arg
                85                  90                  95

Ile Leu Ile Phe Tyr Ile Gly Ala Ile Phe Val Ile Val Ser Ile Tyr
            100                 105                 110

Pro Trp Asn Glu Leu Lys Ser Val Gly Ser Pro Phe Val Glu Thr Phe
        115                 120                 125

Thr Lys Val Gly Ile Thr Gly Ala Ala Gly Ile Ile Asn Phe Val Val
    130                 135                 140

Leu Thr Ala Ala Leu Ser Gly Ala Asn Ser Gly Ile Tyr Ser Ala Ser
145                 150                 155                 160
```

```
Arg Met Leu Phe Lys Leu Ser Val Asp Gly Glu Val Pro Lys Phe Phe
             165                 170                 175

Ser Lys Leu Ser Lys Arg Val Val Pro Asn Val Ala Ile Leu Thr Ile
            180                 185                 190

Ser Ser Trp Ile Phe Leu Gly Phe Val Ile Asn Glu Leu Met Ser Ile
        195                 200                 205

Phe Ser Ser Ala Ala Gln Asn Ile Phe Val Ile Val Tyr Ser Ser Ser
    210                 215                 220

Val Leu Pro Gly Met Val Pro Trp Phe Ile Ile Leu Leu Ser Glu Leu
225                 230                 235                 240

His Phe Arg Lys Glu His Pro Glu Gln Leu Lys Asp His Pro Phe Lys
                245                 250                 255

Met Pro Leu Tyr Pro Ala Tyr Asn Tyr Phe Ser Leu Ile Ala Leu Thr
            260                 265                 270

Val Ile Leu Ile Phe Met Phe Phe Asn Pro Asp Thr Arg Val Ser Val
        275                 280                 285

Ser Val Gly Val Ile Phe Leu Ile Ile Met Ser Ile Ile Tyr Arg Val
    290                 295                 300

Arg Val His Glu Gly Lys Glu Lys
305                 310

<210> SEQ ID NO 29
<211> LENGTH: 600
<212> TYPE: DNA
<213> ORGANISM: Lactobacillus reuteri
<220> FEATURE:
<221> NAME/KEY: CDS
<222> LOCATION: (1)..(597)

<400> SEQUENCE: 29 atg agt aag tgg att aag caa ttc cta ctc gct gga ttg gcg gga tta    48
Met Ser Lys Trp Ile Lys Gln Phe Leu Leu Ala Gly Leu Ala Gly Leu
  1               5                  10                  15 att aga cct aag cat aat cag aag tac tca tta gag act aag tta act    96
Ile Arg Pro Lys His Asn Gln Lys Tyr Ser Leu Glu Thr Lys Leu Thr
                 20                  25                  30 gct gta aaa gct tat ctt tct ggc aag tat act aat caa gca att ctc   144
Ala Val Lys Ala Tyr Leu Ser Gly Lys Tyr Thr Asn Gln Ala Ile Leu
             35                  40                  45 cag cag tat caa att aga aat att tct caa cta cat caa tgg gtt atc   192
Gln Gln Tyr Gln Ile Arg Asn Ile Ser Gln Leu His Gln Trp Val Ile
         50                  55                  60 agt tac aat aat gac aaa ctc cga gtt aat cag aca acg aga aag cga   240
Ser Tyr Asn Asn Asp Lys Leu Arg Val Asn Gln Thr Thr Arg Lys Arg
 65                  70                  75                  80 gtc aga aaa atg gga cga aaa gta acc ttt gat gaa aag agg cag att   288
Val Arg Lys Met Gly Arg Lys Val Thr Phe Asp Glu Lys Arg Gln Ile
                 85                  90                  95 gtc cga tgg aca att gaa cat aac aat aac tat aaa gcg gct gca gag   336
Val Arg Trp Thr Ile Glu His Asn Asn Asn Tyr Lys Ala Ala Ala Glu
            100                 105                 110 aag tat gat att agt tac caa cga gtt tat tct tgg gta cgg aag tac   384
Lys Tyr Asp Ile Ser Tyr Gln Arg Val Tyr Ser Trp Val Arg Lys Tyr
        115                 120                 125 cga gta aat agc gac tgg gaa gta cta aaa gat aac cgt ggg cgt aat   432
Arg Val Asn Ser Asp Trp Glu Val Leu Lys Asp Asn Arg Gly Arg Asn
    130                 135                 140 aaa gga aaa gag ccc act aat gaa cta gaa aaa cta agg aaa cga gtt   480
Lys Gly Lys Glu Pro Thr Asn Glu Leu Glu Lys Leu Arg Lys Arg Val
145                 150                 155                 160
```

```
                    145                 150                 155                 160
cgt gag cta gaa gat cgt gac cgt gaa cgg gag ctg caa atc gct ttc          528
Arg Glu Leu Glu Asp Arg Asp Arg Glu Arg Glu Leu Gln Ile Ala Phe
                165                 170                 175 gca aaa aaa tta gtc gaa ata cgc aat cgg gag gtg aaa cga ccg gac          576
Ala Lys Lys Leu Val Glu Ile Arg Asn Arg Glu Val Lys Arg Pro Asp
            180                 185                 190 gat atc aag cga ttc aag aaa tga                                          600
Asp Ile Lys Arg Phe Lys Lys
        195

<210> SEQ ID NO 30
<211> LENGTH: 199
<212> TYPE: PRT
<213> ORGANISM: Lactobacillus reuteri

<400> SEQUENCE: 30

Met Ser Lys Trp Ile Lys Gln Phe Leu Leu Ala Gly Leu Ala Gly Leu
 1               5                  10                  15

Ile Arg Pro Lys His Asn Gln Lys Tyr Ser Leu Glu Thr Lys Leu Thr
            20                  25                  30

Ala Val Lys Ala Tyr Leu Ser Gly Lys Tyr Thr Asn Gln Ala Ile Leu
        35                  40                  45

Gln Gln Tyr Gln Ile Arg Asn Ile Ser Gln Leu His Gln Trp Val Ile
    50                  55                  60

Ser Tyr Asn Asn Asp Lys Leu Arg Val Asn Gln Thr Thr Arg Lys Arg
65                  70                  75                  80

Val Arg Lys Met Gly Arg Lys Val Thr Phe Asp Glu Lys Arg Gln Ile
                85                  90                  95

Val Arg Trp Thr Ile Glu His Asn Asn Asn Tyr Lys Ala Ala Ala Glu
            100                 105                 110

Lys Tyr Asp Ile Ser Tyr Gln Arg Val Tyr Ser Trp Val Arg Lys Tyr
        115                 120                 125

Arg Val Asn Ser Asp Trp Glu Val Leu Lys Asp Asn Arg Gly Arg Asn
    130                 135                 140

Lys Gly Lys Glu Pro Thr Asn Glu Leu Glu Lys Leu Arg Lys Arg Val
145                 150                 155                 160

Arg Glu Leu Glu Asp Arg Asp Arg Glu Arg Glu Leu Gln Ile Ala Phe
                165                 170                 175

Ala Lys Lys Leu Val Glu Ile Arg Asn Arg Glu Val Lys Arg Pro Asp
            180                 185                 190

Asp Ile Lys Arg Phe Lys Lys
        195

<210> SEQ ID NO 31
<211> LENGTH: 849
<212> TYPE: DNA
<213> ORGANISM: Lactobacillus reuteri
<220> FEATURE:
<221> NAME/KEY: CDS
<222> LOCATION: (1)..(849)

<400> SEQUENCE: 31 atg aac aat gaa ggt tat tcc att agt gaa ttg gcc aag gtc gct gga          48
Met Asn Asn Glu Gly Tyr Ser Ile Ser Glu Leu Ala Lys Val Ala Gly
 1               5                  10                  15 att act aga cag gct tac tac aaa tgg ttg aaa cat gaa ccg act aaa          96
Ile Thr Arg Gln Ala Tyr Tyr Lys Trp Leu Lys His Glu Pro Thr Lys
            20                  25                  30
```

-continued

```
tat gag att gaa gaa tcg gag att ctc caa ttg att aaa cag tta gaa    144
Tyr Glu Ile Glu Glu Ser Glu Ile Leu Gln Leu Ile Lys Gln Leu Glu
         35                  40                  45 aat gaa cat aag caa agc gtt ggt tat gac aaa atg act agg tta atc    192
Asn Glu His Lys Gln Ser Val Gly Tyr Asp Lys Met Thr Arg Leu Ile
 50                  55                  60 aag tta agt cag cag atc tct tat acc gtt aat aag aaa cga gtc att    240
Lys Leu Ser Gln Gln Ile Ser Tyr Thr Val Asn Lys Lys Arg Val Ile
 65                  70                  75                  80 cgt att atg aaa ggc cat agt atc aag gcc gac tat cgt cag cca acc    288
Arg Ile Met Lys Gly His Ser Ile Lys Ala Asp Tyr Arg Gln Pro Thr
                 85                  90                  95 gac aaa cgt att caa gcc cag caa act tat gaa gct gaa aat att ctt    336
Asp Lys Arg Ile Gln Ala Gln Gln Thr Tyr Glu Ala Glu Asn Ile Leu
            100                 105                 110 aac cga caa ttt gac caa act gca gct aac caa gtt tgg gtt acg gat    384
Asn Arg Gln Phe Asp Gln Thr Ala Ala Asn Gln Val Trp Val Thr Asp
        115                 120                 125 acg acg gaa ctg aat tac gga atc tgg ctt aat aaa gtt cgt cta cat    432
Thr Thr Glu Leu Asn Tyr Gly Ile Trp Leu Asn Lys Val Arg Leu His
    130                 135                 140 ata gta tta gat tta tat ggt caa tac cca gta agc tgg tta att aca    480
Ile Val Leu Asp Leu Tyr Gly Gln Tyr Pro Val Ser Trp Leu Ile Thr
145                 150                 155                 160 cct aca gaa acc gct gaa gga gta gtt caa gtg ttc gag caa gca cgg    528
Pro Thr Glu Thr Ala Glu Gly Val Val Gln Val Phe Glu Gln Ala Arg
                165                 170                 175 atg aaa gaa gga gca cta gct ccg tta att cat act gat cgt ggt gcg    576
Met Lys Glu Gly Ala Leu Ala Pro Leu Ile His Thr Asp Arg Gly Ala
            180                 185                 190 gcg tat act tcc aaa gca ttt aat cag tat tta gta gtt aat ggt gcc    624
Ala Tyr Thr Ser Lys Ala Phe Asn Gln Tyr Leu Val Val Asn Gly Ala
        195                 200                 205 caa cac agt tat tca gca cca ggg aca ccg gct gac aat gcc gta ata    672
Gln His Ser Tyr Ser Ala Pro Gly Thr Pro Ala Asp Asn Ala Val Ile
    210                 215                 220 gaa cat tgg tgg gca gat ttt aag gct att tgg atc gca cat cta cct    720
Glu His Trp Trp Ala Asp Phe Lys Ala Ile Trp Ile Ala His Leu Pro
225                 230                 235                 240 aaa gca caa aca tta tta gaa cta gaa gaa caa gtt aga gaa gga att    768
Lys Ala Gln Thr Leu Leu Glu Leu Glu Glu Gln Val Arg Glu Gly Ile
                245                 250                 255 acc tat ttc act gaa aaa ttt atc tca gcg aag aga aat gac ctt acc    816
Thr Tyr Phe Thr Glu Lys Phe Ile Ser Ala Lys Arg Asn Asp Leu Thr
            260                 265                 270 gca gcg gaa tac cgc ttt ggc aag gcc aac taa                        849
Ala Ala Glu Tyr Arg Phe Gly Lys Ala Asn
        275                 280
```

<210> SEQ ID NO 32
<211> LENGTH: 282
<212> TYPE: PRT
<213> ORGANISM: Lactobacillus reuteri

<400> SEQUENCE: 32

```
Met Asn Asn Glu Gly Tyr Ser Ile Ser Glu Leu Ala Lys Val Ala Gly
  1               5                  10                  15

Ile Thr Arg Gln Ala Tyr Tyr Lys Trp Leu Lys His Glu Pro Thr Lys
             20                  25                  30
```

```
Tyr Glu Ile Glu Glu Ser Glu Ile Leu Gln Leu Ile Lys Gln Leu Glu
         35                  40                  45

Asn Glu His Lys Gln Ser Val Gly Tyr Asp Lys Met Thr Arg Leu Ile
 50                  55                  60

Lys Leu Ser Gln Gln Ile Ser Tyr Thr Val Asn Lys Lys Arg Val Ile
 65                  70                  75                  80

Arg Ile Met Lys Gly His Ser Ile Lys Ala Asp Tyr Arg Gln Pro Thr
                 85                  90                  95

Asp Lys Arg Ile Gln Ala Gln Gln Thr Tyr Glu Ala Glu Asn Ile Leu
             100                 105                 110

Asn Arg Gln Phe Asp Gln Thr Ala Ala Asn Gln Val Trp Val Thr Asp
         115                 120                 125

Thr Thr Glu Leu Asn Tyr Gly Ile Trp Leu Asn Lys Val Arg Leu His
    130                 135                 140

Ile Val Leu Asp Leu Tyr Gly Gln Tyr Pro Val Ser Trp Leu Ile Thr
145                 150                 155                 160

Pro Thr Glu Thr Ala Glu Gly Val Val Gln Val Phe Glu Gln Ala Arg
                165                 170                 175

Met Lys Glu Gly Ala Leu Ala Pro Leu Ile His Thr Asp Arg Gly Ala
            180                 185                 190

Ala Tyr Thr Ser Lys Ala Phe Asn Gln Tyr Leu Val Val Asn Gly Ala
        195                 200                 205

Gln His Ser Tyr Ser Ala Pro Gly Thr Pro Ala Asp Asn Ala Val Ile
    210                 215                 220

Glu His Trp Trp Ala Asp Phe Lys Ala Ile Trp Ile Ala His Leu Pro
225                 230                 235                 240

Lys Ala Gln Thr Leu Leu Glu Leu Glu Glu Gln Val Arg Glu Gly Ile
                245                 250                 255

Thr Tyr Phe Thr Glu Lys Phe Ile Ser Ala Lys Arg Asn Asp Leu Thr
            260                 265                 270

Ala Ala Glu Tyr Arg Phe Gly Lys Ala Asn
        275                 280

<210> SEQ ID NO 33
<211> LENGTH: 744
<212> TYPE: DNA
<213> ORGANISM: Lactobacillus reuteri
<220> FEATURE:
<221> NAME/KEY: CDS
<222> LOCATION: (1)..(744)
<220> FEATURE:
<221> NAME/KEY: unsure
<222> LOCATION: (12)
<220> FEATURE:
<221> NAME/KEY: unsure
<222> LOCATION: (297)
<220> FEATURE:
<221> NAME/KEY: misc_feature
<222> LOCATION: (10)..(12)
<223> OTHER INFORMATION: Xaa = Tyr or stop
<220> FEATURE:
<221> NAME/KEY: misc_feature
<222> LOCATION: (295)..(297)
<223> OTHER INFORMATION: Xaa = Tyr or stop

<400> SEQUENCE: 33 atg ctt cgt tan acc ata tta gta aaa ttg ctt att gga aga aaa cca      48
Met Leu Arg Xaa Thr Ile Leu Val Lys Leu Leu Ile Gly Arg Lys Pro
 1               5                  10                  15 gtc aca acg atc aaa aaa aca tta ccg cca act cag gaa cag gct aat      96
Val Thr Thr Ile Lys Lys Thr Leu Pro Pro Thr Gln Glu Gln Ala Asn
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| tca | gtc | tta | act | ccg | gct | gtt | cgc | caa | caa | ctt | ggc | att | tca | att | acc | 144 |
| Ser | Val | Leu | Thr | Pro | Ala | Val | Arg | Gln | Gln | Leu | Gly | Ile | Ser | Ile | Thr |
|  |  | 35 |  |  |  |  | 40 |  |  |  |  | 45 |  |  |  |
| tgg | aac | aaa | gcc | ggt | gcg | ttt | att | atc | aat | aat | aac | caa | aca | aat | ctt | 192 |
| Trp | Asn | Lys | Ala | Gly | Ala | Phe | Ile | Ile | Asn | Asn | Asn | Gln | Thr | Asn | Leu |
| 50 |  |  |  |  | 55 |  |  |  |  | 60 |  |  |  |  |  |
| aac | gct | aag | att | gca | agt | gca | ccc | tat | gct | gta | aat | cat | ctt | gac | cgt | 240 |
| Asn | Ala | Lys | Ile | Ala | Ser | Ala | Pro | Tyr | Ala | Val | Asn | His | Leu | Asp | Arg |
| 65 |  |  |  |  | 70 |  |  |  |  | 75 |  |  |  |  | 80 |
| caa | gga | agg | gcg | tgg | caa | ggt | gat | gcc | tgg | tta | aac | agg | aca | act | cgg | 288 |
| Gln | Gly | Arg | Ala | Trp | Gln | Gly | Asp | Ala | Trp | Leu | Asn | Arg | Thr | Thr | Arg |
|  |  |  |  | 85 |  |  |  |  | 90 |  |  |  |  | 95 |  |
| tca | ata | tan | aag | ccg | aaa | ttt | gcc | aca | ggg | aat | ggt | gct | acg | gat | tgg | 336 |
| Ser | Ile | Xaa | Lys | Pro | Lys | Phe | Ala | Thr | Gly | Asn | Gly | Ala | Thr | Asp | Trp |
|  |  |  | 100 |  |  |  |  | 105 |  |  |  |  | 110 |  |  |
| cga | cca | gct | ggc | ttc | ctt | cag | gcg | cat | aat | ctt | aaa | ggc | ggg | tac | aat | 384 |
| Arg | Pro | Ala | Gly | Phe | Leu | Gln | Ala | His | Asn | Leu | Lys | Gly | Gly | Tyr | Asn |
|  |  |  | 115 |  |  |  |  | 120 |  |  |  |  | 125 |  |  |
| cat | gca | tac | gat | cgc | gga | cac | ctt | ctt | gcc | tat | gca | cta | gtt | ggt | ggt | 432 |
| His | Ala | Tyr | Asp | Arg | Gly | His | Leu | Leu | Ala | Tyr | Ala | Leu | Val | Gly | Gly |
|  |  | 130 |  |  |  |  | 135 |  |  |  |  | 140 |  |  |  |
| att | cat | gga | ttt | gat | gca | tcc | gaa | tca | aat | cca | tct | aat | att | gcc | acg | 480 |
| Ile | His | Gly | Phe | Asp | Ala | Ser | Glu | Ser | Asn | Pro | Ser | Asn | Ile | Ala | Thr |
| 145 |  |  |  |  | 150 |  |  |  |  | 155 |  |  |  |  | 160 |
| caa | act | gcc | tgg | gca | aat | gaa | gca | cga | agt | aag | aac | tca | aca | ggg | caa | 528 |
| Gln | Thr | Ala | Trp | Ala | Asn | Glu | Ala | Arg | Ser | Lys | Asn | Ser | Thr | Gly | Gln |
|  |  |  |  | 165 |  |  |  |  | 170 |  |  |  |  | 175 |  |
| aat | tac | tac | gaa | ggt | ctg | gtg | aga | aaa | gca | tta | gat | cag | aat | aag | caa | 576 |
| Asn | Tyr | Tyr | Glu | Gly | Leu | Val | Arg | Lys | Ala | Leu | Asp | Gln | Asn | Lys | Gln |
|  |  |  | 180 |  |  |  |  | 185 |  |  |  |  | 190 |  |  |
| gtt | cgc | tac | cga | gtt | acc | aat | att | tat | gac | ggt | aat | aat | atc | gtt | ccg | 624 |
| Val | Arg | Tyr | Arg | Val | Thr | Asn | Ile | Tyr | Asp | Gly | Asn | Asn | Ile | Val | Pro |
|  |  | 195 |  |  |  |  | 200 |  |  |  |  | 205 |  |  |  |
| gca | ggt | gct | cat | atc | gaa | gct | aaa | tct | agt | gat | ggt | tct | cta | gaa | tac | 672 |
| Ala | Gly | Ala | His | Ile | Glu | Ala | Lys | Ser | Ser | Asp | Gly | Ser | Leu | Glu | Tyr |
|  | 210 |  |  |  |  | 215 |  |  |  |  | 220 |  |  |  |  |
| aat | gtc | ttt | gtt | ccg | aat | gtc | caa | aga | aac | att | acc | att | aat | tat | tca | 720 |
| Asn | Val | Phe | Val | Pro | Asn | Val | Gln | Arg | Asn | Ile | Thr | Ile | Asn | Tyr | Ser |
| 225 |  |  |  |  | 230 |  |  |  |  | 235 |  |  |  |  | 240 |
| acc | ggt | gca | gta | aaa | caa | aac | taa |  |  |  |  |  |  |  |  | 744 |
| Thr | Gly | Ala | Val | Lys | Gln | Asn |  |  |  |  |  |  |  |  |  |
|  |  |  |  | 245 |  |  |  |  |  |  |  |  |  |  |  |

```
<210> SEQ ID NO 34
<211> LENGTH: 247
<212> TYPE: PRT
<213> ORGANISM: Lactobacillus reuteri
<220> FEATURE:
<221> NAME/KEY: misc_feature
<222> LOCATION: 4
<223> OTHER INFORMATION: Xaa = Tyr or stop
<220> FEATURE:
<221> NAME/KEY: misc_feature
<222> LOCATION: 99
<223> OTHER INFORMATION: Xaa = Tyr or stop

<400> SEQUENCE: 34
```

| Met | Leu | Arg | Xaa | Thr | Ile | Leu | Val | Lys | Leu | Leu | Ile | Gly | Arg | Lys | Pro |
|---|---|---|---|---|---|---|---|---|---|---|---|---|---|---|---|
| 1 |  |  |  | 5 |  |  |  |  | 10 |  |  |  |  | 15 |  |

| Val | Thr | Thr | Ile | Lys | Lys | Thr | Leu | Pro | Pro | Thr | Gln | Glu | Gln | Ala | Asn |
|---|---|---|---|---|---|---|---|---|---|---|---|---|---|---|---|
|  |  |  | 20 |  |  |  |  | 25 |  |  |  |  | 30 |  |  |

```
Ser Val Leu Thr Pro Ala Val Arg Gln Gln Leu Gly Ile Ser Ile Thr
        35                  40                  45

Trp Asn Lys Ala Gly Ala Phe Ile Ile Asn Asn Gln Thr Asn Leu
    50                  55                  60

Asn Ala Lys Ile Ala Ser Ala Pro Tyr Ala Val Asn His Leu Asp Arg
65                  70                  75                  80

Gln Gly Arg Ala Trp Gln Gly Asp Ala Trp Leu Asn Arg Thr Thr Arg
                85                  90                  95

Ser Ile Xaa Lys Pro Lys Phe Ala Thr Gly Asn Gly Ala Thr Asp Trp
            100                 105                 110

Arg Pro Ala Gly Phe Leu Gln Ala His Asn Leu Lys Gly Gly Tyr Asn
            115                 120                 125

His Ala Tyr Asp Arg Gly His Leu Leu Ala Tyr Ala Leu Val Gly Gly
            130                 135                 140

Ile His Gly Phe Asp Ala Ser Glu Ser Asn Pro Ser Asn Ile Ala Thr
145                 150                 155                 160

Gln Thr Ala Trp Ala Asn Glu Ala Arg Ser Lys Asn Ser Thr Gly Gln
                165                 170                 175

Asn Tyr Tyr Glu Gly Leu Val Arg Lys Ala Leu Asp Gln Asn Lys Gln
            180                 185                 190

Val Arg Tyr Arg Val Thr Asn Ile Tyr Asp Gly Asn Asn Ile Val Pro
            195                 200                 205

Ala Gly Ala His Ile Glu Ala Lys Ser Ser Asp Gly Ser Leu Glu Tyr
            210                 215                 220

Asn Val Phe Val Pro Asn Val Gln Arg Asn Ile Thr Ile Asn Tyr Ser
225                 230                 235                 240

Thr Gly Ala Val Lys Gln Asn
                245

<210> SEQ ID NO 35
<211> LENGTH: 1540
<212> TYPE: DNA
<213> ORGANISM: Lactobacillus reuteri
<220> FEATURE:
<221> NAME/KEY: CDS
<222> LOCATION: (1)..(1539)

<400> SEQUENCE: 35 atg gtc atg aca gaa act gct ggt ata aga aaa att cat att gtt ttt      48
Met Val Met Thr Glu Thr Ala Gly Ile Arg Lys Ile His Ile Val Phe
 1               5                  10                  15 gat ggt caa gaa aca cca cca tta aag atc cat caa tta ttt gat tca      96
Asp Gly Gln Glu Thr Pro Pro Leu Lys Ile His Gln Leu Phe Asp Ser
                20                  25                  30 caa aaa tac gat cag tta atc gca gta act ggg aaa att act gct gac     144
Gln Lys Tyr Asp Gln Leu Ile Ala Val Thr Gly Lys Ile Thr Ala Asp
            35                  40                  45 ttc att aat aaa tac ctt agt aat ttt atc agt att aat gta gcg tta     192
Phe Ile Asn Lys Tyr Leu Ser Asn Phe Ile Ser Ile Asn Val Ala Leu
        50                  55                  60 agc tcc caa tca act agt gaa tta agt gct gat gag atg gtg aca aag     240
Ser Ser Gln Ser Thr Ser Glu Leu Ser Ala Asp Glu Met Val Thr Lys
65                  70                  75                  80 gtt gca ctt acc aat gct ctc ctt agt tca gca aat aaa gaa gct gct     288
Val Ala Leu Thr Asn Ala Leu Leu Ser Ser Ala Asn Lys Glu Ala Ala
                85                  90                  95 aaa ctc ttc tca gcg tta acc agt gac aac caa acg aac gtc tta aat     336
```

```
                Lys Leu Phe Ser Ala Leu Thr Ser Asp Asn Gln Thr Asn Val Leu Asn
                                100                 105                 110 aat ctt ttt cgc gta tca atc gcg cct act cag gtt atc cat tct aag                  384
Asn Leu Phe Arg Val Ser Ile Ala Pro Thr Gln Val Ile His Ser Lys
            115                 120                 125 ttt tac ttg tta agt agt tca act act cat gat tcc cgt gtg att ctt                  432
Phe Tyr Leu Leu Ser Ser Ser Thr Thr His Asp Ser Arg Val Ile Leu
        130                 135                 140 ggg agt gta gat tta gac gaa gct tca ttt gat gct cac cga aat caa                  480
Gly Ser Val Asp Leu Asp Glu Ala Ser Phe Asp Ala His Arg Asn Gln
145                 150                 155                 160 ttt gaa gaa gta ttg gta ttt gac aat gat gtc cgc tta tac caa aac                  528
Phe Glu Glu Val Leu Val Phe Asp Asn Asp Val Arg Leu Tyr Gln Asn
                165                 170                 175 ctt act gac cac ttt aaa aag gat ttt aag cca gta ttg aag ccc ttc                  576
Leu Thr Asp His Phe Lys Lys Asp Phe Lys Pro Val Leu Lys Pro Phe
            180                 185                 190 ttt act atg aac cta gta aag gca gct caa aag caa gtt gag gaa gga                  624
Phe Thr Met Asn Leu Val Lys Ala Ala Gln Lys Gln Val Glu Glu Gly
        195                 200                 205 aag aaa gat cag gat agc ggt aag gga ccg gtt atc ctt gat aat gaa                  672
Lys Lys Asp Gln Asp Ser Gly Lys Gly Pro Val Ile Leu Asp Asn Glu
210                 215                 220 aca aca gat aag atc gct gaa aca gac atg gtg gat ctg ttg aag cat                  720
Thr Thr Asp Lys Ile Ala Glu Thr Asp Met Val Asp Leu Leu Lys His
225                 230                 235                 240 gac ctt cag cat gat att gac cat aat ctt gtt cct gaa atg atc aca                  768
Asp Leu Gln His Asp Ile Asp His Asn Leu Val Pro Glu Met Ile Thr
                245                 250                 255 aag tca atg cgt gat att acc ata aat cgt tct caa gca aag gag aaa                  816
Lys Ser Met Arg Asp Ile Thr Ile Asn Arg Ser Gln Ala Lys Glu Lys
            260                 265                 270 att gct aag cag gtt aag caa cat gat acg att tat act ttg caa aaa                  864
Ile Ala Lys Gln Val Lys Gln His Asp Thr Ile Tyr Thr Leu Gln Lys
        275                 280                 285 gaa gcg gtc tct cct cgg gca gct aag cca aaa cta aag act cga gaa                  912
Glu Ala Val Ser Pro Arg Ala Ala Lys Pro Lys Leu Lys Thr Arg Glu
    290                 295                 300 aaa att acc aag cag gtt cag gat gct ttg atc agt gga atg tca cca                  960
Lys Ile Thr Lys Gln Val Gln Asp Ala Leu Ile Ser Gly Met Ser Pro
305                 310                 315                 320 cag caa cgg gat gct gag aaa aag tac acg act ttt ctg tac gat cgg                 1008
Gln Gln Arg Asp Ala Glu Lys Lys Tyr Thr Thr Phe Leu Tyr Asp Arg
                325                 330                 335 cca atg gaa cga aac att gcg aat aac aat agt ggc cta tac gtt cct                 1056
Pro Met Glu Arg Asn Ile Ala Asn Asn Asn Ser Gly Leu Tyr Val Pro
            340                 345                 350 aat gat acg gga act cac cca atc cca ttt ggt aaa att gca act att                 1104
Asn Asp Thr Gly Thr His Pro Ile Pro Phe Gly Lys Ile Ala Thr Ile
        355                 360                 365 tct gaa att cgt gac ggt tta aag agc att gat gct gtt atg aag ggc                 1152
Ser Glu Ile Arg Asp Gly Leu Lys Ser Ile Asp Ala Val Met Lys Gly
    370                 375                 380 tat cag cag ttt gtc gtt gat tat gat gct gac tac ggg aag cgg ttc                 1200
Tyr Gln Gln Phe Val Val Asp Tyr Asp Ala Asp Tyr Gly Lys Arg Phe
385                 390                 395                 400 ttt gaa gca att ttg tat agt ttt act gca ccg ttt tta tgg gaa att                 1248
Phe Glu Ala Ile Leu Tyr Ser Phe Thr Ala Pro Phe Leu Trp Glu Ile
                405                 410                 415
```

```
cgt tct aaa gct agc ctg aac cct gaa gat ggg aat gat gtt cct aat    1296
Arg Ser Lys Ala Ser Leu Asn Pro Glu Asp Gly Asn Asp Val Pro Asn
            420                 425                 430 ttc cta atc cta ggg gca acg gct ggt tcc gga aag tct acc ctt ctt    1344
Phe Leu Ile Leu Gly Ala Thr Ala Gly Ser Gly Lys Ser Thr Leu Leu
        435                 440                 445 cgg att att aat cag ctc acg tgg aac act gat cgc tcg ttg att gac    1392
Arg Ile Ile Asn Gln Leu Thr Trp Asn Thr Asp Arg Ser Leu Ile Asp
    450                 455                 460 ttt gga acg atc tac ccg tcg caa act cct caa aag aag gca aag act    1440
Phe Gly Thr Ile Tyr Pro Ser Gln Thr Pro Gln Lys Lys Ala Lys Thr
465                 470                 475                 480 gtt gag gcg atg gaa cat tat atg aaa ctt ggt agt tca tac ccg gtt    1488
Val Glu Ala Met Glu His Tyr Met Lys Leu Gly Ser Ser Tyr Pro Val
                485                 490                 495 ttg tta gat gaa att gaa ccg tac ttc ttc cag caa gat caa tat agt    1536
Leu Leu Asp Glu Ile Glu Pro Tyr Phe Phe Gln Gln Asp Gln Tyr Ser
            500                 505                 510 cga c                                                              1540
Arg

<210> SEQ ID NO 36
<211> LENGTH: 513
<212> TYPE: PRT
<213> ORGANISM: Lactobacillus reuteri

<400> SEQUENCE: 36

Met Val Met Thr Glu Thr Ala Gly Ile Arg Lys Ile His Ile Val Phe
1               5                   10                  15

Asp Gly Gln Glu Thr Pro Leu Lys Ile His Gln Leu Phe Asp Ser
            20                  25                  30

Gln Lys Tyr Asp Gln Leu Ile Ala Val Thr Gly Lys Ile Thr Ala Asp
        35                  40                  45

Phe Ile Asn Lys Tyr Leu Ser Asn Phe Ile Ser Ile Asn Val Ala Leu
    50                  55                  60

Ser Ser Gln Ser Thr Ser Glu Leu Ser Ala Asp Glu Met Val Thr Lys
65                  70                  75                  80

Val Ala Leu Thr Asn Ala Leu Leu Ser Ser Ala Asn Lys Glu Ala Ala
                85                  90                  95

Lys Leu Phe Ser Ala Leu Thr Ser Asp Asn Gln Thr Asn Val Leu Asn
            100                 105                 110

Asn Leu Phe Arg Val Ser Ile Ala Pro Thr Gln Val Ile His Ser Lys
        115                 120                 125

Phe Tyr Leu Leu Ser Ser Thr Thr His Asp Ser Arg Val Ile Leu
    130                 135                 140

Gly Ser Val Asp Leu Asp Glu Ala Ser Phe Asp Ala His Arg Asn Gln
145                 150                 155                 160

Phe Glu Glu Val Leu Val Phe Asp Asn Asp Val Arg Leu Tyr Gln Asn
                165                 170                 175

Leu Thr Asp His Phe Lys Lys Asp Phe Lys Pro Val Leu Lys Pro Phe
            180                 185                 190

Phe Thr Met Asn Leu Val Lys Ala Ala Gln Lys Gln Val Glu Glu Gly
        195                 200                 205

Lys Lys Asp Gln Asp Ser Gly Lys Gly Pro Val Ile Leu Asp Asn Glu
    210                 215                 220

Thr Thr Asp Lys Ile Ala Glu Thr Asp Met Val Asp Leu Leu Lys His
225                 230                 235                 240
```

-continued

```
Asp Leu Gln His Asp Ile Asp His Asn Leu Val Pro Glu Met Ile Thr
                245                 250                 255
Lys Ser Met Arg Asp Ile Thr Ile Asn Arg Ser Gln Ala Lys Glu Lys
            260                 265                 270
Ile Ala Lys Gln Val Lys Gln His Asp Thr Ile Tyr Thr Leu Gln Lys
        275                 280                 285
Glu Ala Val Ser Pro Arg Ala Ala Lys Pro Lys Leu Lys Thr Arg Glu
    290                 295                 300
Lys Ile Thr Lys Gln Val Gln Asp Ala Leu Ile Ser Gly Met Ser Pro
305                 310                 315                 320
Gln Gln Arg Asp Ala Glu Lys Lys Tyr Thr Thr Phe Leu Tyr Asp Arg
                325                 330                 335
Pro Met Glu Arg Asn Ile Ala Asn Asn Asn Ser Gly Leu Tyr Val Pro
            340                 345                 350
Asn Asp Thr Gly Thr His Pro Ile Pro Phe Gly Lys Ile Ala Thr Ile
        355                 360                 365
Ser Glu Ile Arg Asp Gly Leu Lys Ser Ile Asp Ala Val Met Lys Gly
    370                 375                 380
Tyr Gln Gln Phe Val Val Asp Tyr Asp Ala Asp Tyr Gly Lys Arg Phe
385                 390                 395                 400
Phe Glu Ala Ile Leu Tyr Ser Phe Thr Ala Pro Phe Leu Trp Glu Ile
                405                 410                 415
Arg Ser Lys Ala Ser Leu Asn Pro Glu Asp Gly Asn Asp Val Pro Asn
            420                 425                 430
Phe Leu Ile Leu Gly Ala Thr Ala Gly Ser Gly Lys Ser Thr Leu Leu
        435                 440                 445
Arg Ile Ile Asn Gln Leu Thr Trp Asn Thr Asp Arg Ser Leu Ile Asp
    450                 455                 460
Phe Gly Thr Ile Tyr Pro Ser Gln Thr Pro Gln Lys Lys Ala Lys Thr
465                 470                 475                 480
Val Glu Ala Met Glu His Tyr Met Lys Leu Gly Ser Ser Tyr Pro Val
                485                 490                 495
Leu Leu Asp Glu Ile Glu Pro Tyr Phe Phe Gln Gln Asp Gln Tyr Ser
            500                 505                 510
Arg
```

```
<210> SEQ ID NO 37
<211> LENGTH: 26
<212> TYPE: DNA
<213> ORGANISM: Lactobacillus reuteri
<220> FEATURE:
<221> NAME/KEY: terminator
<222> LOCATION: (1)..(26)

<400> SEQUENCE: 37
aaagaagctg aaatttcggc ttcttt                                    26

<210> SEQ ID NO 38
<211> LENGTH: 28
<212> TYPE: DNA
<213> ORGANISM: Lactobacillus reuteri
<220> FEATURE:
<221> NAME/KEY: misc_feature
<222> LOCATION: (1)..(28)
<223> OTHER INFORMATION: PRIMER

<400> SEQUENCE: 38
```

```
gcagtcgacg gagttaagac tgaattag                                              28

<210> SEQ ID NO 39
<211> LENGTH: 26
<212> TYPE: DNA
<213> ORGANISM: Lactobacillus reuteri
<220> FEATURE:
<221> NAME/KEY: misc_feature
<222> LOCATION: (1)..(26)
<223> OTHER INFORMATION: PRIMER

<400> SEQUENCE: 39
ctagtcgacg cagtttctgt catgac                                                26

<210> SEQ ID NO 40
<211> LENGTH: 32
<212> TYPE: DNA
<213> ORGANISM: Lactobacillus reuteri
<220> FEATURE:
<221> NAME/KEY: misc_feature
<222> LOCATION: (1)..(32)
<223> OTHER INFORMATION: PRIMER

<400> SEQUENCE: 40
catatgtatt attcaaacgg gaattatgaa gc                                         32

<210> SEQ ID NO 41
<211> LENGTH: 30
<212> TYPE: DNA
<213> ORGANISM: Lactobacillus reuteri
<220> FEATURE:
<221> NAME/KEY: misc_feature
<222> LOCATION: (1)..(30)
<223> OTHER INFORMATION: PRIMER

<400> SEQUENCE: 41
tgatcatcta taccagcagt ttctgtcatg                                            30
```